United States Patent
Wallrapp et al.

(10) Patent No.: US 12,161,694 B2
(45) Date of Patent: Dec. 10, 2024

(54) METHODS AND COMPOSITIONS FOR REGULATING INNATE LYMPHOID CELL INFLAMMATORY RESPONSES

(71) Applicants: The Broad Institute, Inc., Cambridge, MA (US); Massachusetts Institute of Technology, Cambridge, MA (US); The Brigham and Women's Hospital, Inc., Boston, MA (US)

(72) Inventors: Antonia Wallrapp, Boston, MA (US); Samantha J. Riesenfeld, Cambridge, MA (US); Patrick R. Burkett, Boston, MA (US); Monika S. Kowalczyk, Cambridge, MA (US); Aviv Regev, Cambridge, MA (US); Vijay K. Kuchroo, Boston, MA (US)

(73) Assignees: The Broad Institute, Inc., Cambridge, MA (US); Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 225 days.

(21) Appl. No.: 16/497,105

(22) PCT Filed: Mar. 23, 2018

(86) PCT No.: PCT/US2018/024082
§ 371 (c)(1),
(2) Date: Sep. 24, 2019

(87) PCT Pub. No.: WO2018/175924
PCT Pub. Date: Sep. 27, 2018

(65) Prior Publication Data
US 2021/0121530 A1 Apr. 29, 2021

Related U.S. Application Data

(60) Provisional application No. 62/476,352, filed on Mar. 24, 2017, provisional application No. 62/558,298, filed on Sep. 13, 2017.

(51) Int. Cl.
| | |
|---|---|
| *A61K 38/20* | (2006.01) |
| *A61K 9/00* | (2006.01) |
| *A61K 38/22* | (2006.01) |
| *A61P 37/08* | (2006.01) |
| *C12Q 1/6883* | (2018.01) |

(52) U.S. Cl.
CPC ............ *A61K 38/20* (2013.01); *A61K 9/0073* (2013.01); *A61K 38/22* (2013.01); *A61P 37/08* (2018.01); *C12Q 1/6883* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | |
|---|---|---|
| 4,737,323 A | 4/1988 | Martin et al. |
| 4,837,028 A | 6/1989 | Allen |
| 5,641,870 A | 6/1997 | Rinderknecht et al. |
| 5,811,097 A | 9/1998 | Allison et al. |
| 5,869,326 A | 2/1999 | Hofmann |
| 6,479,626 B1 | 11/2002 | Kim et al. |
| 6,534,261 B1 | 3/2003 | Cox et al. |
| 6,607,882 B1 | 8/2003 | Cox et al. |
| 6,746,838 B1 | 6/2004 | Choo et al. |
| 6,794,136 B1 | 9/2004 | Eisenberg et al. |
| 6,824,978 B1 | 11/2004 | Cox et al. |
| 6,866,997 B1 | 3/2005 | Choo et al. |
| 6,903,185 B2 | 6/2005 | Kim et al. |
| 6,933,113 B2 | 8/2005 | Case et al. |
| 6,979,539 B2 | 12/2005 | Cox et al. |
| 7,013,219 B2 | 3/2006 | Case et al. |

(Continued)

FOREIGN PATENT DOCUMENTS

| | | |
|---|---|---|
| EP | 0 404 097 A2 | 12/1990 |
| EP | 2 784 162 A1 | 10/2014 |

(Continued)

OTHER PUBLICATIONS

Belobrajdic et al. (2000, Nutr. Cancer 36(2):17-23).*
See "Lung Metastases" (https://www.cancer.org/cancer/managing-cancer/advanced-cancer/lung-metastases.html; accessed Dec. 26, 2023).*
The Broad Institute, Inc., "Notification Concerning Transmittal of International Preliminary Report on Patentability for PCT/US2018/024082", Oct. 3, 2019, 9 pages.

(Continued)

*Primary Examiner* — Elizabeth C. Kemmerer
(74) *Attorney, Agent, or Firm* — Wenderoth, Lind & Ponack, L.L.P.

(57) ABSTRACT

Computational and functional analysis identified the neuropeptide receptor Nmur1 as selectively expressed on Type 2 innate lymphoid cells (ILC2s). While both IL-33 and IL-25 promote ILC activation in vivo, IL-33 induces robust ILC proliferation, whereas ILCs activated with IL-25 do not proliferate as robustly and up-regulate Nmur1 expression. Treatment with neuromedin U (NMU), the neuropeptide ligand of Nmur1, had little effect on its own. Co-administration of IL-25 with NMU, however, dramatically amplified allergic lung inflammation and induced the proliferation and expansion of specific ILC2 subsets, characterized by a molecular signature unique to pro-inflammatory ILC2s. The results demonstrate that Nmur1 signaling strongly modulates IL-25-mediated ILC2 responses, resulting in highly proliferative pro-inflammatory ILCs, and highlights the importance of neuro-immune crosstalk in allergic inflammatory responses at mucosal surfaces.

9 Claims, 37 Drawing Sheets

Specification includes a Sequence Listing.

(56) References Cited

U.S. PATENT DOCUMENTS

| | | |
|---|---|---|
| 7,030,215 B2 | 4/2006 | Liu et al. |
| 7,220,719 B2 | 5/2007 | Case et al. |
| 7,241,573 B2 | 7/2007 | Choo et al. |
| 7,241,574 B2 | 7/2007 | Choo et al. |
| 7,585,849 B2 | 9/2009 | Liu et al. |
| 7,595,376 B2 | 9/2009 | Kim et al. |
| 8,021,867 B2 | 9/2011 | Smith et al. |
| 8,119,361 B2 | 2/2012 | Smith et al. |
| 8,119,381 B2 | 2/2012 | Smith et al. |
| 8,124,369 B2 | 2/2012 | Smith et al. |
| 8,129,134 B2 | 3/2012 | Smith et al. |
| 8,133,697 B2 | 3/2012 | Smith et al. |
| 8,163,514 B2 | 4/2012 | Smith et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,697,359 B1 | 4/2014 | Zhang et al. |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 2004/0171156 A1 | 9/2004 | Hartley et al. |
| 2007/0244048 A1 | 10/2007 | Marsh et al. |
| 2010/0254998 A1 | 10/2010 | Adilov et al. |
| 2010/0286035 A1 | 11/2010 | Ohtaki et al. |
| 2011/0158936 A1* | 6/2011 | Wright ............... A61P 35/04 424/85.2 |
| 2011/0165144 A1* | 7/2011 | Binstadt ............ C07K 14/575 424/130.1 |
| 2011/0265198 A1 | 10/2011 | Gregory et al. |
| 2011/0294735 A1 | 12/2011 | Marsh et al. |
| 2011/0301079 A1 | 12/2011 | Marsh et al. |
| 2012/0017290 A1 | 1/2012 | Cui et al. |
| 2013/0236946 A1 | 9/2013 | Gouble |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2015/0184139 A1 | 7/2015 | Zhang et al. |
| 2016/0024195 A1* | 1/2016 | Economides ........ A61K 38/179 424/134.1 |
| 2016/0208243 A1 | 7/2016 | Zhang et al. |
| 2017/0218064 A1* | 8/2017 | Kim .................. G01N 33/6893 |
| 2019/0151346 A1* | 5/2019 | Al-Daccak .......... C07K 16/2866 |
| 2020/0291105 A1* | 9/2020 | Shimkets ............... A61P 29/00 |

FOREIGN PATENT DOCUMENTS

| | | |
|---|---|---|
| EP | 2 771 468 B1 | 2/2015 |
| EP | 2 764 103 B1 | 8/2015 |
| EP | 3 009 511 A2 | 4/2016 |
| WO | 93/11161 A1 | 6/1993 |
| WO | 96/40281 A2 | 12/1996 |
| WO | 97/49450 A1 | 12/1997 |
| WO | 98/52609 A1 | 11/1998 |
| WO | 2006/086769 A2 | 8/2006 |
| WO | 2007/075439 A2 | 7/2007 |
| WO | 2012/050227 A1 | 4/2012 |
| WO | 2014/018423 A2 | 1/2014 |
| WO | 2014/093595 A1 | 6/2014 |
| WO | 2014/093622 A2 | 6/2014 |
| WO | 2014/093635 A1 | 6/2014 |
| WO | 2014/093655 A2 | 6/2014 |
| WO | 2014/093661 A2 | 6/2014 |
| WO | 2014/093694 A1 | 6/2014 |
| WO | 2014/093701 A1 | 6/2014 |
| WO | 2014/093709 A1 | 6/2014 |
| WO | 2014/093712 A1 | 6/2014 |
| WO | 2014/093718 A1 | 6/2014 |
| WO | 2014/204723 A1 | 12/2014 |
| WO | 2014/204724 A1 | 12/2014 |
| WO | 2014/204725 A1 | 12/2014 |
| WO | 2014/204726 A1 | 12/2014 |
| WO | 2014/204727 A1 | 12/2014 |
| WO | 2014/204728 A1 | 12/2014 |
| WO | 2014/204729 A1 | 12/2014 |
| WO | 2014/210353 A2 | 12/2014 |
| WO | 2015/058052 A1 | 4/2015 |
| WO | 2015/070083 A1 | 5/2015 |
| WO | 2015/089351 A1 | 6/2015 |
| WO | 2015/089354 A1 | 6/2015 |
| WO | 2015/089364 A1 | 6/2015 |
| WO | 2015/089419 A2 | 6/2015 |
| WO | 2015/089427 A1 | 6/2015 |
| WO | 2015/089462 A1 | 6/2015 |
| WO | 2015/089465 A1 | 6/2015 |
| WO | 2015/089473 A1 | 6/2015 |
| WO | 2015/089486 A2 | 6/2015 |
| WO | 2016/028682 A1 | 2/2016 |
| WO | 2016/040476 A1 | 3/2016 |
| WO | 2016/049024 A2 | 3/2016 |
| WO | 2016/049163 A2 | 3/2016 |
| WO | 2016/049258 A2 | 3/2016 |
| WO | 2016/094867 A1 | 6/2016 |
| WO | 2016/094872 A1 | 6/2016 |
| WO | 2016/094874 A1 | 6/2016 |
| WO | 2016/094880 A1 | 6/2016 |
| WO | 2016/106236 A1 | 6/2016 |
| WO | 2016/106244 A1 | 6/2016 |
| WO | 2016/168584 A1 | 10/2016 |
| WO | 2017/070605 A1 | 4/2017 |
| WO | 2017/164936 A1 | 9/2017 |
| WO | 2018/175924 A1 | 9/2018 |

OTHER PUBLICATIONS

Audrit, et al., "The Nervous System of Airways and its Remodeling in Inflammatory Lung Diseases", Cell and Tissue Research, vol. 367, No. 3, Mar. 2017, 571-590.

Bartemes, "IL-33-Responsive Lineage-CD25+ CD44(hi) Lymphoid Cells Mediate Innate Type 2 Immunity and Allergic Inflammation in the Lungs", Journal of Immunology, vol. 188, No. 3, Feb. 1, 2012, 1503-1513.

Beale, "Rhinovirus-Induced IL-25 in Asthma Exacerbation Drives Type 2 Immunity and Allergic Pulmonary Inflammation", Science Translational Medicine, vol. 6, No. 256, Oct. 1, 2014, 26 pages.

Bjorklund, et al., "The Heterogeneity of Human Cd127(+) Innate Lymphoid Cells Revealed by Single-Cell RNA Sequencing", Nature Immunology, vol. 17, No. 4, Apr. 2016, 451-460.

Branchfield, et al., "Pulmonary Neuroendocrine Cells Function as Airway Sensors to Control Lung Immune Response", Science, vol. 351, No. 6274, Feb. 2016, 707-710.

Burrows, et al., "OX40 Blockade Inhibits House Dust Mite Driven Allergic Lung Inflammation in Mice and in Vitro Allergic Responses in Humans", European Journal of Immunology, vol. 45, No. 4, Apr. 2015, 1116-1128.

Chang, et al., "Innate Lymphoid Cells Mediate Influenza-Induced Airway Hyper-Reactivity Independently of Adaptive Immunity", Nature Immunology, vol. 12, No. 7, May 29, 2011, 631-638.

(56) References Cited

OTHER PUBLICATIONS

Cheng, et al., "Epithelial Interleukin-25 is a Key Mediator in Th2-High, Corticosteroid-Responsive Asthma", American Journal of Respiratory and Critical Care Medicine, vol. 190, No. 6, Sep. 15, 2014, 639-648.
Gerbe, et al., "Intestinal Epithelial Tuft Cells Initiate Type 2 Mucosal Immunity to Helminth Parasites", Nature, vol. 529, No. 7585, Jan. 14, 2016, 226-230.
Gu, et al., "Chemosensory Functions for Pulmonary Neuroendocrine Cells", American Journal of Respiratory Cell and Molecular Biology, vol. 50, No. 3, Mar. 2015, 637-646.
Gudbjartsson, et al., "Sequence Variants Affecting Eosinophil Numbers Associate with Asthma and Myocardial Infarction", Nature Genetics, vol. 41, No. 3, Mar. 2009, 342-347.
Gury-Benari, et al., "The Spectrum and Regulatory Landscape of Intestinal Innate Lymphoid Cells Are Shaped by the Microbiome", Cell, vol. 166, No. 5, Aug. 25, 2016, 1231-1246.
Halim, et al., "Group 2 Innate Lymphoid Cells are Critical for the Initiation of Adaptive T Helper 2 Cell-Mediated Allergic Lung Inflammation", Immunity, vol. 40, No. 3, Mar. 20, 2014, 425-435.
Hedrick, "Identification of a Human Gastrointestinal Tract and Immune System Receptor for the Peptide Neuromedin U", Molecular Pharmacology, vol. 58, No. 4, Oct. 2000, 870-875.
Heshmat, "Soluble CD30 Serum Levels in Atopic Dermatitis and Bronchial Asthma and its Relationship with Disease Severity in Pediatric Age", Pediatric Allergy and Immunology, vol. 17, No. 4, Jun. 2006, 297-303.
Howitt, et al., "Tuft Cells Taste-Chemosensory Cells, Orchestrate Parasite Type 2 Immunity in the Gut", Science, vol. 351, No. 6279, Mar. 18, 2016, 1329-1333.
Huang, et al., "IL-25-Responsive, Lineage-Negative KLRG1Hi Cells are Multipotential "Inflammatory" Type 2 Innate Lymphoid Cells", Nature Immunology, vol. 16, No. 2, Feb. 2015, 161-169.
Katsunuma, "Analysis of Gene Expressions of T Cells from Children with Acute Exacerbations of Asthma", International Archives of Allergy and Immunology, vol. 134, No. 1, May 2004, 29-33.
Kowalczyk, et al., "Single Cell RNA-Seq Reveals Changes in Cell Cycle and Differentiation Programs Upon Aging of Hematopoietic Stem Cell", Genome Research, vol. 25, No. 12, Dec. 2015, 1860-1872.
Kurakula, et al., "Nuclear Receptor Nur77 Attenuates Airway Inflammation in Mice by Suppressing NF-kappaB Activity in Lung Epithelial Cells", Journal of Immunology, vol. 195, No. 4, Aug. 15, 2015, 1388-1398.
Modena, et al., "Gene Expression Correlated with Severe Asthma Characteristics Reveals Heterogeneous Mechanisms of Severe Disease", American Journal of Respiratory and Critical Care Medicine, vol. 195, No. 11, Jun. 1, 2017, 1449-1463.
Moltke, et al., "Tuft-Cell-Derived IL-25 Regulates an Intestinal ILC2-Epithelial Response Circuit", Nature, vol. 529, No. 7585, Jan. 14, 2016, 221-225.
Monticelli, et al., "Arginase 1 is an Innate Lymphoid-Cell-Intrinsic Metabolic Checkpoint Controlling Type 2 Inflammation", Nature Immunology, vol. 17, No. 6, Jun. 2016, 656-665.
Monticelli, et al., "Innate Lymphoid Cells Promote Lung-tissue Homeostasis after Infection with Influenza Virus", Nature Immunology, vol. 12, No. 11, Nov. 2011, 1045-1054.
Moriyama, et al., "The Neuropeptide Neuromedin U Activates Eosinophils and is Involved in Allergen-Induced Eosinophilia", The American Journal of Physiology—Lung Cellular and Molecular Physiology, vol. 290, No. 5, May 2006, L971-L977.
Moro, et al., "Innate Production of TH 2 Cytokines by Adipose Tissue-associated c-Kit+ Sca-1+ Lymphoid Cells", Nature, vol. 5, No. 7280, Jan. 28, 2010, 540-544.
Neill, et al., "Nuocytes Represent a new Innate Effector Leukocyte that Mediates Type-2 Immunity", Nature, vol. 464, No. 7293, Apr. 29, 2010, 1367-1370.
Nussbaum, et al., "Type 2 Innate Lymphoid Cells Control Eosinophil Homeostasis", Nature, vol. 502, No. 7470, Oct. 10, 2013, 245-248.

Polte, et al., "Direct Evidence for A Critical Role of CD30 in The Development of Allergic Asthma", The Journal of Allergy and Clinical Immunology, vol. 118, No. 4, Oct. 2006, 942-948.
Prendergast, "Species Dependent Smooth Muscle Contraction to Neuromedin U and Determination of the Receptor Subtypes Mediating Contraction using NMU1 Receptor Knockout Mice", British Journal of Pharmacology, vol. 147, No. 8, Apr. 2006, 886-896.
Robinette, "Transcriptional Programs Define Molecular Characteristics of Innate Lymphoid Cell Classes and Subsets", Nature Immunology, vol. 16, No. 3, Mar. 2015, 306-317.
Salimi, et al., "A Role for IL-25 and IL-33-driven type-2 Innate Lymphoid Cells in Atopic Dermatitis", Journal of Experimental Medicine, vol. 210, No. 13, Dec. 16, 2013, 2939-2950.
Schuliga, et al., "Plasminogen-Stimulated Inflammatory Cytokine Production by Airway Smooth Muscle Cells is Regulated by Annexin A2", American Journal of Respiratory Cell and Molecular Biology, vol. 49, No. 5, Nov. 2013, 751-758.
Sekigawa, et al., "Gene-Expression Profiles 482 in Human Nasal Polyp Tissues and Identification of Genetic Susceptibility in Aspirin-Intolerant Asthma", Clinical & Experimental Allergy, vol. 39, No. 7, Jul. 2009, 972-981.
Shan, et al., "Identification of a Novel Neuromedin U Receptor Subtype Expressed in the Central Nervous System", The Journal of Biological Chemistry, vol. 275, No. 50, Dec. 15, 2000, 39482-39486.
Szekeres, et al., "Neuromedin U is A Potent Agonist at The Orphan G Protein-Coupled Receptor FM3", The Journal of Biological Chemistry, vol. 275, No. 27, Jul. 7, 2000, 20247-20250.
Talbot, et al., "Silencing Nociceptor Neurons Reduces Allergic Airway Inflammation", Neuron, vol. 87, No. 2, Jul. 2015, 341-354.
Tirosh, et al., "Dissecting The Multicellular Ecosystem of Metastatic Melanoma By Single-Cell RNA-Seq", Science, vol. 352, No. 6282, Apr. 8, 2016, 189-196.
Ikutani, et al. "Identification of Innate IL-5-Producing Cells and Their Role in Lung Eosinophil Regulation and Antitumor Immunity", The Journal of Immunology, vol. 188, No. 2, Jan. 15, 2012, 703-713.
Mori, et al., "Identification of Neuromedin S and its Possible Role in The Mammalian Circadian Oscillator System", The EMBO Journal, vol. 24, No. 2, Jan. 26, 2005, 325-335.
Morita, et al., "Innate Lymphoid Cells in Allergic and Nonallergic Inflammation", Journal of Allergy and Clinical Immunology, vol. 138, Issue 5, Nov. 2016, 1253-1264.
Rivas, et al., "IL-4 Production by Group 2 Innate Lymphoid cells Promotes Food Allergy by Blocking Regulatory T cell Function", The Journal of Allergy and Clinical Immunology, vol. 138, No. 3, 2016, 801-811.
Van Rijt, et al., "Type 2 Innate Lymphoid Cells: At the Cross-Roads In Allergic Asthma", Seminars in Immunopathology, vol. 38, Issue 4, Jul. 2016, 483-496.
Doherty, et al., "At the Bench: Understanding Group 2 Innate Lymphoid Cells in Disease", J. Leukoc Biol, 97(3), 2015, pp. 455-467.
Moriyama, et al., "The Neuropeptide Neuromedin U Promotes IL-6 Production from Macrophages and Endotoxin Shock", Biochem Biophys Res Commun, 341(4), 2006, pp. 1149-1154.
The Broad Institute, Inc., et al., "International Search Report for PCT/US2018/024082", Jul. 30, 2018, 7 pages.
Cederberg, et al., "Eosinophils Decrease Pulmonary Metastatic Mammary Tumor Growth", Front Oncol. 2022;12:841921, 16 pages.
Ercolano, et al., "ILC2s: New Actors in Tumor Immunity", Front Immunol. 2019;10, 9 pages.
Human IL-25 (Fc Tag) Recombinant protein, NovoPro, catalog No. 501585, 1 page.
Shabgah, et al., "Interleukin-25: New perspective and state-of-the-art in cancer prognosis and treatment approaches", Cancer Med. 2021; 10(15):5191-5202.
Simson, et al., "Regulation of Carcinogenesis by IL-5 and CCL11: a Potential Role for Eosinophils in Tumor Immune Surveillance", J Immunol. 2007;178(7):4222-4229.
Ducimetière, et al., "The Interplay Between Innate Lymphoid Cells and the Tumor Microenvironment," Frontiers in Immunology, vol. 10, 11 pages, Dec. 2019.

(56) References Cited

OTHER PUBLICATIONS

Ikutani, et al., "Identification of Innate IL-5-Producing Cells and Their Role in Lung Eosinophil Regulation and Antitumor Immunity," The Journal of Immunology, 188(2), pp. 703-713, 2012.
Benatar et al., "IL-17E, a proinflammatory cytokine, has antitumor efficacy against several tumor types in vivo," Cancer Immunol Immunother, 59, pp. 805-817, 2010.

* cited by examiner

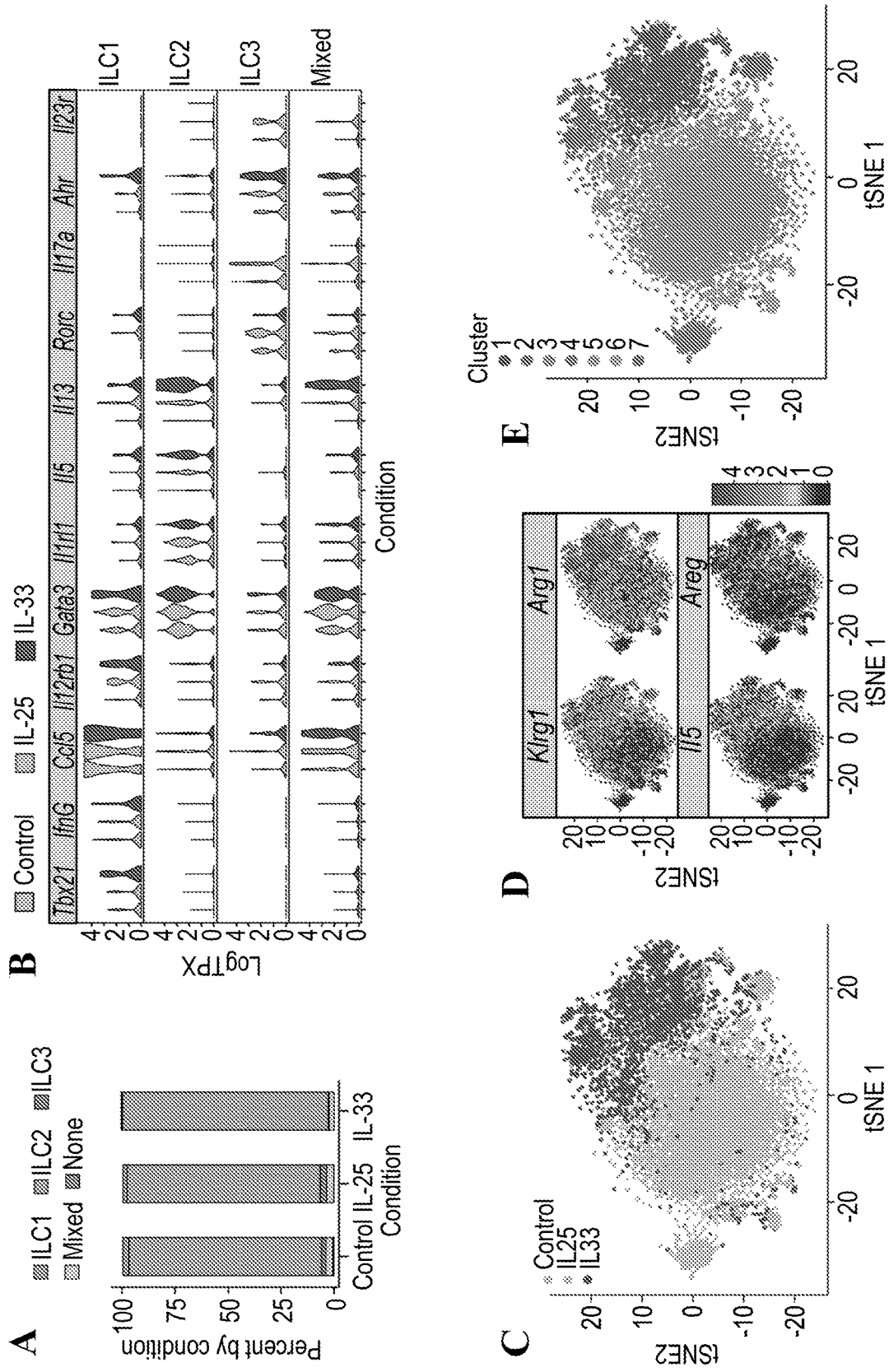
FIG. 1A-E

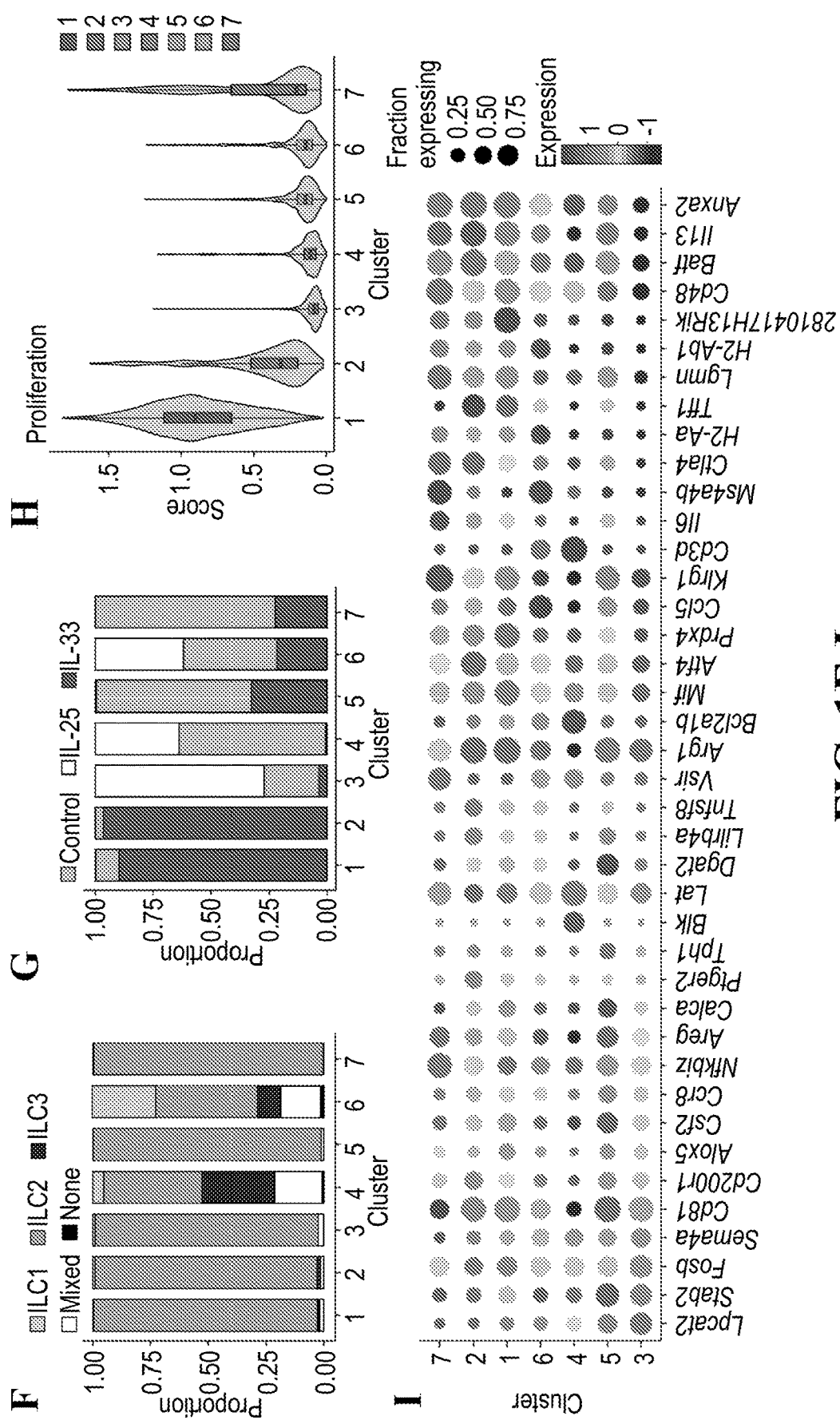
FIG. 1F-I

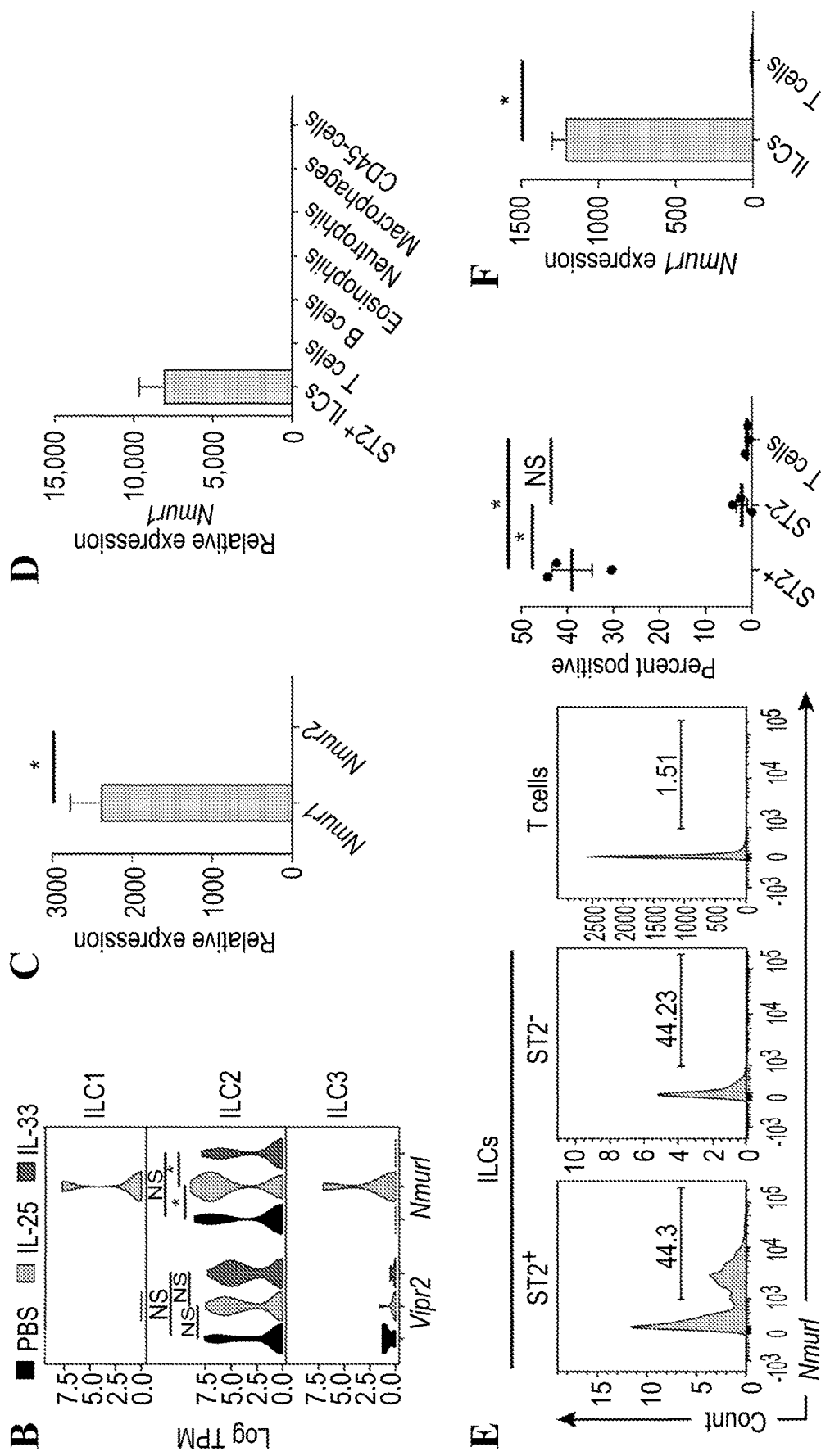
FIG. 2B-F

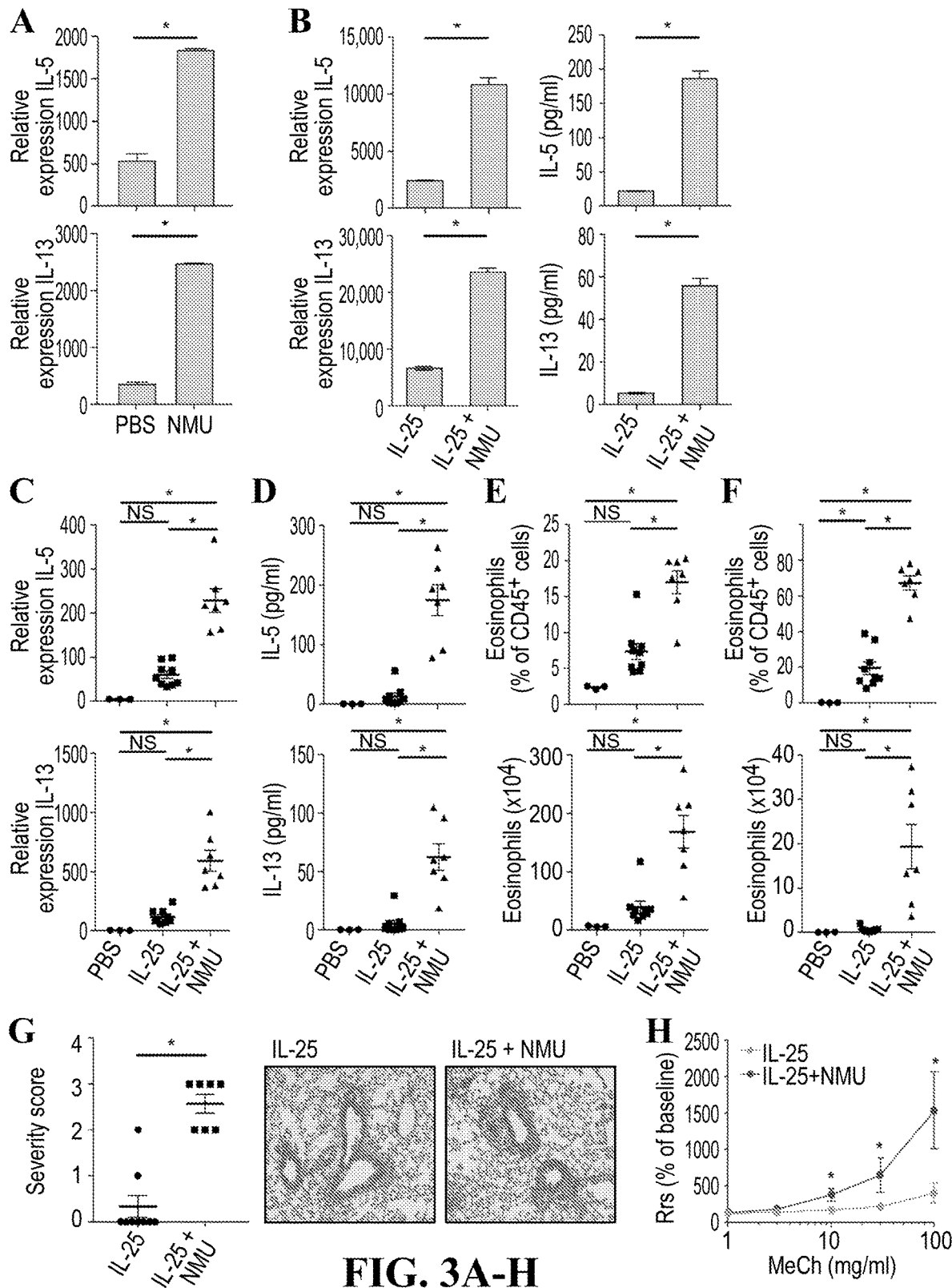
FIG. 3A-H

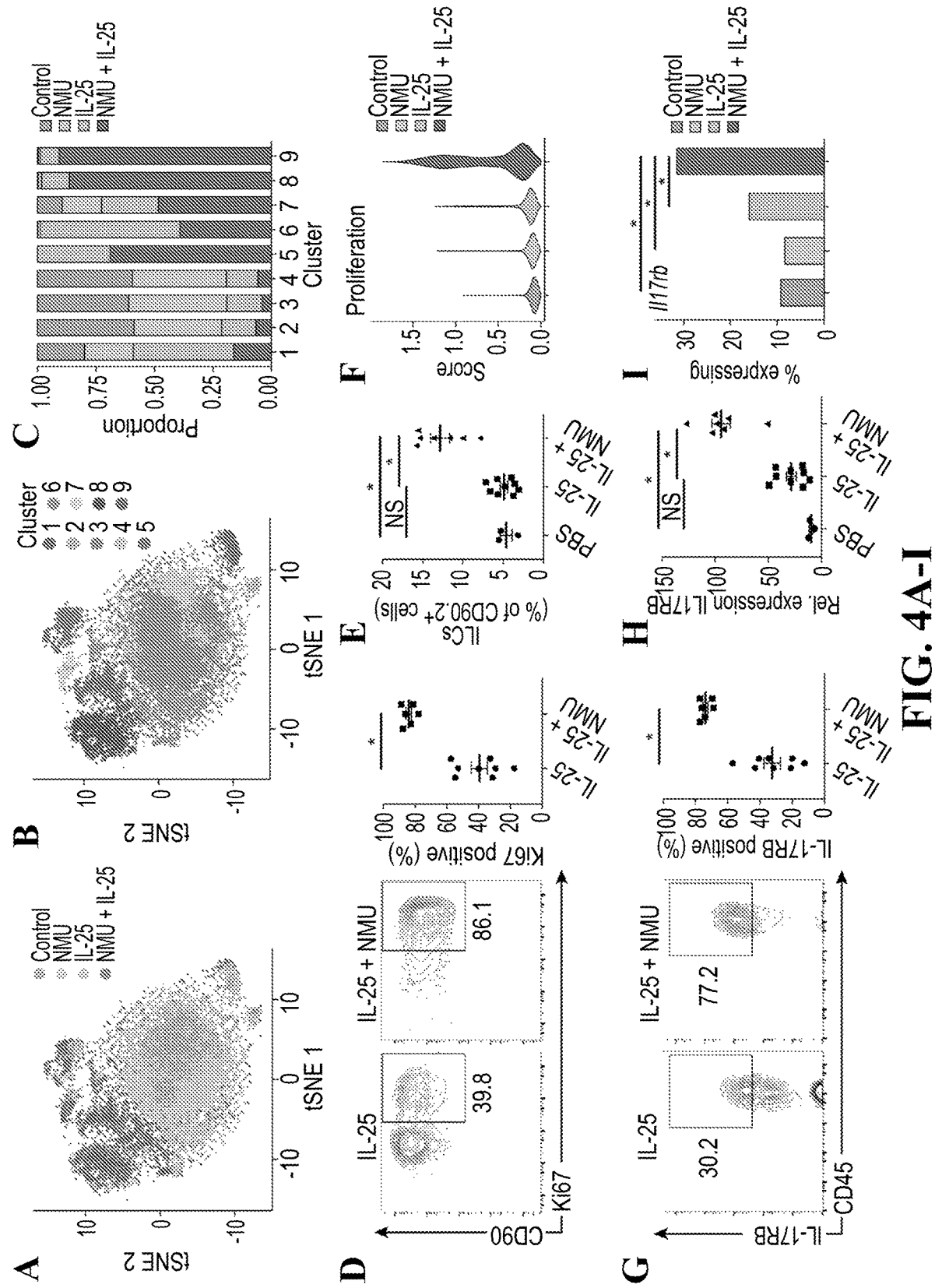
FIG. 4A-I

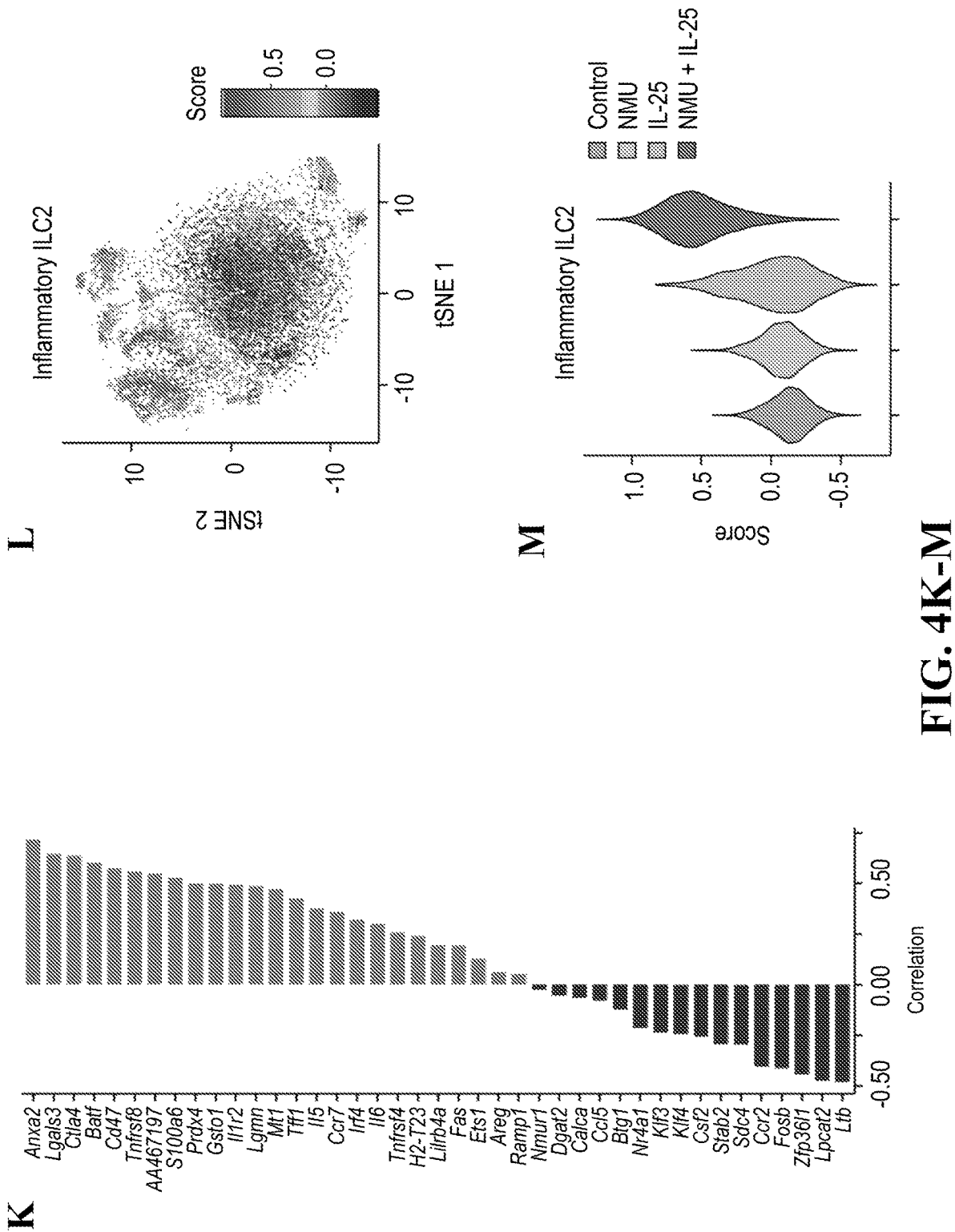
FIG. 4K-M

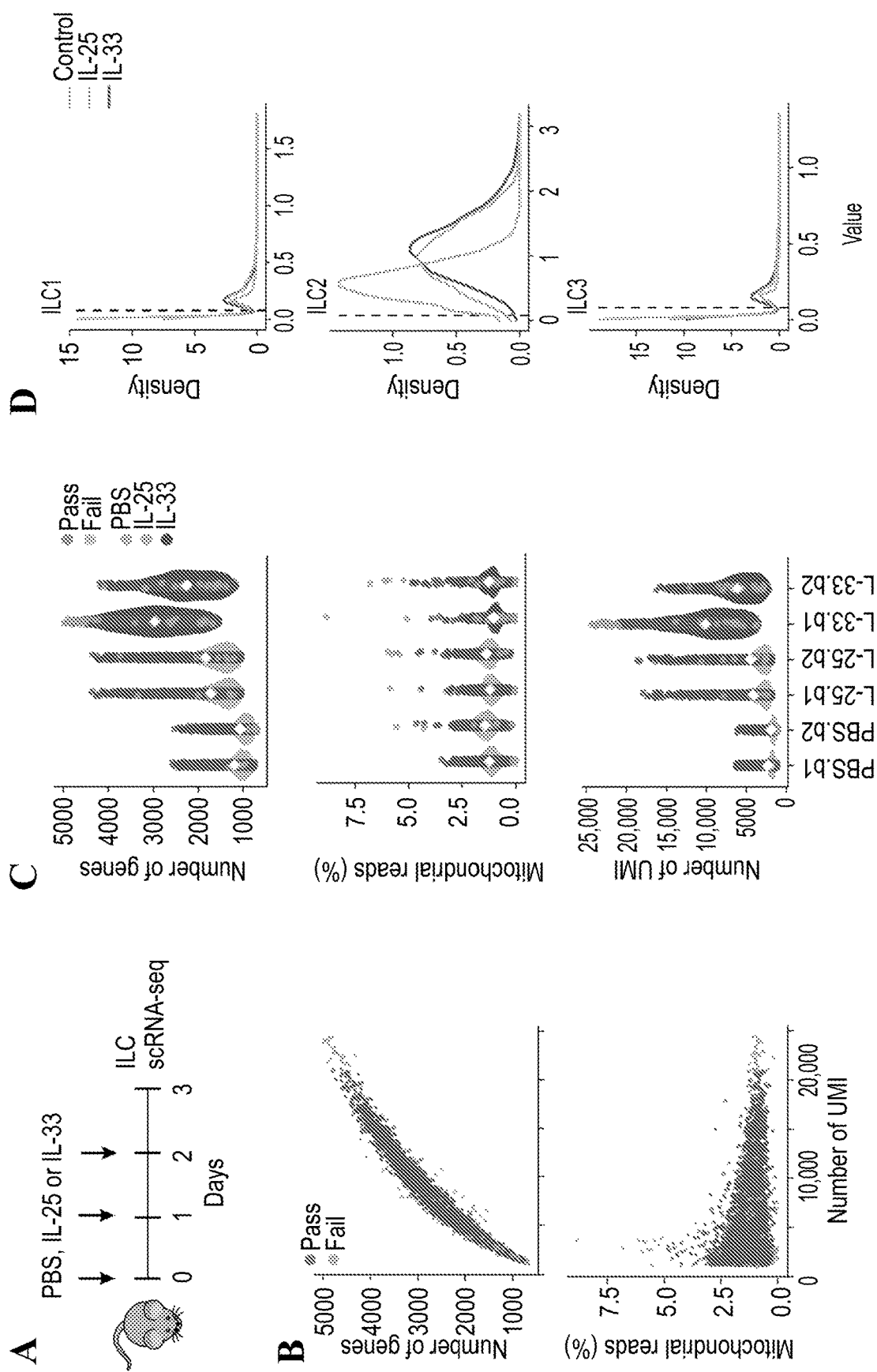
FIG. 5A-D

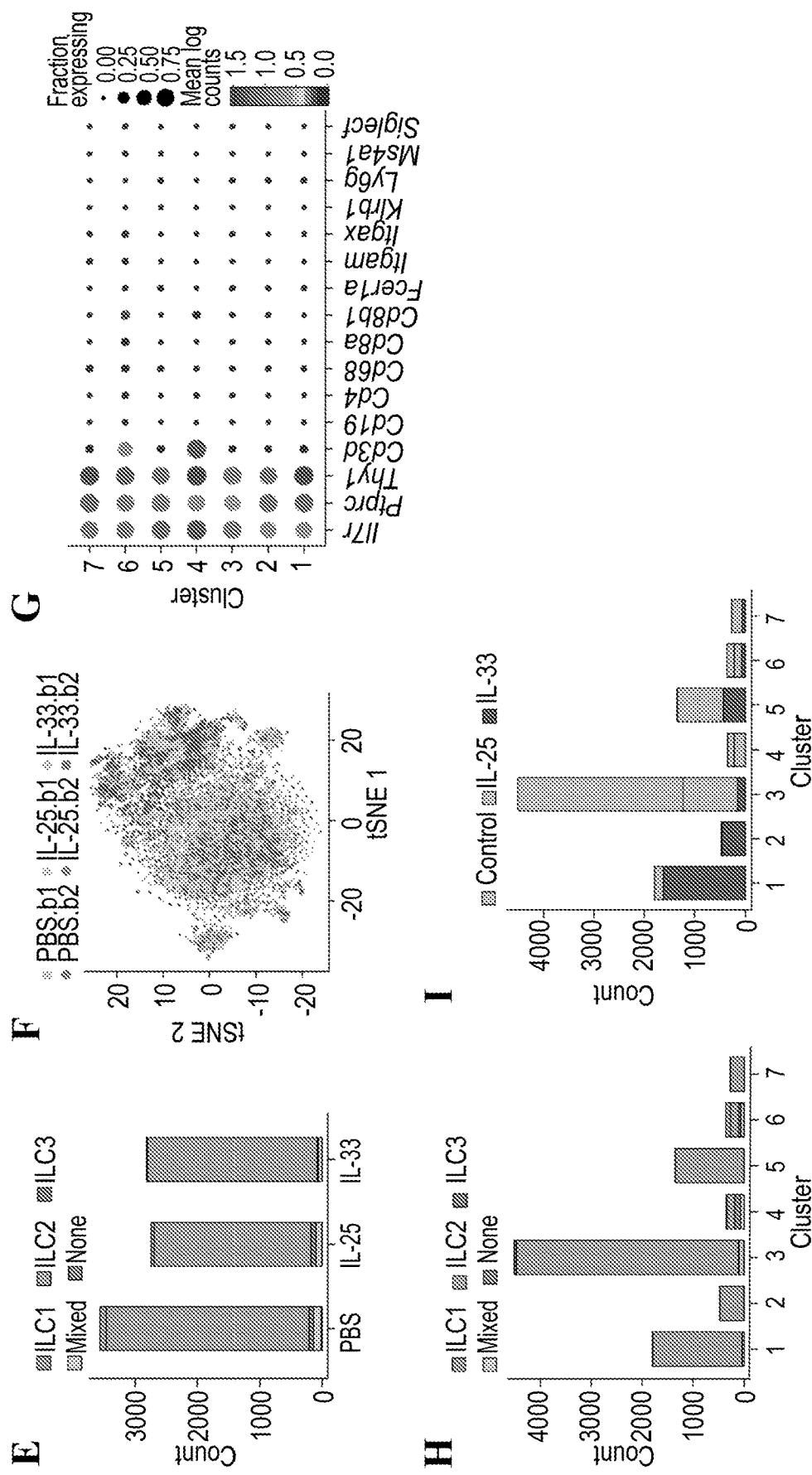
FIG. 5E-I

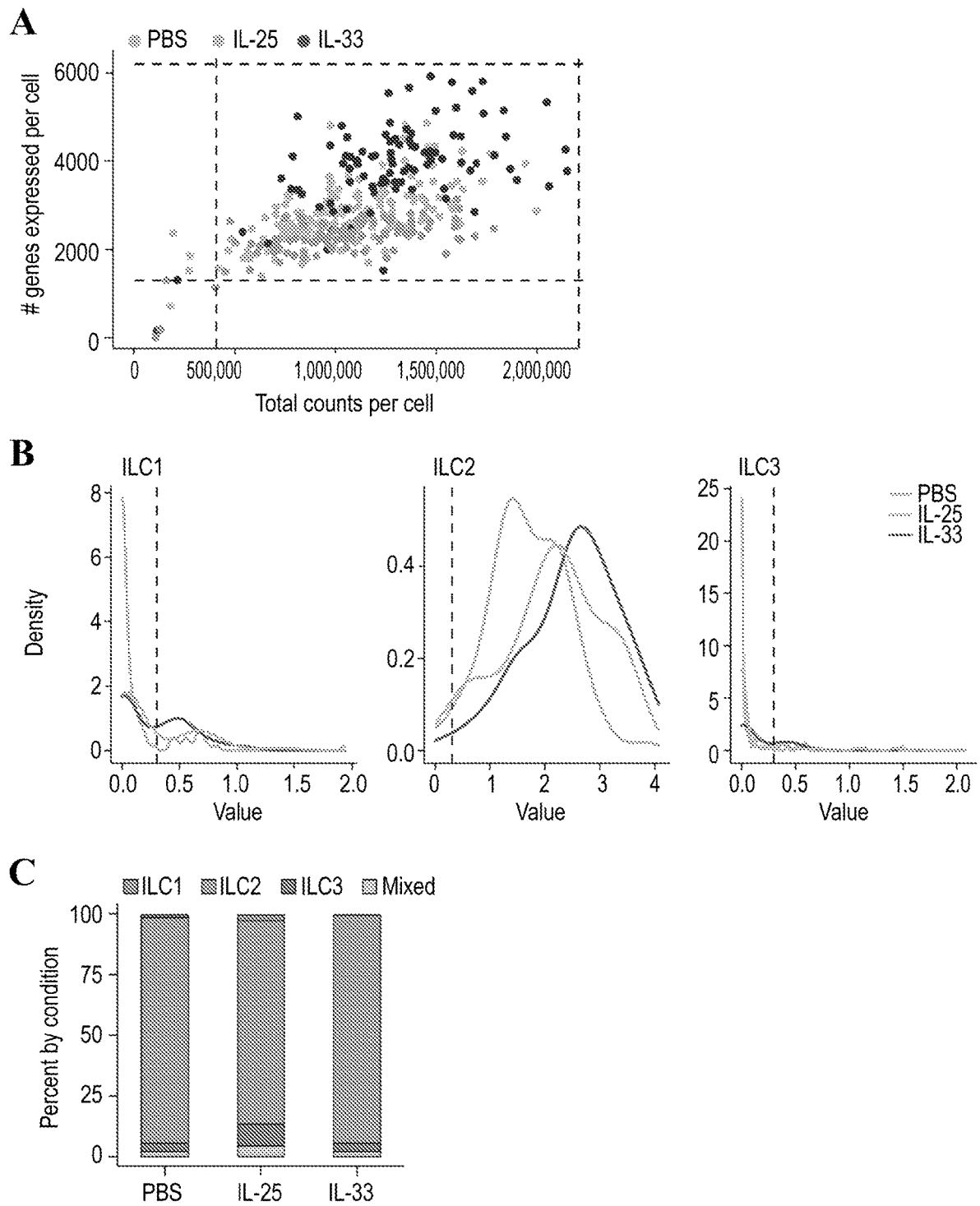
FIG. 7A-C

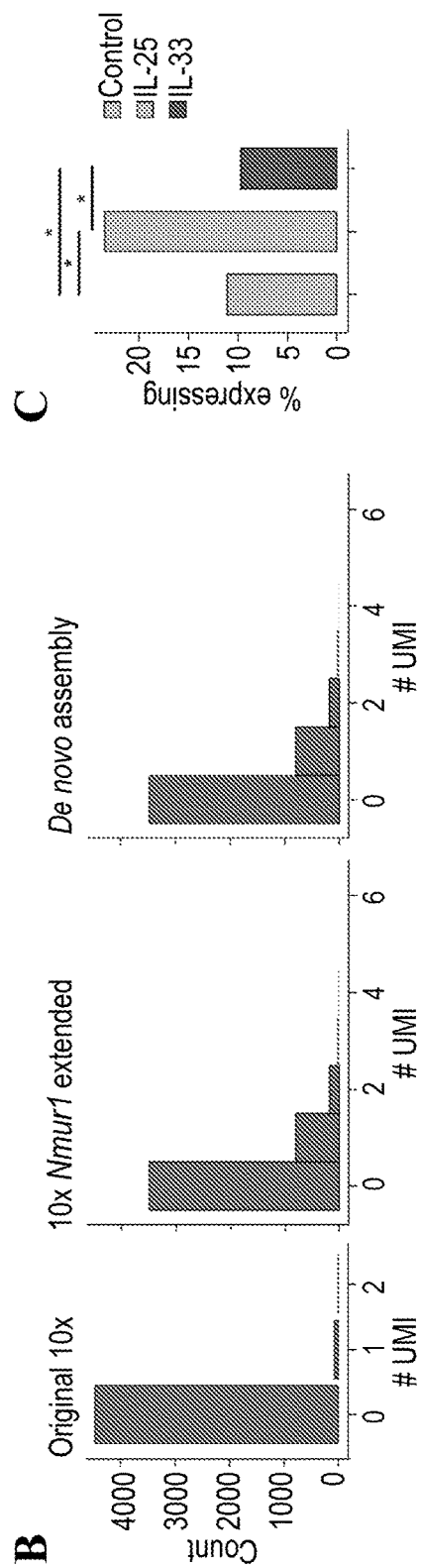
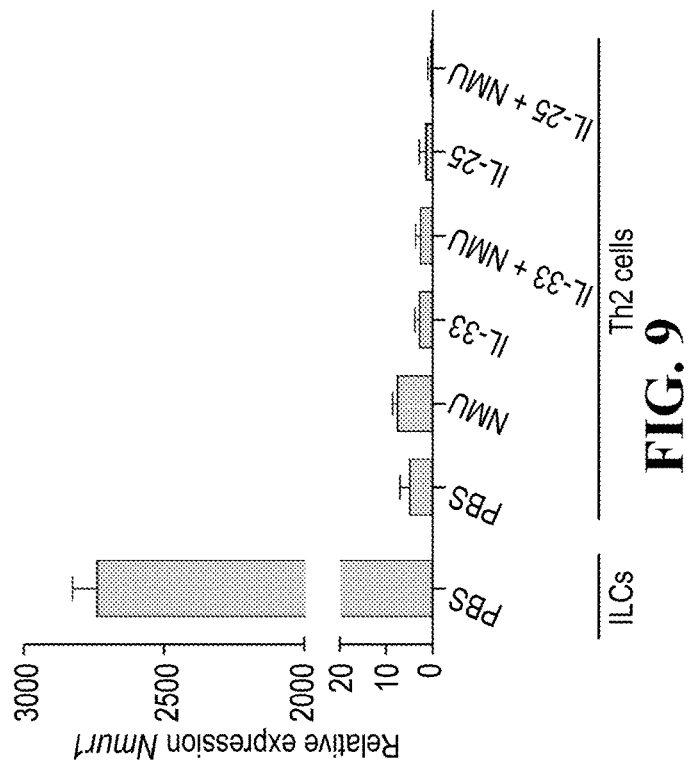
FIG. 8B-C
FIG. 9

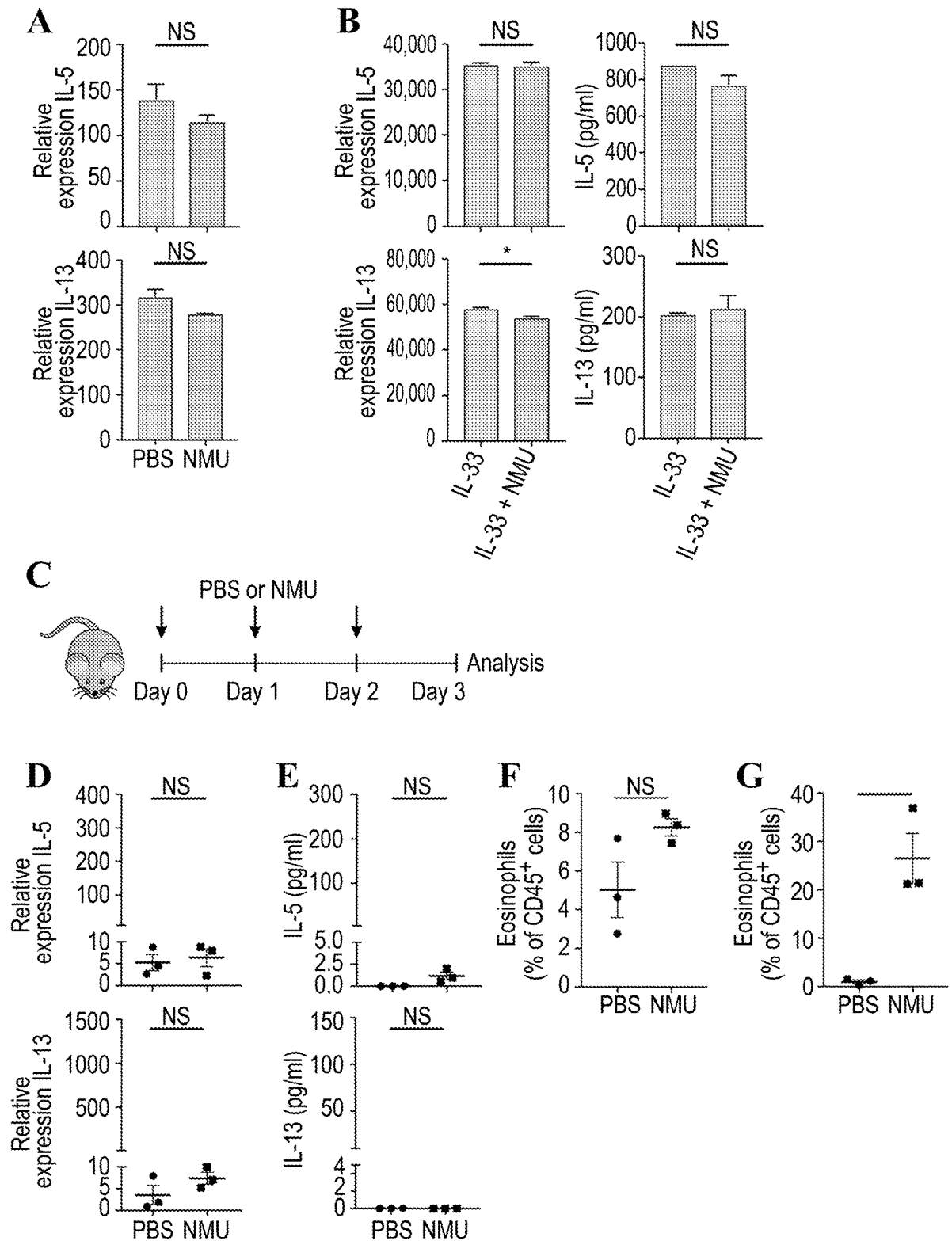
FIG. 10A-G

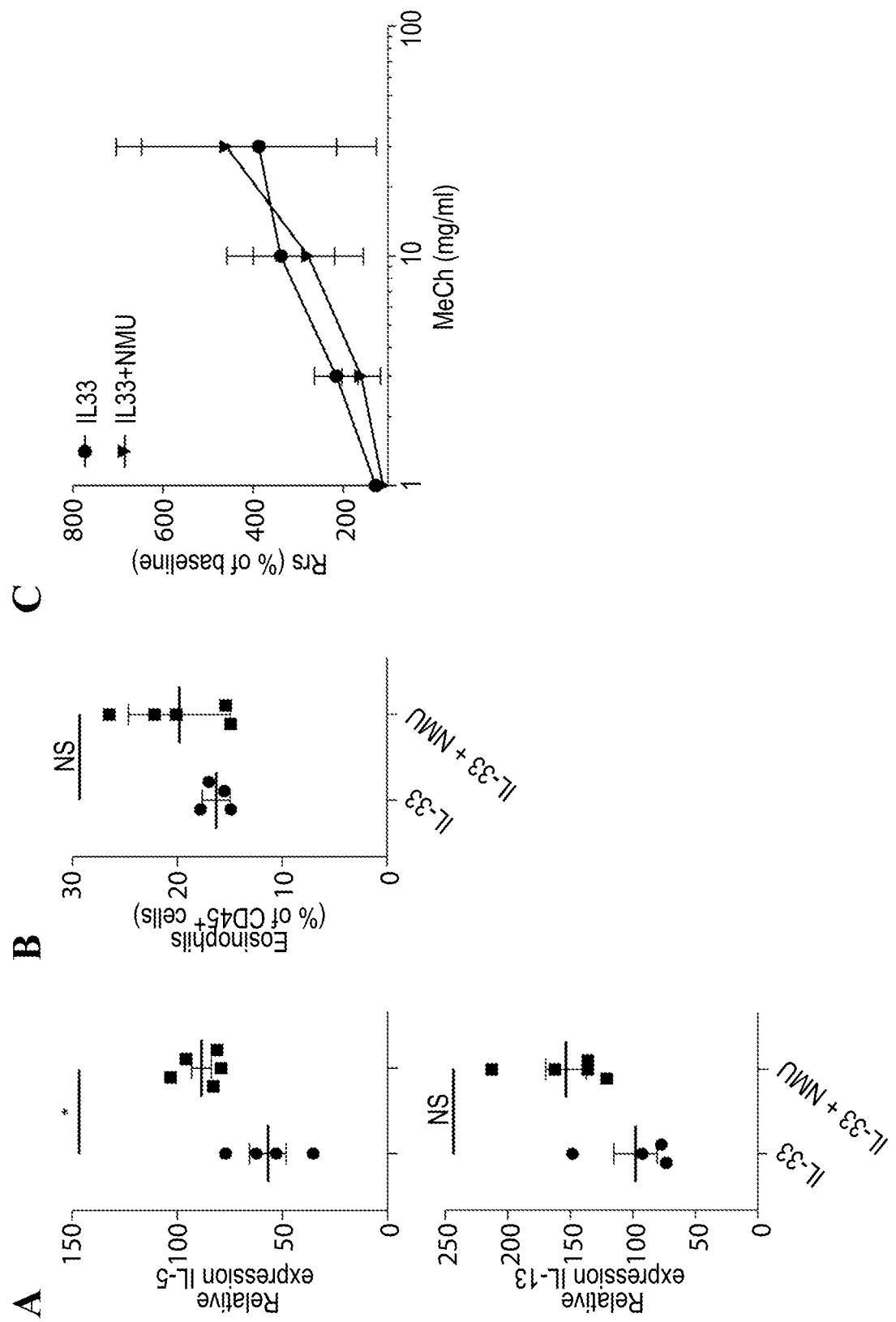
FIG. 11A-C

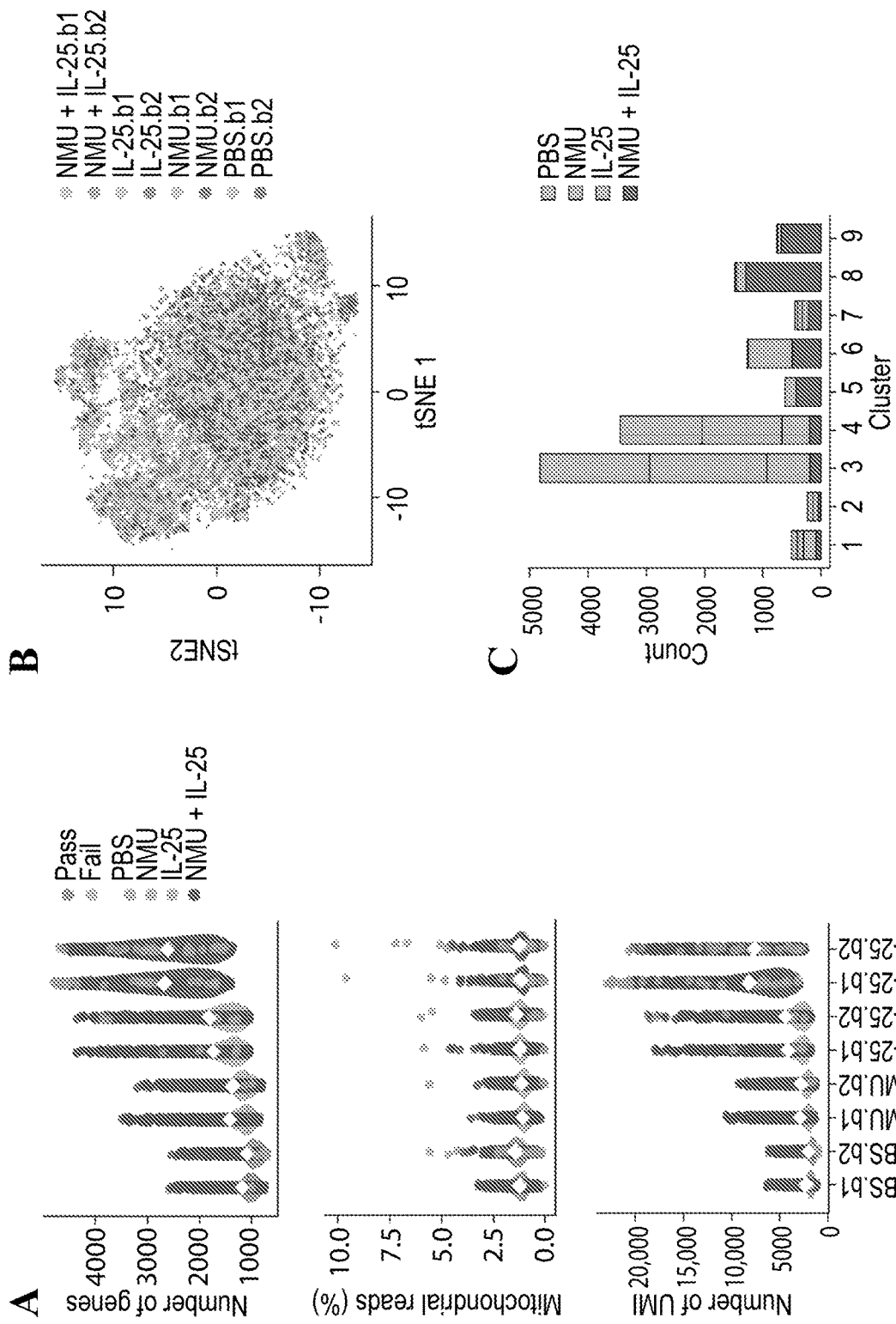
FIG. 12A-C

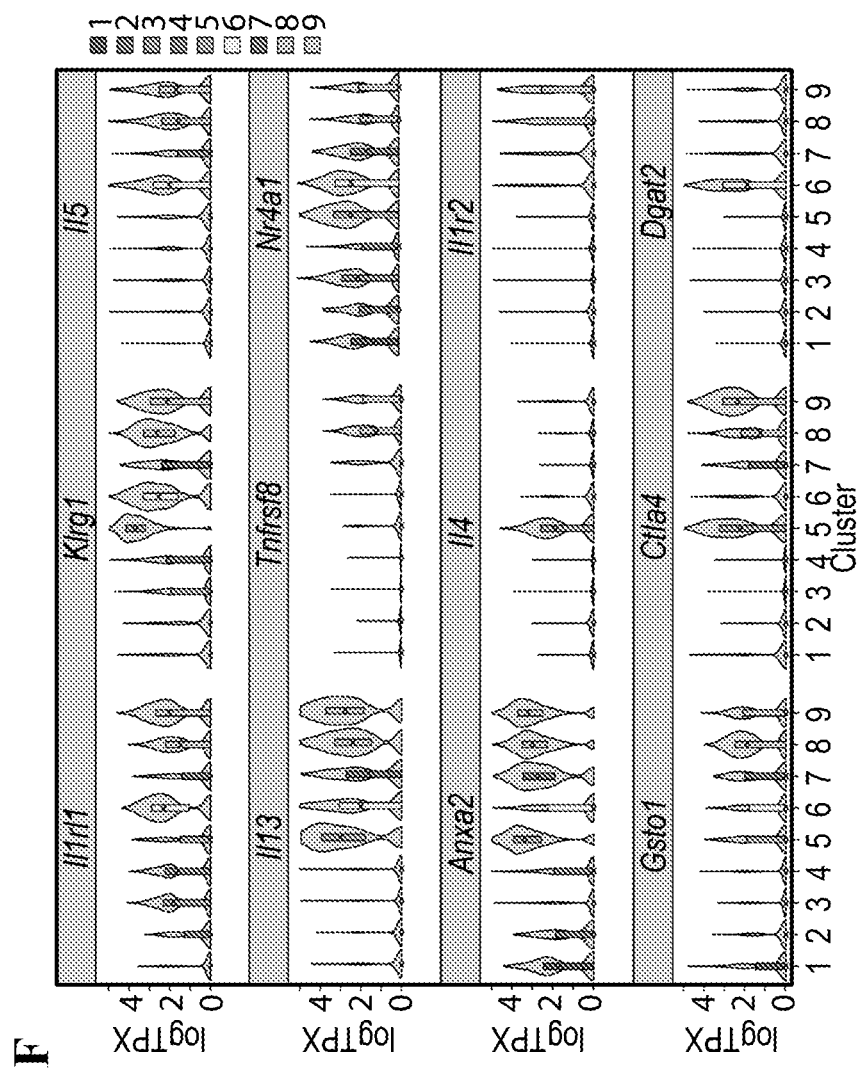
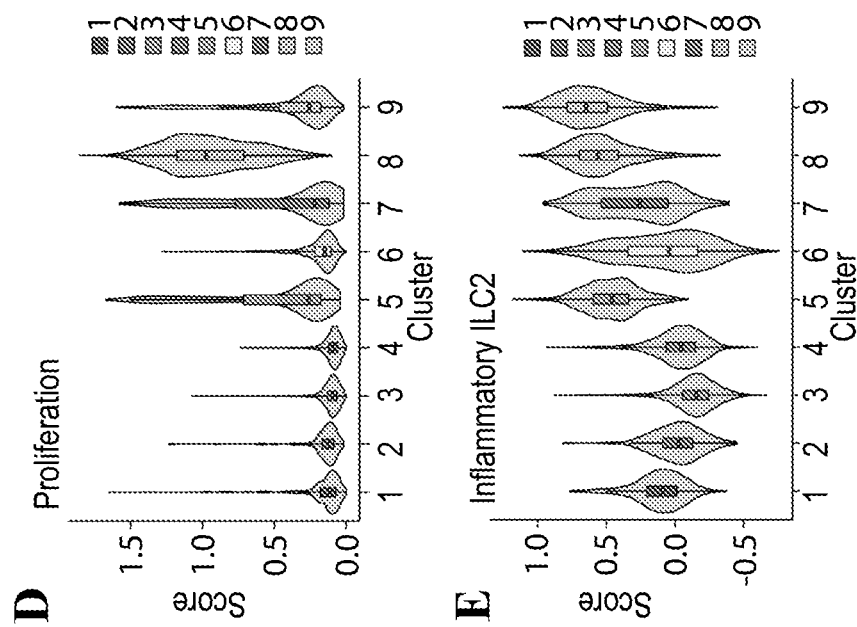
FIG. 12D-F

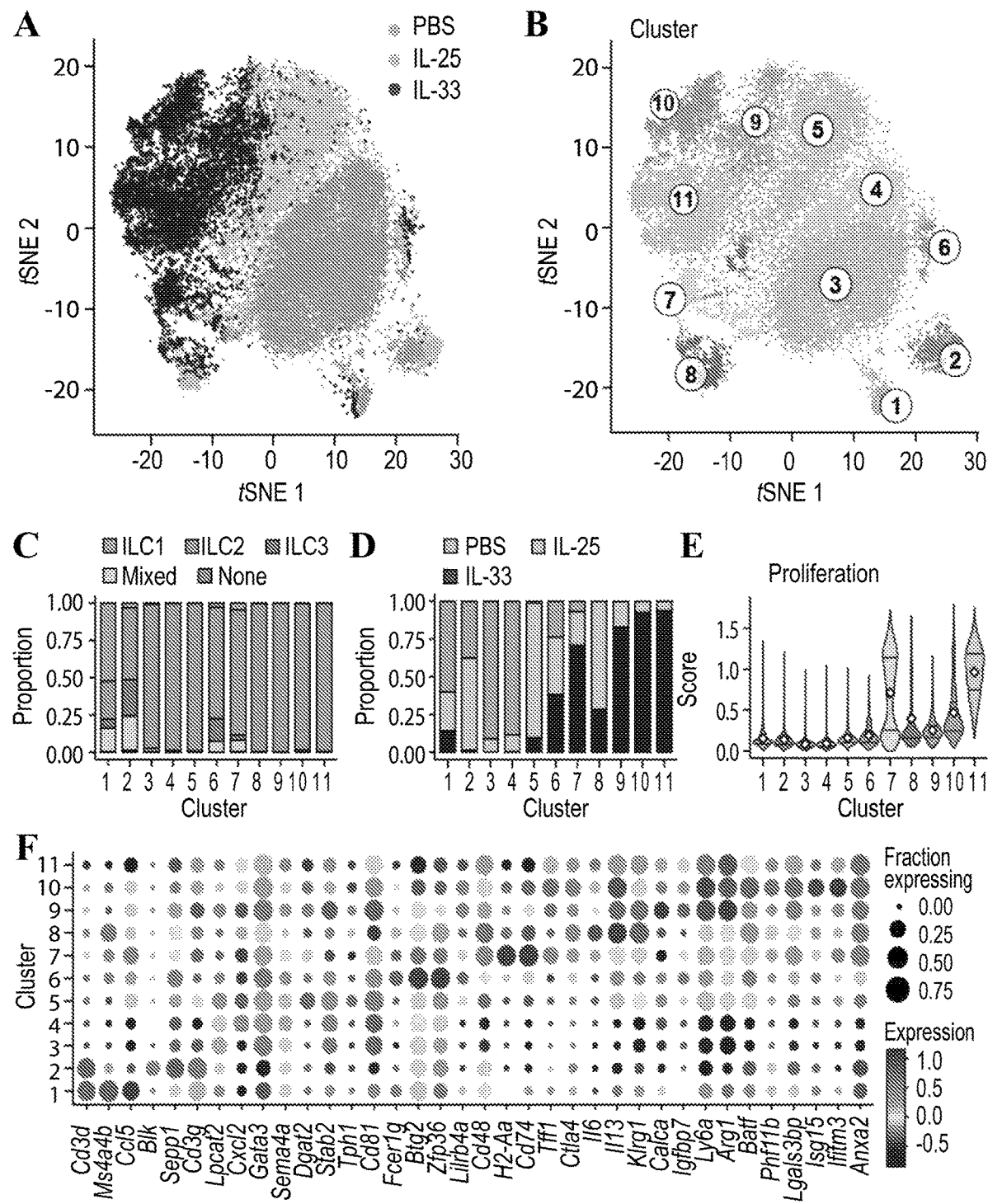
FIG. 13A-F

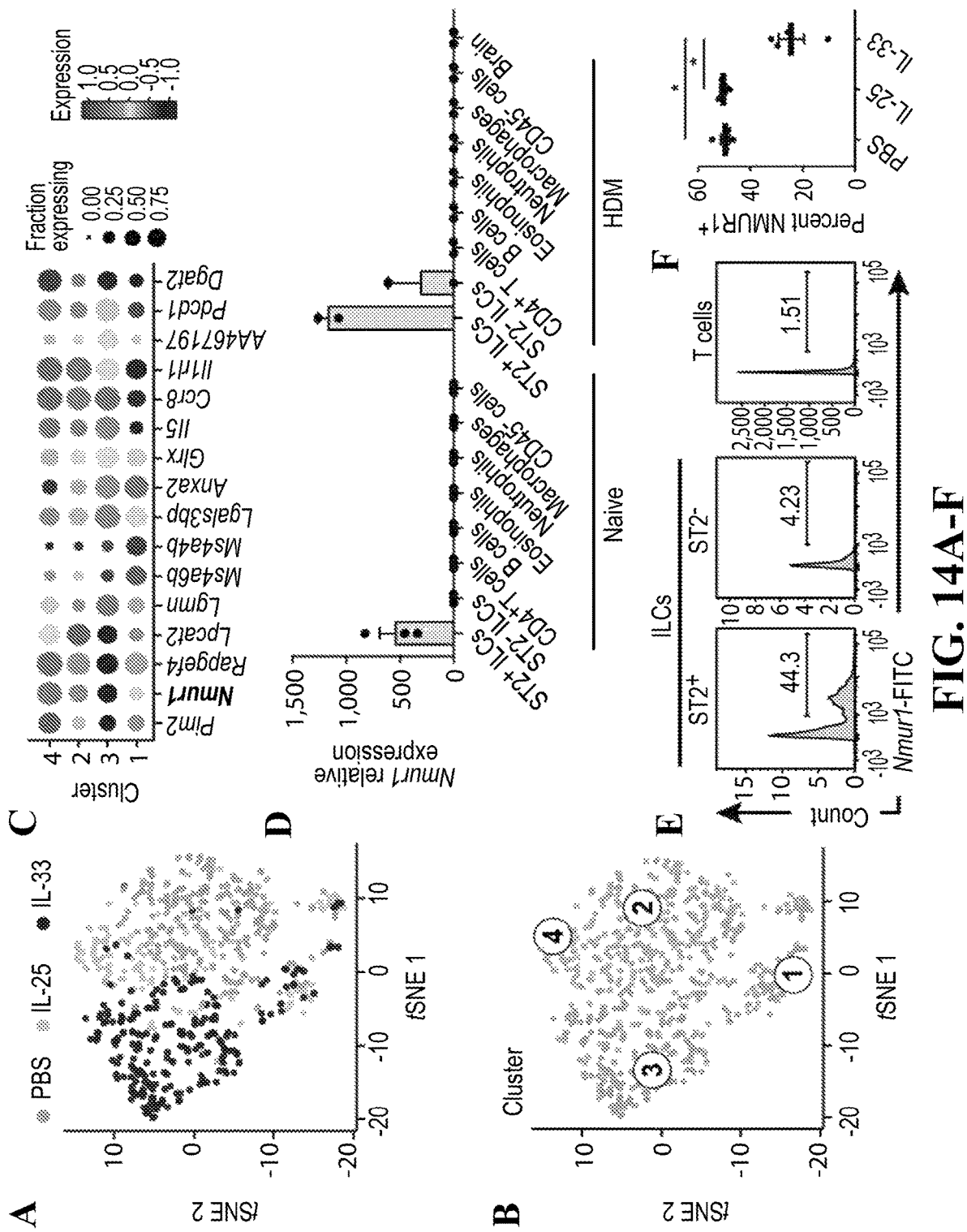
FIG. 14A-F

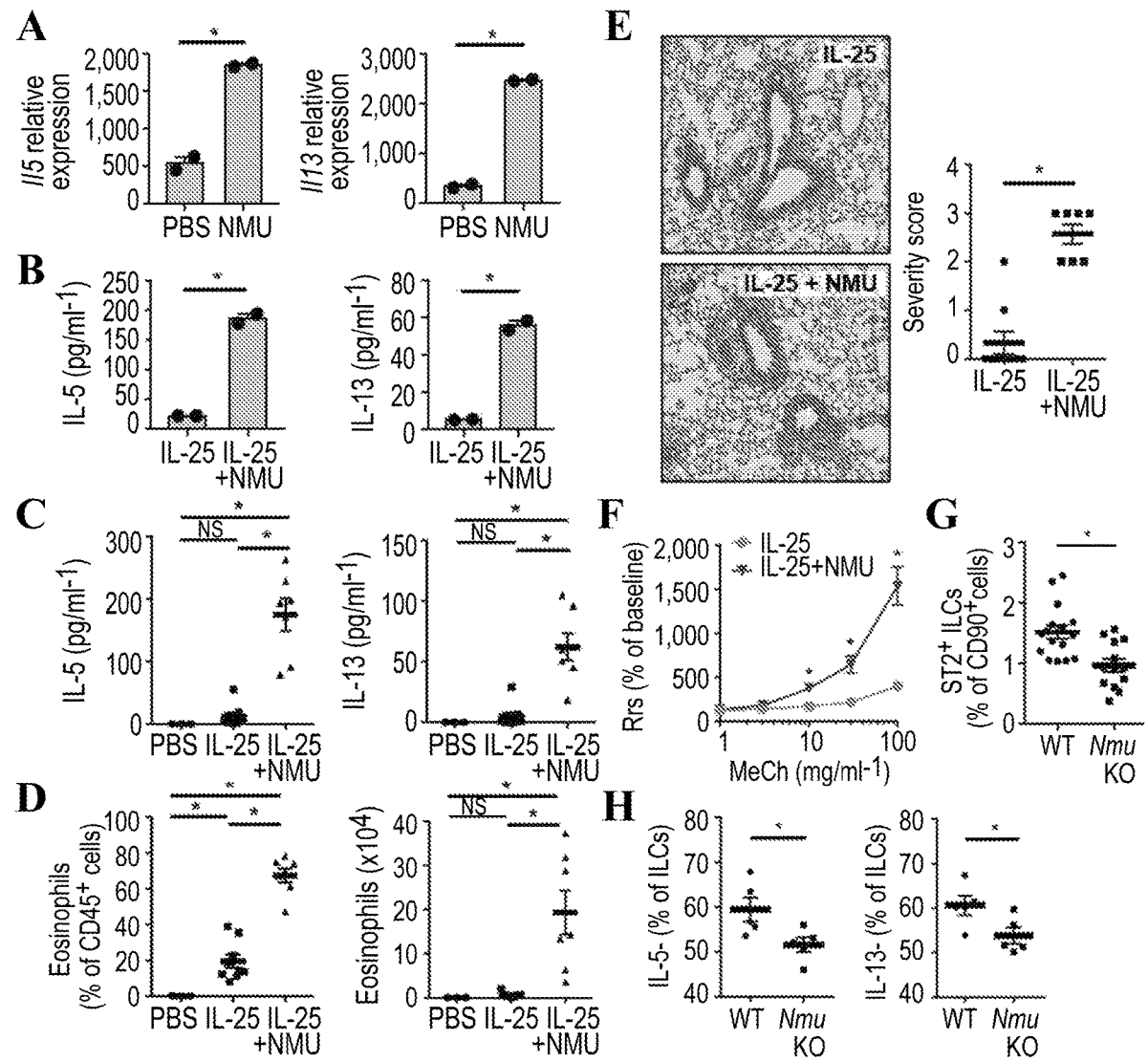
FIG. 15A-H

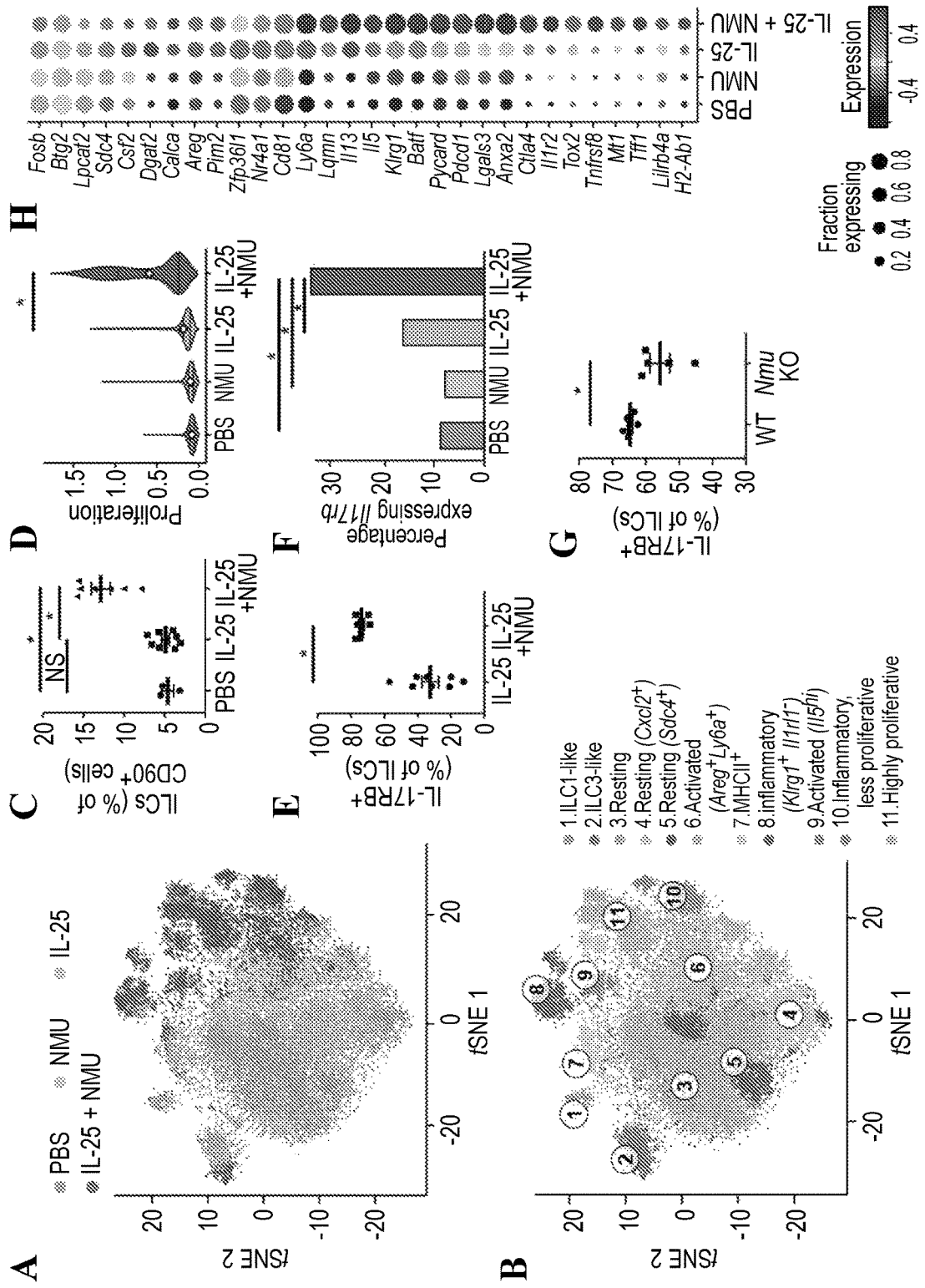
FIG. 16A-G

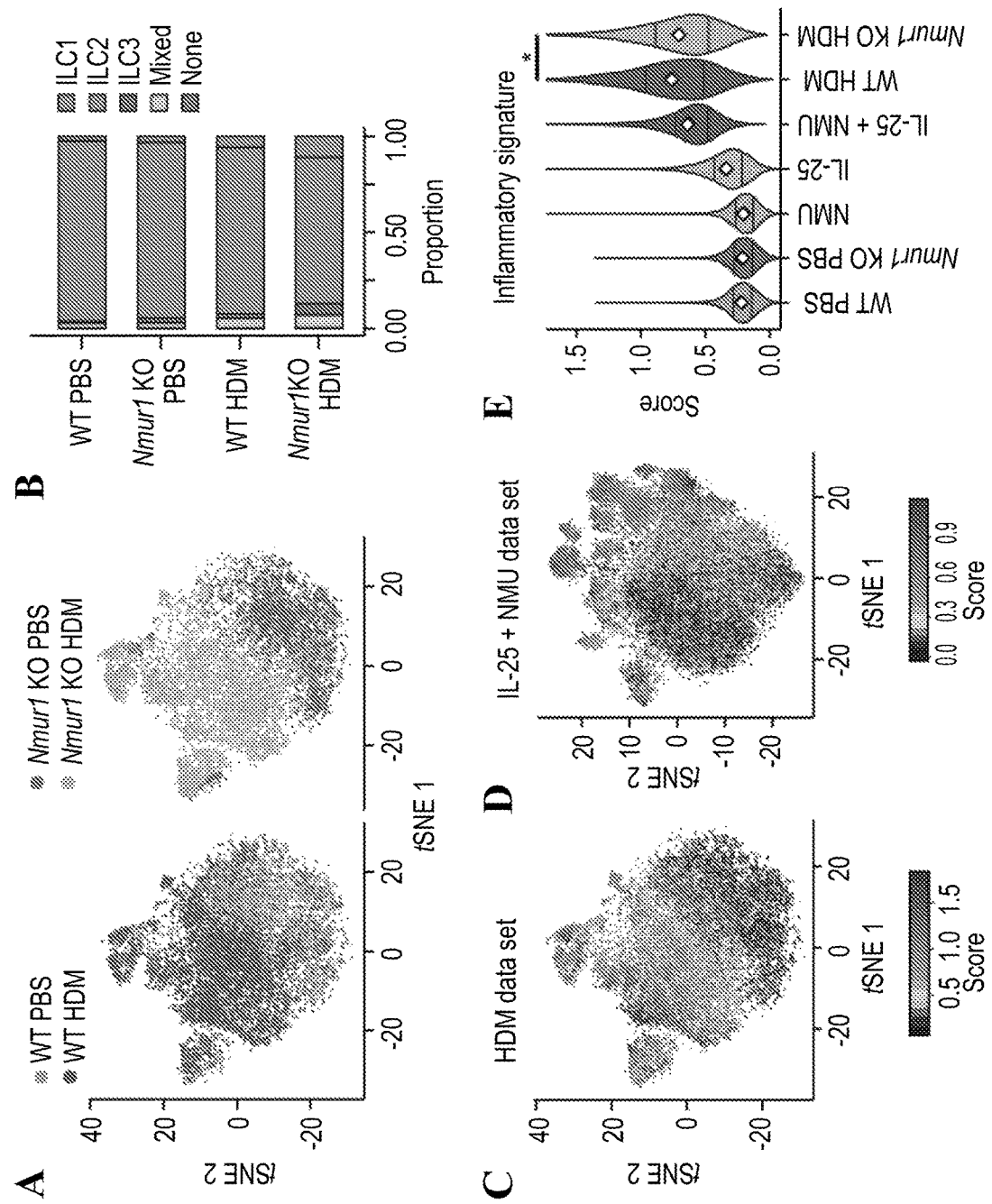
FIG. 17A-E

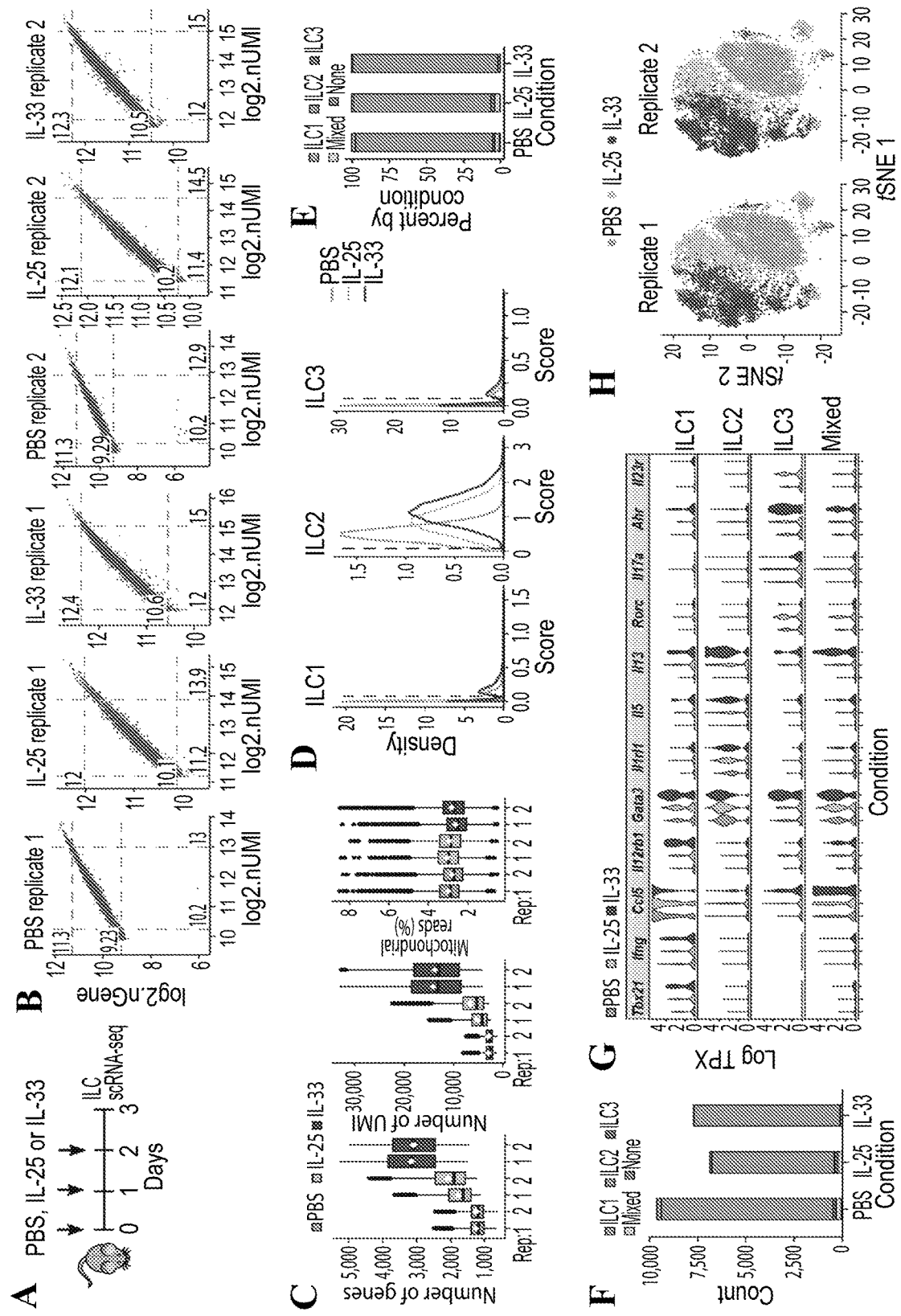
FIG. 18A-H

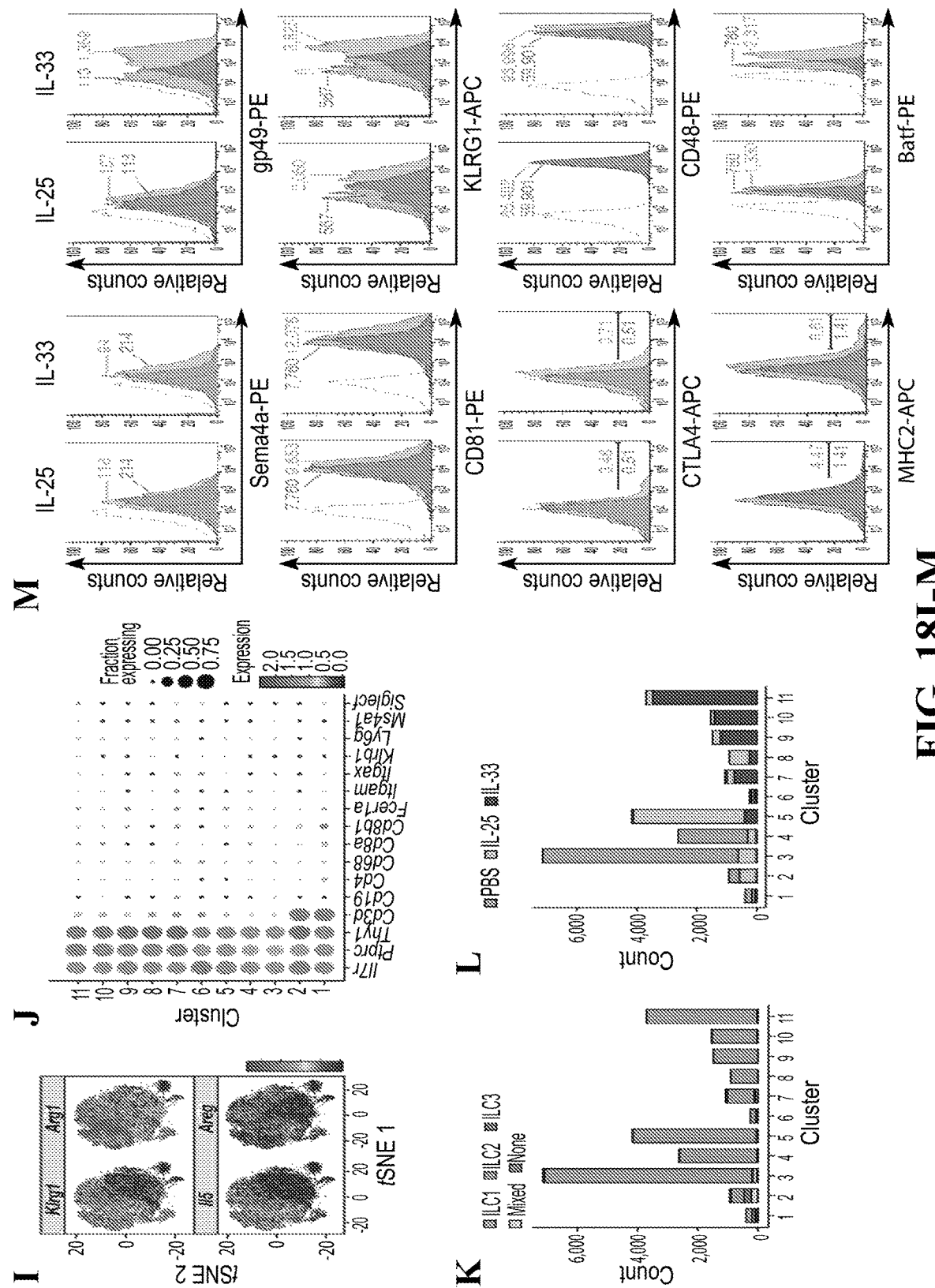
FIG. 18I-M

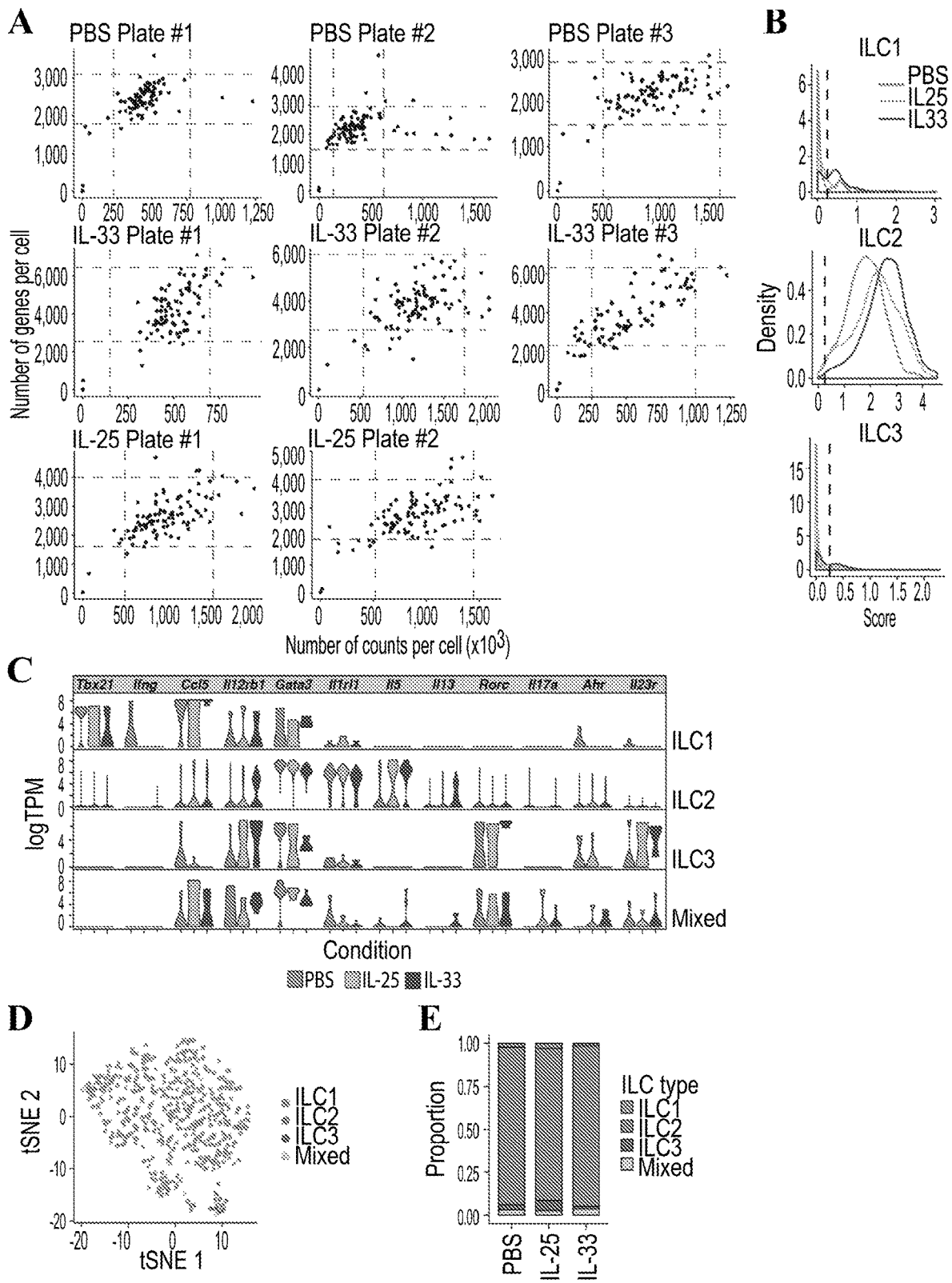
FIG. 20A-E

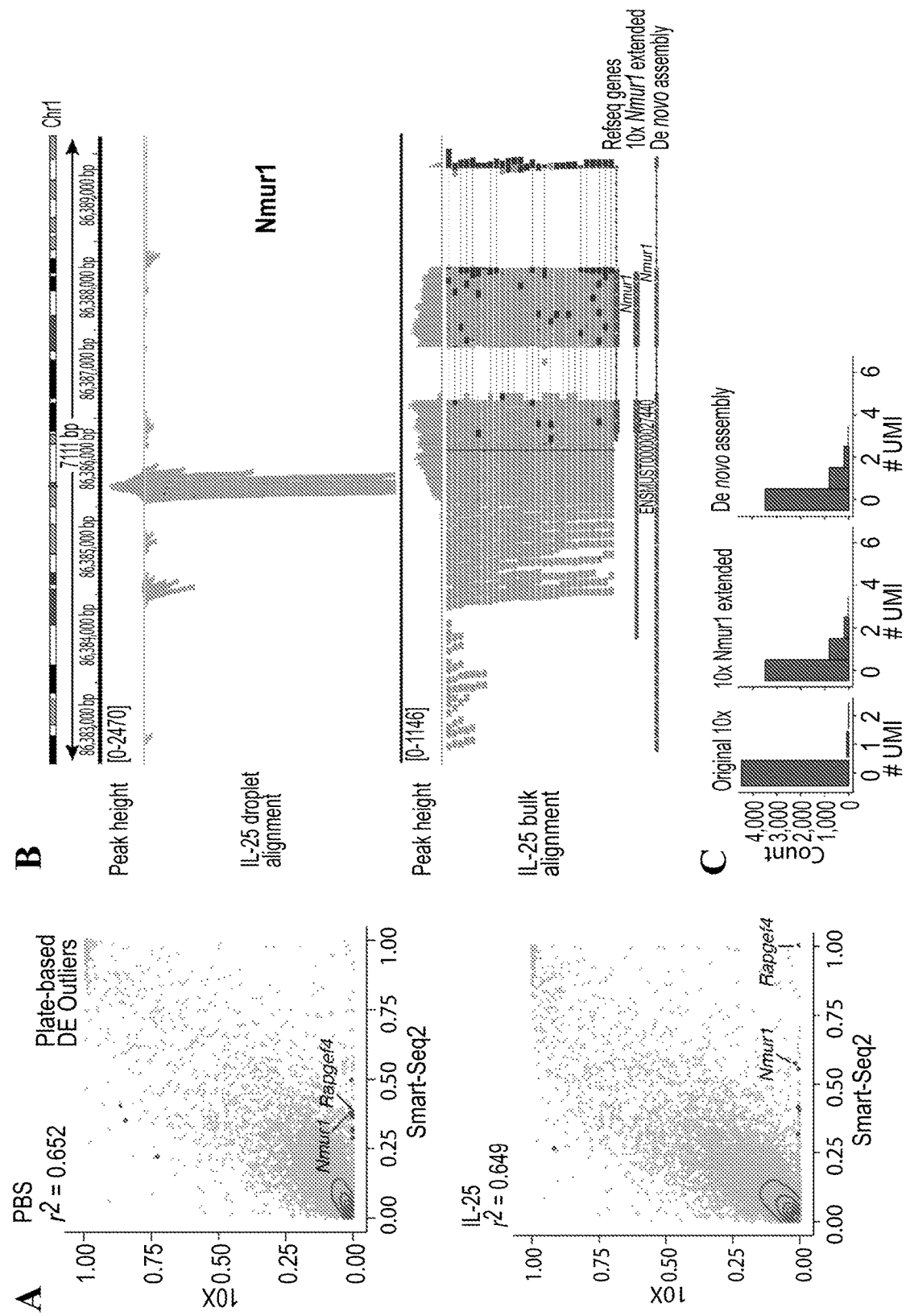
FIG. 21A-C

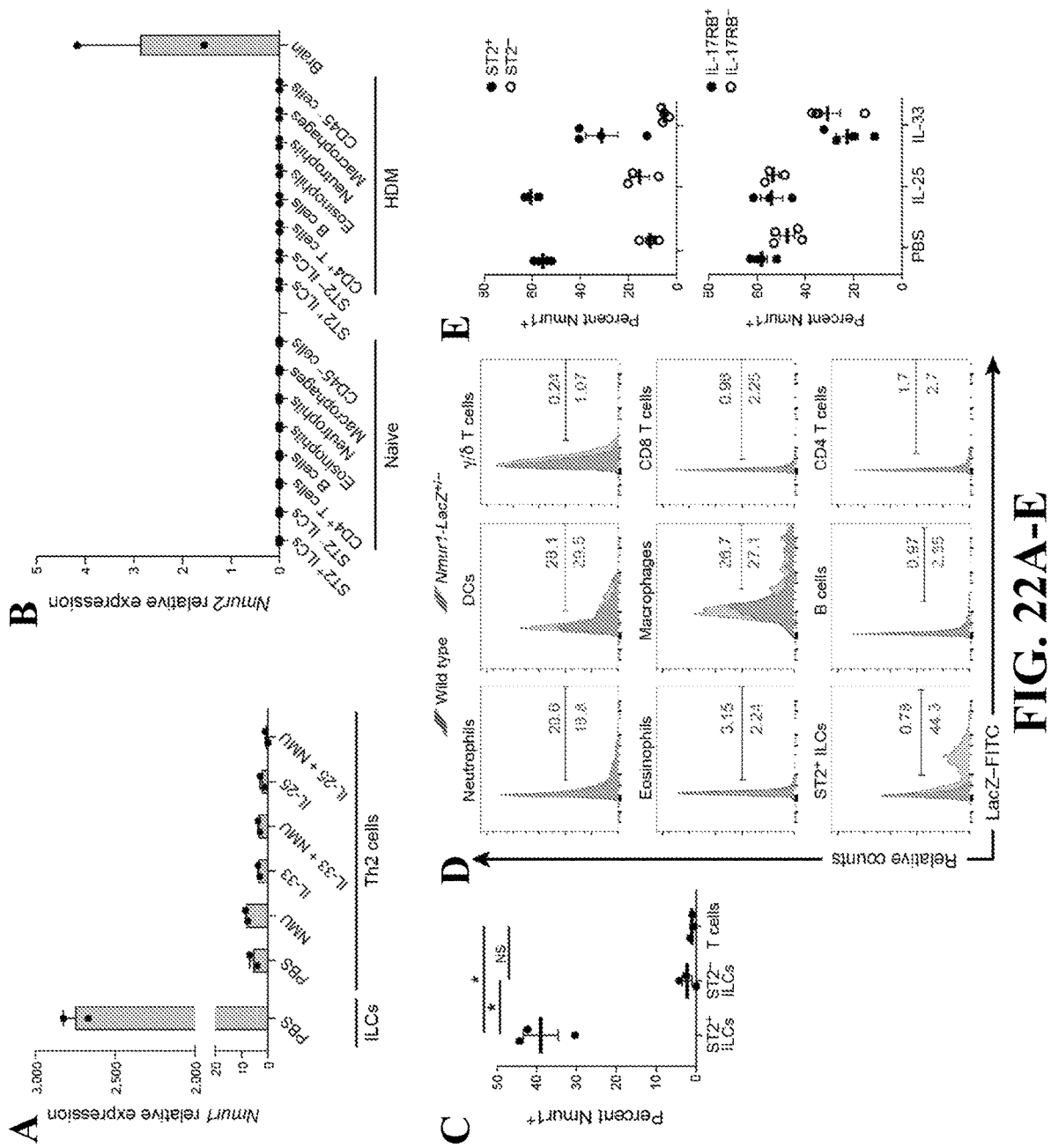
FIG. 22A-E

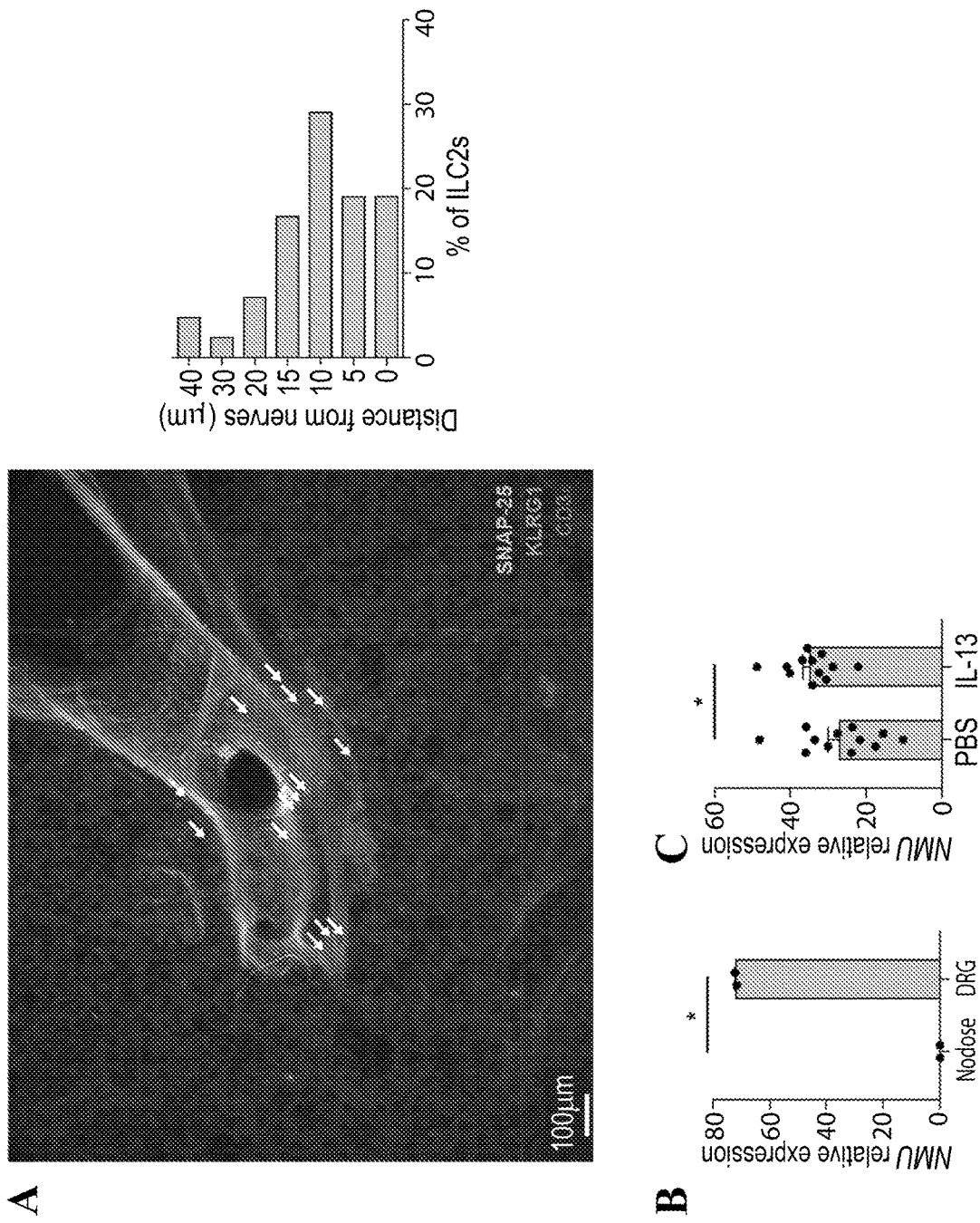
FIG. 23A-B

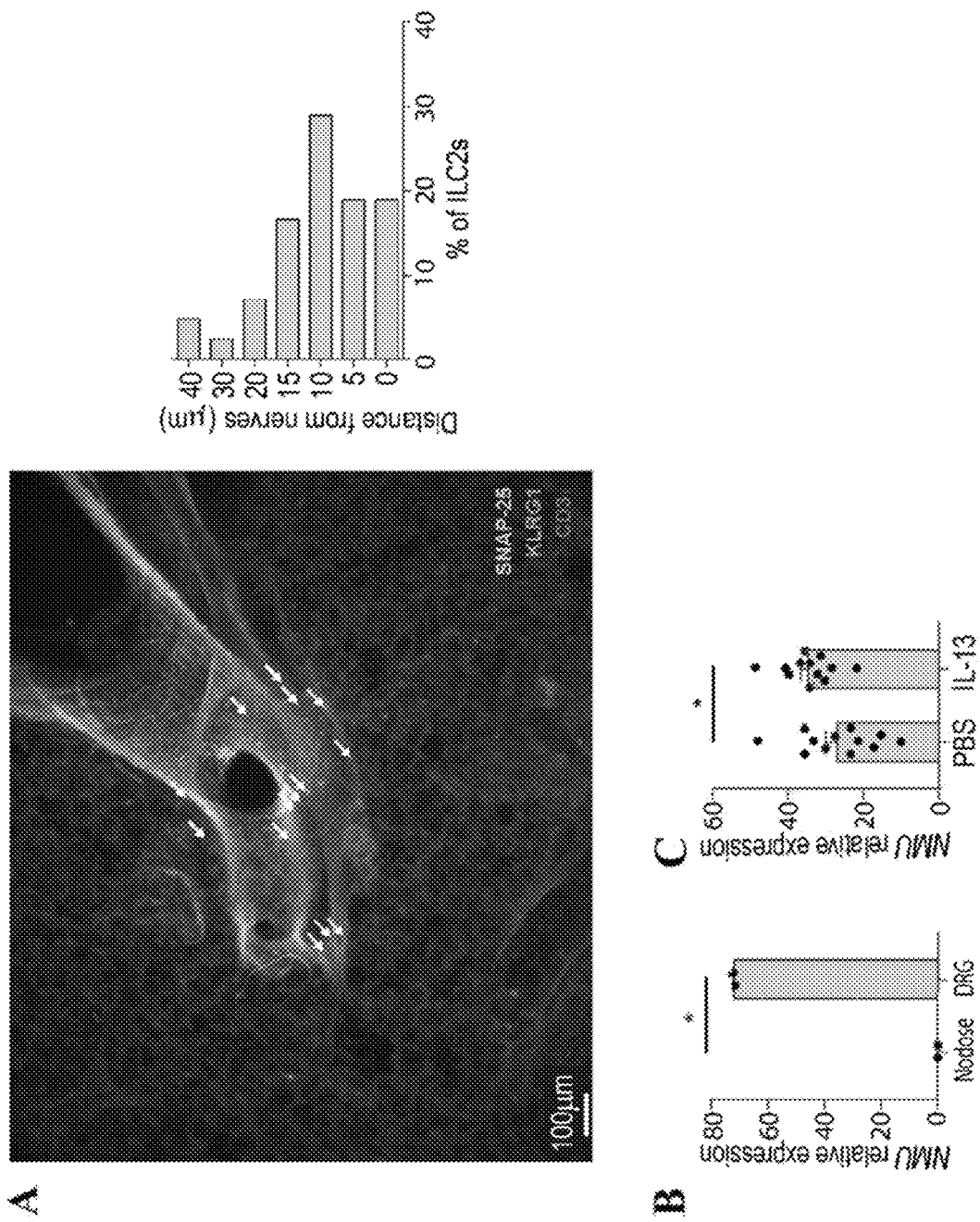
FIG. 23A-C

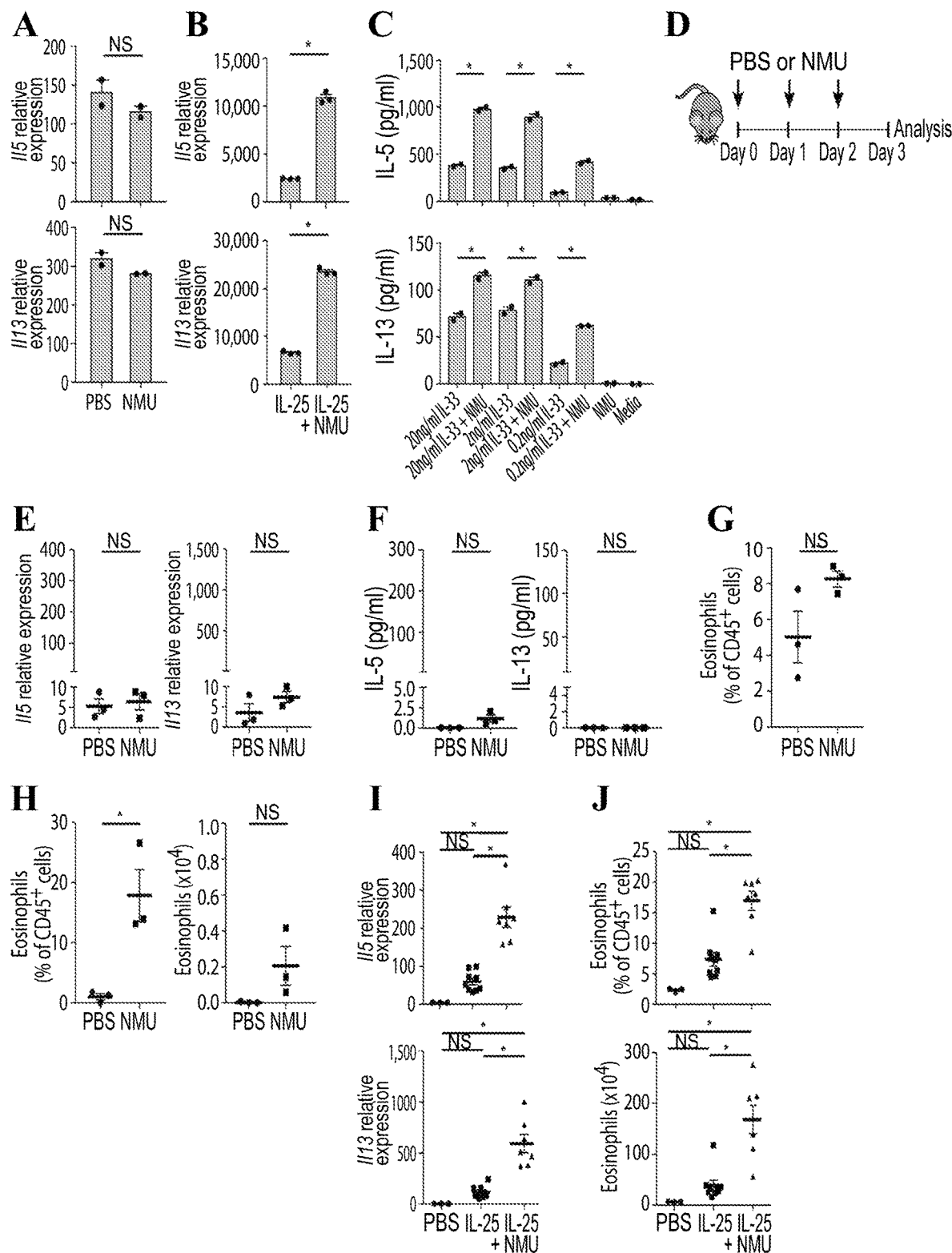
FIG. 24A-J

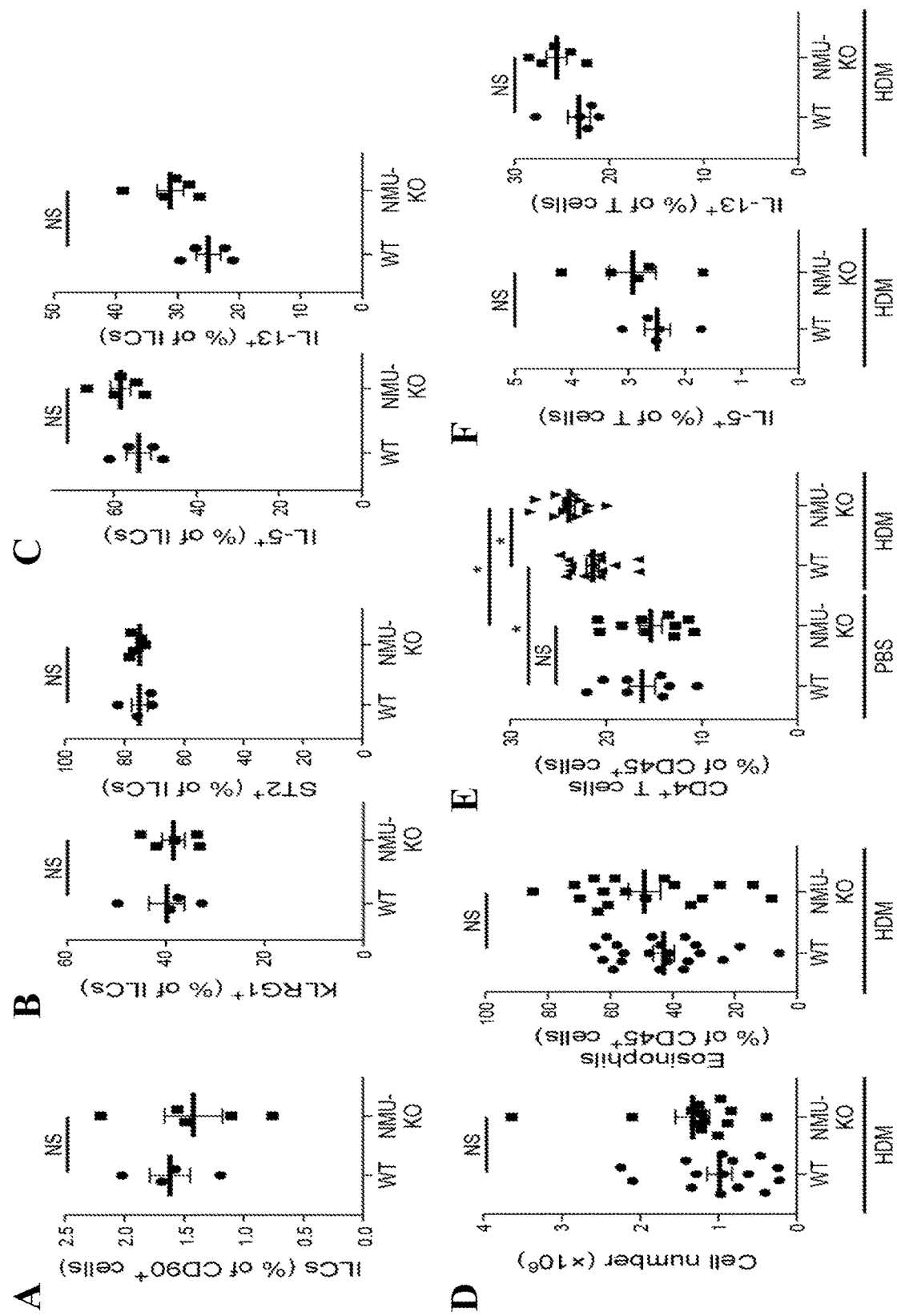
FIG. 25A-F

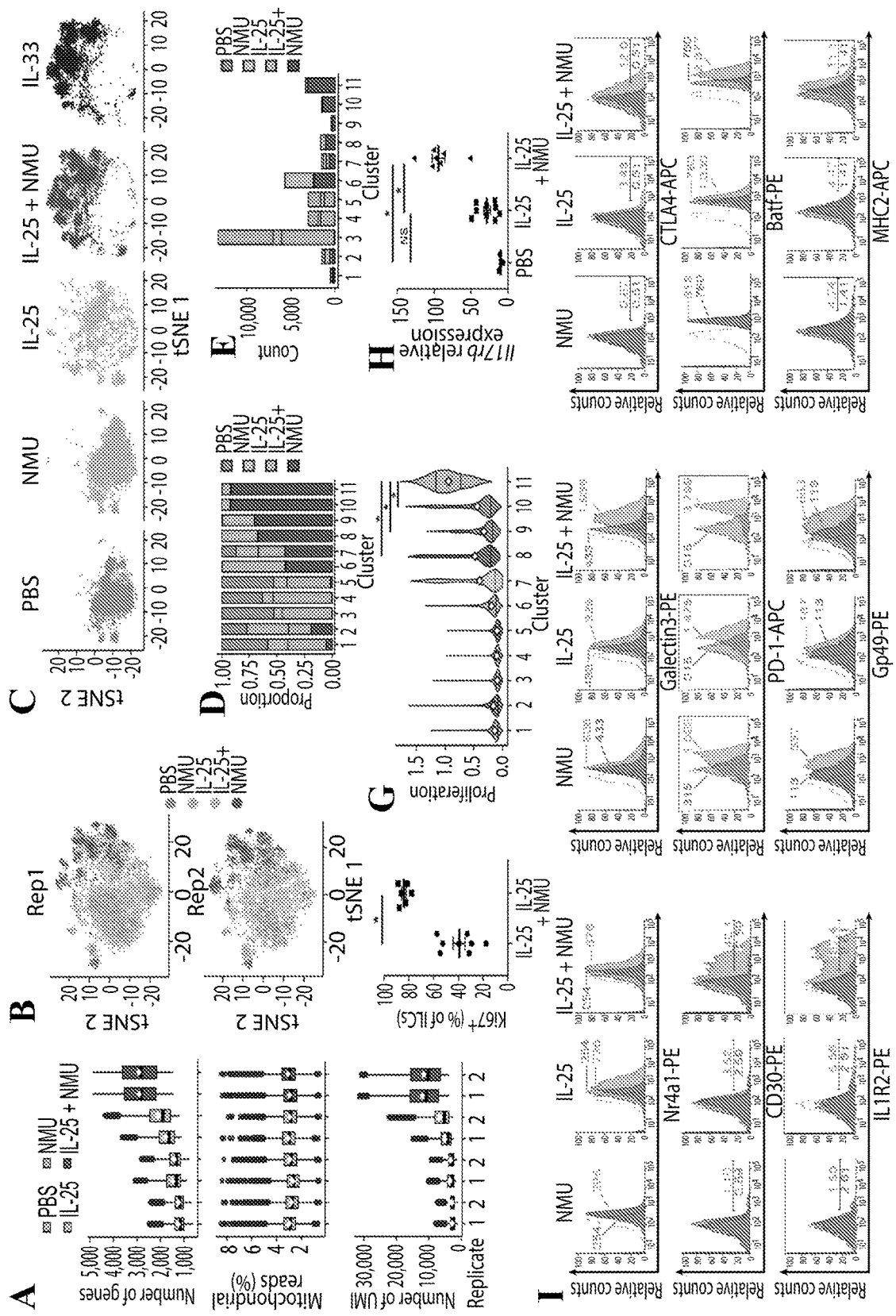
FIG. 26A-I

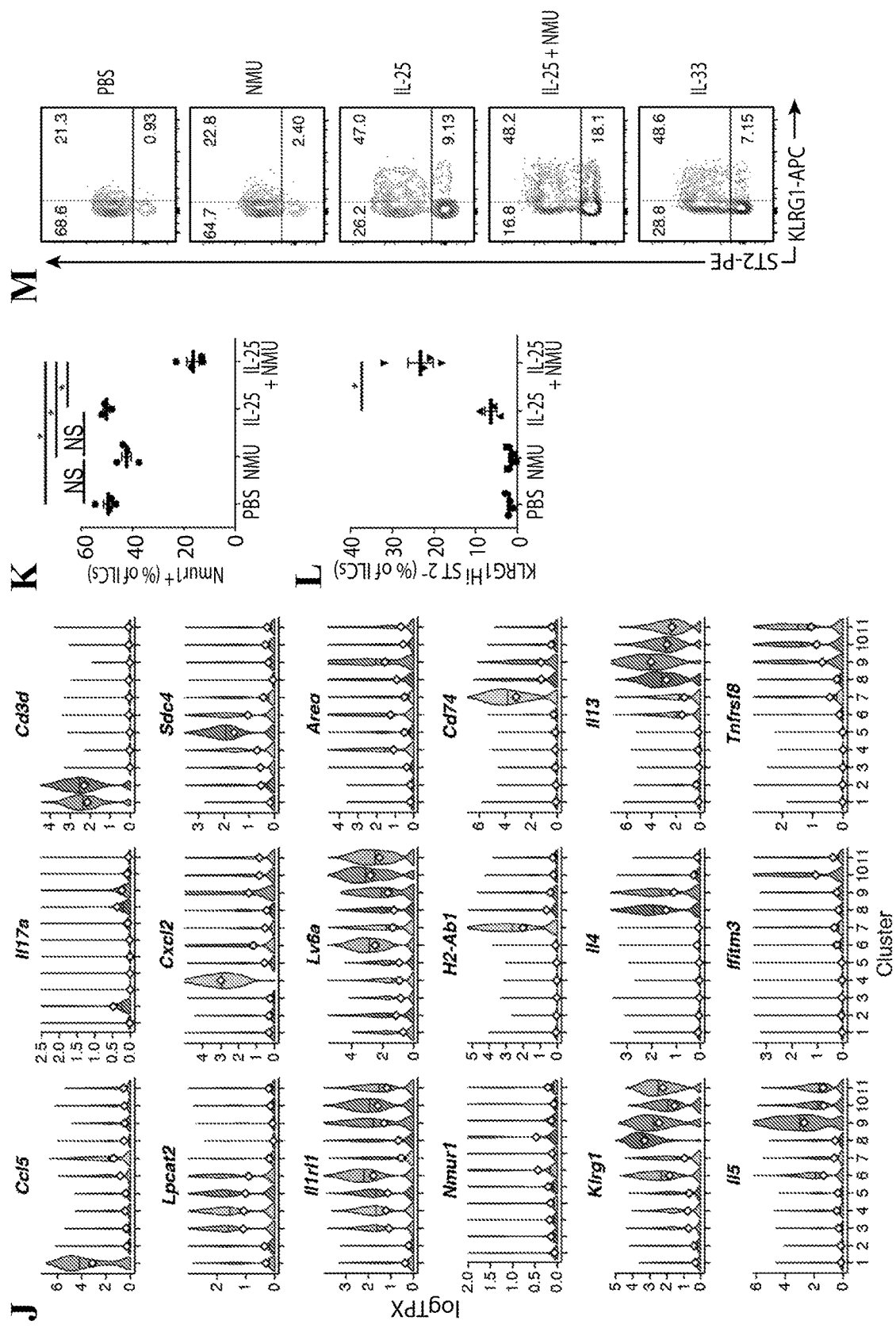
FIG. 26J-M

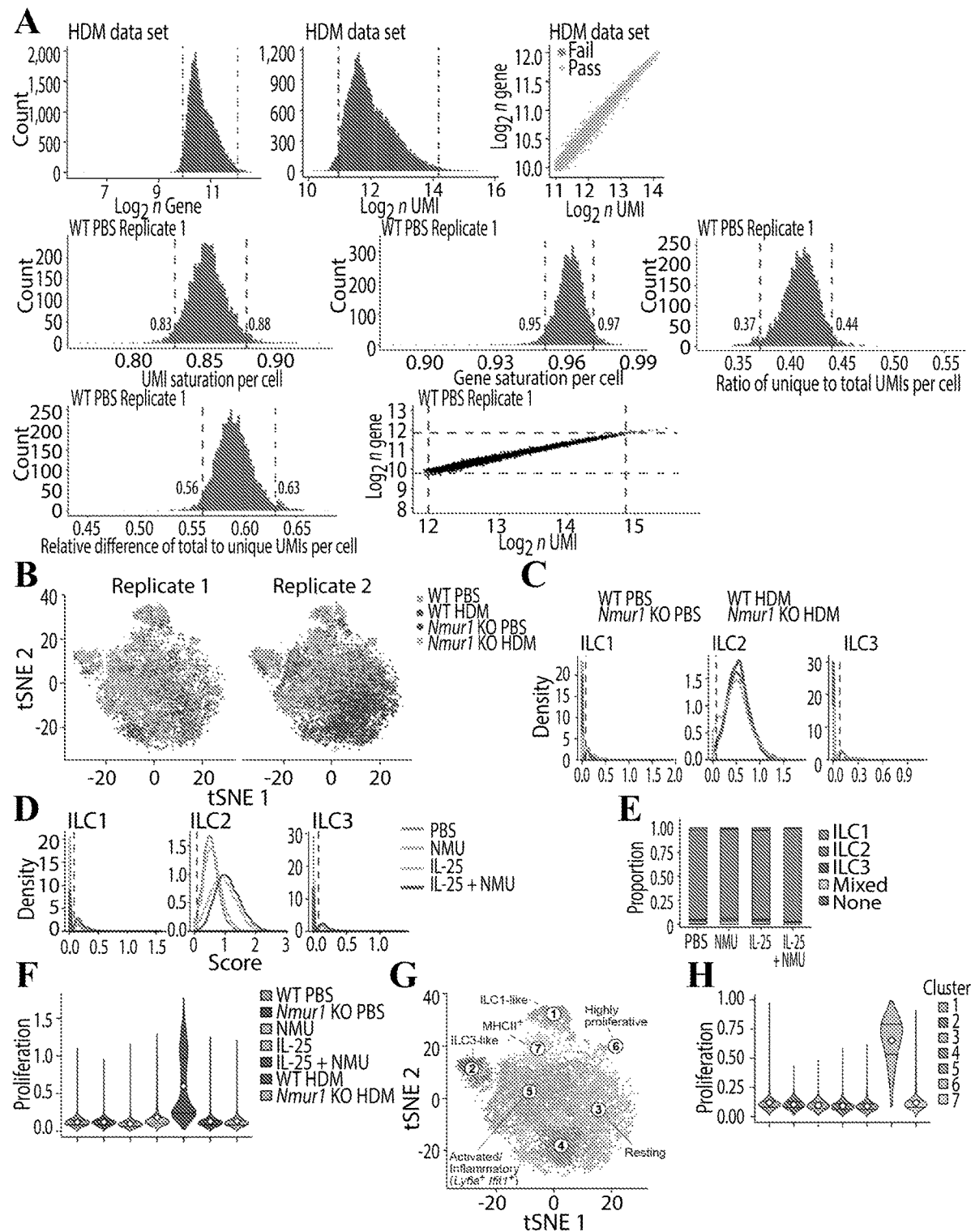
FIG. 27A-H

METHODS AND COMPOSITIONS FOR REGULATING INNATE LYMPHOID CELL INFLAMMATORY RESPONSES

CROSS-REFERENCE TO RELATED APPLICATIONS

This application is a U.S. National Stage of International Application No. PCT/US2018/024082, filed, Mar. 23, 2018, published in English under PCT Article 21(2), which claims the benefit of U.S. Provisional Application Nos. 62/476,352, filed Mar. 24, 2017 and 62/558,298, filed Sep. 13, 2017. The entire contents of the above-identified applications are hereby fully incorporated herein by reference.

STATEMENT REGARDING FEDERALLY SPONSORED RESEARCH

This invention was made with government support under grant numbers AI123516, AI056299 and AI039671 awarded by the National Institutes of Health. The government has certain rights in the invention.

REFERENCE TO AN ELECTRONIC SEQUENCE LISTING

The contents of the electronic sequence listing (BROD_2007WP_ST25.txt"; Size is 35,000 bytes and it was created on Mar. 23, 2018) is herein incorporated by reference in its entirety.

TECHNICAL FIELD

The subject matter disclosed herein is generally directed to compositions and methods for modulating Type 2 innate lymphoid cell responses.

BACKGROUND

Type 2 innate lymphoid cells (ILC2s) regulate the initiation of allergic tissue inflammation at mucosal surfaces, in large part due to their ability to rapidly produce effector cytokines such as IL-5 and IL-13[1,4]. ILC2s are also vital in maintaining tissue homeostasis by promoting epithelial cell proliferation, survival, and barrier integrity[2]. Alarmin cytokines, such as IL-25 and IL-33, activate ILC2s to promote tissue homeostasis in the face of epithelial injury, but also play critical roles in initiating allergic inflammatory responses[6,9,10].

The factors that balance homeostatic and pathological ILC responses are unclear, and it remains unknown if unique subsets or functional states of ILCs mediate these homeostatic vs. pro inflammatory effects. Since there are no known markers of such functional states, it is also challenging to distinguish homeostatic from pro-inflammatory ILCs. Single-cell genomics, especially scRNA-seqg[11,12], can help identify such diversity, even when changes in cell states are continuous across the cells in a population[13], or are unique to a very small sub-population[14,15]. Recently, scRNA-seq-based approaches identified transcriptionally distinct subpopulations within intestinal ILC subsets, demonstrating the utility of scRNA-seq in identifying previously unrecognized subpopulations and cell states within this cell type, although the functional roles of these sub-populations remain to be clarified[16].

Citation or identification of any document in this application is not an admission that such document is available as prior art to the present invention.

SUMMARY

Type 2 innate lymphoid cells (ILC2s) are critical for maintaining mucosal barrier functions and tissue homeostasis, and yet are also important drivers of pathologic type 2 immune responses in allergy and asthma[1-5]. Alarmin cytokines produced by damaged and stressed epithelial cells, such as IL-25 and IL-33, have been shown to activate ILC2s, but it remains unclear if these cytokines are unique in switching homeostatic ILC2s into proinflammatory cells that drive tissue inflammation[6-8].

It is an objective of the present invention to identify molecular cues that modulate ILC responses to alarmins. Applicants collected single-cell RNA-sequencing (scRNA-seq) profiles of lung-resident ILCs at steady state and after in vivo stimulation, combining massively-parallel droplet-based scRNA-seq surveys with full-length scRNA-seq for deeper characterization of markers. Computational and functional analysis identified the neuropeptide receptor Nmur1 as selectively expressed on ILC2s. While both IL-33 and IL-25 promote ILC activation in vivo, IL-33 induces robust ILC proliferation, whereas ILCs activated with IL-25 do not proliferate as robustly and up-regulate Nmur1 expression.

It is another objective of the present invention to modulate ILC2 immune responses and cell states. Treatment of ILC2s with neuromedin U (NMU), the neuropeptide ligand of Nmur1, has little effect on its own in the experimental models used herein. Co-administration of IL-25 with NMU, however, dramatically amplifies allergic lung inflammation and induces the proliferation and expansion of specific ILC2 subsets, characterized by a molecular signature unique to pro-inflammatory ILC2s. The results demonstrated for the first time that Nmur1 signaling strongly modulates IL-25-mediated ILC2 responses, resulting in highly proliferative pro-inflammatory ILCs, and highlights the importance of neuro-immune crosstalk in allergic inflammatory responses at mucosal surfaces.

In one aspect, the present invention provides for a method of treating a disease requiring reduction of an innate lymphoid cell (ILC) Type 2 inflammatory response comprising administering to a subject in need thereof a therapeutically effective amount of an agent capable of inhibiting neuromedin U receptor 1 (Nmur1) or blocking Nmur1 interaction with neuromedin U (NMU). In a further aspect, the present invention provides for a method of reducing an innate lymphoid cell (ILC) Type 2 inflammatory response comprising administering to a subject in need thereof a therapeutically effective amount of an agent capable of inhibiting neuromedin U receptor 1 (Nmur1) or blocking Nmur1 interaction with neuromedin U (NMU). Also provided is an agent capable of inhibiting neuromedin U receptor 1 (Nmur1) or blocking Nmur1 interaction with neuromedin U (NMU) for use in a method of treating a disease requiring reduction of an innate lymphoid cell (ILC) Type 2 inflammatory response. Further provided is an agent capable of inhibiting neuromedin U receptor 1 (Nmur1) or blocking Nmur1 interaction with neuromedin U (NMU) for use in reducing an innate lymphoid cell (ILC) Type 2 inflammatory response. Further provided is the use of an agent capable of inhibiting neuromedin U receptor 1 (Nmur1) or blocking Nmur1 interaction with neuromedin U (NMU) for the manufacture of a medicament for treating a disease requiring reduction of an innate lymphoid cell (ILC) Type 2 inflammatory response. The agent may comprise a therapeutic antibody, antibody fragment, antibody-like protein scaffold, aptamer, nucleic acid molecule, protein or small molecule. Preferably the agent reduces the expression of NMUR1, reduces the expression of NMU, and/or reduces the interaction of NMUR1 with NMU. The disease may be an allergic inflammatory disease. The disease may be asthma.

In another aspect, the present invention provides for a method of treating a disease requiring induction of an innate lymphoid cell (ILC) Type 2 inflammatory response comprising administering to a subject in need thereof a therapeutically effective amount of IL-25 and an agonist of NMUR1. In a further aspect, the present invention provides for a method of increasing or inducing an innate lymphoid cell (ILC) Type 2 inflammatory response comprising administering to a subject in need thereof a therapeutically effective amount of IL-25 and an agonist of NMUR1. Also provided is IL-25 and an agonist of NMUR1 for use in a method of treating a disease requiring induction of an innate lymphoid cell (ILC) Type 2 inflammatory response. Further provided is an agonist of NMUR1 for use in treating a disease requiring induction of an innate lymphoid cell (ILC) Type 2 inflammatory response or for use in increasing or inducing an innate lymphoid cell (ILC) Type 2 inflammatory response. Preferably, said treatment further comprises treatment with IL-25. Further provided is use of IL-25 and an agonist of NMUR1 for the manufacture of a medicament for treating a disease requiring induction of an innate lymphoid cell (ILC) Type 2 inflammatory response. The NMUR1 agonist may be Neuromedin U (NMU), Neuromedin S (NMS) or a derivative thereof. The disease may be cancer. The cancer may be a drug resistant cancer. The cancer may be resistant to an immunotherapy targeting the adaptive immune system. The immunotherapy may be a check point inhibitor. In another aspect, the present invention provides for a pharmaceutical composition comprising a therapeutically effective amount of IL-25 and an agonist of NMUR1, and a pharmaceutically acceptable carrier. Also provided is IL-25 and an agonist of NMUR1 for use as a medicament. IL-25 and the agonist of NMUR1 may be admixed in a pharmaceutical composition or may be comprised in a kit of parts configured for separate, simultaneous or sequential in any order administration of IL-25 and the agonist of NMUR1. Certain preferred embodiments provide for a pharmaceutical composition comprising a therapeutically effective amount of IL-25 and NMU, and a pharmaceutically acceptable carrier. Also, provided in certain further embodiments is IL-25 and NMU for use as a medicament. IL-25 and NMU may be admixed in a pharmaceutical composition or may be comprised in a kit of parts configured for separate, simultaneous or sequential in any order administration of IL-25 and NMU.

In another aspect, the present invention provides for a method of treating a disease requiring modulation of an innate lymphoid cell (ILC) Type 2 inflammatory response comprising administering to a subject in need thereof a therapeutically effective amount of an agent capable of modulating the expression or the activity of one or more genes or polypeptides selected from the group consisting of Anxa1, Anxa2, Areg, Calca, Ccl1, Ccl5, Ccr2, Ccr7, Ccr8, Cd200r1, Cd3d, Cd47, Cd48, Cd81, Csf2, Ctla4, Fas, H2-Aa, H2-Ab1, H2-Q8, H2-T23, Il13, Il1r2, Il2rb, Il5, Il6, Klrg1, Lat, Lgals3, Lilrb4a, Ltb, Mif, Ms4a4b, Nmur1, Pdcd1, Pgk1, Ptger2, Ramp1, Sdc4, Sema4a, Sepp1, Stab2, Tff1, Tmem176a, Tnfrsf4, Tnfrsf8, Tnfsf8, Vsir, Nmu, 2810417H13Rik, AA467197, Alox5, Arg1, Atf4, Batf, Bcl2a1b, Blk, Btg1, Cox5b, Cox6c, Crip1, Dgat1, Dgat2, Dusp1, Ets1, Fos, Fosb, Furin, Gadd45b, Gsto1, Hint1, Ier2, Irf4, Klf3, Klf4, Lgmn, Lpcat2, Mcm3, Mt1, Myl6, Ndufa4, Nfkbia, Nfkbid, Nfkbiz, Nop56, Nr4a1, Prdx4, S100a4, S100a6, Serpinb6a, Snrpd3, Sptssa, Tph1, Vim, Zfp36 and Zfp36l1. Also provided is an agent capable of modulating the expression or the activity of one or more genes or polypeptides selected from the group consisting of Anxa1, Anxa2, Areg, Calca, Ccl1, Ccl5, Ccr2, Ccr7, Ccr8, Cd200r1, Cd3d, Cd47, Cd48, Cd81, Csf2, Ctla4, Fas, H2-Aa, H2-Ab1, H2-Q8, H2-T23, Il13, Il1r2, Il2rb, Il5, Il6, Klrg1, Lat, Lgals3, Lilrb4a, Ltb, Mif, Ms4a4b, Nmur1, Pdcd1, Pgk1, Ptger2, Ramp1, Sdc4, Sema4a, Sepp1, Stab2, Tff1, Tmem176a, Tnfrsf4, Tnfrsf8, Tnfsf8, Vsir, Nmu, 2810417H13Rik, AA467197, Alox5, Arg1, Atf4, Batf, Bcl2a1b, Blk, Btg1, Cox5b, Cox6c, Crip1, Dgat1, Dgat2, Dusp1, Ets1, Fos, Fosb, Furin, Gadd45b, Gsto1, Hint1, Ier2, Irf4, Klf3, Klf4, Lgmn, Lpcat2, Mcm3, Mt1, Myl6, Ndufa4, Nfkbia, Nfkbid, Nfkbiz, Nop56, Nr4a1, Prdx4, S100a4, S100a6, Serpinb6a, Snrpd3, Sptssa, Tph1, Vim, Zfp36, and Zfp36l1, for use in a method of treating a disease requiring modulation of an innate lymphoid cell (ILC) Type 2 inflammatory response or for use in modulating an innate lymphoid cell (ILC) Type 2 inflammatory response. Further provided is use of an agent capable of modulating the expression or the activity of one or more genes or polypeptides selected from the group consisting of Anxa1, Anxa2, Areg, Calca, Ccl1, Ccl5, Ccr2, Ccr7, Ccr8, Cd200r1, Cd3d, Cd47, Cd48, Cd81, Csf2, Ctla4, Fas, H2-Aa, H2-Ab1, H2-Q8, H2-T23, Il13, Il1 r2, Il2rb, Il5, Il6, Klrg1, Lat, Lgals3, Lilrb4a, Ltb, Mif, Ms4a4b, Nmur1, Pdcd1, Pgk1, Ptger2, Ramp1, Sdc4, Sema4a, Sepp1, Stab2, Tff1, Tmem176a, Tnfrsf4, Tnfrsf8, Tnfsf8, Vsir, Nmu, 2810417H13Rik, AA467197, Alox5, Arg1, Atf4, Batf, Bcl2a1b, Blk, Btg1, Cox5b, Cox6c, Crip1, Dgat1, Dgat2, Dusp1, Ets1, Fos, Fosb, Furin, Gadd45b, Gsto1, Hint1, Ier2, Irf4, Klf3, Klf4, Lgmn, Lpcat2, Mcm3, Mt1, Myl6, Ndufa4, Nfkbia, Nfkbid, Nfkbiz, Nop56, Nr4a1, Prdx4, S100a4, S100a6, Serpinb6a, Snrpd3, Sptssa, Tph1, Vim, Zfp36, and Zfp36l1, for the manufacture of a medicament for treating a disease requiring modulation of an innate lymphoid cell (ILC) Type 2 inflammatory response. The agent may be capable of modulating the expression or the activity of one or more genes or polypeptides selected from the group consisting of Anxa1, Areg, Calca, Ccl1, Ccl5, Ccr2, Ccr7, Ccr8, Cd200r1, Cd3d, Cd47, Cd48, Cd81, Csf2, Ctla4, Fas, H2-Aa, H2-Ab1, H2-Q8, H2-T23, IL13, Il2rb, Il5, Il6, Klrg1, Lat, Lgals3, Lilrb4a, Ltb, Mif, Ms4a4b, Nmur1, Pdcd1, Pgk1, Ptger2, Ramp1, Sdc4, Sema4a, Sepp1, Stab2, Tff1, Tmem176a, Tnfsf8, Vsir, Nmu, 2810417H13Rik, AA467197, Alox5, Arg1, Atf4, Batf, Bcl2a1b, Blk, Btg1, Cox5b, Cox6c, Crip1, Dgat1, Dgat2, Dusp1, Ets1, Fos, Fosb, Furin, Gadd45b, Gsto1, Hint1, Ier2, Irf4, Klf3, Klf4, Lgmn, Lpcat2, Mcm3, Mt1, Myl6, Ndufa4, Nfkbia, Nfkbid, Nfkbiz, Nop56, Prdx4, S100a4, S100a6, Serpinb6a, Snrpd3, Sptssa, Tph1, Vim, Zfp36 and Zfp36l1. The agent may be capable of modulating the expression or the activity of one or more genes or polypeptides selected from the group consisting of Anxa1, Anxa2, Areg, Calca, Ccl1, Ccl5, Ccr2, Ccr7, Ccr8, Cd200r1, Cd3d, Cd47, Cd48, Cd81, Csf2, Ctla4, Fas, H2-Aa, H2-Ab1, H2-Q8, H2-T23, Il13, Il1r2, Il2rb, Il5, Il6, Klrg1, Lat, Lgals3, Lilrb4a, Ltb, Mif, Ms4a4b, Nmur1, Pdcd1, Pgk1, Ptger2, Ramp1, Sdc4, Sema4a, Sepp1, Stab2, Tff1, Tmem176a, Tnfrsf4, Tnfrsf8, Tnfsf8, Vsir and Nmu. The agent may be capable of modulating the expression or the activity of one or more genes or polypeptides selected from the group consisting of Anxa1, Areg, Calca, Ccl1, Ccl5, Ccr2, Ccr7, Ccr8, Cd200r1, Cd3d, Cd47, Cd48, Cd81, Csf2, Ctla4, Fas, H2-Aa, H2-Ab1, H2-Q8, H2-T23, Il13, Il2rb, Il5, Il6, Klrg1, Lat, Lgals3, Lilrb4a, Ltb, Mif, Ms4a4b, Nmur1, Pdcd1, Pgk1, Ptger2, Ramp1, Sdc4, Sema4a, Sepp1, Stab2, Tff1, Tmem176a, Tnfsf8, Vsir and Nmu. The agent may be capable of reducing the expression or inhibiting the activity of the one or more genes or polypeptides. The agent may be capable of inducing the expression or increasing the activity of the one or more genes or polypeptides.

Treating the disease may require reduction of an innate lymphoid cell (ILC) Type 2 inflammatory response. The agent may be capable of reducing the expression or inhibiting the activity of one or more genes or polypeptides selected from the group consisting of Anxa2, Lgals3, Ctla4, Batf, Cd47, Tnfrsf8, AA467197, S100a6, Prdx4, Gsto1, Il1r2, Lgmn, Mt1, Tff1, Il5, Ccr7, Irf4, Il6, Tnfrsf4, H2-T23, Lilrb4a, Fas, Ets1, Areg, and Ramp1. The agent may be capable of reducing the expression or inhibiting the activity of one or more genes or polypeptides selected from the group consisting of Lgals3, Ctla4, Batf, Cd47, AA467197, S100a6, Prdx4, Gsto1, Lgmn, Mt1, Tff1, Ccr7, Irf4, Il6, H2-T23, Lilrb4a, Ets1 and Ramp1. The agent may be capable of reducing the expression or inhibiting the activity of one or more genes or polypeptides selected from the group consisting of Lgals3, Ctla4, Cd47, Tff1, Ccr7, Il6, H2-T23, Lilrb4a and Ramp1. The disease may be an allergic inflammatory disease. The disease may be asthma.

Treating the disease may require induction of an innate lymphoid cell (ILC) Type 2 inflammatory response. The agent may be capable of reducing the expression or inhibiting the activity of one or more genes or polypeptides selected from the group consisting of Nmur1, Dgat2, Calca, Ccl5, Btg1, Nr4a1, Klf3, Klf4, Csf2, Stab2, Sdc4, Ccr2, Fosb, Zfp36l1, Lpcat2 and Ltb. The agent may be capable of reducing the expression or inhibiting the activity of one or more genes or polypeptides selected from the group consisting of Nmur1, Dgat2, Calca, Ccl5, Btg1, Klf3, Klf4, Csf2, Stab2, Sdc4, Ccr2, Fosb, Zfp36l1, Lpcat2 and Ltb. The agent may be capable of reducing the expression or inhibiting the activity of one or more genes or polypeptides selected from the group consisting of Nmur1, Calca, Ccl5, Csf2, Stab2, Sdc4, Ccr2 and Ltb. The disease may be cancer. The cancer may be a drug resistant cancer. The cancer may be resistant to an immunotherapy targeting the adaptive immune system. The immunotherapy may be a check point inhibitor.

The agent may comprise a therapeutic antibody, antibody fragment, antibody-like protein scaffold, aptamer, nucleic acid molecule, protein or small molecule. The treatment may be administered to a mucosal surface. The treatment may be administered to the lung, nasal passage, trachea, gut, intestine, or esophagus. The treatment may be administered by aerosol inhalation.

In another aspect, the present invention provides for a method of detecting an innate lymphoid cell type 2 inflammatory response in a subject comprising determining the expression or activity of an ILC type 2 inflammatory gene or polypeptide signature, said signature comprising: a) Anxa2; or b) Ltb; or c) one or more genes or polypeptides selected from the group consisting of Anxa1, Anxa2, Calca, Ccl1, Ccl5, Ccr2, Ccr7, Ccr8, Cd200r1, Cd3d, Cd47, Cd48, Cd81, Csf2, Ctla4, Fas, H2-Aa, H2-Ab1, H2-Q8, H2-T23, Il2r2, Il2rb, Il6, Lat, Lgals3, Lilrb4a, Ltb, Mif, Ms4a4b, Nmur1, Pdcd1, Pgk1, Ptger2, Ramp1, Sdc4, Sema4a, Sepp1, Stab2, Tff1, Tmem176a, Tnfrsf4, Tnfrsf8, Tnfsf8, Vsir, Nmu, 2810417H13Rik, AA467197, Alox5, Atf4, Batf, Bcl2a1b, Blk, Btg1, Cox5b, Cox6c, Crip1, Dgat1, Dgat2, Dusp1, Ets1, Fos, Fosb, Furin, Gadd45b, Gsto1, Hint1, Ier2, Irf4, Klf3, Klf4, Lgmn, Lpcat2, Mcm3, Mt1, Myl6, Ndufa4, Nfkbia, Nfkbid, Nfkbiz, Nop56, Nr4a1, Prdx4, S100a4, S100a6, Serpinb6a, Snrpd3, Sptssa, Tph1, Vim, Zfp36 and Zfp36l1; or d) one or more genes or polypeptides selected from the group consisting of Anxa1, Anxa2, Calca, Ccl1, Ccl5, Ccr2, Ccr7, Ccr8, Cd200r1, Cd3d, Cd47, Cd48, Cd81, Csf2, Ctla4, Fas, H2-Aa, H2-Ab1, H2-Q8, H2-T23, Il1r2, Il2rb, Il6, Lat, Lgals3, Lilrb4a, Ltb, Mif, Ms4a4b, Nmur1, Pdcd1, Pgk1, Ptger2, Ramp1, Sdc4, Sema4a, Sepp1, Stab2, Tff1, Tmem176a, Tnfrsf4, Tnfrsf8, Tnfsf8, Vsir, Nmu, 2810417H13Rik, AA467197, Alox5, Atf4, Batf, Bcl2a1b, Blk, Btg1, Cox5b, Cox6c, Crip1, Dgat1, Dgat2, Dusp1, Ets1, Fos, Fosb, Furin, Gadd45b, Gsto1, Hint1, Ier2, Irf4, Klf3, Klf4, Lgmn, Lpcat2, Mcm3, Mt1, Myl6, Ndufa4, Nfkbia, Nfkbid, Nfkbiz, Nop56, Nr4a1, Prdx4, S100a4, S100a6, Serpinb6a, Snrpd3, Sptssa, Tph1, Vim, Zfp36 and Zfp36l1; and one or more genes or polypeptides selected from the group consisting of Il5, Areg, IL-7Ra, CD90, Tbx21, Il1rl1, Il13, Klrg1, Arg1 and Ptprc; or e) one or more genes or polypeptides selected from the group consisting of Anxa2, Lgals3, Ctla4, Batf, Cd47, Tnfrsf8, AA467197, S100a6, Prdx4, Gsto1, Il1r2, Lgmn, Mt1, Tff1, Ccr7, Irf4, Il6, Tnfrsf4, H2-T23, Lilrb4a, Fas, Ets1, Ramp1, Nmur1, Dgat2, Calca, Ccl5, Btg1, Nr4a1, Klf3, Klf4, Csf2, Stab2, Sdc4, Ccr2, Fosb, Zfp36l1, Lpcat2 and Ltb; or f) one or more genes or polypeptides as in (e) and one or more genes or polypeptides selected from the group consisting of Il5 and Areg; or g) one or more genes or polypeptides as in (e) and one or more genes or polypeptides selected from the group consisting of Il7Ra, CD90, Tbx21, Il1rl1, Il13, Klrg1, Arg1 and Ptprc; or h) one or more genes or polypeptides as in (e) and one or more genes or polypeptides selected from the group consisting of Il5, Areg, Il7Ra, CD90, Tbx21, Il1rl1, Il13, Klrg1, Arg1 and Ptprc; or i) one or more genes or polypeptides selected from the group consisting of Anxa1, Anxa2, Calca, Ccl1, Ccl5, Ccr2, Ccr7, Ccr8, Cd200r1, Cd3d, Cd47, Cd48, Cd81, Csf2, Ctla4, Fas, H2-Aa, H2-Ab1, H2-Q8, H2-T23, Il1r2, Il2rb, Il6, Lat, Lgals3, Lilrb4a, Ltb, Mif, Ms4a4b, Nmur1, Pdcd1, Pgk1, Ptger2, Ramp1, Sdc4, Sema4a, Sepp1, Stab2, Tff1, Tmem176a, Tnfrsf4, Tnfrsf8, Tnfsf8, Vsir, Nmu; or j) one or more genes or polypeptides as in (i) and one or more genes or polypeptides selected from the group consisting of Il5, Areg, Il13 and Klrg1; or k) one or more genes or polypeptides selected from the group consisting of Fosb, Btg2, Lpcat2, Sdc4, Csf2, Dgat2, Calca, Areg, Pim2, Zfp36l1, Nr4a1, Cd81, Ly6a, Lgmn, Il13, Il5, Klrg1, Batf, Pycard, Pdcd1, Lgals3, Anxa2, Ctla4, Il1r2, Tox2, Tnfrsf8, Mt1, Tff1, Lilrb4a and H2-Ab1. The one or more genes or polypeptides selected from the group consisting of Anxa2, Lgals3, Ctla4, Batf, Cd47, Tnfrsf8, AA467197, S100a6, Prdx4, Gsto1, Il1r2, Lgmn, Mt1, Tff1, Ccr7, Irf4, Il6, Tnfrsf4, H2-T23, Lilrb4a, Fas, Ets1, Ramp1, Il5 and Areg may be upregulated. The one or more genes or polypeptides selected from the group consisting of Nmur1, Dgat2, Calca, Ccl5, Btg1, Nr4a1, Klf3, Klf4, Csf2, Stab2, Sdc4, Ccr2, Fosb, Zfp36l1, Lpcat2 and Ltb may be downregulated. The one or more genes may be upregulated or downregulated in comparison to a reference sample or reference expression profile. The reference sample may be an untreated sample or a sample of non-inflammatory ILC2s. Detecting an innate lymphoid cell type 2 inflammatory response may be performed in a subject administered an allergic challenge.

In another aspect, the present invention provides for a method of treatment for a subject in need thereof suffering from allergic inflammation comprising: detecting expression or activity of an innate lymphoid cell type 2 inflammatory gene or polypeptide signature according to any embodiment herein; and treating the subject with an agent capable of inhibiting neuromedin U receptor 1 (Nmur1) or blocking Nmur1 interaction with neuromedin U (NMU).

In another aspect, the present invention provides for a kit comprising reagents to detect an ILC type 2 inflammatory gene or polypeptide signature, said signature comprising: a) Anxa2; or b) Ltb; or c) one or more genes or polypeptides selected from the group consisting of Anxa1, Anxa2, Calca, Ccl1, Ccl5, Ccr2, Ccr7, Ccr8, Cd200r1, Cd3d, Cd47, Cd48, Cd81, Csf2, Ctla4, Fas, H2-Aa, H2-Ab1, H2-Q8, H2-T23, Il1r2, Il2rb, Il6, Lat, Lgals3, Lilrb4a, Ltb, Mif, Ms4a4b, Nmur1, Pdcd1, Pgk1, Ptger2, Ramp1, Sdc4, Sema4a, Sepp1, Stab2, Tff1, Tmem176a, Tnfrsf4, Tnfrsf8, Tnfsf8, Vsir, Nmu, 2810417H13Rik, AA467197, Alox5, Atf4, Batf, Bcl2a1b, Blk, Btg1, Cox5b, Cox6c, Crip1, Dgat1, Dgat2, Dusp1, Ets1, Fos, Fosb, Furin, Gadd45b, Gsto1, Hint1, Ier2, Irf4, Klf3, Klf4, Lgmn, Lpcat2, Mcm3, Mt1, Myl6, Ndufa4, Nfkbia, Nfkbid, Nfkbiz, Nop56, Nr4a1, Prdx4, S100a4, S100a6, Serpinb6a, Snrpd3, Sptssa, Tph1, Vim, Zfp36 and Zfp36l1; or d) one or more genes or polypeptides selected from the group consisting of Anxa1, Anxa2, Calca, Ccl1, Ccl5, Ccr2, Ccr7, Ccr8, Cd200r1, Cd3d, Cd47, Cd48, Cd81, Csf2, Ctla4, Fas, H2-Aa, H2-Ab1, H2-Q8, H2-T23, Il1r2, Il2rb, Il6, Lat, Lgals3, Lilrb4a, Ltb, Mif, Ms4a4b, Nmur1, Pdcd1, Pgk1, Ptger2, Ramp1, Sdc4, Sema4a, Sepp1, Stab2, Tff1, Tmem176a, Tnfrsf4, Tnfrsf8, Tnfsf8, Vsir, Nmu, 2810417H13Rik, AA467197, Alox5, Atf4, Batf, Bcl2a1b, Blk, Btg1, Cox5b, Cox6c, Crip1, Dgat1, Dgat2, Dusp1, Ets1, Fos, Fosb, Furin, Gadd45b, Gsto1, Hint1, Ier2, Irf4, Klf3, Klf4, Lgmn, Lpcat2, Mcm3, Mt1, Myl6, Ndufa4, Nfkbia, Nfkbid, Nfkbiz, Nop56, Nr4a1, Prdx4, S100a4, S100a6, Serpinb6a, Snrpd3, Sptssa, Tph1, Vim, Zfp36 and Zfp36l1; and one or more genes or polypeptides selected from the group consisting of Il5, Areg, IL-7Ra, CD90, Tbx21, Il1rl1, Il13, Klrg1, Arg1 and Ptprc; or e) one or more genes or polypeptides selected from the group consisting of Anxa2, Lgals3, Ctla4, Batf, Cd47, Tnfrsf8, AA467197, S100a6, Prdx4, Gsto1, Il1r2, Lgmn, Mt1, Tff1, Ccr7, Irf4, Il6, Tnfrsf4, H2-T23, Lilrb4a, Fas, Ets1, Ramp1, Nmur1, Dgat2, Calca, Ccl5, Btg1, Nr4a1, Klf3, Klf4, Csf2, Stab2, Sdc4, Ccr2, Fosb, Zfp36l1, Lpcat2 and Ltb; or f) one or more genes or polypeptides as in (e) and one or more genes or polypeptides selected from the group consisting of Il5 and Areg; or g) one or more genes or polypeptides as in (e) and one or more genes or polypeptides selected from the group consisting of IL-7Ra, CD90, Tbx21, Il1rl1, Il13, Klrg1, Arg1 and Ptprc; or h) one or more genes or polypeptides as in (e) and one or more genes or polypeptides selected from the group consisting of Il5, Areg, Il7Ra, CD90, Tbx21, Il1rl1, Il13, Klrg1, Arg1 and Ptprc; or i) one or more genes or polypeptides selected from the group consisting of Anxa1, Anxa2, Calca, Ccl1, Ccl5, Ccr2, Ccr7, Ccr8, Cd200r1, Cd3d, Cd47, Cd48, Cd81, Csf2, Ctla4, Fas, H2-Aa, H2-Ab1, H2-Q8, H2-T23, Il1r2, Il2rb, Il6, Lat, Lgals3, Lilrb4a, Ltb, Mif, Ms4a4b, Nmur1, Pdcd1, Pgk1, Ptger2, Ramp1, Sdc4, Sema4a, Sepp1, Stab2, Tff1, Tmem176a, Tnfrsf4, Tnfrsf8, Tnfsf8, Vsir, Nmu; or j) one or more genes or polypeptides as in (i) and one or more genes or polypeptides selected from the group consisting of Il5, Areg, Il13 and Klrg1. The kit may comprise at least one antibody, antibody fragment, or aptamer. The kit may comprise primers and/or probes for quantitative RT-PCR or fluorescently bar-coded oligonucleotide probes for hybridization to RNA (see e.g., Geiss G K, et al., Direct multiplexed measurement of gene expression with color-coded probe pairs. Nat Biotechnol. 2008 March; 26(3):317-25).

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

FIG. 1 illustrates that IL-25 and IL-33 induce distinct transcriptional programs in ILCs. Lung-resident ILCs were isolated from mice treated intranasally with PBS, IL-25 or IL-33 and profiled by droplet-based scRNA-seq. (a) Cell classification. Bar plots of the proportion of 9,138 cells (y axis) classified in each treatment (x axis) based on transcriptional signatures of known ILC subsets as (from top to bottom of bar plot) ILC1, ILC2, ILC3, mixed (scoring for two or more signatures), or none (scoring for none of the three signatures). (b) Expression of key ILC marker genes. Violin plots show the distribution of expression levels (log(TPX), y axis) of each of 12 ILC marker genes (marked on top) in cells classified in each subtype (rows) in each treatment (x axis). (c-e) Distinct cell subsets by expression profiles. tSNE plots show individual cells (dots) in a two dimensional reduced representation of the top 30 PCs (Methods), with cells shaded by (c) treatment, (d) expression of key genes or (e) cell clusters determined by a graph based algorithm (Methods). (f, g) Cell clustering reflects both ILC type and treatment. Bar plots show the proportion of cells (y axis) in each cluster (x axis) in each subtype (f, classified as in (a)), or from each treatment (g). (h) High levels of proliferation observed in IL-33-dominated clusters. Violin plots show the distribution of proliferation scores (y axis) in cells from each cluster (x axis), with cluster 1 showing significantly more proliferation (Student's t-test, p<4.9×10$^-$7). (i) Differentially expressed genes across clusters, groups of clusters or conditions. For each gene (columns) in each cluster (rows), the proportion of cells in the cluster expressing the gene (dot size) and the mean-centered log TPX expression levels is plotted.

FIG. 3 illustrates that Nmur1 signaling dramatically amplifies IL-25-induced allergic inflammation in vivo. (a,b) NMU synergizes with IL-25 to activate ILCs in vitro. ILCs were sorted from the lungs of naive mice and cultured in vitro with the indicated stimuli. (a) Expression of Il5 and Il13 as determined by qPCR are shown. (b) The combination of NMU and IL-25 markedly enhanced Il5 and Il13 mRNA expression (as measured by qPCR) and secretion (concentration in supernatant measured by LegendPlex) in comparison to IL-25. Panels A and B are representative of three independent experiments. (c-h) NMU amplifies IL-25-induced allergic airway inflammation in vivo. Mice were treated with the indicated stimuli for three days and then lung immune responses were analyzed. (c,d) NMU enhanced IL-25 induced expression of IL-5 and IL-13 in (c) lung mononuclear cells (by qPCR) and in (d) bronchoalveolar lavage fluid (BALF) (by LegendPlex). (e,f) NMU+ IL-25 strongly increased both frequency and number of eosinophils (assessed by flow cytometry) in (e) lung and (f) BALF. (g) NMU+IL-25 results in histopathologically significant perivascular and peribronchial lymphocytic infiltrates compared to IL-25 alone. Representative images are shown. (h) NMU+IL-25 treated mice demonstrate increased airway reactivity to methacholine as determined by measuring airway resistance after graded methacholine challenge. Each data point represents the mean of pooled biological replicates (IL-25, n=7, NMU+IL-25, n=6). Panels C-H represent pooled data from at least two independent experiments. In bar graphs (a,b), the mean of technical replicates is shown, and data are representative of at least two individual experiments. Each data point in panels C-G represents an individual mouse. *=P<0.05.

FIG. 5 illustrates massively parallel scRNA-seq of lung ILCs. (a) Schematic of experimental method for in vivo activation of ILCs. (b,c) Quality measures. (b) Scatter plots show for each cell the relation between the number of UMIs (nUMI, x axis) and either the number of genes (y axis, top) or percent of reads from mitochondrial genes (y axis, bottom). Cells included ("pass") and excluded ("fail") from further analysis by these measures are marked, respectively. (c) Violin plots show the distribution of the number of unique genes (y axis, top), UMIs (y axis, middle) and percent of reads from mitochondrial genes (y axis, bottom) in each treatment and batch (x axis). Cells excluded ("fail") from further analysis are marked in pink. White diamond: mean. (d,e) ILC classification by signatures. (d) Density plots show the distributions of ILC subset signature scores (x axis) for ILC1 (top), ILC2 (middle) and ILC3 (bottom) in each of three treatments (control; IL-25; IL-33). Dashed lines mark the cutoffs used in the ILC classification for each signature. (e) Bar plots show the number of ILCs (y axis) classified to each subset (Top to bottom ILC1, ILC2, ILC3, Mixed, None) in the PBS, IL-25 or IL-33 conditions (x axis). (f) Cell groupings are independent of batch. tSNE plot of cells (as in FIG. 1c), by condition and biological replicate. (g) Gene expression for marker genes of ILCs and other immune cell types. For each gene (columns) in each cluster (rows), the proportion of cells in the cluster expressing the gene (dot size) and the mean-centered log TPX expression levels is plotted (shading). (h,i) Cluster composition. Bar plots show the number of cells (y axis) from each ILC type (h) and condition (i) in each cluster (x axis).

FIG. 7 illustrates plate based scRNA-seq of lung ILCs. (a) Quality measures. Scatter plot of the total number of reads ("counts per cell") (x axis) and number of unique detected genes (y axis) in each cell. Dashed lines indicate cutoffs for passing quality control, and cells in the upper right quadrant were retained for analysis. (b-d) ILC classification by signatures. (b) Density plots show the distributions of ILC subset signature scores (x axis) for ILC1 (left), ILC2 (middle) and ILC3 (right) in each of three treatments (control; IL-25; IL-33). Dashed lines mark the cutoffs used in the ILC classification for each signature. (c) The bar plot shows the proportion of ILCs classified to each subset in the PBS, IL-25 or IL-33 conditions (x axis) (Top to bottom ILC1, ILC2, ILC3, Mixed).

FIG. 9 illustrates that Nmur1 is expressed at extremely low levels in Th2 cells. Naïve CD4 T cells were differentiated in vitro into Th2 cells in the presence of the indicated stimuli. mRNA was then isolated and Nmur1 expression was analyzed by qPCR. Bar chart shows Nmur1 expression in both Th2 cells cultured under the indicated conditions as well as in freshly isolated ILCs. Data are representative of two individual experiments. The mean of technical replicates is shown.

FIG. 10 illustrates that NMU neither amplifies IL-33-induced cytokine production in vitro nor induces significant lung inflammation. (a,b) NMU has little if any effect on key cytokine expression in vitro. (a) Expression of Il5 and Il13 is similar in Th2 cells cultured with or without NMU, as assessed by qPCR. (b) ILCs were isolated from naive mice and cultured in vitro with IL-33 either alone or in combination with NMU. Expression of Il5 and Il13 mRNA was quantified by qPCR, and the concentrations of IL-5 and IL-13 in supernatants were determined by LegendPlex. The mean of technical replicates is shown. (c-g) NMU induces minimal allergic lung inflammation. (c) Schematic of experimental method for activation of ILCs with NMU in vivo. Mice were treated with NMU intranasally for 3 consecutive days and then analyzed the following day. (d) Il5 and Il13 expression was determined in lung mononuclear cells by qPCR. (e) The concentration of IL-5 and IL-13 protein in BALF was analyzed by LegendPlex. (f-g) Eosinophil frequencies in lung parenchyma (f) and BALF (g), as determined by flow cytometry, are shown. Each data point corresponds to an individual mouse. All data are representative of at least two individual experiments. *=P<0.05.

FIG. 11 illustrates that NMU does not significantly amplify IL-33-induced lung inflammation. Mice were treated with the indicated stimuli intranasally for 3 consecutive days and analyzed the following day. (a) Expression of Il5 and Il13 in lung mononuclear cells was analyzed by qPCR. (b) Frequency of eosinophils in lung parenchyma was assessed by flow cytometry. (c) Airway resistance in response to methacholine challenge was assessed after treatment with the indicated stimuli. The mean of biological replicates (IL-33, n=4, IL-33+NMU, n=5) is shown. For panels A-B, each data point corresponds to an individual mouse. Data are representative of two individual experiments. *=P<0.05.

FIG. 12 illustrates massively parallel scRNA-seq of ILCs from NMU- and NMU+IL-25 treated mice. (a) Quality measures. Violin plots show the distribution of the number of unique genes (y axis, top), UMIs (y axis, middle) and percent of reads from mitochondrial genes (y axis, bottom) in each treatment and batch (x axis). Cells excluded ("fail") from further analysis are marked. White diamond: mean. (b) Grouping of ILCs is independent of batch. tSNE plot (as in FIG. 4a) of cells shaded by condition and biological replicate. (c) Cluster composition. Bar plot shows the number of cells (y axis) from each condition in each cluster (x axis). (d,e) Proliferation and ILC2 inflammatory signatures. Violin plots show the distributions of the proliferation (d) and ILC2 inflammatory (e) signature scores (y axis) for the cells in each cluster. Proliferation scores in cluster 8 are significantly higher that those in the NMU+IL-25-dominant clusters 5 and 9 (Student's t-test, $p<2.2\times10^{-16}$) Inflammatory ILC2 scores are significantly higher in clusters 5, 8, and 9 (dominated by NMU+IL-25 activated cells) than in other clusters (Student's t-test, $p<2.2\times10^{-16}$), but not significantly higher in cluster 8 compared to clusters 5 and 9. (f) Distinct patterns of expression of key ILC2 related genes, as well as genes from the inflammatory ILC2 signature across clusters. Violin plots show the distribution of expression levels ($\log^2$ TPX, y axis) for each of the indicated genes across the cells in each of the clusters (x axis).

FIG. 13 illustrates that IL-25 and IL-33 induce multiple distinct transcriptional programs in ILCs. ILCs were profiled by droplet-based scRNA-seq. (a,b) tSNE plots show 24,187 cells (dots) in a nonlinear representation of the top 22 PCs. Cells are shaded by (a) in vivo treatment or (b) cluster. (c,d) Clustering reflects ILC type and treatment. Proportions of (c) ILC subsets or (d) treatment condition within each cluster. (e) Distribution of proliferation scores by cluster. Diamond: mean score; lines: first and third quartiles. (f) Representative differentially expressed genes (x-axis) by cluster (y-axis). Dot size: fraction of cells in the cluster that express the gene; shading: mean expression (log TPX) in expressing cells, relative to other clusters.

FIG. 14 illustrates that ScRNA-seq identifies Nmur1 as a novel ILC2-specific gene. (a-c) Full-length scRNA-seq. (a,b) tSNE plots of 606 cells shaded by (a) in vivo treatment and (b) cell clusters. (c) Differentially expressed genes by cluster. Asterisk: Nmur1. (d) Nmur1 expression by qPCR of lung-resident cell types isolated from control or HDM-challenged mice. Data points: technical replicates (PBS, n=3; HDM, n=2). (e) Representative flow cytometry histograms of Nmur1 expression on the indicated cell types. (f) Frequency of Nmur1 ILCs by flow cytometry after the indicated treatments. Data points: individual mice (PBS and IL-33, n=4; IL-25, n=3). Data in panels (d,f) are representative of two individual experiments. Error bars: SEM. *=P<0.05 (one-way ANOVA).

FIG. 15 illustrates that NMU amplifies IL-25-induced allergic inflammation. (a, b) IL-5 and IL-13 levels in cultured ILCs. (a) RNA levels by qPCR. (b) Protein concentration by LegendPlex. One of three independent experiments are shown. Data points: technical replicates (n=2). (c) BALF IL-5 and IL-13 concentrations by LegendPlex. (d) BAL eosinophil frequency and number after treatment. (e) Lung histology. Representative images (left) and severity score (right). Data points in (c-e) represent individual mice (PBS, n=3; IL-25, n=9; IL-25+NMU, n=7). (f) Airway resistance after graded methacholine challenge. Data points:

Figure 2A:
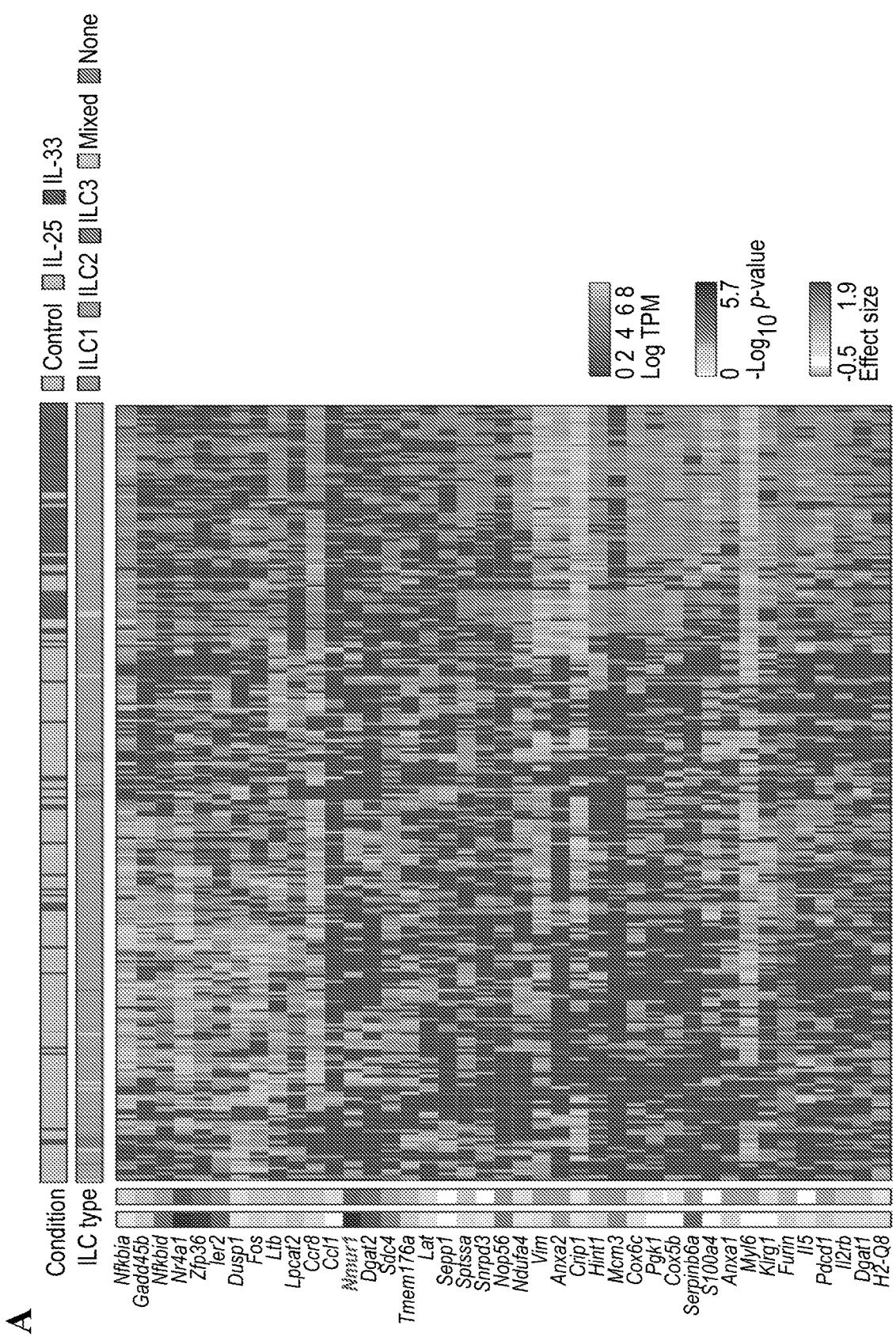
FIG. 2 illustrates that Nmur1 is a novel and specific regulator of ILC2s. (a) Top genes from PCA of individual ILCs. Heatmap shows the expression levels (log TPM; 0-4 low; 5-8 high) of each of five genes associated with the top nine PCs (rows) in each of 270 cells (columns) profiled by full-length scRNA-Seq. Rows above indicate treatment (top) and classified ILC type (bottom) for each cell. Columns on left show the significance ($-\log^{10}$ (p-value)) and effect size (log of the odds ratio) of the frequency of cells expressing the gene under IL-25 vs. IL-33 treatment. Nmur1 is preferentially expressed by IL-25 activated ILCs. (b) Neuropeptide receptor expression is differentially regulated by alarmins. Violin plots show the distribution of expression levels (y axis, log TPM) of Vipr2 (left) and Nmur1 (right) in each ILC subset (rows) and treatment (GLM binomial test, p<3.4× 10−). (c) Lung ILCs express only Nmur1 and not Nmur2 by qPCR. (d) Nmur1 is preferentially expressed by ILC2 cells compared to other lung-resident cell types. Nmur1 expression levels determined by qPCR for different lung-resident cell types are shown. (e) Specific expression of Nmur1 in ILC2s. Representative flow cytometry plots (histograms, left) and a summary graph showing the frequency of Nmur1+ cells (bar plot, right) are shown in different cell populations from Nmur1-LacZ reporter mice as assayed by flow cytometry. Data points in the bar plot (right) represent individual mice. (f) T cells minimally express Nmur1 after induction of airway inflammation, while Nmur1 expression is sustained in ILC2. Nmur1 mRNA levels measured by qPCR are shown. Data are representative of at least two individual experiments. In bar graphs (c, d, f), the mean of technical replicates is shown. *=P<0.05.

mean of biological replicates (IL-25, n=7; IL-25+NMU, n=6). (g,h) ILC responses after HDM challenge. (g) Frequency of ST2+ ILCs by flow cytometry. Data points: individual mice (WT, n=15; KO, n=13). (h) Frequency of ILCs expressing IL-5 or IL-13, by intracellular cytokine staining. Data points: individual mice (n=5) in one of three individual experiments. Error bars: SEM. *=P<0.05 by (a, b, e, g, h) two-tailed t-test, (c,d) one-way ANOVA, or (f) two-way ANOVA.

FIG. 16 illustrates that IL-25+NMU synergize to activate inflammatory ILC2s. (a-b) IL-25+NMU induces distinct transcriptional states. tSNE plots of 35,542 ILCs from mice treated with the indicated stimuli, shaded by (a) treatment and (b) cluster. (c) ILC frequency by flow cytometry. (d) Distribution of proliferation scores by treatment condition. Diamond: mean score; lines: first and third quartiles. (e-g) IL-25+NMU enhances IL-17RB expression on ILCs. (e) IL-17RB+ ILC frequency by flow cytometry in one of two independent experiments. (f) Frequency of Il17rb-expressing ILCs by scRNA-seq. (*=P<2.73×10$^{-10}$, GLM binomial test). (g) IL-17RB+ ILC frequency after HDM-challenge by flow cytometry. (h) Differentially expressed genes (y-axis) by condition (x-axis). Data points (c, e, g): individual mice ((c) PBS, n=3; IL-25, n=9; IL-25+NMU, n=7; (e) IL-25, n=8; IL-25+NMU, n=6; (g) WT, n=5; NMU-KO, n=5). Error bars: SEM. *=P<0.05 by (c) one-way ANOVA or (d, e, g) two-tailed t-test.

FIG. 17 illustrates that Nmur1-signaling regulates ILC responses after allergen challenge. (a) HDM challenge induces distinct transcriptional states. ScRNA-seq profiles of 21,895 ILCs from WT (left) and Nmur1-KO (right), on the same tSNE plot, shaded by treatment and genotype. (b) Proportions of ILC subsets in each condition and genotype. (c-e) An inflammatory ILC2 gene signature based on differential expression between ILCs from PBS- and HDM-treated mice. (c,d) ILCs shaded by inflammatory ILC2 score, from (c) HDM-challenged mice and (d) PBS-, NMU-, IL-25- and IL-25+NMU-treated mice. (e) Distribution of inflammatory ILC2 scores (y-axis) in the indicated conditions. Diamond: mean score; lines: first and third quartiles. *=P<4.9×10$^{-15}$, two-tailed t-test.

FIG. 18 illustrates massively parallel scRNA-seq of lung ILCs. (a) Schematic of experimental method for in vivo activation of ILCs. (b,c) Quality measures. (b) Scatter plots show for each cell the relation between the number of UMIs (nUMI, x-axis) and the number of genes (nGene, y-axis). Cells are shown according to whether they are included or excluded from further analysis by these measures. (c) Box plots show the distribution of the number of unique genes (y-axis, left), UMIs (y-axis, middle) and percent of normalized expression from mitochondrial genes (y-axis, right) in each treatment and replicate ("rep"; x-axis). White diamond: mean. (d-g) ILC classification by signatures. (d) Density plots show the distributions of ILC subset signature scores (x-axis) for ILC1 (left), ILC2 (middle) and ILC3 (right) in each of three treatments (control; IL-25; IL-33). Dashed lines mark the cutoffs used in the ILC classification for each signature. (e) Bar plots of the proportion of 24,187 cells (y-axis) classified in each treatment (x-axis) based on transcriptional signatures of known ILC subsets as ILC1, ILC2, ILC3, mixed (scoring for two or more signatures), or none (scoring for none of the three signatures). (f) Bar plots show the number of ILCs (y-axis) classified to each subset in the PBS, IL-25 or IL-33 conditions (x-axis). (g) Expression of key ILC marker genes. Violin plots show the distribution of expression levels (log TPX, y-axis) of each of 12 ILC marker genes (marked on top) in cells classified in each subtype (rows) in each treatment (x-axis). (h) Cell groupings are independent of batch. tSNE plot of cells (as in FIG. 13a) from replicate 1 (left plot) and replicate 2 (right plot), shaded by condition. (i) Expression of key genes. tSNE is shown by the relative expression of the indicated genes. (j) Gene expression for marker genes of ILCs and other immune cell types. For each gene (columns) in each cluster (rows), the proportion of cells in the cluster expressing the gene (dot size) and the relative mean log TPX expression of expressing cells is plotted. (k,l) Cluster composition. Bar plots show the number of cells (y-axis) from each (k) ILC type and (l) condition in each cluster (x-axis). (m) Validation of expression patterns identified by scRNA-seq using flow cytometry. In each histogram, the expression of proteins encoded by genes identified with scRNA-seq on ILCs from mice treated with PBS vs. one of the alarmins IL-25 or IL-33 is shown, as well as an FMO control (dashed). Numbers indicate the mean fluorescence intensity of the marker in PBS or condition or, for CTLA4 and MHC Class II, the frequency of cells positive for the marker in PBS or condition. Data are representative of at least two individual experiments.

Figure 19:
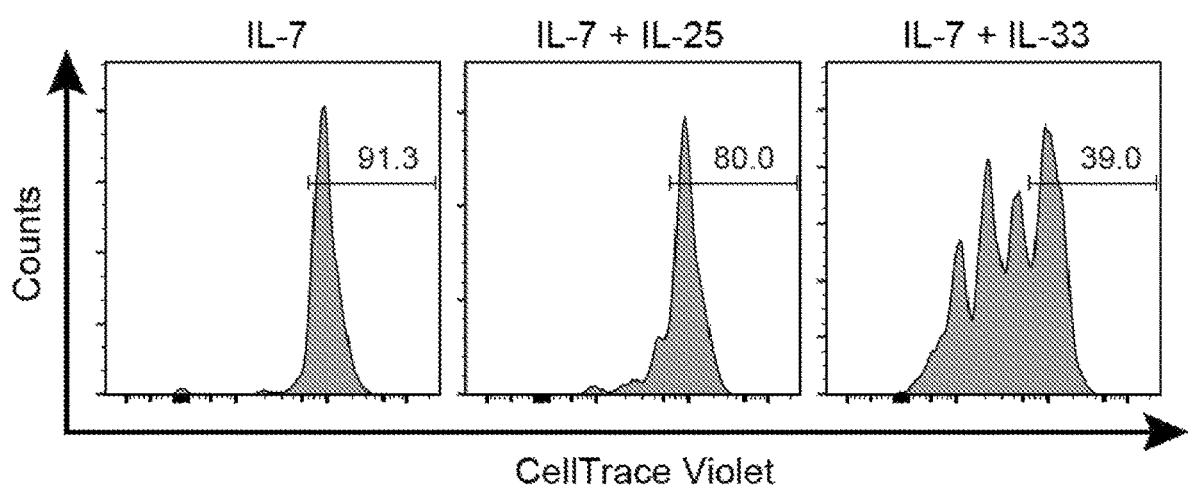

FIG. 19 illustrates Alarmin-induced ILC proliferation in vitro. ILCs were labeled with CellTrace Violet and cultured in vitro under the indicated conditions. After 3 days, proliferation was analyzed by flow cytometric analysis of CellTrace Violet dilution. The frequency of non-proliferating ILCs is indicated. Data are representative of two individual experiments.

FIG. 20 illustrates plate-based scRNA-seq of lung-resident ILCs. (a) Quality measures. Scatter plots for each plate showing the total number of read counts per cell (x-axis) and number of unique detected genes (y-axis) in each cell. Dashed lines indicate cutoffs for passing quality control. Only cells in the central quadrant were retained for analysis. (b-e) ILC subset classification. (b) ILC signature score distributions. Density plots show the distributions of ILC subset signature scores (x-axis) for ILC1 (top), ILC2 (middle) and ILC3 (bottom) in each of three treatments (control; IL-25; IL-33). Dashed lines mark the minimum score cutoff used in the ILC classification for each signature. (c) Expression of key ILC marker genes. Violin plots show the distribution of expression levels (log TPM, y-axis) of each of 12 ILC marker genes (marked on top) in cells classified in each subtype (rows) in each treatment (x-axis). (d) Distinct cell subsets by ILC expression profile. tSNE plot shows individual cells (dots) in a nonlinear reduced representation of the top 9 PCs, with cells by ILC subset. (e) Composition by treatment condition. Bar plots show the proportion of each ILC subtype (y-axis) in each treatment condition (x-axis).

FIG. 21 illustrates that accurate detection of Nmur1 from massively parallel 3' end scRNA-seq requires cell-type specific annotation. (a) Comparison of gene expression estimates from plate-based and droplet-based scRNA-seq. Scatter plots show for each gene (dot) the fraction of cells expressing it according to plate-based scRNA-seq (x-axis) and droplet-based scRNA-seq (y-axis) in the PBS (top) and IL-25 (bottom) conditions. Of the differentially expressed genes in the plate-based data that are expressed in a substantially different proportion of cells compared to droplet-based data, Nmur1 and Rapgef4 are among the highest ranked and are only detected in the plate-based data. (b) Reannotation of the Nmur1 locus by RNA-seq and assembly. Shown is a window of ~7Kb around the annotated Nmur1 locus on chromosome 1 (top) along with read alignments to that region from either droplet-based 3' scRNA-seq (top, 55nt reads) or from population (bulk)

RNA-seq of ILCs (bottom, 75nt reads). The Refseq annotation of Nmur1 (top track) does not extend to the 3' end of the transcript, as defined by either the scRNA-seq reads (10× Nmur1 extended; middle track) or by a transcriptome reassembly from bulk RNA-Seq (StringTie reassembled; bottom track). (c) Corrected annotation recovers Nmur1. Histogram shows the distribution of expression levels of Nmur1 in single cells based on droplet-based scRNA-seq data when expression was calculated by aligning reads with the original RefSeq annotation (left), the scRNA-seq read-based extended annotation (middle) or the reassembled transcript annotation from bulk RNA-Seq (right). (d) Rapgef4 locus correctly annotated. Shown is a plot for Rapgef4, arranged as in (b). The 3' annotation in the RefSeq annotation agrees with the observed end from bulk RNA-seq.

FIG. 22 illustrates expression of Nmur1 and Nmur2 in lung-resident immune cells. (a) Minimal expression of Nmur1 on in vitro differentiated Th2 cells. Bar chart shows Nmur1 mRNA levels by qPCR in both Th2 cells differentiated under the indicated conditions in vitro, and in freshly isolated ILCs. Data points represent technical replicates (n=2). (b) Nmur2 is not expressed by lung-resident immune cells, including ILCs. Bar chart shows Nmur2 mRNA levels by qPCR for the indicated cell types, which were sorted from mice either at steady state (PBS) or after HDM challenge. The mean of technical replicates is shown (n=2). (c) Summary graph of the flow cytometry data, of which a representative is shown in FIG. 14e. Plot shows the frequency of Nmur1$^+$ cells in different cell populations from Nmur1-LacZ reporter mice as assayed by flow cytometry. Data points represent individual mice (n=3). (d) Nmur1-LacZ β-galactosidase activity reveals ILC-specific Nmur1 expression. Representative histograms show the distribution of expression of Nmur1 in the indicated cell types as determined by flow cytometry in cells isolated from WT (top number) and Nmur1-LacZ heterozygous (bottom number) mice. The frequency of Nmur1-LacZ-positive cells is indicated. (e) Nmur1 is preferentially expressed by ST2$^+$ ILCs. The expression of ST2, IL-17RB, and Nmur1 was analyzed by flow cytometry, and the frequency of Nmur1+ ILCs within the indicated populations is shown. Each data point reflects an individual mouse (n=4 for PBS and IL-33; n=3 for IL-25). All panels represent one of two individual experiments, error bars represent SEM, *=P<0.05 by two-tailed t-test.

FIG. 23 illustrates that ILCs and neurons are in proximity in the lung, and NMU is expressed by dorsal root ganglion neurons. (a) Representative image (left) of lung sections stained for the neuronal marker SNAP-25, KLRG1, and CD3ε. Arrows indicate KLRG1$^+$ CD3ε$^-$ cells in close proximity to SNAP-25$^+$ nerve fibers. Scale bar=100 μm. Bar plot (right) shows the frequency of ILCs (x-axis) within indicated distances (y-axis) of SNAP-25$^+$ nerve fibers. All KLRG1$^+$ CD3ε$^-$ cells in the field of view were counted, and the distances between ILCs and the closest SNAP-25$^+$ nerve fiber were measured (3-5 lung sections per mouse, n=3 mice). Data are representative of three independent experiments with similar results. (b,c) Neuromedin U (NMU) is expressed in thoracic dorsal root ganglion (DRG) neurons. NMU expression was examined by qPCR. (b) NMU expression in the nodose/jugular ganglion and DRG ex vivo. Data points represent technical replicates (n=2). (c) NMU expression in DRG neurons stimulated in vitro with IL-13. Data points represent two technical replicates from each of six biologic replicates. All panels are representative of at least two individual experiments, error bars represent the SEM, *=P<0.05 by two-tailed t-test.

FIG. 24 illustrates that NMU induces minimal lung inflammation in the absence of alarmins. (a) NMU does not alter in vitro expression of type 2 cytokines in T cells. Expression of Il5 and Il13 is similar in Th2 cells cultured with or without NMU, as assessed by qPCR. (b-c) ILCs were isolated from naive mice and cultured in vitro with the indicated stimuli. (b) ILCs cultured in vitro have markedly enhanced Il5 and Il13 mRNA expression in response to combination of NMU and IL-25, as measured by qPCR. (c) IL-33-induced IL-5 and IL-13 secretion is enhanced by NMU, as determined by LegendPlex. Data points represent technical replicates, and the mean is indicated. (d-h) NMU alone induces minimal allergic lung inflammation. (d) Schematic of experimental method for activation of ILCs with NMU in vivo. (e) Il5 and Il13 expression was determined in lung mononuclear cells by qPCR. (f) The concentration of IL-5 and IL-13 protein in BALF was analyzed by LegendPlex. (g,h) Eosinophil frequencies in (g) lung parenchyma and (h) BALF (left), and BALF eosinophil numbers (right), as determined by flow cytometry. Data points correspond to individual mice (n=3). (i) The combination of IL-25+NMU markedly enhanced Il5 (top) and Il13 (bottom) mRNA expression in lung mononuclear cells, as measured by qPCR. (j) NMU and IL-25 synergize to promote tissue eosinophilia. Eosinophil frequency (top) and number (bottom) in lung parenchyma was assessed by flow cytometry. Data points correspond to individual mice (PBS, n=3; IL-25, n=9; IL-25+NMU, n=7). For all panels, data are representative of at least two individual experiments, error bars represent the SEM, *=P<0.05 by two-tailed t-test.

FIG. 25 illustrates the phenotype of NMU-KO mice. (a-c) ILC frequency and function are not altered in the absence of NMU in steady state. Lung resident ILCs isolated from WT and NMU-deficient mice were analyzed by flow cytometry. (a) The frequency of ILCs (among CD90$^+$ cells) and (b) expression of KLRG1 and ST2 on ILCs are unchanged in NMU-KO mice compared to control mice. (c) Frequency of IL-5- and IL-13-producing ILCs in NMU-KO mice is comparable to that of control mice. Each data point corresponds to an individual mouse (WT, n=4, NMU-KO, n=5). (d-f) Analysis of BALF and T cell responses in NMU-KO mice after HDM challenge. (d) BALF cell numbers (left) and the frequency of eosinophils (right) were analyzed after HDM challenge in NMU-KO mice. Total cell numbers (WT, n=15, NMU-KO, n=13) and eosinophil frequency are unchanged in NMU-KO mice (n=17) compared to WT mice (n=21). (e) Increased lung-infiltrating CD4 T cells in the absence of NMU. The frequency of lung-infiltrating T cells was determined by flow cytometry after HDM challenge. (WT, n=15, NMU-KO, n=13) (f) Intact Th2 response in the absence of NMU. Expression of IL-5 and IL-13 by CD4 T cells was analyzed by flow cytometry following HDM challenge. Each data point represents an individual mouse (WT, n=5; NMU-KO, n=5). All panels are representative of at least two individual experiments. For all panels, error bars represent the SEM. *=P<0.05 by (a-d,f) two-tailed t-test or (e) one-way ANOVA.

FIG. 26 illustrates massively parallel, droplet-based scRNA-seq of ILCs from NMU- and IL-25+NMU-treated mice. (a) Quality measures. Bar plots show the distribution of the number of unique genes (y-axis, top), percent of reads from mitochondrial genes (y-axis, middle) and number of UMIs (y-axis, bottom) in each treatment and replicate (x-axis). White diamond: mean. (b) Grouping of ILCs is independent of batch. tSNE plots (as in FIG. 16a) of cells from replicate 1 (left) and replicate 2 (right) shaded by condition. (c) Faceted tSNE plot of ILCs from all alarmin and NMU treatments, shaded by condition, shows that IL-25+NMU and IL-33 induce partially overlapping transcriptional responses. (d-e) Cluster composition. (d) Bar plot shows the proportion of ILCs from each condition in each cluster. (e) Bar plot shows the number of cells from each condition in each cluster. (f,g) IL-25+NMU promotes ILC proliferation. (f) The frequency of Ki-67$^+$ ILCs was determined by flow cytometry in IL-25 or IL-25+NMU treated mice. Data points represent individual mice (IL-25, n=8; IL-25+NMU, n=6). (g) Violin plots show the distributions of the proliferation signature scores (y-axis) for the cells in each cluster (x-axis) (white diamond: mean score; lines: first and third quartiles). Proliferation scores in cluster 11 are significantly higher than those in the other IL-25+NMU-dominant clusters 8, 9, and 10 (t-test, $P<2.2\times10^{-16}$). (h) IL-25+NMU enhances expression of Il17rb in mononuclear lung cells, as shown by qPCR. Data points represent individual mice (PBS, n=3; IL-25, n=9; IL-25+NMU, n=7). (i) Validation of expression patterns identified by scRNA-seq using flow cytometry. Expression levels for proteins encoded by genes identified by scRNA-seq on ILCs from mice treated with PBS vs. one of the treatments, as well as an FMO control (dashed open histogram) is shown. Numbers indicate the mean fluorescence intensity of the respective marker or, if a gate is indicated, the frequency of positive ILCs in PBS and in the indicated condition. (j) Distinct patterns of expression of key differentially expressed genes across clusters. Violin plots show the expression levels in log TPX (y-axis) for the indicated genes across the cells in each cluster (x-axis) (white diamond: mean; line: median). (k) Nmur1 is down-regulated after activation with IL-25+NMU. The frequency of Nmur1$^+$ILCs (x-axis) in each condition among ILCs isolated from mice treated with the indicated stimuli is shown. Dots represent individual mice (n=4, except for IL-25, where n=3). (l,m) Increased frequency of KLRG1$^{Hi}$ ST2-inflammatory ILC2s (iILC2s) after treatment with IL-25+NMU. (l) Frequency of iILC2s (of total ILCs) isolated from mice after different treatments. Dots represent individual mice (n=4, except for IL-25, where n=3). (m) Representative flow cytometry plots of ST2 and KLRG1 expression on ILCs for the indicated conditions. For panels (f, h, k, l) error bars represent SEM, *=P<0.05 by (f) two-tailed t-test or (h, k, l).one-way ANOVA.

FIG. 27 illustrates transcriptional analysis by massively parallel scRNA-seq of ILCs from WT and Nmur1-KO mice during airway inflammation. (a) Quality measures. The top row shows the distributions of the number of genes (log scale, x-axis, left histogram) and UMIs (log scale, x-axis, center histogram) per cell and their relation (scatter plot, right) in the aggregated data. The middle row shows the distributions of the estimated saturation for UMIs (x-axis, left histogram) and genes (x-axis, middle histogram) per cell, as well as the ratio of the number of unique UMIs to total number of UMIs per cell (x-axis, right histogram), for a representative sample. The bottom row shows the distribution of the relative difference of the total number of UMIs and number of unique UMIs (x-axis, left histogram), and the relation between the number of UMIs and number of genes (scatter plot, right), for the same representative sample. Dashed lines show lower and upper cutoffs used. Outlier cells (scatter plot) were also removed. (b) Minor batch effects. tSNE plots show cells from replicate 1 (left) and replicate 2 (right) shaded by condition and genotype (PBS-treated WT mice, HDM-treated WT mice, PBS-treated Nmur1-KO mice, HDM-treated Nmur1-KO mice). (c,d) Signature-based scoring of ILCs. Density plots show the distribution of scores for ILC1, 2, and 3 signatures in the cells from indicated treatment conditions. Dashed line: cutoff for each signature used in assigning ILC type. (e) Composition by ILC type. Bar plot shows proportion of each ILC type in the conditions indicated. (f) ILC proliferation is strongly increased by IL-25+NMU. Violin plots show the distribution of proliferation scores (y-axis) across the cells in indicated conditions (x-axis) (white diamond: mean; lines: first and third quartiles). (g) Similar clusters are induced by HDM and by IL-25+NMU treatment. tSNE plot shows ILCs from PBS- and HDM treated WT and Nmur1-KO mice (as in FIG. 17a), shaded by cluster and labeled by post-hoc annotations. Note similarity to clustering in (FIG. 16b). (h) Cluster-specific ILC proliferation in cells from HDM-treated mice. Violin plots show the distribution of proliferation scores (y-axis) across the cells in each cluster (x-axis), as in (g).

The following manuscript contains complete color versions of the figures described above and is hereby fully incorporated herein by reference: Wallrapp et al., The neuropeptide NMU amplifies ILC2-driven allergic lung inflammation, Nature. 2017 Sep. 21; 549(7672):351-356. doi: 10.1038/nature24029. Epub 2017 Sep. 13.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2$^{nd}$ edition (1989) (Sambrook, Fritsch, and Maniatis); Molecular Cloning: A Laboratory Manual, 4$^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2$^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2$^{nd}$ edition (2011)

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +1-5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited in this application are indicative of the level of skill in the art(s) to which the application pertains. All publications, published patent documents, and patent applications cited herein are hereby incorporated by reference to the same extent as though each individual publication, published patent document, or patent application was specifically and individually indicated as being incorporated by reference.

Overview

Type 2 innate lymphoid cells (ILC2s) both contribute to mucosal homeostasis and initiate pathologic inflammation in allergic asthma. However, the signals that direct ILC2s to promote homeostasis versus inflammation were previously. To identify such molecular cues, Applicants profiled lung-resident ILCs using single-cell RNA-seq at steady state and after in vivo stimulation with the alarmin cytokines IL-25 and IL-33. ILC2s were transcriptionally heterogeneous after activation, with subpopulations distinguished by expression of proliferative, homeostatic, and effector genes. The neuropeptide receptor Nmur1 was preferentially expressed by ILC2s at steady state and after IL-25 stimulation. Neuromedin U (NMU), the ligand of Nmur1, activated ILC2s in vitro, and in vivo co-administration of NMU with IL-25 dramatically amplified allergic inflammation. Loss of NMU/Nmur1-signaling reduced ILC2 frequency and effector function, and altered transcriptional programs following allergen challenge in vivo. Thus, Nmur1 signaling promotes inflammatory ILC2 responses, highlighting the importance of neuro-immune crosstalk in allergic inflammation at mucosal surfaces.

Embodiments disclosed herein provide methods and compositions for modulating an innate immune response, in particular an innate lymphoid cell class 2 innate immune response. Using single-cell RNA-sequencing (scRNA-seq) profiles of lung-resident ILCs at steady state and after in vivo stimulation, Applicants have discovered novel ILC2 gene programs and therapeutic targets. Computational and functional analysis identified the neuropeptide receptor Nmur1 as selectively expressed on ILC2s. While both IL-33 and IL-25 promoted ILC activation in vivo, IL-33 induces robust ILC proliferation, whereas ILCs activated with IL-25 did not proliferate as robustly and up-regulate Nmur1 expression. Treatment with neuromedin U (NMU), the neuropeptide ligand of Nmur1, had little effect on its own in the experimental models used herein. Applicants discovered that co-administration of IL-25 with NMU, dramatically amplified allergic lung inflammation and induced the proliferation and expansion of specific ILC2 subsets, characterized by a novel molecular signature unique to pro-inflammatory ILC2s. The results demonstrate for the first time that Nmur1 signaling strongly modulates IL-25-mediated ILC2 responses, resulting in highly proliferative pro-inflammatory ILCs, and highlights the importance of neuro-immune crosstalk in allergic inflammatory responses at mucosal surfaces. Moreover, Applicants have discovered for the first time, regulatory mechanisms for modulating the balance between tissue protective ILCs and tissue inflammatory cells. In certain embodiments, the methods and compositions described herein may be used to shift the balance of ILC2 responses in order to treat inflammatory allergic diseases and cancer.

Gene Signatures

As used herein a "signature" may encompass any gene or genes, protein or proteins, or epigenetic element(s) whose expression profile or whose occurrence is associated with a specific cell type, subtype, or cell state of a specific cell type or subtype within a population of cells (e.g., inflammatory ILC2 cells). In certain embodiments, the expression of the ILC2 inflammatory signature is dependent on epigenetic modification of the genes or regulatory elements associated with the genes. Thus, in certain embodiments, use of signature genes includes epigenetic modifications that may be detected or modulated. For ease of discussion, when discussing gene expression, any of gene or genes, protein or proteins, or epigenetic element(s) may be substituted. As used herein, the terms "signature", "expression profile", or "expression program" may be used interchangeably. It is to be understood that also when referring to proteins (e.g. differentially expressed proteins), such may fall within the definition of "gene" signature. Levels of expression or activity may be compared between different cells in order to characterize or identify, for instance, signatures specific for cell (sub)populations. Increased or decreased expression or activity or prevalence of signature genes may be compared between different cells in order to characterize or identify, for instance, specific cell (sub)populations. The detection of a signature in single cells may be used to identify and quantitate, for instance, specific cell (sub)populations. A signature may include a gene or genes, protein or proteins, or epigenetic element(s) whose expression or occurrence is specific to a cell (sub)population, such that expression or occurrence is exclusive to the cell (sub)population. A gene signature as used herein, may thus refer to any set of up- and/or down-regulated genes that are representative of a cell type or subtype. A gene signature as used herein, may also refer to any set of up- and/or down-regulated genes between different cells or cell (sub)populations derived from a gene-expression profile. For example, a gene signature may comprise a list of genes differentially expressed in a distinction of interest.

The signature as defined herein (being it a gene signature, protein signature or other genetic or epigenetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest, for instance, particular therapies, or to follow up treatment, or to suggest ways to modulate immune systems. The signatures of the present invention may be discovered by analysis of expression profiles of single-cells within a population of cells from isolated samples (e.g. lung ILC2 samples), thus allowing the discovery of novel cell subtypes or cell states that were previously invisible or unrecognized. The presence of subtypes or cell states may be determined by subtype specific or cell state specific signatures. The presence of these specific cell (sub)types or cell states may be determined by applying the signature genes to bulk sequencing data in a sample. Not being bound by a theory the signatures of the present invention may be microenvironment specific, such as their expression in a particular spatio-temporal context. Not being bound by a theory, signatures as discussed herein are specific to a particular pathological context. Not being bound by a theory, a combination of cell subtypes having a particular signature may indicate an outcome. Not being bound by a theory, the signatures can be used to deconvolute the network of cells present in a particular pathological condition. Not being bound by a theory the presence of specific cells and cell subtypes are indicative of a particular response to treatment, such as including increased or decreased susceptibility to treatment. The signature may indicate the presence of one particular cell type. In one embodiment, the novel signatures are used to detect multiple cell states or hierarchies that occur in subpopulations of cells that are linked to particular pathological condition (e.g. inflammation), or linked to a particular outcome or progression of the disease, or linked to a particular response to treatment of the disease.

The signature according to certain embodiments of the present invention may comprise or consist of one or more genes, proteins and/or epigenetic elements, such as for instance 1, 2, 3, 4, 5, 6, 7, 8, 9, 10 or more. In certain embodiments, the signature may comprise or consist of two or more genes, proteins and/or epigenetic elements, such as for instance 2, 3, 4, 5, 6, 7, 8, 9, 10 or more. In certain embodiments, the signature may comprise or consist of three or more genes, proteins and/or epigenetic elements, such as for instance 3, 4, 5, 6, 7, 8, 9, 10 or more. In certain embodiments, the signature may comprise or consist of four or more genes, proteins and/or epigenetic elements, such as for instance 4, 5, 6, 7, 8, 9, 10 or more. In certain embodiments, the signature may comprise or consist of five or more genes, proteins and/or epigenetic elements, such as for instance 5, 6, 7, 8, 9, 10 or more. In certain embodiments, the signature may comprise or consist of six or more genes, proteins and/or epigenetic elements, such as for instance 6, 7, 8, 9, 10 or more. In certain embodiments, the signature may comprise or consist of seven or more genes, proteins and/or epigenetic elements, such as for instance 7, 8, 9, 10 or more. In certain embodiments, the signature may comprise or consist of eight or more genes, proteins and/or epigenetic elements, such as for instance 8, 9, 10 or more. In certain embodiments, the signature may comprise or consist of nine or more genes, proteins and/or epigenetic elements, such as for instance 9, 10 or more. In certain embodiments, the signature may comprise or consist of ten or more genes, proteins and/or epigenetic elements, such as for instance 10, 11, 12, 13, 14, 15, or more. It is to be understood that a signature according to the invention may, for instance, also include genes or proteins as well as epigenetic elements combined.

In certain embodiments, a signature is characterized as being specific for a particular cell or cell (sub)population if it is upregulated or only present, detected or detectable in that particular cell or cell (sub)population, or alternatively is downregulated or only absent, or undetectable in that particular cell or cell (sub)population. In this context, a signature consists of one or more differentially expressed genes/proteins or differential epigenetic elements when comparing different cells or cell (sub)populations, including comparing different immune cells or immune cell (sub)populations (e.g., ILC2 cells), as well as comparing immune cells or immune cell (sub)populations with other immune cells or immune cell (sub)populations. It is to be understood that "differentially expressed" genes/proteins include genes/proteins which are up- or down-regulated as well as genes/proteins which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins, or differential epigenetic elements may be differentially expressed on a single cell level, or may be differentially expressed on a cell population level. Preferably, the differentially expressed genes/proteins or epigenetic elements as discussed herein, such as constituting the gene signatures as discussed herein, when as to the cell population level, refer to genes that are differentially expressed in all or substantially all cells of the population (such as at least 80%, preferably at least 90%, such as at least 95% of the individual cells). This allows one to define a particular subpopulation of cells. As referred to herein, a "subpopulation" of cells preferably refers to a particular subset of cells of a particular cell type (e.g., ILC2) which can be distinguished or are uniquely identifiable and set apart from other cells of this cell type. The cell subpopulation may be phenotypically characterized, and is preferably characterized by the signature as discussed herein. A cell (sub)population as referred to herein may constitute of a (sub)population of cells of a particular cell type characterized by a specific cell state.

When referring to induction, or alternatively suppression of a particular signature, preferable is meant induction or alternatively suppression (or upregulation or downregulation) of at least one gene/protein and/or epigenetic element of the signature, such as for instance at least two, at least three, at least four, at least five, at least six, or all genes/proteins and/or epigenetic elements of the signature.

Various aspects and embodiments of the invention may involve analyzing gene signatures, protein signature, and/or other genetic or epigenetic signature based on single cell analyses (e.g. single cell RNA sequencing) or alternatively based on cell population analyses, as is defined herein elsewhere.

The invention further relates to various uses of the gene signatures, protein signatures, and/or other genetic or epigenetic signatures as defined herein, as well as various uses of the immune cells or immune cell (sub)populations as defined herein. Particular advantageous uses include methods for identifying agents capable of inducing or suppressing particular immune cell (sub)populations based on the gene signatures, protein signatures, and/or other genetic or epigenetic signatures as defined herein. The invention further relates to agents capable of inducing or suppressing particular immune cell (sub)populations based on the gene signatures, protein signatures, and/or other genetic or epigenetic signatures as defined herein, as well as their use for modulating, such as inducing or repressing, a particular gene signature, protein signature, and/or other genetic or epigenetic signature. In one embodiment, genes in one population of cells may be activated or suppressed in order to affect the cells of another population. In related aspects, modulating, such as inducing or repressing, a particular gene signature, protein signature, and/or other genetic or epigenetic signature may modify overall immune composition, such as immune cell composition, such as immune cell subpopulation composition or distribution, or functionality.

The signature genes of the present invention were discovered by analysis of expression profiles of single-cells within a population of lung resident innate lymphoid cells (ILC), thus allowing the discovery of novel cell subtypes that were previously invisible in a population of cells within ILCs. The presence of subtypes may be determined by subtype specific signature genes. The presence of these specific cell types may be determined by applying the signature genes to bulk sequencing data in a patient. Not being bound by a theory, many cells make up a microenvironment, whereby the cells communicate and affect each other in specific ways. As such, specific cell types within this microenvironment may express signature genes specific for this microenvironment. Not being bound by a theory the signature genes of the present invention may be microenvironment specific, such as their expression at a site of inflammation. The signature gene may indicate the presence of one particular cell type. In one embodiment, the expression may indicate the presence of inflammatory or protective cell types. Not being bound by a theory, a combination of cell subtypes in a subject may indicate an outcome.

In one embodiment, the signature genes may be detected by immunofluorescence, immunohistochemistry, fluorescence activated cell sorting (FACS), mass cytometry (CyTOF), Drop-seq, RNA-seq, scRNA-seq, InDrop, single cell qPCR, MERFISH (multiplex (in situ) RNA FISH) and/or by in situ hybridization. Other methods, including absorbance assays and colorimetric assays, are known in the art and may be used herein.

All gene name symbols refer to the gene as commonly known in the art. The examples described herein refer to the mouse gene names and it is to be understood that the present invention also encompasses human genes (e.g., homologous genes). Gene symbols may be those referred to by the HUGO Gene Nomenclature Committee (HGNC) or National Center for Biotechnology Information (NCBI). Any reference to the gene symbol is a reference made to the entire gene or variants of the gene. The signature as described herein may encompass any of the genes described herein.

In certain embodiments, the gene signature includes the following genes. In certain embodiments, the gene signature includes surface expressed proteins. Not being bound by a theory, surface proteins may be targeted for detection and isolation of cell types, or may be targeted therapeutically to modulate an immune response.

The gene name Anxa1 may refer to the Annexin A1 gene or polypeptide according to NCBI Reference Sequence accession number NM_010730.2. The gene name Anxa2 may refer to the Annexin A2 gene or polypeptide according to NCBI Reference Sequence accession number NM_007585.3. The gene name Areg may refer to the Amphiregulin gene or polypeptide according to NCBI Reference Sequence accession number NM_009704.4. The gene name Calca may refer to the Calcitonin/calcitonin-related polypeptide, alpha gene or polypeptide according to NCBI Reference Sequence accession numbers NM_001033954.3, NM_007587.2. The gene name Ccl1 may refer to the Chemokine (C-C motif) ligand 1 gene or polypeptide according to NCBI Reference Sequence accession number NM_011329.3. The gene name Ccl5 may refer to the Chemokine (C-C motif) ligand 5 gene or polypeptide according to NCBI Reference Sequence accession number NM_013653.3. The gene name Ccr2 may refer to the Chemokine (C-C motif) receptor 2 gene or polypeptide according to NCBI Reference Sequence accession number NM_009915.2. The gene name Ccr7 may refer to the Chemokine (C-C motif) receptor 7 gene or polypeptide according to NCBI Reference Sequence accession number NM_007719.2. The gene name Ccr8 may refer to the Chemokine (C-C motif) receptor 8 gene or polypeptide according to NCBI Reference Sequence accession number NM_007720.2. The gene name Cd200r1 may refer to the CD200 receptor 1 gene or polypeptide according to NCBI Reference Sequence accession number NM_021325.3. The gene name Cd3d may refer to the CD3 antigen, delta polypeptide gene or polypeptide according to NCBI Reference Sequence accession number NM_013487.3. The gene name Cd47 may refer to the CD47 antigen (Rh-related antigen, integrin-associated signal transducer) gene or polypeptide according to NCBI Reference Sequence accession numbers NM_010581.3, AK164165.1. The gene name Cd48 may refer to the CD48 antigen gene or polypeptide according to NCBI Reference Sequence accession number NM_007649.4. The gene name Cd81 may refer to the CD81 antigen gene or polypeptide according to NCBI Reference Sequence accession number NM_133655.2. The gene name Csf2 may refer to the Colony stimulating factor 2 (granulocyte-macrophage) gene or polypeptide according to NCBI Reference Sequence accession number NM_009969.4. The gene name Ctla4 may refer to the Cytotoxic T-lymphocyte-associated protein 4 gene or polypeptide according to NCBI Reference Sequence accession number NM_009843.4. The gene name Fas may refer to the Fas (TNF receptor superfamily member 6) gene or polypeptide according to NCBI Reference Sequence accession numbers NM 007987.2, NM_001146708.1. The gene name H2-Aa may refer to the Histocompatibility 2, class II antigen A, alpha gene or polypeptide according to NCBI Reference Sequence accession number NM_010378.2. The gene name H2-Ab1 may refer to the Histocompatibility 2, class II antigen A, beta 1 gene or polypeptide according to NCBI Reference Sequence accession number NM_207105.3. The gene name H2-Q8 may refer to the histocompatibility 2, Q region locus 8 gene or polypeptide according to NCBI Reference Sequence accession number NM_023124.5. The gene name H2-T23 may refer to the histocompatibility 2, T region locus 23 gene or polypeptide according to NCBI Reference Sequence accession numbers XM_003945738.3, NM_010398.3. The gene name Il13 may refer to the Interleukin 13 gene or polypeptide according to NCBI Reference Sequence accession number NM_008355.3. The gene name Il1r2 may refer to the Interleukin 1 receptor, type II gene or polypeptide according to NCBI Reference Sequence accession number NM_010555.4. The gene name Il2rb may refer to the Interleukin 2 receptor, beta chain gene or polypeptide according to NCBI Reference Sequence accession number NM_008368.4. The gene name Il5 may refer to the Interleukin 5 gene or polypeptide according to NCBI Reference Sequence accession number NM_010558.1. The gene name Il6 may refer to the Interleukin 6 gene or polypeptide according to NCBI Reference Sequence accession number NM_031168.2. The gene name Klrg1 may refer to the Killer cell lectin-like receptor subfamily G, member 1 gene or polypeptide according to NCBI Reference Sequence accession number NM_016970.1. The gene name Lat may refer to the Linker for activation of T cells gene or polypeptide according to NCBI Reference Sequence accession number NM_010689.3. The gene name Lgals3 may refer to the Lectin, galactose binding, soluble 3 gene or polypeptide according to NCBI Reference Sequence accession numbers NM_001145953.1, NM_010705.3. The gene name Ltb may refer to the Lymphotoxin B gene or polypeptide according to NCBI Reference Sequence accession number NM_008518.2. The gene name Mif may refer to the Macrophage migration inhibitory factor gene or polypeptide according to NCBI Reference Sequence accession number NM_010798.2. The gene name Ms4a4b may refer to the Membrane-spanning 4-domains, subfamily A, member 4B gene or polypeptide according to NCBI Reference Sequence accession number NM_021718.2. The gene name Nmur1 may refer to the Neuromedin U receptor 1 gene or polypeptide according to NCBI Reference Sequence accession number NM_010341.1. The gene name Pdcd1 may refer to the Programmed cell death 1 gene or polypeptide according to NCBI Reference Sequence accession number NM_008798.2. The gene name Pgk1 may refer to the Phosphoglycerate kinase 1 gene or polypeptide according to NCBI Reference Sequence accession number NM_008828.3. The gene name Ptger2 may refer to the Prostaglandin E receptor 2 (subtype EP2) gene or polypeptide according to NCBI Reference Sequence accession number NM_008964.4. The gene name Ramp1 may refer to the Receptor (calcitonin) activity modifying protein 1 gene or polypeptide according to NCBI Reference Sequence accession number NM_016894.3, NM_001168392.1. The gene name Sdc4 may refer to the Syndecan 4 gene or polypeptide according to NCBI Reference Sequence accession number NM_011521.2. The gene name Sema4a may refer to the Sema domain, immunoglobulin domain (Ig), transmembrane domain (TM) and short cytoplasmic domain, (semaphorin) 4A gene or polypeptide according to NCBI Reference Sequence accession numbers NM_013658.3, NM_001163490.1, NM_001163491.1, NM_001163489.1. The gene name Sepp1 may refer to the Selenoprotein P, plasma, 1 gene or polypeptide according to NCBI Reference Sequence accession numbers NM_001042614.2, NM_009155.4, NM_001042613.2. The gene name Stab2 may refer to the Stabilin 2 gene or polypeptide according to NCBI Reference Sequence accession numbers NM_138673.2. The gene name Tff1 may refer to the Trefoil factor 1 gene or polypeptide according to NCBI Reference Sequence accession number NM_009362.2. The gene name Tmem176a may refer to the Transmembrane protein 176A gene or polypeptide according to NCBI Reference Sequence accession numbers NM_025326.4, NM_001098271.1. The gene name Tnfrsf4 may refer to the Tumor necrosis factor receptor superfamily, member 4 gene or polypeptide according to NCBI Reference Sequence accession number NM_011659.2. The gene name Tnfrsf8 may refer to the Tumor necrosis factor receptor superfamily, member 8 gene or polypeptide according to NCBI Reference Sequence accession number NM_009401.2. The gene name Tnfsf8 may refer to the Tumor necrosis factor (ligand) superfamily, member 8 gene or polypeptide according to NCBI Reference Sequence accession number NM_009403.3. The gene name Nmu may refer to the Neuromedin U gene or polypeptide according to NCBI Reference Sequence accession number NM_019515.1. The gene Lilrb4a may refer to the leukocyte immunoglobulin-like receptor, subfamily B, member 4A gene or polypeptide according to NCBI Reference Sequence accession number NM_001291894.1. The gene Vsir may refer to the V-set immunoregulatory receptor gene or polypeptide according to NCBI Reference Sequence accession numbers NM_001159572.1, NM_028732.4. The gene name Il7r may refer to the interleukin 7 receptor gene or polypeptide according to NCBI Reference Sequence accession number NM_008372.4. The gene name Thy1, CD90 may refer to the thymus cell antigen 1 gene or polypeptide according to NCBI Reference Sequence accession number NM_009382.3. The gene name Tbx21 may refer to the T-box 21 gene or polypeptide according to NCBI Reference Sequence accession number NM_019507.2. The gene name Il1rl1 may refer to the interleukin 1 receptor-like 1 gene or polypeptide according to NCBI Reference Sequence accession numbers NM_001294171.1, NM_010743.3, NM_001025602.3. The gene name Ptprc may refer to the protein tyrosine phosphatase, receptor type C allele gene or polypeptide according to NCBI Reference Sequence accession numbers AH011622.2, AH011623.2.

The gene name ANXA1 may refer to the annexin A1 gene or polypeptide according to NCBI Reference Sequence accession number NM_000700.2. The gene name ANXA2 may refer to the annexin A2 gene or polypeptide according to NCBI Reference Sequence accession numbers NM_001002857.1, NM_001002858.2, NM_001136015.2, NM_004039.2. The gene name AREG may refer to the amphiregulin gene or polypeptide according to NCBI Reference Sequence accession number NM_001657.3. The gene name CALCA may refer to the calcitonin-related polypeptide alpha gene or polypeptide according to NCBI Reference Sequence accession number NM 001033952.2, NM_001033953.2, NM_001741.2. The gene name CCL1 may refer to the chemokine (C-C motif) ligand 1 gene or polypeptide according to NCBI Reference Sequence accession number NM_002981.2. The gene name CCL5 may refer to the chemokine (C-C motif) ligand 5 gene or polypeptide according to NCBI Reference Sequence accession number NM_002985.2. The gene name CCR2 may refer to the chemokine (C-C motif) receptor 2 gene or polypeptide according to NCBI Reference Sequence accession number NM_001123041.2, NM_001123396.1. The gene name CCR7 may refer to the chemokine (C-C motif) receptor 7 gene or polypeptide according to NCBI Reference Sequence accession number NM_001838.3. The gene name CCR8 may refer to the chemokine (C-C motif) receptor 8 gene or polypeptide according to NCBI Reference Sequence accession number NM_005201.3. The gene name CD200R1 may refer to the CD200 receptor 1 gene or polypeptide according to NCBI Reference Sequence accession number NM_138806.3, NM_138939.2, NM_138940.2, NM_170780.2. The gene name CD3D may refer to the CD3d molecule, delta (CD3-TCR complex) gene or polypeptide according to NCBI Reference Sequence accession number NM_000732.4, NM_001040651.1. The gene name CD47 may refer to the CD47 molecule gene or polypeptide according to NCBI Reference Sequence accession number NM_001777.3, NM_198793.2. The gene name CD48 may refer to the CD48 molecule gene or polypeptide according to NCBI Reference Sequence accession number NM_001256030.1, NM_001778.3. The gene name CD81 may refer to the CD81 molecule gene or polypeptide according to NCBI Reference Sequence accession number NM_004356.3. The gene name CSF2 may refer to the colony stimulating factor 2 (granulocyte-macrophage) gene or polypeptide according to NCBI Reference Sequence accession number NM_000758.3. The gene name CTLA4 may refer to the cytotoxic T-lymphocyte-associated protein 4 gene or polypeptide according to NCBI Reference Sequence accession number NM_001037631.2, NM_005214.4. The gene name FAS may refer to the Fas (TNF receptor superfamily, member 6) gene or polypeptide according to NCBI Reference Sequence accession number NM_000043.5, NM_152871.3, NM_152872.3, NR_028033.3, NR_028034.3, NR_028035.3, NR_028036.3. The gene name HLA-DQA1 may refer to the major histocompatibility complex, class II, DQ alpha 1 gene or polypeptide according to NCBI Reference Sequence accession number NM_002122.3. The gene name HLA-DQB1 may refer to the major histocompatibility complex, class II, DQ beta 1 gene or polypeptide according to NCBI Reference Sequence accession number NM_001243961.1, NM_001243962.1, NM_002123.4. The gene name HLA-E may refer to the major histocompatibility complex, class I, E gene or polypeptide according to NCBI Reference Sequence accession number NM_005516.5. The gene name IL13 may refer to the interleukin 13 gene or polypeptide according to NCBI Reference Sequence accession number NM_002188.2. The gene name IL1R2 may refer to the interleukin 1 receptor, type II gene or polypeptide according to NCBI Reference Sequence accession number NM_001261419.1, NM_004633.3, NR_048564.1. The gene name IL2RB may refer to the interleukin 2 receptor, beta gene or polypeptide according to NCBI Reference Sequence accession number NM_000878.4. The gene name IL5 may refer to the interleukin 5 (colony-stimulating factor, eosinophil) gene or polypeptide according to NCBI Reference Sequence accession number NM_000879.2. The gene name IL6 may refer to the interleukin 6 (interferon, beta 2) gene or polypeptide according to NCBI Reference Sequence accession number NM_000600.4. The gene name KLRG1 may refer to the killer cell lectin-like receptor subfamily G, member 1 gene or polypeptide according to NCBI Reference Sequence accession number NM_005810.3. The gene name LAT may refer to the linker for activation of T cells gene or polypeptide according to NCBI Reference Sequence accession number NM_001014987.1, NM_001014988.1, NM_001014989.1, NM_014387.3. The gene name LGALS3 may refer to the lectin, galactoside-binding, soluble, 3 gene or polypeptide according to NCBI Reference Sequence accession number NM_001177388.1, NM_002306.3, NR_003225.2. The gene name LILRB1 may refer to the leukocyte immunoglobulin-like receptor, subfamily B (with TM and ITIM domains), member 1 gene or polypeptide according to NCBI Reference Sequence accession number NM_001081637.2, NM_001081638.3, NM_001081639.3, NM_006669.6. The gene name LILRA1 may refer to the leukocyte immunoglobulin-like receptor, subfamily A (with TM domain), member 1 gene or polypeptide according to NCBI Reference Sequence accession number NM_006863.3. The gene name LILRB2 may refer to the leukocyte immunoglobulin-like receptor, subfamily B (with TM and ITIM domains), member 2 gene or polypeptide according to NCBI Reference Sequence accession number NM_001080978.3, NM_005874.4. The gene name LILRA2 may refer to the leukocyte immunoglobulin-like receptor, subfamily A (with TM domain), member 2 gene or polypeptide according to NCBI Reference Sequence accession number NM_001130917.2, NM_006866.3. The gene name LTB may refer to the lymphotoxin beta (TNF superfamily, member 3) gene or polypeptide according to NCBI Reference Sequence accession number NM_002341.1, NM_009588.1. The gene name MIF may refer to the macrophage migration inhibitory factor (glycosylation-inhibiting factor) gene or polypeptide according to NCBI Reference Sequence accession number NM_002415.1. The gene name MS4A4A may refer to the membrane-spanning 4-domains, subfamily A, member 4A gene or polypeptide according to NCBI Reference Sequence accession number NM_001243266.1, NM_024021.3, NM_148975.2. The gene name NMUR1 may refer to the neuromedin U receptor 1 gene or polypeptide according to NCBI Reference Sequence accession number NM_006056.4. The gene name PDCD1 may refer to the programmed cell death 1 gene or polypeptide according to NCBI Reference Sequence accession number NM_005018.2. The gene name PGK1 may refer to the phosphoglycerate kinase 1 gene or polypeptide according to NCBI Reference Sequence accession number NM_000291.3. The gene name PTGER2 may refer to the prostaglandin E receptor 2 (subtype EP2), 53 kDa gene or polypeptide according to NCBI Reference Sequence accession number NM_000956.3. The gene name RAMP1 may refer to the receptor (G protein-coupled) activity modifying protein 1 gene or polypeptide according to NCBI Reference Sequence accession number NM_005855.3. The gene name SDC4 may refer to the syndecan 4 gene or polypeptide according to NCBI Reference Sequence accession number NM_002999. The gene name SEMA4A may refer to the sema domain, immunoglobulin domain (Ig), transmembrane domain (TM) and short cytoplasmic domain, (semaphorin) 4A gene or polypeptide according to NCBI Reference Sequence accession number NM_001193300.1, NM_001193301.1, NM_001193302.1, NM_022367.3. The gene name SEPP1 may refer to the selenoprotein P, plasma, 1 gene or polypeptide according to NCBI Reference Sequence accession number NM_001085486.2, NM_001093726.2, NM_005410.3. The gene name STAB2 may refer to the stabilin 2 gene or polypeptide according to NCBI Reference Sequence accession number NM_017564.9. The gene name TFF1 may refer to the trefoil factor 1 gene or polypeptide according to NCBI Reference Sequence accession number NM_003225.2. The gene name TMEM176A may refer to the transmembrane protein 176A gene or polypeptide according to NCBI Reference Sequence accession number NM_018487.2. The gene name TNFRSF4 may refer to the tumor necrosis factor receptor superfamily, member 4 gene or polypeptide according to NCBI Reference Sequence accession number NM_003327.3. The gene name TNFRSF8 may refer to the tumor necrosis factor receptor superfamily, member 8 gene or polypeptide according to NCBI Reference Sequence accession number NM_001243.4. The gene name TNFSF8 may refer to the tumor necrosis factor (ligand) superfamily, member 8 gene or polypeptide according to NCBI Reference Sequence accession number NM_001244.3, NM_001252290.1. The gene name NMU may refer to the neuromedin U gene or polypeptide according to NCBI Reference Sequence accession number NM_006681.3. The gene name Il7r may refer to the interleukin 7 receptor gene or polypeptide according to NCBI Reference Sequence accession number NM_002185.3. The gene name THY1, CD90 may refer to the Thy-1 cell surface antigen gene or polypeptide according to NCBI Reference Sequence accession numbers NM_001311162.1, NM_001311160.1, NM_006288.4. The gene name TBX21 may refer to the T-box 21 gene or polypeptide according to NCBI Reference Sequence accession number NM_013351.1. The gene name IL1RL1 may refer to the interleukin 1 receptor like 1 gene or polypeptide according to NCBI Reference Sequence accession numbers NM_001282408.1, NM_003856.3, NM_016232.4. The gene name PTPRC may refer to the protein tyrosine phosphatase, receptor type C gene or polypeptide according to NCBI Reference Sequence accession numbers NM_002838.4, NM_080921.3, NM_001267798.1.

The gene name 2810417H13Rik may refer to the PCNA clamp associated factor (Pclaf) gene or polypeptide according to NCBI Reference Sequence accession number NM_026515.2. The gene name AA467197 may refer to the Expressed sequence AA467197 according to NCBI Reference Sequence accession number NM_001004174.1. The gene name Alox5 may refer to the Arachidonate 5-lipoxygenase gene or polypeptide according to NCBI Reference Sequence accession number NM_009662.2. The gene name Arg1 may refer to the Arginase, liver gene or polypeptide according to NCBI Reference Sequence accession number NM_007482.3. The gene name Atf4 may refer to the Activating transcription factor 4 gene or polypeptide according to NCBI Reference Sequence accession number NM_009716.3. The gene name Batf may refer to the Basic leucine zipper transcription factor, ATF-like gene or polypeptide according to NCBI Reference Sequence accession number NM_016767.2. The gene name Bcl2a1b may refer to the B cell leukemia/lymphoma 2 related protein A1b gene or polypeptide according to NCBI Reference Sequence accession number NM_007534.3. The gene name Blk may refer to the B lymphoid kinase gene or polypeptide according to NCBI Reference Sequence accession number NM_007549.2. The gene name Btg1 may refer to the B cell translocation gene 1, anti-proliferative gene or polypeptide according to NCBI Reference Sequence accession number NM_007569.2. The gene name Cox5b may refer to the Cytochrome c oxidase, subunit Vb gene or polypeptide according to NCBI Reference Sequence accession number NM_009942.2. The gene name Cox6c may refer to the Cytochrome c oxidase, subunit VIc gene or polypeptide according to NCBI Reference Sequence accession number NM_053071.2. The gene name Crip1 may refer to the Cysteine-rich protein 1 (intestinal) gene or polypeptide according to NCBI Reference Sequence accession number NM_007763.3. The gene name Dgat1 may refer to the Diacylglycerol O-acyltransferase 1 gene or polypeptide according to NCBI Reference Sequence accession number NM_010046.3. The gene name Dgat2 may refer to the Diacylglycerol O-acyltransferase 2 gene or polypeptide according to NCBI Reference Sequence accession number NM_026384.3. The gene name Dusp1 may refer to the Dual specificity phosphatase 1 gene or polypeptide according to NCBI Reference Sequence accession number NM_013642.3. The gene name Ets1 may refer to the E26 avian leukemia oncogene 1, 5' domain gene or polypeptide according to NCBI Reference Sequence accession number NM_011808.2, NM_001038642.1. The gene name Fos may refer to the FBJ osteosarcoma oncogene gene or polypeptide according to NCBI Reference Sequence accession number NM_010234.2. The gene name Fosb may refer to the FBJ osteosarcoma oncogene B gene or polypeptide according to NCBI Reference Sequence accession number NM_008036.2. The gene name Furin may refer to the Furin (paired basic amino acid cleaving enzyme) gene or polypeptide according to NCBI Reference Sequence accession numbers NM_011046.3, NM_001081454.2. The gene name Gadd45b may refer to the Growth arrest and DNA-damage-inducible 45 beta gene or polypeptide according to NCBI Reference Sequence accession number NM_008655.1. The gene name Gsto1 may refer to the Glutathione S-transferase omega 1 gene or polypeptide according to NCBI Reference Sequence accession number NM_010362.3. The gene name Hint1 may refer to the Histidine triad nucleotide binding protein 1 gene or polypeptide according to NCBI Reference Sequence accession number NM_008248.2. The gene name Ier2 may refer to the Immediate early response 2 gene or polypeptide according to NCBI Reference Sequence accession number NM_010499.4. The gene name Irf4 may refer to the Interferon regulatory factor 4 gene or polypeptide according to NCBI Reference Sequence accession number NM_013674.2. The gene name Klf3 may refer to the Kruppel-like factor 3 (basic) gene or polypeptide according to NCBI Reference Sequence accession number NM_008453.5. The gene name Klf4 may refer to the Kruppel-like factor 4 (gut) gene or polypeptide according to NCBI Reference Sequence accession number NM_010637.3. The gene name Lgmn may refer to the Legumain gene or polypeptide according to NCBI Reference Sequence accession number NM_011175.3. The gene name Lpcat2 may refer to the Lysophosphatidylcholine acyltransferase 2 gene or polypeptide according to NCBI Reference Sequence accession number NM 173014.1. The gene name Mcm3 may refer to the Minichromosome maintenance complex 3 gene or polypeptide according to NCBI Reference Sequence accession number NM_008563.2. The gene name Mt1 may refer to the Metallothionein 1 gene or polypeptide according to NCBI Reference Sequence accession number NM_013602.3. The gene name Myl6 may refer to the Myosin, light polypeptide 6, alkali, smooth muscle and non-muscle gene or polypeptide according to NCBI Reference Sequence accession number NM_010860.4. The gene name Ndufa4 may refer to the NADH dehydrogenase (ubiquinone) 1 alpha subcomplex, 4 gene or polypeptide according to NCBI Reference Sequence accession number NM_010886.2. The gene name Nfkbia may refer to the Nuclear factor of kappa light polypeptide gene enhancer in B cells inhibitor, alpha gene or polypeptide according to NCBI Reference Sequence accession number NM_010907.2. The gene name Nfkbid may refer to the Nuclear factor of kappa light polypeptide gene enhancer in B cells inhibitor, delta gene or polypeptide according to NCBI Reference Sequence accession number NM_172142.3. The gene name Nfkbiz may refer to the Nuclear factor of kappa light polypeptide gene enhancer in B cells inhibitor, zeta gene or polypeptide according to NCBI Reference Sequence accession number NM_030612.3, NM_001159394.1, NM_001159395.1. The gene name Nop56 may refer to the NOP56 ribonucleoprotein gene or polypeptide according to NCBI Reference Sequence accession number NM_024193.2. The gene name Nr4a1 may refer to the Nuclear receptor subfamily 4, group A, member 1 gene or polypeptide according to NCBI Reference Sequence accession number NM_010444.2. The gene name Prdx4 may refer to the Peroxiredoxin 4 gene or polypeptide according to NCBI Reference Sequence accession number NM_016764.5. The gene name S100a4 may refer to the S100 calcium binding protein A4 gene or polypeptide according to NCBI Reference Sequence accession number NM_011311.2. The gene name S100a6 may refer to the S100 calcium binding protein A6 (calcyclin) gene or polypeptide according to NCBI Reference Sequence accession number NM_011313.2. The gene name Serpinb6a may refer to the Serine (or cysteine) peptidase inhibitor, clade B, member 6a gene or polypeptide according to NCBI Reference Sequence accession number NM_001164118.1, NM_001164117.1, NM_001243192.1, NM_009254.3. The gene name Ripk1 may refer to the Receptor (TNFRSF)-interacting serine-threonine kinase 1 gene or polypeptide according to NCBI Reference Sequence accession number NM_009068.3. The gene name Snrpd3 may refer to the Small nuclear ribonucleoprotein D3 gene or polypeptide according to NCBI Reference Sequence accession number NM_026095.4. The gene name 1110002B05Rik may refer to the serine palmitoyltransferase, small subunit A (Sptssa) gene or polypeptide according to NCBI Reference Sequence accession number NM_134054.2. The gene name Tph1 may refer to the Tryptophan hydroxylase 1 gene or polypeptide according to NCBI Reference Sequence accession number NM_009414.3, NM_001136084.2. The gene name Vim may refer to the Vimentin gene or polypeptide according to NCBI Reference Sequence accession number NM_011701.4. The gene name Zfp36 may refer to the Zinc finger protein 36 gene or polypeptide according to NCBI Reference Sequence accession number NM_011756.4. The gene name Zfp36l1 may refer to the Zinc finger protein 36, C3H type-like 1 gene or polypeptide according to NCBI Reference Sequence accession number NM_007564.5.

The gene name 2810417H13Rik may refer to the PCNA clamp associated factor (Pclaf) gene or polypeptide according to NCBI Reference Sequence accession numbers NM_014736.5, NM_001029989.2. The gene name ALOX5 may refer to the arachidonate 5-lipoxygenase gene or polypeptide according to NCBI Reference Sequence accession numbers NM 000698.4, NM_001256153.2, NM_001256154.2. The gene name ARG1 may refer to the arginase, liver gene or polypeptide according to NCBI Reference Sequence accession numbers NM_000045.3, NM_001244438.1. The gene name ATF4 may refer to the activating transcription factor 4 (tax-responsive enhancer element B67) gene or polypeptide according to NCBI Reference Sequence accession numbers NM_001675.4, NM_182810.2. The gene name BATF may refer to the basic leucine zipper transcription factor, ATF-like gene or polypeptide according to NCBI Reference Sequence accession number NM_006399.3. The gene name BLK may refer to the B lymphoid tyrosine kinase gene or polypeptide according to NCBI Reference Sequence accession number NM_001715.2. The gene name BTG1 may refer to the B-cell translocation gene 1, anti-proliferative gene or polypeptide according to NCBI Reference Sequence accession number NM_001731.2. The gene name COX5B may refer to the cytochrome c oxidase subunit Vb gene or polypeptide according to NCBI Reference Sequence accession number NM_001862.2. The gene name COX6C may refer to the cytochrome c oxidase subunit 6C gene or polypeptide according to NCBI Reference Sequence accession number NM_004374.3. The gene name CRIP1 may refer to the cysteine-rich protein 1 gene or polypeptide according to NCBI Reference Sequence accession number NM_001311.4. The gene name DGAT1 may refer to the diacylglycerol O-acyltransferase 1 gene or polypeptide according to NCBI Reference Sequence accession number NM_012079.5. The gene name DGAT2 may refer to the diacylglycerol O-acyltransferase 2 gene or polypeptide according to NCBI Reference Sequence accession numbers NM_001253891.1, NM_032564.4. The gene name DUSP1 may refer to the dual specificity phosphatase 1 gene or polypeptide according to NCBI Reference Sequence accession number NM_004417.3. The gene name ETS1 may refer to the ETS proto-oncogene 1 gene or polypeptide according to NCBI Reference Sequence accession numbers NM_001143820.1, NM_001162422.1, NM_005238.3. The gene name FOS may refer to the Fos proto-oncogene or AP-1 transcription factor subunit (FOS) gene or polypeptide according to NCBI Reference Sequence accession number NM_005252.3. The gene name FOSB may refer to the Fos proto-oncogene or AP-1 transcription factor subunit (FOSB) gene or polypeptide according to NCBI Reference Sequence accession numbers NM_001114171.1, NM_006732.2. The gene name FURIN may refer to the furin (paired basic amino acid cleaving enzyme) gene or polypeptide according to NCBI Reference Sequence accession number NM_002569.3. The gene name GADD45B may refer to the growth arrest and DNA-damage-inducible, beta gene or polypeptide according to NCBI Reference Sequence accession number NM_015675.3. The gene name GSTO1 may refer to the glutathione S-transferase omega 1 gene or polypeptide according to NCBI Reference Sequence accession numbers NM_001191002.1, NM_001191003.1, NM_004832.2. The gene name HINT1 may refer to the histidine triad nucleotide binding protein 1 gene or polypeptide according to NCBI Reference Sequence accession number NM_005340.6. The gene name IER2 may refer to the immediate early response 2 gene or polypeptide according to NCBI Reference Sequence accession number NM_004907.2. The gene name IRF4 may refer to the interferon regulatory factor 4 gene or polypeptide according to NCBI Reference Sequence accession numbers NM_001195286.1, NM_002460.3. The gene name KLF3 may refer to the Kruppel-like factor 3 (basic) gene or polypeptide according to NCBI Reference Sequence accession numbers NM_016531.5. The gene name KLF4 may refer to the Kruppel-like factor 4 (gut) gene or polypeptide according to NCBI Reference Sequence accession number NM_004235.5. The gene name LGMN may refer to the legumain gene or polypeptide according to NCBI Reference Sequence accession numbers NM_001008530.2, NM_005606.6. The gene name LPCAT2 may refer to the lysophosphatidylcholine acyltransferase 2 gene or polypeptide according to NCBI Reference Sequence accession number NM_017839.4. The gene name MCM3 may refer to the minichromosome maintenance complex component 3 gene or polypeptide according to NCBI Reference Sequence accession numbers NM_001270472.1, NM_002388.4. The gene name MT1x may refer to the Metallothionein 1x gene or polypeptide according to NCBI Reference Sequence accession number NM_005952.3. The gene name MT1B may refer to the Metallothionein 113 gene or polypeptide according to NCBI Reference Sequence accession number NM 005947.2. The gene name MT1H may refer to the Metallothionein 1H gene or polypeptide according to NCBI Reference Sequence accession number NM_005951.2. The gene name MTNR1A may refer to the Melatonin receptor 1A gene or polypeptide according to NCBI Reference Sequence accession number NM_005958.4. The gene name MT1A may refer to the Metallothionein 1A gene or polypeptide according to NCBI Reference Sequence accession number NM_005946.2. The gene name MT1F may refer to the Metallothionein 1F gene or polypeptide according to NCBI Reference Sequence accession number NM_005949.3. The gene name MT1E may refer to the Metallothionein 1E gene or polypeptide according to NCBI Reference Sequence accession number NM_175617.3. The gene name MT1M may refer to the Metallothionein 1M gene or polypeptide according to NCBI Reference Sequence accession number NM_176870.2. The gene name MT1G may refer to the Metallothionein 1G gene or polypeptide according to NCBI Reference Sequence accession number NM_005950.2. The gene name MYL6 may refer to the myosin, light chain 6, alkali, smooth muscle and non-muscle gene or polypeptide according to NCBI Reference Sequence accession numbers NM_021019.4, NM_079423.3. The gene name NDUFA4 may refer to the NADH dehydrogenase (ubiquinone) 1 alpha subcomplex gene or polypeptide according to NCBI Reference Sequence accession numbers NM_002489.3. The gene name NFKBIA may refer to the nuclear factor of kappa light polypeptide gene enhancer in B-cells inhibitor, alpha gene or polypeptide according to NCBI Reference Sequence accession number NM_020529.2. The gene name NFKBID may refer to the nuclear factor of kappa light polypeptide gene enhancer in B-cells inhibitor, delta gene or polypeptide according to NCBI Reference Sequence accession number NM_139239.2. The gene name NFKBIZ may refer to the nuclear factor of kappa light polypeptide gene enhancer in B-cells inhibitor, zeta gene or polypeptide according to NCBI Reference Sequence accession numbers NM_001005474.2, NM_031419.3. The gene name NOP56 may refer to the NOP56 ribonucleoprotein gene or polypeptide according to NCBI Reference Sequence accession number NM_006392.3. The gene name NR4A1 may refer to the nuclear receptor subfamily 4, group A, member 1 gene or polypeptide according to NCBI Reference Sequence accession numbers NM_001202233.1, NM_002135.4, NM_173157.2, NM_001202234.1. The gene name NR4A1 may refer to the nuclear receptor subfamily 4, group A, member 1 gene or polypeptide according to NCBI Reference Sequence accession numbers NM_001202233.1, NM_002135.4, NM_173157.2, NM_001202234.1. The gene name PRDX4 may refer to the peroxiredoxin 4 gene or polypeptide according to NCBI Reference Sequence accession number NM_006406.1. The gene name S100A4 may refer to the S100 calcium binding protein A4 gene or polypeptide according to NCBI Reference Sequence accession numbers NM_002961.2, NM_019554.2. The gene name S100A6 may refer to the S100 calcium binding protein A6 gene or polypeptide according to NCBI Reference Sequence accession number NM_014624.3. The gene name SNRPD3 may refer to the small nuclear ribonucleoprotein D3 polypeptide gene or polypeptide according to NCBI Reference Sequence accession number NM_004175.4. The gene name SPTSSA may refer to the serine palmitoyltransferase, small subunit A gene or polypeptide according to NCBI Reference Sequence accession number NM_138288.3. The gene name TPH1 may refer to the tryptophan hydroxylase 1 gene or polypeptide according to NCBI Reference Sequence accession number NM_004179.2. The gene name VIM may refer to the vimentin gene or polypeptide according to NCBI Reference Sequence accession number NM_003380.3. The gene name ZFP36 may refer to the ZFP36 ring finger protein gene or polypeptide according to NCBI Reference Sequence accession number NM_003407.3. The gene name ZFP36L1 may refer to the ZFP36 ring finger protein-like 1 gene or polypeptide according to NCBI Reference Sequence accession numbers NM_001244698.1, NM_001244701.1, NM_004926.3.

The amino acid sequence of NMUR1 may be derived from:

(SEQ ID No: 1)
MTPLCLNCSVLPGDLYPGGARNPMACNGSAARGHFDPEDLNLTDEALRLK

YLGPQQTELFMPICATYLLIFVVGAVGNGLTCLVILRHKAMRTPTNYYLF

SLAVSDLLVLLVGLPLELYEMWHNYPFLLGVGGCYFRTLLFEMVCLASVL

NVTALSVERYVAVVHPLQARSMVTRAHVRRVLGAVWGLAMLCSLPNTSLH

GIRQLHVPCRGPVPDSAVCMLVRPRALYNMVVQTTALLFFCLPMAIMSVL

YLLIGLRLRRERLLLMQEAKGRGSAAARSRYTCRLQQHDRGRRQVTKMLF

VLVVVFGICWAPFHADRVMWSVVSQWTDGLHLAFQHVHVISGIFFYLGSA

ANPVLYSLMSSRFRETFQEALCLGACCHRLRPRHSSHSLSRMTTGSTLCD

VGSLGSWVHPLAGNDGPEAQQETDPS.

The amino acid sequence of NMU may be derived from:

(SEQ ID No: 2)
MLRTESCRPRSPAGQVAAASPLLLLLLLLAWCAGACRGAPILPQGLQPEQ

QLQLWNEIDDTCSSFLSIDSQPQASNALEELCFMIMGMLPKPQEQDEKDN

TKRFLFHYSKTQKLGKSNVVSSVVHPLLQLVPHLHERRMKRFRVDEEFQS

PFASQSRGYFLFRPRNGRRSAGFI.

The gene name IL-25 may refer to the interleukin 25 gene or polypeptide according to NCBI Reference Sequence accession numbers BC104931.1, BC104929.1, or BC069565.1. The amino acid sequence of IL-25 may be derived from:

(SEQ ID No: 3)
MRERPRLGEDSSLISLFLQVVAFLAMVMGTHTYSHWPSCCPSKGQDTSEE

LLRWSTVPVPPLEPARPNRHPESCRASEDGPLNSRAISPWRYELDRDLNR

LPQDLYHARCLCPHCVSLQTGSHMDPRGNSELLYHNQTVFYRRPCHGEKG

THKGYCLERRLYRVSLACVCVRPRVMG.

As used herein, "modulating" or "to modulate" generally means either reducing or inhibiting the expression or activity of, or alternatively increasing the expression or activity of a target or antigen (e.g., Nmur1, NMU). In particular, "modulating" or "to modulate" can mean either reducing or inhibiting the activity of, or alternatively increasing a (relevant or intended) biological activity of, a target or antigen as measured using a suitable in vitro, cellular or in vivo assay (which will usually depend on the target involved), by at least 5%, at least 10%, at least 25%, at least 50%, at least 60%, at least 70%, at least 80%, at least 90%, or more, compared to activity of the target in the same assay under the same conditions but without the presence of an agent. An "increase" or "decrease" refers to a statistically significant increase or decrease respectively. For the avoidance of doubt, an increase or decrease will be at least 10% relative to a reference, such as at least 10%, at least 20%, at least 30%, at least 40%, at least 50%, at least 60%, at least 70%, at least 80%, at least 90%, at least 95%, at least 97%, at least 98%, or more, up to and including at least 100% or more, in the case of an increase, for example, at least 2-fold, at least 3-fold, at least 4-fold, at least 5-fold, at least 6-fold, at least 7-fold, at least 8-fold, at least 9-fold, at least 10-fold, at least 50-fold, at least 100-fold, or more. "Modulating" can also involve effecting a change (which can either be an increase or a decrease) in affinity, avidity, specificity and/or selectivity of a target or antigen, such as Nmur1 or NMU. "Modulating" can also mean effecting a change with respect to one or more biological or physiological mechanisms, effects, responses, functions, pathways or activities in which the target or antigen (or in which its substrate(s), ligand(s) or pathway(s) are involved, such as its signaling pathway or metabolic pathway and their associated biological or physiological effects) is involved. Again, as will be clear to the skilled person, such an action as an agonist or an antagonist can be determined in any suitable manner and/or using any suitable assay known or described herein (e.g., in vitro or cellular assay), depending on the target or antigen involved.

Modulating can, for example, also involve allosteric modulation of the target and/or reducing or inhibiting the binding of the target to one of its substrates or ligands and/or competing with a natural ligand, substrate for binding to the target. Modulating can also involve activating the target or the mechanism or pathway in which it is involved. Modulating can, for example, also involve effecting a change in respect of the folding or confirmation of the target, or in respect of the ability of the target to fold, to change its conformation (for example, upon binding of a ligand), to associate with other (sub)units, or to disassociate. Modulating can, for example, also involve effecting a change in the ability of the target to signal, phosphorylate, dephosphorylate, and the like.

As used herein, an "agent" can refer to a protein-binding agent that permits modulation of activity of proteins or disrupts interactions of proteins and other biomolecules, such as, but not limited to, disrupting protein-protein interaction, ligand-receptor interaction, or protein-nucleic acid interaction. Agents can also refer to DNA targeting or RNA targeting agents. Agents may include a fragment, derivative and analog of an active agent. The terms "fragment," "derivative" and "analog" when referring to polypeptides as used herein refers to polypeptides which either retain substantially the same biological function or activity as such polypeptides. An analog includes a proprotein which can be activated by cleavage of the proprotein portion to produce an active mature polypeptide. Such agents include, but are not limited to, antibodies ("antibodies" includes antigen-binding portions of antibodies such as epitope- or antigen-binding peptides, paratopes, functional CDRs; recombinant antibodies; chimeric antibodies; humanized antibodies; nanobodies; tribodies; midibodies; or antigen-binding derivatives, analogs, variants, portions, or fragments thereof), protein-binding agents, nucleic acid molecules, small molecules, recombinant protein, peptides, aptamers, avimers and protein-binding derivatives, portions or fragments thereof. An "agent" as used herein, may also refer to an agent that inhibits expression of a gene, such as, but not limited to, a DNA targeting agent (e.g., CRISPR system, TALE, Zinc finger protein) or RNA targeting agent (e.g., inhibitory nucleic acid molecules such as RNAi, miRNA, ribozyme).

In certain embodiments, the agent modulates the Nmur1/NMU interaction or Nmur1 signaling. In certain embodiments, the agent is an agonist or antagonist of Nmur1 activity.

In one embodiment, the agonist is NMU or a derivative or analog thereof. Not being bound by a theory, NMU is a pan Nmur1/2 agonist. In one embodiment, the agonist is a Nmur1 specific agonist. In one embodiment, the agonist is a Nmur1/2 pan specific agonist. In preferred embodiments, the Nmur1 agonist is used in combination with IL-25 or a derivative thereof to induce an ILC2 inflammatory response. Not being bound by a theory, treatment alone with an Nmur1 agonist has no or little effect on inducing an inflammatory response in the experimental models used herein, but does have an effect in ILC2 cells already exposed to a sufficient amount of IL-25. Not being bound by a theory, treatment with IL-25 or a derivative thereof and an Nmur1 agonist induces an ILC2 inflammatory response. Not being bound by a theory, treatment with IL-25 or a derivative thereof without an Nmur1 agonist induces a protective ILC2 immune response. In some embodiments, the Nmur1 or Nmur1/2 agonist is an agonistic antibody. The Nmur1/2 agonist may be any agonist or NMU derivative as described in US patent application serial numbers US20070244048A1, US20100286035A1, US20110294735AI and international publication number WO2012050227A1. The Nmur1 agonist may also comprise derivatives and analogs of neuromedin S (NMS), (Mori et al. (EMBO J. 24: 325-335 (2005)) such as described in US patent application publication number US20110301079A1. NMS has also been disclosed in International publication numbers WO2006/086769, WO2007/0221123, and WO2007/075439. The NMUR1 agonists disclosed are incorporated herein by reference. Thus, in exemplary embodiments, the NMUR1 agonist may comprise any peptide described in Table 1.

TABLE 1

| SEQ ID NO. | Peptides | Neuromedin U Receptor Agonist Sequences |
|---|---|---|
| 4 | NMU | FRVDEEFQSPFASQSRGYFLFRPRN-CONH$_2$ |
| 5 | NMU1 | P$_1$-FRVDEEFQSPFASQSRGYFLFRPRN-CONH$_2$ |
| 6 | NMU2 | Ac-FRVDEEFQSPFASQSRGYFLFRPRN-CONH$_2$ |
| 7 | NMU3 | GYFLFRPRN-CONH$_2$ |
| 8 | NMU4 | FRVDEEFQSPFASQSRPYFLFRPRN-CONH$_2$ |
| 9 | NMU5 | Ac-FRVDEEFQSPFASQSRPYFLFRPRN-CONH$_2$ |
| 10 | Pre-1 | Ac-CGYFLFRPRN-CONH$_2$ |
| 11 | NMU6 | Ac-C$_1$GYFLFRPRN-CONH$_2$ |
| 12 | NMU7 | Ac-C$_2$GYFLFRPRN-CONH$_2$ |
| 13 | NMU11 | Ac-C$_3$GYFLFRPRN-CONH$_2$ |
| 14 | Pre-2 | Ac-CFRVDEEFQSPFASQSRGYFLFRPRN-CONH$_2$ |
| 15 | NMU8 | Ac-C$_1$FRVDEEFQSPFASQSRGYFLFRPRN-CONH$_2$ |

TABLE 1 -continued

| SEQ ID NO. | Peptides | Neuromedin U Receptor Agonist Sequences |
|---|---|---|
| 16 | NMU9 | Ac-C$_2$FRVDEEFQSPFASQSRGYFLFRPRN-CONH$_2$ |
| 17 | NMU12 | Ac-C$_2$FRVDEEFQSPFASQSRGYFLFRPRN-CONH$_2$ |
| 18 | NMU10 | Ac-C$_3$FRVDEEFQSPFASQSRGYFLFRPRN-CONH$_2$ |
| 19 | NMU21 | Ac-C$_4$FRVDEEFQSPFASQSRGYFLFRPRN-CONH$_2$ |
| 20 | NMU26 | Ac-C$_5$FRVDEEFQSPFASQSRGYFLFRPRN-CONH$_2$ |
| 21 | Pre-3 | Ac-CFRVDEEFQSPFASQSRGYFaWRPRN-CONH$_2$ |
| 22 | NMU13 | Ac-C$_1$FRVDEEFQSPFASQSRGYFaWRPRN-CONH$_2$ |
| 23 | NMU14 | Ac-C$_2$FRVDEEFQSPFASQSRGYFaWRPRN-CONH$_2$ |
| 24 | Pre-4 | Ac-C-Ttds-FLFRPRN-CONH$_2$ |
| 25 | NMU15 | Ac-C$_1$-Ttds-FLFRPRN-CONH$_2$ |
| 26 | NMU16 | Ac-C$_2$-Ttds-FLFRPRN-CONH$_2$ |
| 27 | Pre-5 | Ac-CASQSRGYFLFRPRN-CONH$_2$ |
| 28 | NMU17 | Ac-C$_1$ASQSRGYFLFRPRN-CONH$_2$ |
| 29 | NMU18 | Ac-C$_2$ASQSRGYFLFRPRN-CONH$_2$ |
| 30 | Pre-6 | Ac-CFQSPFASQSRGYFLFRPRN-CONH$_2$ |
| 31 | NMU19 | Ac-C$_1$FQSPFASQSRGYFLFRPRN-CONH$_2$ |
| 32 | NMU20 | Ac-C$_2$FQSPFASQSRGYFLFRPRN-CONH$_2$ |
| 33 | Pre-7 | Ac-C-C-FRVDEEFQSPFASQSRGYFLFRPRN-CONH$_2$ |
| 34 | NMU22 | Ac-C1-C1-FRVDEEFQSPFASQSRGYFLFRPRN-CONH$_2$ |
| 35 | NMU23 | Ac-C$_4$-C$_4$-FRVDEEFQSPFASQSRGYFLFRPRN-CONH$_2$ |
| 36 | Pre-8 | Pam-CFRVDEEFQSPFASQSRGYFLFRPRN-CONH$_2$ |
| 37 | NMU24 | Pam-C$_1$FRVDEEFQSPFASQSRGYFLFRPRN-CONH$_2$ |
| 38 | NMU25 | Pam-C$_2$FRVDEEFQSPFASQSRGYFLFRPRN-CONH$_2$ |
| 39 | NMU27 | Ac-C$_6$FRVDEEFQSPFASQSRGYFLFRPRN-CONH$_2$ |
| 40 | Pre-9 | Ac-C-Ttds-GYFLFRPRN-CONH$_2$ |
| 41 | NMU28 | Ac-C$_1$-Ttds-GYFLFRPRN-CONH$_2$ |
| 42 | NMU29 | Ac-C$_2$-Ttds-GYFLFRPRN-CONH$_2$ |
| 43 | NMU30 | Ac-C$_1$FRVDEEFQSPFASQSRPYFLFRPRN-CONH$_2$ |
| 44 | NMU31 | Ac-C$_2$FRVDEEFQSPFASQSRPYFLFRPRN-CONH$_2$ |
| 45 | A | YFWRPRN-CONH$_2$ |
| 46 | B | YF-(D-L)-WRPRN-CONH$_2$ |
| 47 | C | YFGWRPRN-CONH$_2$ |
| 48 | D | YF-(D-A)-WRPRN-CONH$_2$ |
| 49 | E | Ac-F-(D-L)-WRPRN-CONH$_2$ |
| 50 | F | Ac-FFRPRN-CONH$_2$ |
| 51 | G | FRVDEEFQSPFASQSRGYFWRPRN-CONH$_2$ |
| 52 | H | FRVDEEFQSPFASQSRGYF-(D-L)-WRPRN-CONH$_2$ |
| 53 | I | FWLFRP-(Harg)-N-CONH$_2$ |
| 54 | J | FWLFRA-(Harg)-N-CONH$_2$ |

TABLE 1 -continued

| SEQ ID NO. | Peptides | Neuromedin U Receptor Agonist Sequences |
|---|---|---|
| 55 | K | WFLFRAR-(D-Nle)-CONH$_2$ |
| 56 | L | FWLFRARN-CONH$_2$ |
| 57 | M | WALFRARN-CONH$_2$ |
| 58 | N | FALFRPRN-CONH$_2$ |
| 59 | O | FRVDEEFQSPFASQSRGFWLFRP-(Harg)-N-CONH$_2$ |
| 60 | P | FRVDEEFQSPFASQSRGFWLFRA-(Harg)-N-CONH$_2$ |
| 61 | Q | FRVDEEFQSPFASQSRGFWLFRPR-(D-Nle)-CONH$_2$ |
| 62 | NMS | ILQRGSGTAAVDFTKKDHTATWGRPFFLFRPRN-CONH$_2$ |
| 63 | NMS' | Ac-CILQRGSGTAAVDFTKKDHTATWGRPFFLFRPRN-CONH$_2$ |
| 64 | NMS3 | Ac-C$_1$ILQRGSGTAAVDFTKKDHTATWGRPFFLFRPRN-CONH$_2$ |
| 65 | NMS1 | Ac-C$_2$ILQRGSGTAAVDFTKKDHTATWGRPFFLFRPRN-CONH$_2$ |
| 66 | NMS2 | Ac-C$_3$ILQRGSGTAAVDFTKKDHTATWGRPFFLFRPRN-CONH$_2$ |
| 67 | NMS4 | Ac-C$_4$ILQRGSGTAAVDFTKKDHTATWGRPFFLFRPRN-CONH$_2$ |
| 68 | NMS5 | Pam-ILQRGSGTAAVDFTKKDHTATWGRPFFLFRPRN-CONH$_2$ |

C = cysteine;
P$_1$ = (PEG)$_2$40 kDa;
C$_1$ = Cys(N-ethylmaleimidyl),
C$_2$ = Cys(PEG)$_2$40 kDa,
C$_4$ = Cys(PEG)20 kDa,
C$_5$ = Cys(PEG)$_2$20 kDa,
C$_6$ = CyS(PEG)40 kDa;
each corresponding to a cysteine residue PEGylated via the side-chain thiol with a branched PEG [(PEG)$_2$]or a linear PEG of the indicated MW;
C$_3$ = Cys(Cholesteroyl), corresponding to a cysteine residue linked to cholesterol via the side-chain thiol;
Ttds, 1-amino-4,7,10-trioxa-13-tridecanamine succinimic acid;
a, D-Alanine;
Ac = acetyl;
Pam = palmitoyl;
Harg = Homoarginine;
Nle = Norleucine.

In certain embodiments, the agent is capable of inhibiting NMUR1 or blocking NMUR1 interaction with NMU. Such agents may also be referred to as NMUR1 inhibitors or antagonists and can inhibit either the expression and/or the activity of NMUR1. In some embodiments, NMUR1 expression is inhibited, e.g., by a DNA targeting agent (e.g., CRISPR system, TALE, Zinc finger protein) or a RNA targeting agent (e.g., inhibitory nucleic acid molecules). In some embodiments, NMUR1 activity is inhibited. Such inhibition includes, e.g., reducing the expression of its ligand, NMU, or by blocking the interaction of NMUR1 with NMU. In certain embodiments, the antagonist is an antibody or fragment thereof. In certain embodiments, the antibody is specific for NMU or NMUR1. In one embodiment, the agent is an antibody or fragment thereof as described in US patent application publication number US20100254998A.

The agents of the present invention may be modified, such that they acquire advantageous properties for therapeutic use (e.g., stability and specificity), but maintain their biological activity.

It is well known that the properties of certain proteins can be modulated by attachment of polyethylene glycol (PEG) polymers, which increases the hydrodynamic volume of the protein and thereby slows its clearance by kidney filtration. (See, e.g., Clark et al., J. Biol. Chem. 271: 21969-21977 (1996)). Therefore, it is envisioned that certain agents can be PEGylated (e.g., on peptide residues) to provide enhanced therapeutic benefits such as, for example, increased efficacy by extending half-life in vivo. In certain embodiments, PEGylation of the agents may be used to extend the serum half-life of the agents (e.g., neuromedin U receptor agonists or antagonists) and allow for particular agents to be capable of crossing the blood-brain barrier. Thus, in one embodiment, PEGylating the neuromedin U receptor agonists or antagonists improve the pharmacokinetics and pharmacodynamics of the neuromedin U receptor agonists or antagonists.

In regards to peptide PEGylation methods, reference is made to Lu et al., Int. J. Pept. Protein Res. 43: 127-38 (1994); Lu et al., Pept. Res. 6: 140-6 (1993); Felix et al., Int. J. Pept. Protein Res. 46: 253-64 (1995); Gaertner et al., Bioconjug. Chem. 7: 38-44 (1996); Tsutsumi et al., Thromb. Haemost. 77: 168-73 (1997); Francis et al., hit. J. Hematol. 68: 1-18 (1998); Roberts et al., J. Pharm. Sci. 87: 1440-45 (1998); and Tan et al., Protein Expr. Purif. 12: 45-52 (1998). Polyethylene glycol or PEG is meant to encompass any of the forms of PEG that have been used to derivatize other proteins, including, but not limited to, mono-(C1-10) alkoxy or aryloxy-polyethylene glycol. Suitable PEG moieties include, for example, 40 kDa methoxy poly(ethylene glycol) propionaldehyde (Dow, Midland, Mich.); 60 kDa methoxy poly(ethylene glycol) propionaldehyde (Dow, Midland, Mich.); 40 kDa methoxy poly(ethylene glycol) maleimido-propionamide (Dow, Midland, Mich.); 31 kDa alpha-methyl-w-(3-oxopropoxy), polyoxyethylene (NOF Corporation, Tokyo); mPEG2-NHS-40k (Nektar); mPEG2-MAL-40k (Nektar), SUNBRIGHT GL2-400MA ((PEG)240 kDa) (NOF Corporation, Tokyo), SUNBRIGHT ME-200MA (PEG20 kDa) (NOF Corporation, Tokyo). The PEG groups are generally attached to the peptide (e.g., neuromedin U receptor agonists or antagonists) via acylation or alkylation through a reactive group on the PEG moiety (for example, a maleimide, an aldehyde, amino, thiol, or ester group) to a reactive group on the peptide (for example, an aldehyde, amino, thiol, a maleimide, or ester group).

The PEG molecule(s) may be covalently attached to any Lys, Cys, or $K(CO(CH_2)_2SH)$ residues at any position in a peptide. In certain embodiments, the neuromedin U receptor agonists described herein can be PEGylated directly to any amino acid at the N-terminus by way of the N-terminal amino group. A "linker arm" may be added to a peptide to facilitate PEGylation. PEGylation at the thiol side-chain of cysteine has been widely reported (see, e.g., Caliceti & Veronese, Adv. Drug Deliv. Rev. 55: 1261-77 (2003)). If there is no cysteine residue in the peptide, a cysteine residue can be introduced through substitution or by adding a cysteine to the N-terminal amino acid. In certain embodiments, neuromedin U receptor agonists are PEGylated through the side chains of a cysteine residue added to the N-terminal amino acid.

In exemplary embodiments, the PEG molecule(s) may be covalently attached to an amide group in the C-terminus of a peptide, such as in the neuromedin U receptor agonist. In preferred embodiments, there is at least one PEG molecule covalently attached to the neuromedin U receptor agonist. In certain embodiments, the PEG molecule used in modifying an agent of the present invention is branched while in other embodiments, the PEG molecule may be linear. In particular aspects, the PEG molecule is between 1 kDa and 100 kDa in molecular weight. In further aspects, the PEG molecule is selected from 10, 20, 30, 40, 50, 60, and 80 kDa. In further still aspects, it is selected from 20, 40, or 60 kDa. Where there are two PEG molecules covalently attached to the agent of the present invention, each is 1 to 40 kDa and in particular aspects, they have molecular weights of 20 and 20 kDa, 10 and 30 kDa, 30 and 30 kDa, 20 and 40 kDa, or 40 and 40 kDa. In particular aspects, the agent (e.g., neuromedin U receptor agonists or antagonists) contain mPEG-cysteine. The mPEG in mPEG-cysteine can have various molecular weights. The range of the molecular weight is preferably 5 kDa to 200 kDa, more preferably 5 kDa to 100 kDa, and further preferably 20 kDa to 60 kDA. The mPEG can be linear or branched.

In particular embodiments, the agents (e.g., neuromedin U receptor agonist or antagonists) include a protecting group covalently joined to the N-terminal amino group. In exemplary embodiments, a protecting group covalently joined to the N-terminal amino group of the neuromedin U receptor agonists reduces the reactivity of the amino terminus under in vivo conditions. Amino protecting groups include —C1-10 alkyl, —C1-10 substituted alkyl, —C2-10 alkenyl, —C2-10 substituted alkenyl, aryl, —C1-6 alkyl aryl, —C(O)—CH2)1-6-COOH, —C(O)—C1-6 alkyl, —C(O)-aryl, —C(O)—O—C1-6 alkyl, or —C(O)—O-aryl. In particular embodiments, the amino terminus protecting group is selected from the group consisting of acetyl, propyl, succinyl, benzyl, benzyloxycarbonyl, and t-butyloxycarbonyl. In other embodiments, deamination of the N-terminal amino acid is another modification that may be used for reducing the reactivity of the amino terminus under in vivo conditions.

Chemically modified compositions of the agents (e.g., neuromedin U receptor agonists or antagonists) wherein the agent is linked to a polymer are also included within the scope of the present invention. The polymer selected is usually modified to have a single reactive group, such as an active ester for acylation or an aldehyde for alkylation, so that the degree of polymerization may be controlled. Included within the scope of polymers is a mixture of polymers. Preferably, for therapeutic use of the end-product preparation, the polymer will be pharmaceutically acceptable. The polymer or mixture thereof may include, but is not limited to, polyethylene glycol (PEG), monomethoxy-polyethylene glycol, dextran, cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (for example, glycerol), and polyvinyl alcohol.

In other embodiments, the agents (e.g., neuromedin U receptor agonists or antagonists) are modified by PEGylation, cholesterylation, or palmitoylation. The modification can be to any amino acid residue. In preferred embodiments, the modification is to the N-terminal amino acid of the agent (e.g., neuromedin U receptor agonist or antagonists), either directly to the N-terminal amino acid or by way coupling to the thiol group of a cysteine residue added to the N-terminus or a linker added to the N-terminus such as trimesoyl tris(3,5-dibromosalicylate) (Ttds). In certain embodiments, the N-terminus of the agent (e.g., neuromedin U receptor agonist or antagonist) comprises a cysteine residue to which a protecting group is coupled to the N-terminal amino group of the cysteine residue and the cysteine thiolate group is derivatized with N-ethylmaleimide, PEG group, cholesterol group, or palmitoyl group. In other embodiments, an acetylated cysteine residue is added to the N-terminus of the agents, and the thiol group of the cysteine is derivatized with N-ethylmaleimide, PEG group, cholesterol group, or palmitoyl group. In certain embodiments, the agent of the present invention is a conjugate. In certain embodiments, the agent of the present invention (e.g., neuromedin U receptor agonists or antagonists) is a polypeptide consisting of an amino acid sequence which is bound with a methoxypolyethylene glycol(s) via a linker (e.g., an amino acid sequence containing at least 8 amino acids of the C-terminus of the amino acid sequence of neuromedin U).

Substitutions of amino acids may be used to modify an agent of the present invention. The phrase "substitution of amino acids" as used herein encompasses substitution of amino acids that are the result of both conservative and non-conservative substitutions. Conservative substitutions are the replacement of an amino acid residue by another similar residue in a polypeptide. Typical but not limiting conservative substitutions are the replacements, for one another, among the aliphatic amino acids Ala, Val, Leu and Ile; interchange of Ser and Thr containing hydroxy residues, interchange of the acidic residues Asp and Glu, interchange between the amide-containing residues Asn and Gln, interchange of the basic residues Lys and Arg, interchange of the aromatic residues Phe and Tyr, and interchange of the small-sized amino acids Ala, Ser, Thr, Met, and Gly. Non-conservative substitutions are the replacement, in a polypeptide, of an amino acid residue by another residue which is not biologically similar. For example, the replacement of an amino acid residue with another residue that has a substantially different charge, a substantially different hydrophobicity, or a substantially different spatial configuration.

The term "antibody" (e.g., anti-NMU antibody) is used interchangeably with the term "immunoglobulin" herein, and includes intact antibodies, fragments of antibodies, e.g., Fab, F(ab')2 fragments, and intact antibodies and fragments that have been mutated either in their constant and/or variable region (e.g., mutations to produce chimeric, partially humanized, or fully humanized antibodies, as well as to produce antibodies with a desired trait, e.g., enhanced binding and/or reduced FcR binding). The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc, Fd, dAb, $V_{HH}$ and scFv and/or Fv fragments.

As used herein, a preparation of antibody protein having less than about 50% of non-antibody protein (also referred to herein as a "contaminating protein"), or of chemical precursors, is considered to be "substantially free." 40%, 30%, 20%, 10% and more preferably 5% (by dry weight), of non-antibody protein, or of chemical precursors is considered to be substantially free. When the antibody protein or biologically active portion thereof is recombinantly produced, it is also preferably substantially free of culture medium, i.e., culture medium represents less than about 30%, preferably less than about 20%, more preferably less than about 10%, and most preferably less than about 5% of the volume or mass of the protein preparation.

The term "antigen-binding fragment" refers to a polypeptide fragment of an immunoglobulin or antibody that binds antigen or competes with intact antibody (i.e., with the intact antibody from which they were derived) for antigen binding (i.e., specific binding). As such these antibodies or fragments thereof are included in the scope of the invention, provided that the antibody or fragment binds specifically to a target molecule.

It is intended that the term "antibody" encompass any Ig class or any Ig subclass (e.g. the IgG1, IgG2, IgG3, and IgG4 subclasses of IgG) obtained from any source (e.g., humans and non-human primates, and in rodents, lagomorphs, caprines, bovines, equines, ovines, etc.).

The term "Ig class" or "immunoglobulin class", as used herein, refers to the five classes of immunoglobulin that have been identified in humans and higher mammals, IgG, IgM, IgA, IgD, and IgE. The term "Ig subclass" refers to the two subclasses of IgM (H and L), three subclasses of IgA (IgA1, IgA2, and secretory IgA), and four subclasses of IgG (IgG1, IgG2, IgG3, and IgG4) that have been identified in humans and higher mammals. The antibodies can exist in monomeric or polymeric form; for example, IgM antibodies exist in pentameric form, and IgA antibodies exist in monomeric, dimeric or multimeric form.

The term "IgG subclass" refers to the four subclasses of immunoglobulin class IgG —IgG1, IgG2, IgG3, and IgG4 that have been identified in humans and higher mammals by the heavy chains of the immunoglobulins, V1-γ4, respectively. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by p pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of an antibody light chain are referred to interchangeably as "light chain constant regions", "light chain constant domains", "CL" regions or "CL" domains. The "constant" domains of an antibody heavy chain are referred to interchangeably as "heavy chain constant regions", "heavy chain constant domains", "CH" regions or "CH" domains. The "variable" domains of an antibody light chain are referred to interchangeably as "light chain variable regions", "light chain variable domains", "VL" regions or "VL" domains. The "variable" domains of an antibody heavy chain are referred to interchangeably as "heavy chain constant regions", "heavy chain constant domains", "VH" regions or "VH" domains.

The term "region" can also refer to a part or portion of an antibody chain or antibody chain domain (e.g., a part or portion of a heavy or light chain or a part or portion of a constant or variable domain, as defined herein), as well as more discrete parts or portions of said chains or domains. For example, light and heavy chains or light and heavy chain variable domains include "complementarity determining regions" or "CDRs" interspersed among "framework regions" or "FRs", as defined herein.

The term "conformation" refers to the tertiary structure of a protein or polypeptide (e.g., an antibody, antibody chain, domain or region thereof). For example, the phrase "light (or heavy) chain conformation" refers to the tertiary structure of a light (or heavy) chain variable region, and the phrase "antibody conformation" or "antibody fragment conformation" refers to the tertiary structure of an antibody or fragment thereof.

The term "antibody-like protein scaffolds" or "engineered protein scaffolds" broadly encompasses proteinaceous non-immunoglobulin specific-binding agents, typically obtained by combinatorial engineering (such as site-directed random mutagenesis in combination with phage display or other molecular selection techniques). Usually, such scaffolds are derived from robust and small soluble monomeric proteins (such as Kunitz inhibitors or lipocalins) or from a stably folded extra-membrane domain of a cell surface receptor (such as protein A, fibronectin or the ankyrin repeat).

Such scaffolds have been extensively reviewed in Binz et al. (Engineering novel binding proteins from nonimmunoglobulin domains. Nat Biotechnol 2005, 23:1257-1268), Gebauer and Skerra (Engineered protein scaffolds as next-generation antibody therapeutics. Curr Opin Chem Biol. 2009, 13:245-55), Gill and Damle (Biopharmaceutical drug discovery using novel protein scaffolds. Curr Opin Biotechnol 2006, 17:653-658), Skerra (Engineered protein scaffolds for molecular recognition. J Mol Recognit 2000, 13:167-187), and Skerra (Alterative non-antibody scaffolds for molecular recognition. Curr Opin Biotechnol 2007, 18:295-304), and include without limitation affibodies, based on the Z-domain of staphylococcal protein A, a three-helix bundle of 58 residues providing an interface on two of its alpha-helices (Nygren, Alternative binding proteins: Affibody binding proteins developed from a small three-helix bundle scaffold. FEBS J 2008, 275:2668-2676); engineered Kunitz domains based on a small (ca. 58 residues) and robust, disulphide-crosslinked serine protease inhibitor, typically of human origin (e.g. LACI-D1), which can be engineered for different protease specificities (Nixon and Wood, Engineered protein inhibitors of proteases. Curr Opin Drug Discov Dev 2006, 9:261-268); monobodies or adnectins based on the 10th extracellular domain of human fibronectin III (10fn3), which adopts an Ig-like beta-sandwich fold (94 residues) with 2-3 exposed loops, but lacks the central disulphide bridge (Koide and Koide, Monobodies: antibody mimics based on the scaffold of the fibronectin type III domain. Methods Mol Biol 2007, 352:95-109); anticalins derived from the lipocalins, a diverse family of eight-stranded beta-barrel proteins (ca. 180 residues) that naturally form binding sites for small ligands by means of four structurally variable loops at the open end, which are abundant in humans, insects, and many other organisms (Skerra, Alternative binding proteins: Anticalins-harnessing the structural plasticity of the lipocalin ligand pocket to engineer novel binding activities. FEBS J 2008, 275:2677-2683); DARPins, designed ankyrin repeat domains (166 residues), which provide a rigid interface arising from typically three repeated beta-turns (Stumpp et al., DARPins: a new generation of protein therapeutics. Drug Discov Today 2008, 13:695-701); avimers (multimerized LDLR-A module) (Silverman et al., Multivalent avimer proteins evolved by exon shuffling of a family of human receptor domains. Nat Biotechnol 2005, 23:1556-1561); and cysteine-rich knottin peptides (Kolmar, Alternative binding proteins: biological activity and therapeutic potential of cystine-knot miniproteins. FEBS J 2008, 275:2684-2690).

Specific binding" of an antibody means that the antibody exhibits appreciable affinity for a particular antigen or epitope and, generally, does not exhibit significant cross reactivity. "Appreciable" binding includes binding with an affinity of at least 25 µM. Antibodies with affinities greater than $1 \times 10^7$ M$^{-1}$ (or a dissociation coefficient of 1 µM or less or a dissociation coefficient of 1 nm or less) typically bind with correspondingly greater specificity. Values intermediate of those set forth herein are also intended to be within the scope of the present invention and antibodies of the invention bind with a range of affinities, for example, 100 nM or less, 75 nM or less, 50 nM or less, 25 nM or less, for example 10 nM or less, 5 nM or less, 1 nM or less, or in embodiments 500 pM or less, 100 pM or less, 50 pM or less or 25 pM or less. An antibody that "does not exhibit significant crossreactivity" is one that will not appreciably bind to an entity other than its target (e.g., a different epitope or a different molecule). For example, an antibody that specifically binds to a target molecule will appreciably bind the target molecule but will not significantly react with non-target molecules or peptides. An antibody specific for a particular epitope will, for example, not significantly cross-react with remote epitopes on the same protein or peptide. Specific binding can be determined according to any art-recognized means for determining such binding. Preferably, specific binding is determined according to Scatchard analysis and/or competitive binding assays.

As used herein, the term "affinity" refers to the strength of the binding of a single antigen-combining site with an antigenic determinant. Affinity depends on the closeness of stereochemical fit between antibody combining sites and antigen determinants, on the size of the area of contact between them, on the distribution of charged and hydrophobic groups, etc. Antibody affinity can be measured by equilibrium dialysis or by the kinetic BIACORE™ method. The dissociation constant, Kd, and the association constant, Ka, are quantitative measures of affinity.

As used herein, the term "monoclonal antibody" refers to an antibody derived from a clonal population of antibody-producing cells (e.g., B lymphocytes or B cells) which is homogeneous in structure and antigen specificity. The term "polyclonal antibody" refers to a plurality of antibodies originating from different clonal populations of antibody-producing cells which are heterogeneous in their structure and epitope specificity but which recognize a common antigen. Monoclonal and polyclonal antibodies may exist within bodily fluids, as crude preparations, or may be purified, as described herein.

The term "binding portion" of an antibody (or "antibody portion") includes one or more complete domains, e.g., a pair of complete domains, as well as fragments of an antibody that retain the ability to specifically bind to a target molecule. It has been shown that the binding function of an antibody can be performed by fragments of a full-length antibody. Binding fragments are produced by recombinant DNA techniques, or by enzymatic or chemical cleavage of intact immunoglobulins. Binding fragments include Fab, Fab', F(ab')2, Fabc, Fd, dAb, Fv, single chains, single-chain antibodies, e.g., scFv, and single domain antibodies.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, FR residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

Examples of portions of antibodies or epitope-binding proteins encompassed by the present definition include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the CHI domain; (v) the Fv fragment having the $V_L$ and $V_H$ domains of a single arm of an antibody; (vi) the dAb fragment (Ward et al., 341

Nature 544 (1989)) which consists of a $V_H$ domain or a $V_L$ domain that binds antigen; (vii) isolated CDR regions or isolated CDR regions presented in a functional framework; (viii) F(ab')$_2$ fragments which are bivalent fragments including two Fab' fragments linked by a disulphide bridge at the hinge region; (ix) single chain antibody molecules (e.g., single chain Fv; scFv) (Bird et al., 242 Science 423 (1988); and Huston et al., 85 PNAS 5879 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; Hollinger et al., 90 PNAS 6444 (1993)); (xi) "linear antibodies" comprising a pair of tandem Fd segments ($V_H$-$C_h$1-$V_H$-$C_h$1) which, together with complementary light chain polypeptides, form a pair of antigen binding regions (Zapata et al., Protein Eng. 8(10): 1057-62 (1995); and U.S. Pat. No. 5,641,870).

As used herein, a "blocking" antibody or an antibody "antagonist" is one which inhibits or reduces biological activity of the antigen(s) it binds. For example, an antagonist antibody may bind Nmur1 or NMU and inhibit the ability of Nmur1 and NMU to induce an ILC class 2 inflammatory response. In certain embodiments, the blocking antibodies or antagonist antibodies or portions thereof described herein completely inhibit the biological activity of the antigen(s).

Antibodies may act as agonists or antagonists of the recognized polypeptides. For example, the present invention includes antibodies which disrupt receptor/ligand interactions either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or of one of its down-stream substrates by immunoprecipitation followed by western blot analysis. In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex. Likewise, encompassed by the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides disclosed herein. The antibody agonists and antagonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16): 3668-3678 (1998); Harrop et al., J. Immunol. 161(4):1786-1794 (1998); Zhu et al., Cancer Res. 58(15):3209-3214 (1998); Yoon et al., J. Immunol. 160(7):3170-3179 (1998); Prat et al., J. Cell. Sci. III (Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996).

The antibodies as defined for the present invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Simple binding assays can be used to screen for or detect agents that bind to a target protein, or disrupt the interaction between proteins (e.g., a receptor and a ligand). Because certain targets of the present invention are transmembrane proteins, assays that use the soluble forms of these proteins rather than full-length protein can be used, in some embodiments. Soluble forms include, for example, those lacking the transmembrane domain and/or those comprising the IgV domain or fragments thereof which retain their ability to bind their cognate binding partners. Further, agents that inhibit or enhance protein interactions for use in the compositions and methods described herein, can include recombinant peptido-mimetics.

Detection methods useful in screening assays include antibody-based methods, detection of a reporter moiety, detection of cytokines as described herein, and detection of a gene signature as described herein.

Another variation of assays to determine binding of a receptor protein to a ligand protein is through the use of affinity biosensor methods. Such methods may be based on the piezoelectric effect, electrochemistry, or optical methods, such as ellipsometry, optical wave guidance, and surface plasmon resonance (SPR).

The disclosure also encompasses nucleic acid molecules, in particular those that inhibit NMUR1 or NMU. Exemplary nucleic acid molecules include aptamers, siRNA, artificial microRNA, interfering RNA or RNAi, dsRNA, ribozymes, antisense oligonucleotides, and DNA expression cassettes encoding said nucleic acid molecules. Preferably, the nucleic acid molecule is an antisense oligonucleotide. Antisense oligonucleotides (ASO) generally inhibit their target by binding target mRNA and sterically blocking expression by obstructing the ribosome. ASOs can also inhibit their target by binding target mRNA thus forming a DNA-RNA hybrid that can be a substance for RNase H. Preferred ASOs include Locked Nucleic Acid (LNA), Peptide Nucleic Acid (PNA), and morpholinos Preferably, the nucleic acid molecule is an RNAi molecule, i.e., RNA interference molecule. Preferred RNAi molecules include siRNA, shRNA, and artificial miRNA. The design and production of siRNA molecules is well known to one of skill in the art (e.g., Hajeri P B, Singh S K. Drug Discov Today. 2009 14(17-18):851-8). The nucleic acid molecule inhibitors may be chemically synthesized and provided directly to cells of interest. The nucleic acid compound may be provided to a cell as part of a gene delivery vehicle. Such a vehicle is preferably a liposome or a viral gene delivery vehicle.

It will be understood by the skilled person that treating as referred to herein encompasses enhancing treatment, or improving treatment efficacy. Treatment may include inhibition of an inflammatory response, tumor regression as well as inhibition of tumor growth, metastasis or tumor cell proliferation, or inhibition or reduction of otherwise deleterious effects associated with the tumor.

Efficaciousness of treatment is determined in association with any known method for diagnosing or treating the particular disease. The invention comprehends a treatment method comprising any one of the methods or uses herein discussed.

The phrase "therapeutically effective amount" as used herein refers to a sufficient amount of a drug, agent, or compound to provide a desired therapeutic effect.

As used herein "patient" refers to any human being receiving or who may receive medical treatment and is used interchangeably herein with the term "subject".

Therapy or treatment according to the invention may be performed alone or in conjunction with another therapy, and may be provided at home, the doctor's office, a clinic, a hospital's outpatient department, or a hospital. Treatment generally begins at a hospital so that the doctor can observe the therapy's effects closely and make any adjustments that are needed. The duration of the therapy depends on the age and condition of the patient, the stage of the cancer, and how the patient responds to the treatment. Additionally, a person having a greater risk of developing an inflammatory response (e.g., a person who is genetically predisposed or predisposed to allergies or a person having a disease characterized by episodes of inflammation) may receive prophylactic treatment to inhibit or delay symptoms of the disease.

The disclosure provides NMUR1 inhibitors for treating disease. A skilled person can readily determine diseases that can be treated by reducing an ILC2 inflammatory response. ILC2 cells and ILC2 inflammatory responses have been associated with allergic asthma, therapy resistant-asthma, steroid-resistant severe allergic airway inflammation, systemic steroid-dependent severe eosinophilic asthma, chronic rhino-sinusitis (CRS), atopic dermatitis, food allergies, persistence of chronic airway inflammation, and primary eosinophilic gastrointestinal disorders (EGIDs), including, but not limited to, eosinophilic esophagitis (EoE), eosinophilic gastritis, eosinophilic gastroenteritis, and eosinophilic colitis (see, e.g., Van Rijt et al., Type 2 innate lymphoid cells: at the cross-roads in allergic asthma, Seminars in Immunopathology July 2016, Volume 38, Issue 4, pp 483-496; Rivas et al., IL-4 production by group 2 innate lymphoid cells promotes food allergy by blocking regulatory T-cell function, J Allergy Clin Immunol. 2016 September; 138(3):801-811.e9; and Morita, Hideaki et al. Innate lymphoid cells in allergic and nonallergic inflammation, Journal of Allergy and Clinical Immunology, Volume 138, Issue 5, 1253-1264). Asthma is characterized by recurrent episodes of wheezing, shortness of breath, chest tightness, and coughing. Sputum may be produced from the lung by coughing but is often hard to bring up. During recovery from an attack, it may appear pus-like due to high levels of eosinophils. Symptoms are usually worse at night and in the early morning or in response to exercise or cold air. Some people with asthma rarely experience symptoms, usually in response to triggers, whereas others may have marked and persistent symptoms. CRS is characterized by inflammation of the mucosal surfaces of the nose and para-nasal sinuses, and it often coexists with allergic asthma. Atopic dermatitis is a chronic inflammatory skin disease that is characterized by eosinophilic infiltration and high serum IgE levels. Similar to allergic asthma and CRS, atopic dermatitis has been associated with increased expression of TSLP, IL-25, and IL-33 in the skin. Primary eosinophilic gastrointestinal disorders (EGIDs), including eosinophilic esophagitis (EoE), eosinophilic gastritis, eosinophilic gastroenteritis, and eosinophilic colitis, are disorders that exhibit eosinophil-rich inflammation in the gastrointestinal tract in the absence of known causes for eosinophilia, such as parasite infection and drug reaction. Not being bound by a theory, corticosteroids suppress TH2 cells, but not ILC2s and cannot be used to modulate ILC2 inflammatory responses. Applicants have discovered factors that balance homeostatic and pathological pro-inflammatory ILC2 responses. In certain embodiments, modulation of these factors, as described herein, may be used to treat the diseases described. In preferred embodiments, Nmur1 signaling is modulated.

The disclosure also provides methods for enhancing an ILC2 type response and treating disease. In certain embodiments, tissue inflammatory ILC2s are switched to activated, tissue protective ILC2s. ILC2 cells have been shown to promote an eosinophil cytotoxic response, antitumor response and metastasis suppression (Ikutani et al., Identification of Innate IL-5-Producing Cells and Their Role in Lung Eosinophil Regulation and Antitumor Immunity, J Immunol 2012; 188:703-713). Specifically, innate IL-5-producing cells were increased in response to tumor invasion, and their regulation of eosinophils was critical to suppress tumor metastasis. Thus, in one embodiment induction of an ILC2 inflammatory response may be used in treating cancer. In other embodiments, the cancer is resistant to therapies targeting the adaptive immune system (see e.g., Rooney et al., Molecular and genetic properties of tumors associated with local immune cytolytic activity, Cell. 2015 Jan. 15; 160(1-2): 48-61). In one embodiment, modulation of one or more of the signature genes are used for inducing an inflammatory immune response state for the treatment of a subpopulation of tumor cells that are linked to resistance to targeted therapies and progressive tumor growth. Not being bound by a theory, in cases where tumors are resistant to therapies targeting the adaptive immune system, treatments targeting the innate immune system may be therapeutically effective in treating the tumor.

The cancer may include, without limitation, liquid tumors such as leukemia (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease, non-Hodgkin's disease), Waldenstrom's macroglobulinemia, heavy chain disease, or multiple myeloma.

The cancer may include, without limitation, solid tumors such as sarcomas and carcinomas. Examples of solid tumors include, but are not limited to, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, epithelial carcinoma, bronchogenic carcinoma, hepatoma, colorectal cancer (e.g., colon cancer, rectal cancer), anal cancer, pancreatic cancer (e.g., pancreatic adenocarcinoma, islet cell carcinoma, neuroendocrine tumors), breast cancer (e.g., ductal carcinoma, lobular carcinoma, inflammatory breast cancer, clear cell carcinoma, mucinous carcinoma), ovarian carcinoma (e.g., ovarian epithelial carcinoma or surface epithelial-stromal tumour including serous tumour, endometrioid tumor and mucinous cystadenocarcinoma, sex-cord-stromal tumor), prostate cancer, liver and bile duct carcinoma (e.g., hepatocelluar carcinoma, cholangiocarcinoma, hemangioma), choriocarcinoma, seminoma, embryonal carcinoma, kidney cancer (e.g., renal cell carcinoma, clear cell carcinoma, Wilm's tumor, nephroblastoma), cervical cancer, uterine cancer (e.g., endometrial adenocarcinoma, uterine papillary serous carcinoma, uterine clear-cell carcinoma, uterine sarcomas and leiomyosarcomas, mixed mullerian tumors), testicular cancer, germ cell tumor, lung cancer (e.g., lung adenocarcinoma, squamous cell carcinoma, large cell carcinoma, bronchioloalveolar carcinoma, non-small-cell carcinoma, small cell carcinoma, mesothelioma), bladder carcinoma, signet ring cell carcinoma, cancer of the head and neck (e.g., squamous cell carcinomas), esophageal carcinoma (e.g., esophageal adenocarcinoma), tumors of the brain (e.g., glioma, glioblastoma, medullablastoma, astrocytoma, medulloblastoma, craniopharyngioma, ependymoma, pinealoma, hemangioblastoma, acoustic neuroma, oligodenroglioma, schwannoma, meningioma), neuroblastoma, retinoblastoma, neuroendocrine tumor, melanoma, cancer of the stomach (e.g., stomach adenocarcinoma, gastrointestinal stromal tumor), or carcinoids. Lymphoproliferative disorders are also considered to be proliferative diseases.

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, PA (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

The medicaments of the invention are prepared in a manner known to those skilled in the art, for example, by means of conventional dissolving, lyophilizing, mixing, granulating or confectioning processes. Methods well known in the art for making formulations are found, for example, in Remington: The Science and Practice of Pharmacy, 20th ed., ed. A. R. Gennaro, 2000, Lippincott Williams & Wilkins, Philadelphia, and Encyclopedia of Pharmaceutical Technology, eds. J. Swarbrick and J. C. Boylan, 1988-1999, Marcel Dekker, New York.

Administration of medicaments of the invention may be by any suitable means that results in a compound concentration that is effective for treating or inhibiting (e.g., by delaying) the development of a disease. The compound is admixed with a suitable carrier substance, e.g., a pharmaceutically acceptable excipient that preserves the therapeutic properties of the compound with which it is administered. One exemplary pharmaceutically acceptable excipient is physiological saline. The suitable carrier substance is generally present in an amount of 1-95% by weight of the total weight of the medicament. The medicament may be provided in a dosage form that is suitable for administration. Thus, the medicament may be in form of, e.g., tablets, capsules, pills, powders, granulates, suspensions, emulsions, solutions, gels including hydrogels, pastes, ointments, creams, plasters, drenches, delivery devices, injectables, implants, sprays, or aerosols.

The agents disclosed herein (e.g., neuromedin U receptor agonists or antagonists) may be used in a pharmaceutical composition when combined with a pharmaceutically acceptable carrier. Such compositions comprise a therapeutically-effective amount of the agent and a pharmaceutically acceptable carrier. Such a composition may also further comprise (in addition to an agent and a carrier) diluents, fillers, salts, buffers, stabilizers, solubilizers, and other materials well known in the art. Compositions comprising the agent can be administered in the form of salts provided the salts are pharmaceutically acceptable. Salts may be prepared using standard procedures known to those skilled in the art of synthetic organic chemistry.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. It will be understood that, as used herein, references to specific agents (e.g., neuromedin U receptor agonists or antagonists), also include the pharmaceutically acceptable salts thereof.

Methods of administrating the pharmacological compositions, including agonists, antagonists, antibodies or fragments thereof, to an individual include, but are not limited to, intradermal, intrathecal, intramuscular, intraperitoneal, intravenous, subcutaneous, intranasal, epidural, by inhalation, and oral routes. The compositions can be administered by any convenient route, for example by infusion or bolus injection, by absorption through epithelial or mucocutaneous linings (for example, oral mucosa, rectal and intestinal mucosa, and the like), ocular, and the like and can be administered together with other biologically-active agents. Administration can be systemic or local. In addition, it may be advantageous to administer the composition into the central nervous system by any suitable route, including intraventricular and intrathecal injection. Pulmonary administration may also be employed by use of an inhaler or nebulizer, and formulation with an aerosolizing agent. It may also be desirable to administer the agent locally to the area in need of treatment; this may be achieved by, for example, and not by way of limitation, local infusion during surgery, topical application, by injection, by means of a catheter, by means of a suppository, or by means of an implant.

Various delivery systems are known and can be used to administer the pharmacological compositions including, but not limited to, encapsulation in liposomes, microparticles, microcapsules, minicells, polymers, capsules, tablets, and the like. In one embodiment, the agent may be delivered in a vesicle, in particular a liposome. In a liposome, the agent is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,837,028 and 4,737,323. In yet another embodiment, the pharmacological compositions can be delivered in a controlled release system including, but not limited to: a delivery pump (see, for example, Saudek, et al., New Engl. J. Med. 321: 574 (1989) and a semi-permeable polymeric material (see, for example, Howard, et al., J. Neurosurg. 71: 105 (1989)). Additionally, the controlled release system can be placed in proximity of the therapeutic target (e.g., a tumor), thus requiring only a fraction of the systemic dose. See, for example, Goodson, In: Medical Applications of Controlled Release, 1984. (CRC Press, Boca Raton, Fla.).

The amount of the agents (e.g., NMUR1 agonist, NMU derivatives) which will be effective in the treatment of a particular disorder or condition will depend on the nature of the disorder or condition, and may be determined by standard clinical techniques by those of skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. Ultimately, the attending physician will decide the amount of the agent with which to treat each individual patient. In certain embodiments, the attending physician will administer low doses of the agent and observe the patient's response. Larger doses of the agent may be administered until the optimal therapeutic effect is obtained for the patient, and at that point the dosage is not increased further. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases. In certain embodiments, suitable dosage ranges for intravenous administration of the agent (e.g., neuromedin U receptor agonist or antagonist) are generally about 5-500 micrograms (μg) of active compound per kilogram (Kg) body weight. Suitable dosage ranges for intranasal administration are generally about 0.01 pg/kg body weight to 1 mg/kg body weight. In certain embodiments, a composition containing an agent of the present invention is subcutaneously injected in adult patients with dose ranges of approximately 5 to 5000 μg/human and preferably approximately 5 to 500 μg/human as a single dose. It is desirable to administer this dosage 1 to 3 times daily. Effective doses may be extrapolated from dose-response curves derived from in vitro or animal model test systems. Suppositories generally contain active ingredient in the range of 0.5% to 10% by weight; oral formulations preferably contain 10% to 95% active ingredient. Ultimately the attending physician will decide on the appropriate duration of therapy using compositions of the present invention. Dosage will also vary according to the age, weight and response of the individual patient.

Methods for administering antibodies for therapeutic use is well known to one skilled in the art. In certain embodiments, small particle aerosols of antibodies or fragments thereof may be administered (see e.g., Piazza et al., J. Infect. Dis., Vol. 166, pp. 1422-1424, 1992; and Brown, Aerosol Science and Technology, Vol. 24, pp. 45-56, 1996). In certain embodiments, antibodies (e.g., anti-NMU antibodies) are administered in metered-dose propellant driven aerosols. In preferred embodiments, antibodies are used as inhibitors or antagonists to depress inflammatory diseases or allergen-induced asthmatic responses. In certain embodiments, antibodies may be administered in liposomes, i.e., immunoliposomes (see, e.g., Maruyama et al., Biochim. Biophys. Acta, Vol. 1234, pp. 74-80, 1995). In certain embodiments, immunoconjugates, immunoliposomes or immunomicrospheres containing an agent of the present invention is administered by inhalation.

In certain embodiments, antibodies may be topically administered to mucosa, such as the oropharynx, nasal cavity, respiratory tract, gastrointestinal tract, eye such as the conjunctival mucosa, vagina, urogenital mucosa, or for dermal application. In certain embodiments, antibodies are administered to the nasal, bronchial or pulmonary mucosa. In order to obtain optimal delivery of the antibodies to the pulmonary cavity in particular, it may be advantageous to add a surfactant such as a phosphoglyceride, e.g. phosphatidylcholine, and/or a hydrophilic or hydrophobic complex of a positively or negatively charged excipient and a charged antibody of the opposite charge.

Other excipients suitable for pharmaceutical compositions intended for delivery of antibodies to the respiratory tract mucosa may be a) carbohydrates, e.g., monosaccharides such as fructose, galactose, glucose. D-mannose, sorbose, and the like; disaccharides, such as lactose, trehalose, cellobiose, and the like; cyclodextrins, such as 2-hydroxypropyl-β-cyclodextrin; and polysaccharides, such as raffinose, maltodextrins, dextrans, and the like; b) amino acids, such as glycine, arginine, aspartic acid, glutamic acid, cysteine, lysine and the like; c) organic salts prepared from organic acids and bases, such as sodium citrate, sodium ascorbate, magnesium gluconate, sodium gluconate, tromethamine hydrochloride, and the like: d) peptides and proteins, such as aspartame, human serum albumin, gelatin, and the like; e) alditols, such mannitol, xylitol, and the like, and f) polycationic polymers, such as chitosan or a chitosan salt or derivative.

For dermal application, the antibodies of the present invention (e.g. NMU antibodies) may suitably be formulated with one or more of the following excipients: solvents, buffering agents, preservatives, humectants, chelating agents, antioxidants, stabilizers, emulsifying agents, suspending agents, gel-forming agents, ointment bases, penetration enhancers, and skin protective agents.

Examples of solvents are e.g. water, alcohols, vegetable or marine oils (e.g. edible oils like almond oil, castor oil, cacao butter, coconut oil, corn oil, cottonseed oil, linseed oil, olive oil, palm oil, peanut oil, poppy seed oil, rapeseed oil, sesame oil, soybean oil, sunflower oil, and tea seed oil), mineral oils, fatty oils, liquid paraffin, polyethylene glycols, propylene glycols, glycerol, liquid polyalkylsiloxanes, and mixtures thereof.

Examples of buffering agents are e.g. citric acid, acetic acid, tartaric acid, lactic acid, hydrogenphosphoric acid, diethyl amine etc. Suitable examples of preservatives for use in compositions are parabenes, such as methyl, ethyl, propyl p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodopropynyl butylcarbamate, EDTA, benzalconium chloride, and benzylalcohol, or mixtures of preservatives.

Examples of humectants are glycerin, propylene glycol, sorbitol, lactic acid, urea, and mixtures thereof.

Examples of antioxidants are butylated hydroxy anisole (BHA), ascorbic acid and derivatives thereof, tocopherol and derivatives thereof, cysteine, and mixtures thereof.

Examples of emulsifying agents are naturally occurring gums, e.g. gum acacia or gum tragacanth; naturally occurring phosphatides, e.g. soybean lecithin, sorbitan monooleate derivatives: wool fats; wool alcohols; sorbitan esters; monoglycerides; fatty alcohols; fatty acid esters (e.g. triglycerides of fatty acids); and mixtures thereof.

Examples of suspending agents are e.g. celluloses and cellulose derivatives such as, e.g., carboxymethyl cellulose, hydroxyethylcellulose, hydroxypropylcellulose, hydroxypropylmethylcellulose, carraghenan, acacia gum, arabic gum, tragacanth, and mixtures thereof.

Examples of gel bases, viscosity-increasing agents or components which are able to take up exudate from a wound are: liquid paraffin, polyethylene, fatty oils, colloidal silica or aluminum, zinc soaps, glycerol, propylene glycol, tragacanth, carboxyvinyl polymers, magnesium-aluminum silicates, Carbopol®, hydrophilic polymers such as, e.g. starch or cellulose derivatives such as, e.g., carboxymethylcellulose, hydroxyethylcellulose and other cellulose derivatives, water-swellable hydrocolloids, carragenans, hyaluronates (e.g. hyaluronate gel optionally containing sodium chloride), and alginates including propylene glycol alginate.

Examples of ointment bases are e.g. beeswax, paraffin, cetanol, cetyl palmitate, vegetable oils, sorbitan esters of fatty acids (Span), polyethylene glycols, and condensation products between sorbitan esters of fatty acids and ethylene oxide, e.g. polyoxyethylene sorbitan monooleate (Tween).

Examples of hydrophobic or water-emulsifying ointment bases are paraffins, vegetable oils, animal fats, synthetic glycerides, waxes, lanolin, and liquid polyalkylsiloxanes. Examples of hydrophilic ointment bases are solid macrogols (polyethylene glycols). Other examples of ointment bases are triethanolamine soaps, sulphated fatty alcohol and polysorbates.

Examples of other excipients are polymers such as carmelose, sodium carmelose, hydroxypropylmethylcellulose, hydroxyethylcellulose, hydroxypropylcellulose, pectin, xanthan gum, locust bean gum, acacia gum, gelatin, carbomer, emulsifiers like vitamin E, glyceryl stearates, cetanyl glucoside, collagen, carrageenan, hyaluronates and alginates and chitosans.

The dose of antibody required in humans to be effective in the treatment or prevention of allergic inflammation differs with the type and severity of the allergic condition to be treated, the type of allergen, the age and condition of the patient, etc. Typical doses of antibody to be administered are in the range of 1 μg to 1 g, preferably 1-1000 μg, more preferably 2-500 μg, even more preferably 5-50 μg, most preferably 10-20 μg per unit dosage form. In certain embodiments, infusion of antibodies of the present invention may range from 10-500 mg/m$^2$.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection.

Suitable doses of IL-25 are generally in the range of between about 1 and about 250 μg/kg body weight, and may be administered from once a week up to about six times daily. Treatment may continue for a period of between one day and six months, or for as long as is deemed necessary and safe in the treatment of the aforementioned disorders, as is readily ascertained by standard tests by the attending physician, depending upon the nature of the disorder being treated. In some embodiments, a patient may first undergo IL-25 treatment (e.g., for several days or weeks) followed by treatment with an NMUR1 agonist.

In another aspect, provided is a pharmaceutical pack or kit, comprising one or more containers filled with one or more of the ingredients of the pharmaceutical compositions and neuromedin U receptor agonists or antagonists (e.g., NMU derivatives and IL-25, NMU antibodies).

In another aspect, provided is a kit for detecting the gene signature as described herein.

Genetic Modifying Agents

In certain embodiments, the one or more modulating agents may be a genetic modifying agent. The genetic modifying agent may comprise a CRISPR system, a zinc finger nuclease system, a TALEN, or a meganuclease.

In general, a CRISPR-Cas or CRISPR system as used in herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g, Shmakov et al. (2015) "Discovery and Functional Characterization of Diverse Class 2 CRISPR-Cas Systems", Molecular Cell, DOI: dx.doi.org/10.1016/j.molcel.2015.10.008.

In certain embodiments, a protospacer adjacent motif (PAM) or PAM-like motif directs binding of the effector protein complex as disclosed herein to the target locus of interest. In some embodiments, the PAM may be a 5' PAM (i.e., located upstream of the 5' end of the protospacer). In other embodiments, the PAM may be a 3' PAM (i.e., located downstream of the 5' end of the protospacer). The term "PAM" may be used interchangeably with the term "PFS" or "protospacer flanking site" or "protospacer flanking sequence".

In a preferred embodiment, the CRISPR effector protein may recognize a 3' PAM. In certain embodiments, the CRISPR effector protein may recognize a 3' PAM which is 5'H, wherein H is A, C or U.

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to a RNA polynucleotide being or comprising the target sequence. In other words, the target RNA may be a RNA polynucleotide or a part of a RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell.

In certain example embodiments, the CRISPR effector protein may be delivered using a nucleic acid molecule encoding the CRISPR effector protein. The nucleic acid molecule encoding a CRISPR effector protein, may advantageously be a codon optimized CRISPR effector protein. An example of a codon optimized sequence, is in this instance a sequence optimized for expression in eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR effector protein is a codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way the Cas transgene is introduced in the cell may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell;

159(2):440-455 (2014)), describing a Cas9 knock-in mouse, which is incorporated herein by reference. The Cas transgene can further comprise a Lox-Stop-polyA-Lox(LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in, for instance, eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus.

In certain aspects the invention involves vectors, e.g. for delivering or introducing in a cell Cas and/or RNA capable of guiding Cas to a target locus (i.e. guide RNA), but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety. Thus, the embodiments disclosed herein may also comprise transgenic cells comprising the CRISPR effector system. In certain example embodiments, the transgenic cell may function as an individual discrete volume. In other words samples comprising a masking construct may be delivered to a cell, for example in a suitable delivery vesicle and if the target is present in the delivery vesicle the CRISPR effector is activated and a detectable signal generated.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s); and, when a single vector provides for more than 16 RNA(s), one or more promoter(s) can drive expression of more than one of the RNA(s), e.g., when there are 32 RNA(s), each promoter can drive expression of two RNA(s), and when there are 48 RNA(s), each promoter can drive expression of three RNA(s). By simple arithmetic and well established cloning protocols and the teachings in this disclosure one skilled in the art can readily practice the invention as to the RNA(s) for a suitable exemplary vector such as AAV, and a suitable promoter such as the U6 promoter. For example, the packaging limit of AAV is ~4.7 kb. The length of a single U6-gRNA (plus restriction sites for cloning) is 361 bp. Therefore, the skilled person can readily fit about 12-16, e.g., 13 U6-gRNA cassettes in a single vector. This can be assembled by any suitable means, such as a golden gate strategy used for TALE assembly (genome-engineering.org/taleffectors/). The skilled person can also use a tandem guide strategy to increase the number of U6-gRNAs by approximately 1.5 times, e.g., to increase from 12-16, e.g., 13 to approximately 18-24, e.g., about 19 U6-gRNAs. Therefore, one skilled in the art can readily reach approximately 18-24, e.g., about 19 promoter-RNAs, e.g., U6-gRNAs in a single vector, e.g., an AAV vector. A further means for increasing the number of promoters and RNAs in a vector is to use a single promoter (e.g., U6) to express an array of RNAs separated by cleavable sequences. And an even further means for increasing the number of promoter-RNAs in a vector, is to express an array of promoter-RNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals.org/content/34/7/e53.short and nature.com/mt/journal/v16/n9/abs/mt2008144a.html). In an advantageous embodiment, AAV may package U6 tandem gRNA targeting up to about 50 genes. Accordingly, from the knowledge in the art and the teachings in this disclosure the skilled person can readily make and use vector(s), e.g., a single vector, expressing multiple RNAs or guides under the control or operatively or functionally linked to one or more promoters—especially as to the numbers of RNAs or guides discussed herein, without any undue experimentation.

The guide RNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter. An advantageous promoter is the promoter is U6.

Additional effectors for use according to the invention can be identified by their proximity to cas1 genes, for example, though not limited to, within the region 20 kb from the start of the cas1 gene and 20 kb from the end of the cas1 gene. In certain embodiments, the effector protein comprises at least one HEPN domain and at least 500 amino acids, and wherein the C2c2 effector protein is naturally present in a prokaryotic genome within 20 kb upstream or downstream of a Cas gene or a CRISPR array. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In certain example embodiments, the C2c2 effector protein is naturally present in a prokaryotic genome within 20 kb upstream or downstream of a Cas 1 gene. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related.

Guide Molecules

The methods described herein may be used to screen inhibition of CRISPR systems employing different types of guide molecules. As used herein, the term "guide sequence" and "guide molecule" in the context of a CRISPR-Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. The guide sequences made using the methods disclosed herein may be a full-length guide sequence, a truncated guide sequence, a full-length sgRNA sequence, a truncated sgRNA sequence, or an E+F sgRNA sequence. In some embodiments, the degree of complementarity of the guide sequence to a given target sequence, when optimally aligned using a suitable alignment algorithm, is about or more than about 50%, 60%, 75%, 80%, 85%, 90%, 95%, 97.5%, 99%, or more. In certain example embodiments, the guide molecule comprises a guide sequence that may be designed to have at least one mismatch with the target sequence, such that a RNA duplex formed between the guide sequence and the target sequence. Accordingly, the degree of complementarity is preferably less than 99%. For instance, where the guide sequence consists of 24 nucleotides, the degree of complementarity is more particularly about 96% or less. In particular embodiments, the guide sequence is designed to have a stretch of two or more adjacent mismatching nucleotides, such that the degree of complementarity over the entire guide sequence is further reduced. For instance, where the guide sequence consists of 24 nucleotides, the degree of complementarity is more particularly about 96% or less, more particularly, about 92% or less, more particularly about 88% or less, more particularly about 84% or less, more particularly about 80% or less, more particularly about 76% or less, more particularly about 72% or less, depending on whether the stretch of two or more mismatching nucleotides encompasses 2, 3, 4, 5, 6 or 7 nucleotides, etc. In some embodiments, aside from the stretch of one or more mismatching nucleotides, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence (or a sequence in the vicinity thereof) may be evaluated in a test tube by providing the target nucleic acid sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art. A guide sequence, and hence a nucleic acid-targeting guide RNA may be selected to target any target nucleic acid sequence.

In certain embodiments, the guide sequence or spacer length of the guide molecules is from 15 to 50 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer. In certain example embodiment, the guide sequence is 15, 16, 17, 18, 19, 20, 21, 22, 23, 24, 25, 26, 27, 28, 29, 30, 31, 32, 33, 34, 35, 36, 37, 38, 39 40, 41, 42, 43, 44, 45, 46, 47 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nt.

In some embodiments, the guide sequence is an RNA sequence of between 10 to 50 nt in length, but more particularly of about 20-30 nt advantageously about 20 nt, 23-25 nt or 24 nt. The guide sequence is selected so as to ensure that it hybridizes to the target sequence. This is described more in detail below. Selection can encompass further steps which increase efficacy and specificity.

In some embodiments, the guide sequence has a canonical length (e.g., about 15-30 nt) is used to hybridize with the target RNA or DNA. In some embodiments, a guide molecule is longer than the canonical length (e.g., >30 nt) is used to hybridize with the target RNA or DNA, such that a region of the guide sequence hybridizes with a region of the RNA or DNA strand outside of the Cas-guide target complex. This can be of interest where additional modifications, such as deamination of nucleotides, is of interest. In alternative embodiments, it is of interest to maintain the limitation of the canonical guide sequence length.

In some embodiments, the sequence of the guide molecule (direct repeat and/or spacer) is selected to reduce the degree secondary structure within the guide molecule. In some embodiments, about or less than about 75%, 50%, 40%, 30%, 25%, 20%, 15%, 10%, 5%, 1%, or fewer of the nucleotides of the nucleic acid-targeting guide RNA participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and PA Carr and GM Church, 2009, Nature Biotechnology 27(12):1151-62).

In some embodiments, it is of interest to reduce the susceptibility of the guide molecule to RNA cleavage, such as to cleavage by Cas13. Accordingly, in particular embodiments, the guide molecule is adjusted to avoid cleavage by Cas13 or other RNA-cleaving enzymes.

In certain embodiments, the guide molecule comprises non-naturally occurring nucleic acids and/or non-naturally occurring nucleotides and/or nucleotide analogs, and/or chemically modifications. Preferably, these non-naturally occurring nucleic acids and non-naturally occurring nucleotides are located outside the guide sequence. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromo-uridine, pseudouridine, inosine, 7-methylguanosine.

Examples of guide RNA chemical modifications include, without limitation, incorporation of 2'-O-methyl (M), 2'-O-methyl 3' phosphorothioate (MS), S-constrained ethyl(cEt), or 2'-O-methyl 3' thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015 Ragdarm et al., 0215, PNAS, E7110-E7111; Allerson et al., J. Med. Chem. 2005, 48:901-904; Bramsen et al., Front. Genet., 2012, 3:154; Deng et al., PNAS, 2015, 112:11870-11875; Sharma et al., MedChemComm., 2014, 5:1454-1471; Hendel et al., Nat. Biotechnol. (2015) 33(9): 985-989; Li et al., Nature Biomedical Engineering, 2017, 1, 0066 DOI:10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, J. Biotech. 233:74-83). In certain embodiments, a guide comprises ribonucleotides in a region that binds to a target RNA and one or more deoxyribonucleotides and/or nucleotide analogs in a region that binds to Cas13. In an embodiment of the invention, deoxyribonucleotides and/or nucleotide analogs are incorporated in engineered guide structures, such as, without limitation, stem-loop regions, and the seed region. For Cas13 guide, in certain embodiments, the modification is not in the 5'-handle of the stem-loop regions. Chemical modification in the 5'-handle of the stem-loop region of a guide may abolish its function (see Li, et al., Nature Biomedical Engineering, 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl 3' phosphorothioate (MS), S-constrained ethyl(cEt), or 2'-O-methyl 3' thioPACE (MSP). Such modification can enhance genome editing efficiency (see Hendel et al., Nat. Biotechnol. (2015) 33(9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemically modified with 2'-0-Me, 2'-F or S-constrained ethyl(cEt). Such chemically modified guide can mediate enhanced levels of gene disruption (see Ragdarm et al., 0215, PNAS, E7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., eLife, 2017, 6:e25312, DOI:10.7554).

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromo-uridine, pseudouridine (Ψ), N1-methylpseudouridine (melΨ), 5-methoxyuridine (5moU), inosine, 7-methylguanosine, 2'-O-methyl 3' phosphorothioate (MS), S-constrained ethyl(cEt), phosphorothioate (PS), or 2'-O-methyl 3' thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 to 10 nucleotides in the 3'-terminus are chemically modified. Such chemical modifications at the 3'-terminus of the Cas13 CrRNA may improve Cas13 activity. In a specific embodiment, 1, 2, 3, 4, 5, 6, 7, 8, 9 or 10 nucleotides in the 3'-terminus are replaced with 2'-fluoro analogues. In a specific embodiment, 1, 2, 3, 4, 5, 6, 7, 8, 9 or 10 nucleotides in the 3'-terminus are replaced with 2'-O-methyl (M) analogs.

In some embodiments, the loop of the 5'-handle of the guide is modified. In some embodiments, the loop of the 5'-handle of the guide is modified to have a deletion, an insertion, a split, or chemical modifications. In certain embodiments, the modified loop comprises 3, 4, or 5 nucleotides. In certain embodiments, the loop comprises the sequence of UCUU, UUUU, UAUU, or UGUU (SEQ. I.D. Nos. 1-4).

In some embodiments, the guide molecule forms a stem-loop with a separate non-covalently linked sequence, which can be DNA or RNA. In particular embodiments, the sequences forming the guide are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, these sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sufonyl, ally, propargyl, diene, alkyne, and azide. Once this sequence is functionalized, a covalent chemical bond or linkage can be formed between this sequence and the direct repeat sequence. Examples of chemical bonds include, but are not limited to, those based on carbamates, ethers, esters, amides, imines, amidines, aminotrizines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, these stem-loop forming sequences can be chemically synthesized. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In certain embodiments, the guide molecule comprises (1) a guide sequence capable of hybridizing to a target locus and (2) a tracr mate or direct repeat sequence whereby the direct repeat sequence is located upstream (i.e., 5') from the guide sequence. In a particular embodiment the seed sequence (i.e. the sequence essential critical for recognition and/or hybridization to the sequence at the target locus) of th guide sequence is approximately within the first 10 nucleotides of the guide sequence.

In a particular embodiment the guide molecule comprises a guide sequence linked to a direct repeat sequence, wherein the direct repeat sequence comprises one or more stem loops or optimized secondary structures. In particular embodiments, the direct repeat has a minimum length of 16 nts and a single stem loop. In further embodiments the direct repeat has a length longer than 16 nts, preferably more than 17 nts, and has more than one stem loops or optimized secondary structures. In particular embodiments the guide molecule comprises or consists of the guide sequence linked to all or part of the natural direct repeat sequence. A typical Type V or Type VI CRISPR-cas guide molecule comprises (in 3' to 5' direction or in 5' to 3' direction): a guide sequence a first complimentary stretch (the "repeat"), a loop (which is typically 4 or 5 nucleotides long), a second complimentary stretch (the "anti-repeat" being complimentary to the repeat), and a poly A (often poly U in RNA) tail (terminator). In certain embodiments, the direct repeat sequence retains its natural architecture and forms a single stem loop. In particular embodiments, certain aspects of the guide architecture can be modified, for example by addition, subtraction, or substitution of features, whereas certain other aspects of guide architecture are maintained. Preferred locations for engineered guide molecule modifications, including but not limited to insertions, deletions, and substitutions include guide termini and regions of the guide molecule that are exposed when complexed with the CRISPR-Cas protein and/or target, for example the stemloop of the direct repeat sequence.

In particular embodiments, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-10 and Y2-10 (wherein X and Y represent any complementary set of nucleotides) may be contemplated. In one aspect, the stem made of the X and Y nucleotides, together with the loop will form a complete hairpin in the overall secondary structure; and, this may be advantageous and the amount of base pairs can be any amount that forms a complete hairpin. In one aspect, any complementary X:Y basepairing sequence (e.g., as to length) is tolerated, so long as the secondary structure of the entire guide molecule is preserved. In one aspect, the loop that connects the stem made of X:Y basepairs can be any sequence of the same length (e.g., 4 or 5 nucleotides) or longer that does not interrupt the overall secondary structure of the guide molecule. In one aspect, the stemloop can further comprise, e.g. an MS2 aptamer. In one aspect, the stem comprises about 5-7 bp comprising complementary X and Y sequences, although stems of more or fewer basepairs are also contemplated. In one aspect, non-Watson Crick basepairing is contemplated, where such pairing otherwise generally preserves the architecture of the stemloop at that position.

In particular embodiments the natural hairpin or stemloop structure of the guide molecule is extended or replaced by an extended stemloop. It has been demonstrated that extension of the stem can enhance the assembly of the guide molecule with the CRISPR-Cas protein (Chen et al. Cell. (2013); 155(7): 1479-1491). In particular embodiments the stem of the stemloop is extended by at least 1, 2, 3, 4, 5 or more complementary basepairs (i.e. corresponding to the addition of 2, 4, 6, 8, 10 or more nucleotides in the guide molecule). In particular embodiments these are located at the end of the stem, adjacent to the loop of the stemloop.

In particular embodiments, the susceptibility of the guide molecule to RNAses or to decreased expression can be reduced by slight modifications of the sequence of the guide molecule which do not affect its function. For instance, in particular embodiments, premature termination of transcription, such as premature transcription of U6 Pol-III, can be removed by modifying a putative Pol-III terminator (4 consecutive U's) in the guide molecules sequence. Where such sequence modification is required in the stemloop of the guide molecule, it is preferably ensured by a basepair flip.

In a particular embodiment the direct repeat may be modified to comprise one or more protein-binding RNA aptamers. In a particular embodiment, one or more aptamers may be included such as part of optimized secondary structure. Such aptamers may be capable of binding a bacteriophage coat protein as detailed further herein.

In some embodiments, the guide molecule forms a duplex with a target RNA comprising at least one target cytosine residue to be edited. Upon hybridization of the guide RNA molecule to the target RNA, the cytidine deaminase binds to the single strand RNA in the duplex made accessible by the mismatch in the guide sequence and catalyzes deamination of one or more target cytosine residues comprised within the stretch of mismatching nucleotides.

A guide sequence, and hence a nucleic acid-targeting guide RNA may be selected to target any target nucleic acid sequence. The target sequence may be mRNA.

In certain embodiments, the target sequence should be associated with a PAM (protospacer adjacent motif) or PFS (protospacer flanking sequence or site); that is, a short sequence recognized by the CRISPR complex. Depending on the nature of the CRISPR-Cas protein, the target sequence should be selected such that its complementary sequence in the DNA duplex (also referred to herein as the non-target sequence) is upstream or downstream of the PAM. In the embodiments of the present invention where the CRISPR-Cas protein is a Cas13 protein, the complementary sequence of the target sequence is downstream or 3' of the PAM or upstream or 5' of the PAM. The precise sequence and length requirements for the PAM differ depending on the Cas13 protein used, but PAMs are typically 2-5 base pair sequences adjacent the protospacer (that is, the target sequence). Examples of the natural PAM sequences for different Cas13 orthologues are provided herein below and the skilled person will be able to identify further PAM sequences for use with a given Cas13 protein.

Further, engineering of the PAM Interacting (PI) domain may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523 (7561):481-5. doi: 10.1038/nature14592. As further detailed herein, the skilled person will understand that Cas13 proteins may be modified analogously.

In particular embodiment, the guide is an escorted guide. By "escorted" is meant that the CRISPR-Cas system or complex or guide is delivered to a selected time or place within a cell, so that activity of the CRISPR-Cas system or complex or guide is spatially or temporally controlled. For example, the activity and destination of the 3 CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time.

The escorted CRISPR-Cas systems or complexes have a guide molecule with a functional structure designed to improve guide molecule structure, architecture, stability, genetic expression, or any combination thereof. Such a structure can include an aptamer.

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928.). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

Accordingly, in particular embodiments, the guide molecule is modified, e.g., by one or more aptamer(s) designed to improve guide molecule delivery, including delivery across the cellular membrane, to intracellular compartments, or into the nucleus. Such a structure can include, either in addition to the one or more aptamer(s) or without such one or more aptamer(s), moiety(ies) so as to render the guide molecule deliverable, inducible or responsive to a selected effector. The invention accordingly comprehends an guide molecule that responds to normal or pathological physiological conditions, including without limitation pH, hypoxia, $O_2$ concentration, temperature, protein concentration, enzymatic concentration, lipid structure, light exposure, mechanical disruption (e.g. ultrasound waves), magnetic fields, electric fields, or electromagnetic radiation.

Light responsiveness of an inducible system may be achieved via the activation and binding of cryptochrome-2 and CIB1. Blue light stimulation induces an activating conformational change in cryptochrome-2, resulting in recruitment of its binding partner CIB1. This binding is fast and reversible, achieving saturation in <15 sec following pulsed stimulation and returning to baseline <15 min after the end of stimulation. These rapid binding kinetics result in a system temporally bound only by the speed of transcription/translation and transcript/protein degradation, rather than uptake and clearance of inducing agents. Crytochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

The invention contemplates energy sources such as electromagnetic radiation, sound energy or thermal energy to induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 mW/cm$^2$. In a preferred embodiment, a stimulation paradigm of as low as 0.25 sec every 15 sec should result in maximal activation.

The chemical or energy sensitive guide may undergo a conformational change upon induction by the binding of a chemical source or by the energy allowing it act as a guide and have the Cas13 CRISPR-Cas system or complex function. The invention can involve applying the chemical source or energy so as to have the guide function and the Cas13 CRISPR-Cas system or complex function; and optionally further determining that the expression of the genomic locus is altered.

There are several different designs of this chemical inducible system: 1. ABI-PYL based system inducible by Abscisic Acid (ABA) (see, e.g., stke.sciencemag.org/cgi/content/abstract/sigtrans;4/164/rs2), 2. FKBP-FRB based system inducible by rapamycin (or related chemicals based on rapamycin) (see, e.g., www.nature.com/nmeth/journal/v2/n6/full/nmeth763.html), 3. GID1-GAI based system inducible by Gibberellin (GA) (see, e.g., www.nature.com/nchembio/journal/v8/n5/full/nchembio.922.html).

A chemical inducible system can be an estrogen receptor (ER) based system inducible by 4-hydroxytamoxifen (4OHT) (see, e.g., www.pnas.org/content/104/3/1027.abstract). A mutated ligand-binding domain of the estrogen receptor called ERT2 translocates into the nucleus of cells upon binding of 4-hydroxytamoxifen. In further embodiments of the invention any naturally occurring or engineered derivative of any nuclear receptor, thyroid hormone receptor, retinoic acid receptor, estrogren receptor, estrogen-related receptor, glucocorticoid receptor, progesterone receptor, androgen receptor may be used in inducible systems analogous to the ER based inducible system.

Another inducible system is based on the design using Transient receptor potential (TRP) ion channel based system inducible by energy, heat or radio-wave (see, e.g., www.sciencemag.org/content/336/6081/604). These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the Cas13 CRISPR-Cas complex or system, and the binding will induce the change of sub-cellular localization of the polypeptide, leading to the entire polypeptide entering the nucleus of cells. Once inside the nucleus, the guide protein and the other components of the Cas13 CRISPR-Cas complex will be active and modulating target gene expression in cells.

While light activation may be an advantageous embodiment, sometimes it may be disadvantageous especially for in vivo applications in which the light may not penetrate the skin or other organs. In this instance, other methods of energy activation are contemplated, in particular, electric field energy and/or ultrasound which have a similar effect.

Electric field energy is preferably administered substantially as described in the art, using one or more electric pulses of from about 1 Volt/cm to about 10 kVolts/cm under in vivo conditions. Instead of or in addition to the pulses, the electric field may be delivered in a continuous manner. The electric pulse may be applied for between 1 μs and 500 milliseconds, preferably between 1 μs and 100 milliseconds. The electric field may be applied continuously or in a pulsed manner for 5 about minutes.

As used herein, 'electric field energy' is the electrical energy to which a cell is exposed. Preferably the electric field has a strength of from about 1 Volt/cm to about 10 kVolts/cm or more under in vivo conditions (see WO97/49450).

As used herein, the term "electric field" includes one or more pulses at variable capacitance and voltage and including exponential and/or square wave and/or modulated wave and/or modulated square wave forms. References to electric fields and electricity should be taken to include reference the presence of an electric potential difference in the environment of a cell. Such an environment may be set up by way of static electricity, alternating current (AC), direct current (DC), etc, as known in the art. The electric field may be uniform, non-uniform or otherwise, and may vary in strength and/or direction in a time dependent manner.

Single or multiple applications of electric field, as well as single or multiple applications of ultrasound are also possible, in any order and in any combination. The ultrasound and/or the electric field may be delivered as single or multiple continuous applications, or as pulses (pulsatile delivery).

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of Genetronics, Inc (see U.S. Pat. No. 5,869,326).

The known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100.mu.s duration. Such a pulse may be generated, for example, in known applications of the Electro Square Porator T820.

Preferably, the electric field has a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800 V/cm, 900 V/cm, 1 kV/cm, 2 kV/cm, 5 kV/cm, 10 kV/cm, 20 kV/cm, 50 kV/cm or more. More preferably from about 0.5 kV/cm to about 4.0 kV/cm under in vitro conditions. Preferably the electric field has a strength of from about 1 V/cm to about 10 kV/cm under in vivo conditions. However, the electric field strengths may be lowered where the number of pulses delivered to the target site are increased. Thus, pulsatile delivery of electric fields at lower field strengths is envisaged.

Preferably the application of the electric field is in the form of multiple pulses such as double pulses of the same strength and capacitance or sequential pulses of varying strength and/or capacitance. As used herein, the term "pulse" includes one or more electric pulses at variable capacitance and voltage and including exponential and/or square wave and/or modulated wave/square wave forms.

Preferably the electric pulse is delivered as a waveform selected from an exponential wave form, a square wave form, a modulated wave form and a modulated square wave form.

A preferred embodiment employs direct current at low voltage. Thus, Applicants disclose the use of an electric field which is applied to the cell, tissue or tissue mass at a field strength of between 1V/cm and 20V/cm, for a period of 100 milliseconds or more, preferably 15 minutes or more.

Ultrasound is advantageously administered at a power level of from about 0.05 W/cm2 to about 100 W/cm2. Diagnostic or therapeutic ultrasound may be used, or combinations thereof.

As used herein, the term "ultrasound" refers to a form of energy which consists of mechanical vibrations the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz' (From Ultrasonics in Clinical Diagnosis, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound is typically used in an energy density range of up to about 100 mW/cm2 (FDA recommendation), although energy densities of up to 750 mW/cm2 have been used. In physiotherapy, ultrasound is typically used as an energy source in a range up to about 3 to 4 W/cm2 (WHO recommendation). In other therapeutic applications, higher intensities of ultrasound may be employed, for example, HIFU at 100 W/cm up to 1 kW/cm2 (or even higher) for short periods of time. The term "ultrasound" as used in this specification is intended to encompass diagnostic, therapeutic and focused ultrasound.

Focused ultrasound (FUS) allows thermal energy to be delivered without an invasive probe (see Morocz et al 1998 Journal of Magnetic Resonance Imaging Vol. 8, No. 1, pp. 136-142. Another form of focused ultrasound is high intensity focused ultrasound (HIFU) which is reviewed by Moussatov et al in Ultrasonics (1998) Vol. 36, No. 8, pp. 893-900 and TranHuuHue et al in Acustica (1997) Vol. 83, No. 6, pp. 1103-1106.

Preferably, a combination of diagnostic ultrasound and a therapeutic ultrasound is employed. This combination is not intended to be limiting, however, and the skilled reader will appreciate that any variety of combinations of ultrasound may be used. Additionally, the energy density, frequency of ultrasound, and period of exposure may be varied.

Preferably the exposure to an ultrasound energy source is at a power density of from about 0.05 to about 100 Wcm-2. Even more preferably, the exposure to an ultrasound energy source is at a power density of from about 1 to about 15 Wcm-2.

Preferably the exposure to an ultrasound energy source is at a frequency of from about 0.015 to about 10.0 MHz. More preferably the exposure to an ultrasound energy source is at a frequency of from about 0.02 to about 5.0 MHz or about 6.0 MHz. Most preferably, the ultrasound is applied at a frequency of 3 MHz.

Preferably the exposure is for periods of from about 10 milliseconds to about 60 minutes. Preferably the exposure is for periods of from about 1 second to about 5 minutes. More preferably, the ultrasound is applied for about 2 minutes. Depending on the particular target cell to be disrupted, however, the exposure may be for a longer duration, for example, for 15 minutes.

Advantageously, the target tissue is exposed to an ultrasound energy source at an acoustic power density of from about 0.05 Wcm-2 to about 10 Wcm-2 with a frequency ranging from about 0.015 to about 10 MHz (see WO 98/52609). However, alternatives are also possible, for example, exposure to an ultrasound energy source at an acoustic power density of above 100 Wcm-2, but for reduced periods of time, for example, 1000 Wcm-2 for periods in the millisecond range or less.

Preferably the application of the ultrasound is in the form of multiple pulses; thus, both continuous wave and pulsed wave (pulsatile delivery of ultrasound) may be employed in any combination. For example, continuous wave ultrasound may be applied, followed by pulsed wave ultrasound, or vice versa. This may be repeated any number of times, in any order and combination. The pulsed wave ultrasound may be applied against a background of continuous wave ultrasound, and any number of pulses may be used in any number of groups.

Preferably, the ultrasound may comprise pulsed wave ultrasound. In a highly preferred embodiment, the ultrasound is applied at a power density of 0.7 Wcm-2 or 1.25 Wcm-2 as a continuous wave. Higher power densities may be employed if pulsed wave ultrasound is used.

Use of ultrasound is advantageous as, like light, it may be focused accurately on a target. Moreover, ultrasound is advantageous as it may be focused more deeply into tissues unlike light. It is therefore better suited to whole-tissue penetration (such as but not limited to a lobe of the liver) or whole organ (such as but not limited to the entire liver or an entire muscle, such as the heart) therapy. Another important advantage is that ultrasound is a non-invasive stimulus which is used in a wide variety of diagnostic and therapeutic applications. By way of example, ultrasound is well known in medical imaging techniques and, additionally, in orthopedic therapy. Furthermore, instruments suitable for the application of ultrasound to a subject vertebrate are widely available and their use is well known in the art.

In particular embodiments, the guide molecule is modified by a secondary structure to increase the specificity of the CRISPR-Cas system and the secondary structure can protect against exonuclease activity and allow for 5' additions to the guide sequence also referred to herein as a protected guide molecule.

In one aspect, the invention provides for hybridizing a "protector RNA" to a sequence of the guide molecule, wherein the "protector RNA" is an RNA strand complementary to the 3' end of the guide molecule to thereby generate a partially double-stranded guide RNA. In an embodiment of the invention, protecting mismatched bases (i.e. the bases of the guide molecule which do not form part of the guide sequence) with a perfectly complementary protector sequence decreases the likelihood of target RNA binding to the mismatched basepairs at the 3' end. In particular embodiments of the invention, additional sequences comprising an extended length may also be present within the guide molecule such that the guide comprises a protector sequence within the guide molecule. This "protector sequence" ensures that the guide molecule comprises a "protected sequence" in addition to an "exposed sequence" (comprising the part of the guide sequence hybridizing to the target sequence). In particular embodiments, the guide molecule is modified by the presence of the protector guide to comprise a secondary structure such as a hairpin. Advantageously there are three or four to thirty or more, e.g., about 10 or more, contiguous base pairs having complementarity to the protected sequence, the guide sequence or both. It is advantageous that the protected portion does not impede thermodynamics of the CRISPR-Cas system interacting with its target. By providing such an extension including a partially double stranded guide molecule, the guide molecule is considered protected and results in improved specific binding of the CRISPR-Cas complex, while maintaining specific activity.

In particular embodiments, use is made of a truncated guide (tru-guide), i.e. a guide molecule which comprises a guide sequence which is truncated in length with respect to the canonical guide sequence length. As described by Nowak et al. (Nucleic Acids Res (2016) 44 (20): 9555-9564), such guides may allow catalytically active CRISPR-Cas enzyme to bind its target without cleaving the target RNA. In particular embodiments, a truncated guide is used which allows the binding of the target but retains only nickase activity of the CRISPR-Cas enzyme.

The present invention may be further illustrated and extended based on aspects of CRISPR-Cas development and use as set forth in the following articles and particularly as relates to delivery of a CRISPR protein complex and uses of an RNA guided endonuclease in cells and organisms:

Multiplex genome engineering using CRISPR-Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR-Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Nature12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, LA., Bao, G., & Zhang, F. Nat Biotechnol doi:10.1038/nbt.2647 (2013);

Genome engineering using the CRISPR-Cas9 system. Ran, FA., Hsu, PD., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013);

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR-Cas9 system, Wang T, Wei J J, Sabatini D M, Lander E S., Science. January 3; 343(6166): 80-84. doi:10.1126/science.1246981(2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh 00, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546):186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR-Cas9 cleavage of viral DNA efficiently suppresses hepatitis B virus," Scientific Reports 5:10833. doi: 10.1038/srep10833 (Jun. 2, 2015)

Nishimasu et al., Crystal Structure of *Staphylococcus aureus* Cas9," Cell 162, 1113-1126 (Aug. 27, 2015)

BCL11A enhancer dissection by Cas9-mediated in situ saturating mutagenesis, Canver et al., Nature 527(7577): 192-7 (Nov. 12, 2015) doi: 10.1038/nature15521. Epub 2015 September 16.

*Cpf1 Is a Single RNA-Guided Endonuclease of a Class 2 CRISPR-Cas System*, Zetsche et al., Cell 163, 759-71 (Sep. 25, 2015).

*Discovery and Functional Characterization of Diverse Class 2 CRISPR-Cas Systems*, Shmakov et al., Molecular Cell, 60(3), 385-397 doi: 10.1016/j.molcel.2015.10.008 Epub Oct. 22, 2015.

*Rationally engineered Cas9 nucleases with improved specificity*, Slaymaker et al., Science 2016 Jan. 1 351(6268): 84-88 doi: 10.1126/science.aad5227. Epub 2015 Dec. 1.

Gao et al, "Engineered Cpf1 Enzymes with Altered PAM Specificities," bioRxiv 091611; doi: http://dx.doi.org/10.1101/091611 (Dec. 4, 2016).

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR-Cas system for the one-step generation of mice carrying mutations in multiple genes which were traditionally generated in multiple steps by sequential recombination in embryonic stem cells and/or time-consuming intercrossing of mice with a single mutation. The CRISPR-Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and guide RNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knock-out (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knock-out approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR-Cas9 knockout and nucleotide preference at the cleavage site. The authors also found that the sequence preference for CRISPRi/a is substantially different from that for CRISPR-Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements. The authors Applicants developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from *Francisella novicida* U112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al (2016) reported the use of structure-guided protein engineering to improve the specificity of *Streptococcus pyogenes* Cas9 (SpCas9). The authors developed "enhanced specificity" SpCas9 (eSpCas9) variants which maintained robust on-target cleavage with reduced off-target effects.

The methods and tools provided herein are may be designed for use with or Cas13, a type II nuclease that does not make use of tracrRNA. Orthologs of Cas13 have been identified in different bacterial species as described herein. Further type II nucleases with similar properties can be identified using methods described in the art (Shmakov et al. 2015, 60:385-397; Abudayeh et al. 2016, Science, 5; 353 (6299)). In particular embodiments, such methods for identifying novel CRISPR effector proteins may comprise the steps of selecting sequences from the database encoding a seed which identifies the presence of a CRISPR Cas locus, identifying loci located within 10 kb of the seed comprising Open Reading Frames (ORFs) in the selected sequences, selecting therefrom loci comprising ORFs of which only a single ORF encodes a novel CRISPR effector having greater than 700 amino acids and no more than 90% homology to a known CRISPR effector. In particular embodiments, the seed is a protein that is common to the CRISPR-Cas system, such as Cas1. In further embodiments, the CRISPR array is used as a seed to identify new effector proteins.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

With respect to general information on CRISPR/Cas Systems, components thereof, and delivery of such components, including methods, materials, delivery vehicles, vectors, particles, and making and using thereof, including as to amounts and formulations, as well as CRISPR-Cas-expressing eukaryotic cells, CRISPR-Cas expressing eukaryotes, such as a mouse, reference is made to: U.S. Pat. Nos. 8,999,641, 8,993,233, 8,697,359, 8,771,945, 8,795,965, 8,865,406, 8,871,445, 8,889,356, 8,889,418, 8,895,308, 8,906,616, 8,932,814, and 8,945,839; US Patent Publications US 2014-0310830 (U.S. application Ser. No. 14/105, 031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256, 912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); Ser. No. 14/054,414 European Patent Applications EP 2 771 468 (EP13818570.7), EP 2 764 103 (EP13824232.6), and EP 2 784 162 (EP14170383.5); and PCT Patent Publications WO2014/093661 (PCT/US2013/074743), WO2014/093694 (PCT/US2013/074790), WO2014/093595 (PCT/US2013/074611), WO2014/093718 (PCT/US2013/074825), WO2014/093709 (PCT/US2013/074812), WO2014/093622 (PCT/US2013/074667), WO2014/093635 (PCT/US2013/074691), WO2014/093655 (PCT/US2013/074736), WO2014/093712 (PCT/US2013/074819), WO2014/093701 (PCT/US2013/074800), WO2014/018423 (PCT/US2013/051418), WO2014/204723 (PCT/US2014/041790), WO2014/204724 (PCT/US2014/041800), WO2014/204725 (PCT/US2014/041803), WO2014/204726 (PCT/US2014/041804), WO2014/204727 (PCT/US2014/041806), WO2014/204728 (PCT/US2014/041808), WO2014/204729 (PCT/US2014/041809), WO2015/089351 (PCT/US2014/069897), WO2015/089354 (PCT/US2014/069902), WO2015/089364 (PCT/US2014/069925), WO2015/089427 (PCT/US2014/070068), WO2015/089462 (PCT/US2014/070127), WO2015/089419 (PCT/US2014/070057), WO2015/089465 (PCT/US2014/070135), WO2015/089486 (PCT/US2014/070175), WO2015/058052 (PCT/US2014/061077), WO2015/070083 (PCT/US2014/064663), WO2015/089354 (PCT/US2014/069902), WO2015/089351 (PCT/US2014/069897), WO2015/089364 (PCT/US2014/069925), WO2015/089427 (PCT/US2014/070068), WO2015/089473 (PCT/US2014/070152), WO2015/089486 (PCT/US2014/070175), WO2016/049258 (PCT/US2015/051830), WO2016/094867 (PCT/US2015/065385), WO2016/094872 (PCT/US2015/065393), WO2016/094874 (PCT/US2015/065396), WO2016/106244 (PCT/US2015/067177).

Mention is also made of U.S. application 62/180,709, 17 Jun. 2015, PROTECTED GUIDE RNAS (PGRNAS); U.S.

application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. application 62/091,462, 12 Dec. 2014, 62/096,324, 23 Dec. 2014, 62/180,681, 17 Jun. 2015, and 62/237,496, 5 Oct. 2015, DEAD GUIDES FOR CRISPR TRANSCRIPTION FACTORS; U.S. application 62/091,456, 12 Dec. 2014 and 62/180,692, 17 Jun. 2015, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, 62/181,641, 18 Jun. 2015, and 62/181,667, 18 Jun. 2015, RNA-TARGETING SYSTEM; U.S. application 62/096,656, 24 Dec. 2014 and 62/181,151, 17 Jun. 2015, CRISPR HAVING OR ASSOCIATED WITH DESTABILIZATION DOMAINS; U.S. application 62/096,697, 24 Dec. 2014, CRISPR HAVING OR ASSOCIATED WITH AAV; U.S. application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 61/939,154, 12 Feb. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/054,675, 24 Sep. 2014 and 62/181,002, 17 Jun. 2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014 and 62/181,690, 18 Jun. 2015, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014 and 62/181,687, 18 Jun. 2015, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Mention is made of U.S. application 62/181,659, 18 Jun. 2015 and 62/207,318, 19 Aug. 2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of U.S. application 62/181,663, 18 Jun. 2015 and 62/245,264, 22 Oct. 2015, NOVEL CRISPR ENZYMES AND SYSTEMS, U.S. application 62/181,675, 18 Jun. 2015, 62/285,349, 22 Oct. 2015, 62/296,522, 17 Feb. 2016, and 62/320,231, 8 Apr. 2016, NOVEL CRISPR ENZYMES AND SYSTEMS, U.S. application 62/232,067, 24 Sep. 2015, U.S. application Ser. No. 14/975,085, 18 Dec. 2015, European application No. 16150428.7, U.S. application 62/205,733, 16 Aug. 2015, U.S. application 62/201,542, 5 Aug. 2015, U.S. application 62/193,507, 16 Jul. 2015, and U.S. application 62/181,739, 18 Jun. 2015, each entitled NOVEL CRISPR ENZYMES AND SYSTEMS and of U.S. application 62/245,270, 22 Oct. 2015, NOVEL CRISPR ENZYMES AND SYSTEMS. Mention is also made of U.S. application 61/939,256, 12 Feb. 2014, and WO 2015/089473 (PCT/US2014/070152), 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, 15 Aug. 2015, U.S. application 62/180,699, 17 Jun. 2015, and U.S. application 62/038,358, 17 Aug. 2014, each entitled GENOME EDITING USING CAS9 NICKASES.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Tale Systems

As disclosed herein editing can be made by way of the transcription activator-like effector nucleases (TALENs) system. Transcription activator-like effectors (TALEs) can be engineered to bind practically any desired DNA sequence. Exemplary methods of genome editing using the TALEN system can be found for example in Cermak T. Doyle E L. Christian M. Wang L. Zhang Y. Schmidt C, et al. Efficient design and assembly of custom TALEN and other TAL effector-based constructs for DNA targeting. Nucleic Acids Res. 2011; 39:e82; Zhang F. Cong L. Lodato S. Kosuri S. Church G M. Arlotta P Efficient construction of sequence-specific TAL effectors for modulating mammalian transcription. Nat Biotechnol. 2011; 29:149-153 and U.S. Pat. Nos. 8,450,471, 8,440,431 and 8,440,432, all of which are specifically incorporated by reference.

In advantageous embodiments of the invention, the methods provided herein use isolated, non-naturally occurring, recombinant or engineered DNA binding proteins that comprise TALE monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", or "TALE monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is X1-11-(X12X13)-X14-33 or 34 or 35, where the subscript indicates the amino acid position and X represents any amino acid. X12X13 indicate the RVDs. In some polypeptide monomers, the variable amino acid at position 13 is missing or absent and in such polypeptide monomers, the RVD consists of a single amino acid. In such cases the RVD may be alternatively represented as X*, where X represents X12 and (*) indicates that X13 is absent. The DNA binding domain comprises several repeats of TALE monomers and this may be represented as (X1-11-(X12X13)-X14-33 or 34 or 35)z, where in an advantageous embodiment, z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), polypeptide monomers with an RVD of NG preferentially bind to thymine (T), polypeptide monomers with an RVD of HD preferentially bind to cytosine (C) and polypeptide monomers with an RVD of NN preferentially bind to both adenine (A) and guanine (G). In yet another embodiment of the invention, polypeptide monomers with an RVD of IG preferentially bind to T. Thus, the number and order of the polypeptide monomer repeats in the nucleic acid binding domain of a TALE determines its nucleic acid target specificity. In still further embodiments of the invention, polypeptide monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

The TALE polypeptides used in methods of the invention are isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In a preferred embodiment of the invention, polypeptide monomers having RVDs RN, NN, NK, SN, NH, KN, IN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of TALE polypeptides with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of TALE polypeptides with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine. In more preferred embodiments of the invention, polypeptide monomers having RVDs of H*, HA, KA, N*, NA, NC, NS, RA, and S* bind to adenine, guanine, cytosine and thymine with comparable affinity.

The predetermined N-terminal to C-terminal order of the one or more polypeptide monomers of the nucleic acid or DNA binding domain determines the corresponding predetermined target nucleic acid sequence to which the TALE polypeptides will bind. As used herein the polypeptide monomers and at least one or more half polypeptide monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases this region may be referred to as repeat 0. In animal genomes, TALE binding sites do not necessarily have to begin with a thymine (T) and TALE polypeptides may target DNA sequences that begin with T, A, G or C. The tandem repeat of TALE monomers always ends with a half-length repeat or a stretch of sequence that may share identity with only the first 20 amino acids of a repetitive full length TALE monomer and this half repeat may be referred to as a half-monomer (FIG. 8), which is included in the term "TALE monomer". Therefore, it follows that the length of the nucleic acid or DNA being targeted is equal to the number of full polypeptide monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

(SEQ. I.D. No. 69)
M D P I R S R T P S P A R E L L S G P Q P D G V Q

P T A D R G V S P P A G G P L D G L P A R R T M S

R T R L P S P P A P S P A F S A D S F S D L L R Q

F D P S L F N T S L F D S L P P F G A H H T E A A

T G E W D E V Q S G L R A A D A P P P T M R V A V

T A A R P P R A K P A P R R R A A Q P S D A S P A

A Q V D L R T L G Y S Q Q Q Q E K I K P K V R S T

V A Q H H E A L V G H G F T H A H I V A L S Q H P

A A L G T V A V K Y Q D M I A A L P E A T H E A I

V G V G K Q W S G A R A L E A L L T V A G E L R G

P P L Q L D T G Q L L K I A K R G G V T A V E A V

H A W R N A L T G A P L N

An exemplary amino acid sequence of a C-terminal capping region is:

(SEQ. I.D. No. 70)
R P A L E S I V A Q L S R P D P A L A A L T N D H

L V A L A C L G G R P A L D A V K K G L P H A P A

L I K R T N R R I P E R T S H R V A D H A Q V V R

V L G F F Q C H S H P A Q A F D D A M T Q F G M S

R H G L L Q L F R R V G V T E L E A R S G T L P P

A S Q R W D R I L Q A S G M K R A K P S P T S T Q

T P D Q A S L H A F A D S L E R D L D A P S P M H

E G D Q T R A S

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full length capping region, while fragments that include the C-terminal 20 amino acids retain greater than 50% of the efficacy of the full length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies may be generated by any of a number of computer programs known in the art, which include but are not limited to BLAST or FASTA. Suitable computer program for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In advantageous embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4X domain or a Krüppel-associated box (KRAB) or fragments of the KRAB domain. In some embodiments the effector domain is an enhancer of transcription (i.e. an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

ZN-Finger Nucleases

Other preferred tools for genome editing for use in the context of this invention include zinc finger systems and TALE systems. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

Meganucleases

As disclosed herein editing can be made by way of meganucleases, which are endodeoxyribonucleases characterized by a large recognition site (double-stranded DNA sequences of 12 to 40 base pairs). Exemplary method for using meganucleases can be found in U.S. Pat. Nos. 8,163, 514; 8,133,697; 8,021,867; 8,119,361; 8,119,381; 8,124, 369; and 8,129,134, which are specifically incorporated by reference.

In certain embodiments, the invention involves targeted nucleic acid profiling (e.g., sequencing, quantitative reverse transcription polymerase chain reaction, and the like) (see e.g., Geiss G K, et al., Direct multiplexed measurement of gene expression with color-coded probe pairs. Nat Biotechnol. 2008 March; 26(3):317-25). In certain embodiments, a target nucleic acid molecule (e.g., RNA molecule), may be sequenced by any method known in the art, for example, methods of high-throughput sequencing, also known as next generation sequencing or deep sequencing. A nucleic acid target molecule labeled with a barcode (for example, an origin-specific barcode) can be sequenced with the barcode to produce a single read and/or contig containing the sequence, or portions thereof, of both the target molecule and the barcode. Exemplary next generation sequencing technologies include, for example, Illumina sequencing, Ion Torrent sequencing, 454 sequencing, SOLiD sequencing, and nanopore sequencing amongst others.

In certain embodiments, the invention involves plate based single cell RNA sequencing (see, e.g., Picelli, S. et al., 2014, "Full-length RNA-seq from single cells using Smart-seq2" Nature protocols 9, 171-181, doi:10.1038/nprot.2014.006).

In certain embodiments, the invention involves high-throughput single-cell RNA-seq and/or targeted nucleic acid profiling (for example, sequencing, quantitative reverse transcription polymerase chain reaction, and the like) where the RNAs from different cells are tagged individually, allowing a single library to be created while retaining the cell identity of each read. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; and Gierahn et al., "Seq-Well: portable, low-cost RNA sequencing of single cells at high throughput" Nature Methods 14, 395-398 (2017), all the contents and disclosure of each of which are herein incorporated by reference in their entirety.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14(10):955-958; and International patent application number PCT/US2016/059239, published as WO2017164936 on Sep. 28, 2017, which are herein incorporated by reference in their entirety.

The invention is further described in the following examples, which do not limit the scope of the invention described in the claims.

EXAMPLES

Example 1

Methods

Mice and in vivo ILC activation. C57Bl/6J mice were purchased from the Jackson Laboratory. Nmur1-LacZ reporter mice with a LacZ cassette knocked into the Nmur1 locus were rederived from Nmur1$^{tm1.1(KOMP)Vleg}$ sperm obtained from the trans-NIH Knock-Out Mouse Project (KOMP) Repository. Mice were housed under specific-pathogen-free conditions. For experiments, mice were matched for sex and age, and most mice were 6-10 weeks old. Where indicated, mice were anesthetized with Isoflurane and treated intranasally with the indicated stimuli (500 ng IL-25, 500 ng IL-33, or 20 µg Neuromedin U) daily for three consecutive days. The total administered volume was 20 µl for all conditions. Mice received 250 ng IL-33 and 10 µg Neuromedin U in the experiment shown in FIG. 11. Mice were randomly assigned to treatment groups after matching for sex and age. Airway inflammation was also induced with house dust mite (HDM) extract (Greer Laboratories). Mice were treated intranasally with 10 µg HDM on day 0, 7, 8, and 9, prior to sacrifice on day 10. All experiments were conducted in accordance with animal protocols approved by the Harvard Medical Area Standing Committee on Animals or BWH IACUC.

Flow cytometry. The following antibodies were used: CD45 (clone: 30-F11), CD90.2 (clone: 30-H12), CD127 (clone: A7R34), ST2 (clone: DIH9), 7AAD, CD11b (clone: M1/70), CD11 c (clone: N418), CD19 (clone: 6D5), NK1.1 (clone: PK136), CD3ε (clone: 145-2C11), CD4 (clone: RM4-5), CD8a (clone: 53-6.7), TCRβ (clone: H57-597), TCRγδ (clone: GL3), Siglec-F (clone: E50-2440), IL17RB (clone: Munc33), Fixable Viability Dye eFluor 506. All antibodies were purchased from BioLegend, except 7-AAD (BD Pharmingen), Siglec-F (BD Bioscience), IL17RB (eBioscience) and Fixable Viability Dye eFluor 506 (eBioscience). Cells were stained on ice with antibodies for surface molecules and the live/dead marker 7AAD and analyzed on a LSRFortessa (BD Biosciences). Different cell types were identified by the following gating strategies: ST2$^+$ ILCs (7AAD–CD45$^+$ CD4– Lineage-CD90.2$^+$ CD127$^+$ ST2$^+$), T cells (7AAD– CD45$^+$ CD4$^+$), B cells (7AAD–CD45$^+$ CD19$^+$), eosinophils (7AAD–CD45$^+$ CD11 b$^+$ CD11c$^{low}$ Siglec-F$^+$ SSC$^{high}$), neutrophils (7AAD$^-$ CD45$^+$ CD11 c$^{low}$ CD11b$^+$ Ly6G$^+$ CD 11b$^+$), alveolar macrophages (7AAD–CD45$^+$ CD11c$^{high}$ CD 11b$^{intermediate}$) and CD45– cells (7AAD– CD45$^-$).

Lung analysis. Mice were sacrificed and perfused with cold PBS. Where indicated, after perfusion, broncho alveolar lavage (BAL) was obtained by injecting 1.5 ml cold PBS into the lungs via a secured tracheal cannula. BALF was centrifuged, and the supernatant was used for analyzing cytokine levels and the cell pellet was resuspended, counted, and used for flow cytometry. Following BAL, lung lobes were dissected. The post-caval lobe was fixed in buffered formalin for histological analysis. Single cell suspensions of the remaining lung parenchymal tissue were prepared with the GentleMACS lung dissociation kit (Miltenyi Biotec) according to the manufacturer's instructions. Where indicated, cells were diluted in 10% Trypan Blue and viable cells counted using a hemocytometer.

Fluorescence-activated cell sorting of innate lymphoid cells. After dissociation, single cell suspensions were incubated with CD90.2 MicroBeads (Miltenyi Biotec) on ice and enriched for CD90.2$^+$ cells by magnetic separation using LS columns according to the manufacturer's protocol. CD90.2$^+$ lung cells were then stained on ice with antibodies for sorting. ILCs were defined as 7AAD$^-$ CD45$^+$ CD90.2$^+$ CD127$^+$ Lineage (CD11b, CD11c, CD19, NK1.1, CD3ε, CD4, CD8a, TCRβ, TCRγδ)$^-$ cells and sorted on a BD FACS Aria (BD Biosciences).

RNA-Seq. For population (bulk) RNA-seq, sorted ILCs were lysed with RLT Plus buffer and RNA was extracted using the RNeasy Plus Mini Kit (Qiagen). Full-length RNA-seq libraries were prepared as previously described[1] and paired-end sequenced (75 bp×2) with a 150 cycle Nextseq 500 high output V2 kit.

For droplet-based 3' end massively parallel single-cell RNA sequencing (scRNA-seq), sorted ILCs were encapsulated into droplets, and libraries were prepared using Chromium™ Single Cell 3' Reagent Kits v2 according to manufacturer's protocol (10× Genomics). The generated scRNA-seq libraries were sequenced using a 75 cycle Nextseq 500 high output V2 kit.

For full-length scRNA-Seq, single ILCs were sorted into 96-well plates containing 5 µl TCL Buffer (QIAGEN) with 1% 2-Mercaptoethanol, centrifuged and frozen at –80° C. SMART-Seq2 protocol was carried out as previously described[2] with minor modifications in the reverse transcription step (M.S.K. and A.R., in preparation). cDNA was amplified with 22 cycles and tagmented with one-eighth of the standard Illumina NexteraXT reaction volume. Single-cell libraries were pooled and paired-end sequenced (38 bp×2) with a 75 cycle Nextseq 500 high output V2 kit. All RNA-Seq data represent pooled data from at least two distinct biological replicates.

ILC in vitro culture. For in vitro experiments 5,000 ILCs/well were cultured in a 96 well round bottom plate with 20 ng/ml IL-7 (R&D Systems), 200 ng/ml IL-33 (BioLegend) or 200 ng/ml IL-25 (R&D Systems) with or without 1 µg/ml Neuromedin U (US Biological). In some cases purified CD90.2$^+$ lung cells were first labeled with CellTrace Violet (Thermo Fisher Scientific), then sorted as described above, and cultured for 3 days under the indicated conditions.

Histology. Following paraffin embedding, sections of the formalin-fixed lung lobe were stained by H&E staining. Tissue sections were scored by a histopathologist in a blinded manner for severity of lung inflammation according to the following scoring system: 0=normal, 1=very mild, 2=mild, 3=moderate or 4=severe.

Methacholine challenge. Airway hyperresponsiveness was determined as previously described[3] using a flexiVent rodent ventilator (SciReq).

LacZ reporter assay. The Nmur1 null allele contains a LacZ reporter cassette. Single cell suspensions of lung cells from Nmur1-LacZ$^{+/-}$ mice were stained with the FluoReporter lacZ flow cytometry kit (Thermo Fisher Scientific) according to the manufacturer's protocol, except that propidium iodide and PETG were not used. Immediately after fluorescein di-V-galactoside (FDG) loading was stopped with 1.8 ml ice-cold medium, cells were stained with 7AAD and antibodies against surface markers and analyzed by flow cytometry.

Quantitative real-time PCR. RNA was isolated using RNeasy Plus Mini Kit (Qiagen) and reverse transcribed to cDNA with iScript cDNA Synthesis Kit (Bio-Rad). Gene expression was analyzed by quantitative real-time PCR on a ViiA7 System (Thermo Fisher Scientific) using TaqMan Fast Advanced Master Mix (Thermo Fisher Scientific) with the following primer/probe sets: IL-5 (Mm00439646_m1), IL-13 (Mm00434204_m1), IL-17RB (Mm00444709_m1), Nmur1 (Mm04207994 m1), Nmur2 (Mm00600704_m1), and β-Actin (Applied Biosystems). Expression values were calculated relative to β-Actin detected in the same sample by duplex qPCR.

Cytokine quantification. Cytokine concentrations in BAL fluid, lung and supernatant of in vitro ILC cultures were analyzed by the LegendPlex Mouse Th Cytokine Panel (13-plex) (BioLegend) according to the manufacturer's instructions and analyzed on a FACS Calibur (BD Biosciences).

T cell in vitro culture. CD4$^+$ T cells were isolated as described previously[4] and sorted for naive T cells (CD4$^+$ CD62L$^+$ CD44$^{low}$) on a FACS Aria. Naive T cells were cultured in the presence of plate-bound anti-CD3 (1 µg/ml; Bio X Cell) and anti-CD28 (1 µg/ml; Bio X Cell) antibodies. Th2 cells were generated by addition of 20 ng/ml IL-4 (Miltenyi Biotec) and 20 ng/ml anti-IFNγ (Bio X Cell) antibody. On day 3 of in vitro differentiation, PBS, 200 ng/ml IL-33 (BioLegend) or 100 ng/ml IL-25 (R&D Systems) were added to the T cell culture either with or without 1 µg/ml NMU (US Biological). After 2 additional days, RNA was isolated.

Statistical analysis of functional data. No data were excluded from analysis. Prism 7 (GraphPad Software) was used to perform two tailed Student's t-test and ordinary one-way ANOVA with Tukey's multiple comparisons test on datasets for which statistical significance is indicated (except the RNA-sequencing data). All figures of functional data show mean±SEM.

Analysis of droplet-based scRNA-Seq data: Initial QC. Gene counts were obtained by aligning reads to the mm10 genome using CellRanger software (10× Genomics), with the genome reannotated at the 3' end of Nmur1 (see main text). To remove doublets and poor-quality cells, cells were excluded from subsequent analysis if they were outliers in their sample of origin in terms of number of genes, number of UMIs, and percentage of mitochondrial genes (FIG. 5b,c). The number of UMIs per cell and number of genes expressed per cell are tightly correlated with condition (FIG. 5c), likely due to the effect of proliferation on transcript numbers (see main text). Sample-specific cutoffs ranged from 700-2,650 genes per cell for a PBS treated sample to 1,550-5,100 genes per cell for an IL-33 treated sample. At least 89% of cells were retained for each sample. Parts of the subsequent analysis utilized the R package Seurat[44], which includes sparse matrix support for large datasets. To normalize gene counts while accounting for widely varying UMI counts among conditions, Applicants used a scaling factor reflecting the expected number of UMIs in each condition. Let $w_{c,i}$ be the mean number of UMIs per cell in condition c, batch i. Seurat's LogNormalize ( ) function was called on cells from condition c with the scale factor argument set to:

$$10{,}000 \times (w_{c,i}/\mathrm{mean}_i(w_{control,i}))$$

Applicants refer to the output values as log TPX (as opposed to the default log TPM).

The 41,255 high quality cell profiles were combined into two (non-exclusive) groups, and, since initial analysis suggested the overall complexity was well captured by subsampling, each group was subsequently down-sampled and analyzed analogously.

Group A (9,138 cells) is a random sample of 40% of cells stimulated with PBS (3,568 cells), IL-25 (2,746 cells), or IL-33 (2,824 cells).

Group B (13,699 cells) is a random sample of 40% of cells stimulated with PBS (3,577 cells), NMU (3,734 cells), IL-25 (2,758), or NMU+IL-25 (3,630 cells).

Additional QC was performed on each group of samples to remove remaining outlier cells.

To verify that the dataset consists of ILCs, Applicants checked the raw counts for the expression of major markers of other immune cell groups (FIG. 5g).

Analysis of droplet-based scRNA-Seq samples: Signature scores. Applicants calculated signature scores as the log of the geometric mean of the TPX values for the genes in the signature. That is, let S be a set of m genes defining a signature, and for any gene g in S and a given cell, let $x_g$ be the expression of g in the cell in TPX. Then the signature score for that cell is calculated as $$\log(\Pi_g(x_g+1)^{1/m})$$

which is equivalent to the arithmetic mean of the log TPX values. The geometric mean lessens the impact of any specific gene's range of expression on the score. Actual expression values, rather than centered or z-scored expression values were used. For several of our signatures, centering (or z-scoring) expression values before computing signatures leads to misleading scores that are close to 0 across the whole dataset, though the corresponding gene expression is high. This is in large part due to ILC2s composing the majority of the cells that Applicants analyzed, and hence genes that are highly expressed by ILC2s lack sufficient variance over the data set to be useful in a mean-centered signature.

Applicants also deliberately did not replace these scores with a statistical comparison of them to randomized signatures selected from a null distribution (in contrast to our other studies[19,42]). Due to the varying proliferative responses in our cells, it is difficult to find a true null set of signatures, even after matching genes for dataset-wide mean and variance profiles. Signature scores are independent of the expression levels of unrelated genes in the same cell, similar to, but less noisy than, single-gene expression values.

The ILC subset signatures (ILC1, 2, 3 as used in FIGS. 1 and 2) were curated based on established markers for ILC subsets (Table 2). The proliferation signature was created by combining Applicants previously published gene signatures[18,19] that define G1-S and G2-M phases (Table 3). For both ILC subset and proliferative signatures, all genes contribute positively to the signature score. For the inflammatory ILC2 signature, genes contribute negatively to the score if they are down-regulated in NMU+IL-25 relative to IL-25 (and positively otherwise) (Table 6).

TABLE 2

| Signature | Sign | Gene |
|---|---|---|
| ILC1 | plus | Tbx21 |
| ILC1 | plus | Ifng |
| ILC1 | plus | Il21r |
| ILC1 | plus | Ccl5 |
| ILC1 | plus | Ccl4 |
| ILC1 | plus | Ccl3 |
| ILC1 | plus | Ncr1 |

TABLE 2-continued

| Signature | Sign | Gene |
| --- | --- | --- |
| ILC1 | plus | Il15r |
| ILC1 | plus | Eomes |
| ILC1 | plus | Cxcr3 |
| ILC1 | plus | Il12rb1 |
| ILC2 | plus | Gata3 |
| ILC2 | plus | Lmo4 |
| ILC2 | plus | Areg |
| ILC2 | plus | Ccl1 |
| ILC2 | plus | Csf2 |
| ILC2 | plus | Il4 |
| ILC2 | plus | Il5 |
| ILC2 | plus | Il13 |
| ILC2 | plus | Cxcl2 |
| ILC2 | plus | Il9 |
| ILC2 | plus | Il1rl1 |
| ILC2 | plus | Il9r |
| ILC2 | plus | Il17rb |
| ILC2 | plus | Klrg1 |
| ILC3 | plus | Rorc |
| ILC3 | plus | Tcf7 |
| ILC3 | plus | Batf3 |
| ILC3 | plus | Il17f |
| ILC3 | plus | Il17a |
| ILC3 | plus | Il22 |
| ILC3 | plus | Ncr1 |
| ILC3 | plus | Il1rl |
| ILC3 | plus | Ahr |
| ILC3 | plus | Il23r |
| ILC3 | plus | Cxcr5 |
| ILC3 | plus | Ccr6 |

TABLE 3

| Signature | Sign | Gene |
| --- | --- | --- |
| Proliferation | plus | Mcm5 |
| Proliferation | plus | Pcna |
| Proliferation | plus | Tyms |
| Proliferation | plus | Fen1 |
| Proliferation | plus | Mcm2 |
| Proliferation | plus | Mcm4 |
| Proliferation | plus | Rrm1 |
| Proliferation | plus | Ung |
| Proliferation | plus | Gins2 |
| Proliferation | plus | Mcm6 |
| Proliferation | plus | Cdca7 |
| Proliferation | plus | Dtl |
| Proliferation | plus | Prim1 |
| Proliferation | plus | Uhrf1 |
| Proliferation | plus | Mlf1ip |
| Proliferation | plus | Hells |
| Proliferation | plus | Rfc2 |
| Proliferation | plus | Rpa2 |
| Proliferation | plus | Nasp |
| Proliferation | plus | Rad51ap1 |
| Proliferation | plus | Gmnn |
| Proliferation | plus | Wdr76 |
| Proliferation | plus | Slbp |
| Proliferation | plus | Ccne2 |
| Proliferation | plus | Ubr7 |
| Proliferation | plus | Pold3 |
| Proliferation | plus | Msh2 |
| Proliferation | plus | Atad2 |
| Proliferation | plus | Rad51 |
| Proliferation | plus | Rrm2 |
| Proliferation | plus | Cdc45 |
| Proliferation | plus | Cdc6 |
| Proliferation | plus | Exo1 |
| Proliferation | plus | Tipin |
| Proliferation | plus | Dscc1 |
| Proliferation | plus | Blm |
| Proliferation | plus | Casp8ap2 |
| Proliferation | plus | Usp1 |
| Proliferation | plus | Clspn |
| Proliferation | plus | Pola1 |

TABLE 3-continued

| Signature | Sign | Gene |
| --- | --- | --- |
| Proliferation | plus | Chaf1b |
| Proliferation | plus | Brip1 |
| Proliferation | plus | E2f8 |
| Proliferation | plus | Hmgb2 |
| Proliferation | plus | Cdk1 |
| Proliferation | plus | Nusap1 |
| Proliferation | plus | Ube2c |
| Proliferation | plus | Birc5 |
| Proliferation | plus | Tpx2 |
| Proliferation | plus | Top2a |
| Proliferation | plus | Ndc80 |
| Proliferation | plus | Cks2 |
| Proliferation | plus | Nuf2 |
| Proliferation | plus | Cks1b |
| Proliferation | plus | Mki67 |
| Proliferation | plus | Tmpo |
| Proliferation | plus | Cenpf |
| Proliferation | plus | Tacc3 |
| Proliferation | plus | Fam64a |
| Proliferation | plus | Smc4 |
| Proliferation | plus | Ccnb2 |
| Proliferation | plus | Ckap2l |
| Proliferation | plus | Ckap2 |
| Proliferation | plus | Aurkb |
| Proliferation | plus | Bub1 |
| Proliferation | plus | Kif11 |
| Proliferation | plus | Anp32e |
| Proliferation | plus | Tubb4b |
| Proliferation | plus | Gtse1 |
| Proliferation | plus | Kif20b |
| Proliferation | plus | Hjurp |
| Proliferation | plus | Hjurp |
| Proliferation | plus | Cdca3 |
| Proliferation | plus | Hn1 |
| Proliferation | plus | Cdc20 |
| Proliferation | plus | Ttk |
| Proliferation | plus | Cdc25c |
| Proliferation | plus | Kif2c |
| Proliferation | plus | Rangap1 |
| Proliferation | plus | Ncapd2 |
| Proliferation | plus | Dlgap5 |
| Proliferation | plus | Cdca2 |
| Proliferation | plus | Cdca8 |
| Proliferation | plus | Ect2 |
| Proliferation | plus | Kif23 |
| Proliferation | plus | Hmmr |
| Proliferation | plus | Aurka |
| Proliferation | plus | Psrc1 |
| Proliferation | plus | Anln |
| Proliferation | plus | Lbr |
| Proliferation | plus | Ckap5 |
| Proliferation | plus | Cenpe |
| Proliferation | plus | Ctcf |
| Proliferation | plus | Nek2 |
| Proliferation | plus | G2e3 |
| Proliferation | plus | Gas2l3 |
| Proliferation | plus | Cbx5 |

Analysis of droplet-based scRNA-Seq samples: Assigning ILC type. ILC signatures were used to assign each cell to one of the following categories: ILC1, ILC2, ILC3, Mixed (i.e., scoring highly for multiple ILC types), and None (i.e., not scoring highly for any ILC type). Based upon the distributions of ILC subset signature scores (FIG. 5d, 7b), the minimum score for assignment to a given category is 0.08 (droplet) or 0.3 (plates). To be uniquely assigned to a category, the ratio of the highest score to the next highest score had to be at least 1.25. If a cell did not score at least the minimum score in any category, it was noted as "None", while if a cell could be assigned to multiple categories it was classified as "Mixed."

Analysis of droplet-based scRNA-Seq samples: PCA, clustering, and tSNE. For subsequent analysis, genes expressed in at less than 1% of cells were excluded. To strengthen signal for the PCA, variable genes were selected using the MeanVarPlot( ) function in Seurat with the x.low-.cutoff and y.cutoff parameters set to 0.1 and 0.6, respectively. PCAFast( ) was run on mean-centered (not scaled) variable genes to compute a limited number of PCs. To reduce the effect of outliers on downstream analysis, particularly because PC1 is strongly correlated with number of UMIs, cells were eliminated if they fell at the extreme ends of the distributions of the top four PCs or outside coarse clusters found by density-based clustering in pairs of these PCs. Due to the decrease in marginal proportion of variance explained beyond PC 30 in both groups, the top 30 PCs were included for subsequent analysis of each group.

Using these 30 PCs, the cells were clustered via Seurat's FindClusters( ) function, which optimizes a modularity function on a nearest-neighbor graph computed from the data. Cluster resolution parameters of 0.6 and 0.7 were chosen for Groups A and B, respectively. A hierarchical overview of cluster relationships was calculated by the BuildClusterTree( ) function in Seurat, with cluster distances calculated using the set of variable genes.

To visualize the data, tSNE plots were created by calling Seurat's RunTSNE( ) function, with the dims.use parameter set to the first 30 PCs and the do.fast parameter set to TRUE. A number of perplexity parameter choices were evaluated before selecting 50 for Group A and 150 for Group B. TSNE plots of cells colored by batch indicate that experimental batches appear to have a relatively minor impact on the PCA and clustering (FIG. 5f, 12b).

Analysis of droplet-based scRNA-Seq samples: Differential gene expression. To avoid spurious results due to cells in different conditions or clusters having vastly different amounts of mRNA, differential expression (DE) testing had to account for the varying number of transcripts and genes in each condition. To this end, Applicants fit raw counts to a mixture of generalized linear models that include covariates for the number of UMIs in a cell and the number of genes detected in a cell, as well as a factor for the batch. Specifically, Applicants fit a zero-inflated negative binomial model using the zeroinfl( ) function[45] from the pscl R package[46]. The zero-inflated negative binomial model combines a count component and a point mass at zero, which is relevant for scRNA-Seq data where zero values are significantly inflated due to the technology not capturing expressed genes, particularly those with low expression[12]. The model requires a substantial amount of data to fit, and hence is well suited to the large number of sparsely profiled cells from massively-parallel methods. As an alternative to the zero-inflated negative binomial, Applicants also fit a generalized linear model using the binomial family with a logit link.

DE tests included the following models. For Group A: (1) a cluster-based model with indicator coefficients for each cluster except the reference (cluster 3); (2) tree-based models each corresponding to a node in a hierarchical tree on the clusters, such that there is a coefficient indicating whether cells descend from the left (or right) child of the node, with the larger of the groups serving as the reference; (3) a condition-wide model with indicator coefficients for each condition (with the control condition as reference); and (4) a direct comparison of IL-25 versus IL-33, with IL-33 as reference. For Group B: (1) a condition-based model with indicator coefficients for NMU and IL-25, and an additional interaction term (with the control condition as reference) to detect non-additive effects; (2) a condition-based model with a coefficient for each condition, with NMU+IL-25 included as a condition, to capture main effects (with control as reference); (3) a direct comparison between NMU+IL-25 and IL-25, with IL-25 as reference; and (4) a comparison between cells in clusters 8 and 9 versus those in cluster 6.

Many cell-cycle genes and ribosomal protein genes are differentially expressed across conditions and clusters. To detect other types of differentially expressed genes as well, before ranking DE results, Applicants removed the genes in our cell-cycle signature, as well as ribosomal protein genes.

The DE tests report coefficients and associated p-values for each variable of interest (e.g., cluster or condition), separately for each model component. A coefficient in the count component corresponds to the log of the marginal expected fold change in counts, whereas a coefficient in the zero component corresponds to the log of the odds ratio. To rank the results for any given model, Applicants created a list of differentially expressed candidate genes that are detected in at least 10% of the cells in one of the groups in the model and have a coefficient for a term of interest with absolute value at least $\log(1.1)$ and corresponding FDR-adjusted p-value $<0.001$, for at least one component. Applicants ranked these candidates by lowest p-value and also by largest absolute value of coefficient. For Group A, for condition-based models, the top 40 genes according to each ranking were reported, with a minimum of 10 genes, if available, selected from the set of candidates with positive coefficients and from those with negative coefficients. For cluster-based models, the analogous numbers were 20 and 5, respectively. For Group B, the top 75 genes (100 genes, in the case the model has an interaction term) according to each ranking were reported, with a minimum of 15 genes, if available, selected from the set of candidates with positive coefficients and from those with negative coefficients.

Figure 4J:
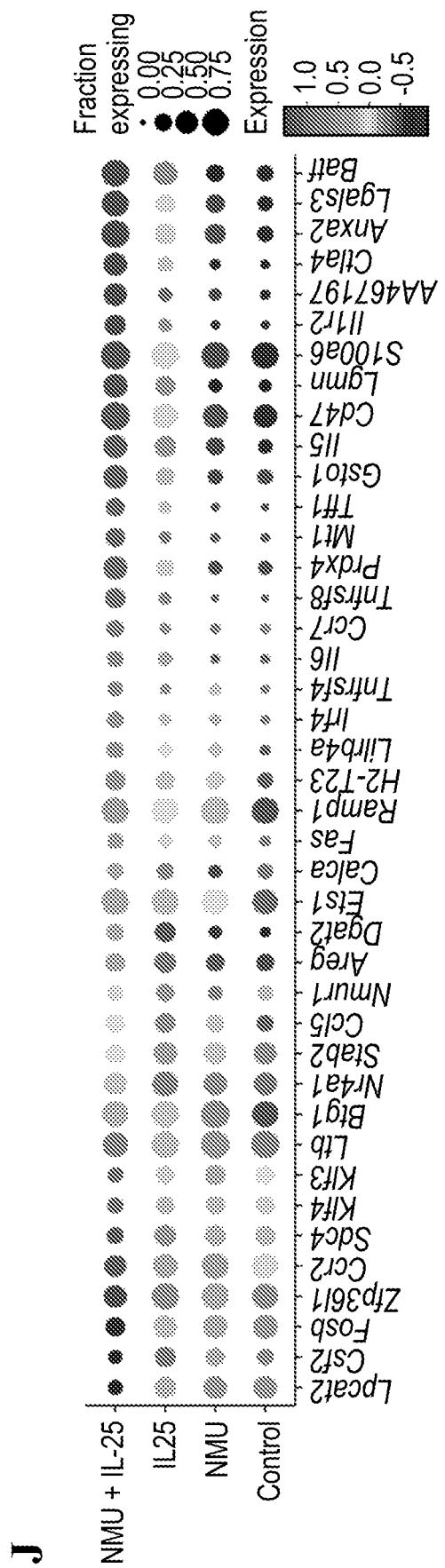
FIG. 4 illustrates that NMU amplifies proliferative, IL-25-responsive inflammatory ILCs, characterized by an inflammatory ILC2 gene signature. (a,b) NMU+IL-25 but not NMU dramatically enhances several transcriptional states observed following IL-25-treatment. tSNE plots of 13,590 ILCs from the lungs of mice treated intranasally with PBS, NMU, IL-25, or the combination NMU+IL-25, shaded by treatment (a) or by cluster (b). (c) Several clusters are dominated by cells from NMU+IL-25 treated mice. Bar chart shows the proportions (y axis) of ILCs from PBS, NMU, IL-25 and NMU+IL-25 treated mice in each cluster (x axis). (d-f) NMU+IL-25 enhances ILC proliferation and frequency. (d) The frequency of Ki-67 expressing cells was determined by flow cytometry in IL-25 or IL-25+NMU treated mice and representative flow cytometry plots and summary data are shown. (e) The frequency of ILCs in each treatment is shown. (f) Violin plots show the distribution of proliferation scores (y axis) in the cells from each treatment (x axis). The distribution of scores in ILCs from NMU+IL-25 treated mice is bimodal with a subset of highly scoring cells, not observed in other treatments, and a significantly higher mean (Student's t-test, P<2.2×10$^{-16}$). (g-i) IL-17RB expression on ILCs is enhanced after stimulation with NMU+IL-25. Representative flow cytometry plots (g, left) and summary data (g, right) of IL-17RB+ cells in IL-25 or NMU+IL-25 treated mice are shown. (h) The level of IL-17RB mRNA by qPCR in mononuclear lung cells is shown. (i) The frequency of ILCs expressing Il17rb after activation with NMU+IL-25 is significantly increased compared to other conditions (GLM binomial test, P<2.2×10$^{-5}$). (j-m) Inflammatory ILC gene signature. U) For each gene from the inflammatory signature (columns, Methods) the proportion of cells in each condition (row) expressing the gene (dot size) and the mean-centered log TPX expression levels (shaded) is plotted. (k) The correlation (x axis) of each signature gene (y axis) with the inflammatory ILC2 signature scores is shown. (l) tSNE plot as in (a) but with cells 41 shaded by the Inflammatory ILC2 signature score described in FIG. 4K. (m) Violin plots show the distributions of inflammatory ILC2 signature scores (y axis) across the cells in each condition (x axis). The scores of NMU+IL-25 activated cells are significantly higher than in the other conditions (Student's t-test, P<2.2×10$^{-16}$). For panels D, E, G, and H, each data point represents an individual mouse. Data are representative of at least two independent experiments. *=P<0.05.

Applicants curated a selection from the highest-ranked results to represent, in FIG. 1i, common, distinctive patterns across clusters, and, in FIG. 4j, patterns that distinguish NMU+IL-25 from the other conditions and shed light on the non-linear interactions between NMU and IL-25 in our pro-inflammatory ILC2 signature (Table 6).

TABLE 6

| Signature | Sign | Gene | clu_8_9.v. clu_6 | NMU_IL25. v.IL25 | wint_cond_ all.bin | wint_cond_ all | cond_ all | cond_all. bin |
|---|---|---|---|---|---|---|---|---|
| Inflammatory_ILC2 | plus | AA467197 | TRUE | TRUE | NA | NA | TRUE | TRUE |
| Inflammatory_ILC2 | plus | Anxa2 | TRUE | TRUE | FALSE | TRUE | TRUE | TRUE |
| Inflammatory_ILC2 | plus | Batf | NA | NA | NA | NA | TRUE | TRUE |
| Inflammatory_ILC2 | plus | Ccr7 | TRUE | TRUE | TRUE | NA | NA | NA |
| Inflammatory_ILC2 | plus | Cd47 | NA | TRUE | TRUE | FALSE | FALSE | FALSE |

TABLE 6-continued

| Signature | Sign | Gene | clu_8_9.v. clu_6 | NMU_IL25. v.IL25 | wint_cond_ all.bin | wint_cond_ all | cond_ all | cond_all. bin |
|---|---|---|---|---|---|---|---|---|
| Inflammatory_ILC2 | plus | Ctla4 | TRUE | TRUE | NA | NA | TRUE | TRUE |
| Inflammatory_ILC2 | plus | Ets1 | NA | NA | FALSE | TRUE | NA | FALSE |
| Inflammatory_ILC2 | plus | Fas | NA | NA | FALSE | TRUE | NA | FALSE |
| Inflammatory_ILC2 | plus | Gsto1 | NA | FALSE | TRUE | TRUE | FALSE | FALSE |
| Inflammatory_ILC2 | plus | H2-T23 | NA | NA | TRUE | TRUE | NA | NA |
| Inflammatory_ILC2 | plus | Il1r2 | NA | TRUE | NA | NA | NA | TRUE |
| Inflammatory_ILC2 | plus | Il5 | NA | NA | FALSE | TRUE | TRUE | TRUE |
| Inflammatory_ILC2 | plus | Il6 | NA | NA | NA | NA | NA | TRUE |
| Inflammatory_ILC2 | plus | Irf4 | NA | NA | TRUE | NA | NA | TRUE |
| Inflammatory_ILC2 | plus | Lgals3 | TRUE | TRUE | FALSE | TRUE | TRUE | TRUE |
| Inflammatory_ILC2 | plus | Lgmn | NA | NA | NA | NA | TRUE | TRUE |
| Inflammatory_ILC2 | plus | Lilrb4a | NA | NA | TRUE | TRUE | NA | FALSE |
| Inflammatory_ILC2 | plus | Mt1 | NA | TRUE | NA | NA | NA | TRUE |
| Inflammatory_ILC2 | plus | Prdx4 | FALSE | FALSE | TRUE | NA | FALSE | FALSE |
| Inflammatory_ILC2 | plus | Ramp1 | NA | NA | TRUE | TRUE | NA | FALSE |
| Inflammatory_ILC2 | plus | S100a6 | NA | NA | TRUE | TRUE | FALSE | FALSE |
| Inflammatory_ILC2 | plus | Tff1 | TRUE | TRUE | NA | NA | NA | NA |
| Inflammatory_ILC2 | plus | Tnfrsf4 | NA | NA | NA | NA | NA | TRUE |
| Inflammatory_ILC2 | plus | Tnfrsf8 | TRUE | TRUE | NA | NA | NA | NA |
| Inflammatory_ILC2 | minus | Areg | TRUE | NA | TRUE | TRUE | NA | FALSE |
| Inflammatory_ILC2 | minus | Btg1 | NA | NA | TRUE | TRUE | NA | FALSE |
| Inflammatory_ILC2 | minus | Calca | TRUE | NA | NA | TRUE | NA | FALSE |
| Inflammatory_ILC2 | minus | Ccl5 | TRUE | NA | TRUE | FALSE | FALSE | NA |
| Inflammatory_ILC2 | minus | Ccr2 | NA | NA | TRUE | TRUE | FALSE | TRUE |
| Inflammatory_ILC2 | minus | Csf2 | TRUE | TRUE | TRUE | TRUE | TRUE | TRUE |
| Inflammatory_ILC2 | minus | Dgat2 | TRUE | TRUE | TRUE | TRUE | TRUE | FALSE |
| Inflammatory_ILC2 | minus | Fosb | TRUE | TRUE | TRUE | FALSE | TRUE | TRUE |
| Inflammatory_ILC2 | minus | Klf3 | NA | NA | TRUE | NA | FALSE | FALSE |
| Inflammatory_ILC2 | minus | Klf4 | NA | TRUE | FALSE | TRUE | TRUE | FALSE |
| Inflammatory_ILC2 | minus | Lpcat2 | NA | TRUE | TRUE | NA | TRUE | TRUE |
| Inflammatory_ILC2 | minus | Ltb | NA | NA | TRUE | TRUE | NA | FALSE |
| Inflammatory_ILC2 | minus | Nr4a1 | TRUE | NA | TRUE | TRUE | NA | FALSE |
| Inflammatory_ILC2 | minus | Sdc4 | TRUE | TRUE | TRUE | TRUE | NA | FALSE |
| Inflammatory_ILC2 | minus | Stab2 | FALSE | TRUE | TRUE | NA | NA | FALSE |
| Inflammatory_ILC2 | minus | Zfp36l1 | TRUE | TRUE | TRUE | TRUE | NA | FALSE |
| Inflammatory_ILC2 | minus | Nmur1 | NA | TRUE | FALSE | NA | NA | FALSE |

Analysis of SMART-Seq2 plate-based scRNA-Seq data. Reads were aligned to mm 10 using Kallisto[47]. The R package tximport[48] was used to convert the output to gene counts and traditional TPM values. Genes were removed from further analysis if they did not express at a level of 2 log TPM in at least three cells. Cells were removed if the number of genes expressed was not in the range 1,200-7,300 or if the total counts was not in the range $7 \times 10^4 - 2.1 \times 10^6$ (FIG. 7a). Of the 684 cells that met QC criteria (252 from control, 179 from IL-25, and 253 from IL-33 treated mice), 90 from each condition in the same batch were selected by random down-sampling for analysis by PCA, which was performed on mean-centered gene expression for genes expressed in more than nine cells. The genes shown in the heatmap in FIG. 2a are the top five genes for the top nine PCs. These genes were tested for differential expression between the cells from IL-25 and IL-33 conditions using a generalized linear model with the binomial family and a logit link function. In addition, Applicants used all 684 cells to test for differential expression according to the same type of model, but with indicator coefficients for each condition (with the control condition as reference), covariates for the number of genes detected in a cell and the number of reads in a cell, and a factor for the batch, which has a significant effect in the plate data. Applicants created a list of candidate differentially expressed genes that contains those genes detected in at least 10% of the cells in one of the conditions and have a coefficient for a term of interest with absolute value at least log(1.2), with corresponding FDR-adjusted P<0.1 (Tables 4,5). The p-value threshold is relaxed compared to droplets, due to lack of power in smaller cell numbers.

TABLE 4

(IL-25)

| | gp.IL25.coeff | gp.IL33.coeff | gp.IL25.pvalue.adj | gp.IL33.pvalue.adj | candidate |
|---|---|---|---|---|---|
| Ms4a4b | 3.49 | 2.44 | 0.070200529 | 0.004529229 | TRUE |
| Epsti1 | 1.79 | 1.72 | 0.070200529 | 0.0044865 | TRUE |
| Tiam1 | -2.1 | -0.828 | 0.060941625 | 0.197952975 | TRUE |
| Lcmt2 | -2.32 | -1.12 | 0.0583245 | 0.058832406 | TRUE |
| Marf1 | 3.17 | 1.15 | 0.055547143 | 0.023928 | TRUE |
| Tet3 | 1.62 | 1.32 | 0.05518395 | 0.006605125 | TRUE |
| Irak3 | 1.76 | 0.157 | 0.036116325 | 0.897030621 | TRUE |
| Pip5k1c | -2.36 | -0.697 | 0.029956015 | 0.258752199 | TRUE |
| Ncoa3 | 2.88 | 1.22 | 0.02413737 | 0.173189351 | TRUE |
| Dgat2 | 2.05 | 0.513 | 0.02413737 | 0.616403736 | TRUE |
| Picalm | 1.79 | 1 | 0.02171466 | 0.049903316 | TRUE |
| Zcchc10 | -1.82 | -0.914 | 0.02171466 | 0.076665862 | TRUE |
| Pim2 | 2.28 | 0.0475 | 0.00661011 | 0.986617099 | TRUE |
| Rel | 2.1 | 0.837 | 0.003517416 | 0.173527438 | TRUE |
| Npy1r | -1.6 | -1.03 | 0.075421703 | 0.035375568 | TRUE |
| Sipa1 | 1.56 | 1.34 | 0.070200529 | 0.006605125 | TRUE |
| Atrx | 1.5 | 0.485 | 0.070200529 | 0.460472954 | TRUE |
| Plb4 | 1.5 | 0.668 | 0.070200529 | 0.283775088 | TRUE |
| Akirin1 | 1.61 | 0.632 | 0.06388776 | 0.313364769 | TRUE |
| Snrk | 1.55 | 0.356 | 0.05518395 | 0.634918159 | TRUE |
| Ctbp1 | -1.88 | -0.324 | 0.090749659 | 0.737612653 | TRUE |
| Mtfmt | -2.15 | -1.57 | 0.089521326 | 0.057100909 | TRUE |
| Clec2i | 1.98 | 0.974 | 0.085670786 | 0.23789802 | TRUE |
| Rdh1 | -2.49 | -1.91 | 0.082137462 | 0.061611843 | TRUE |
| Gas7 | 1.67 | 0.482 | 0.075421703 | 0.457035981 | TRUE |
| Stat1 | 1.88 | 1.23 | 0.070200529 | 0.026525447 | TRUE |
| Top1 | 1.5 | 0.863 | 0.085670786 | 0.127700851 | TRUE |
| Pik3cd | 1.43 | 0.807 | 0.085670786 | 0.155738276 | TRUE |

TABLE 5

(IL-33)

| | gp.IL25.coeff | gp.IL33.coeff | gp.IL25.pvalue.adj | gp.IL33.pvalue.adj | candidate |
|---|---|---|---|---|---|
| Igfbp4 | -2.9 | -2.3 | 0.328922287 | 0.006043579 | TRUE |
| Shank2 | -3.19 | -3.62 | 0.131681688 | 0.004462572 | TRUE |
| Lilrb4 | 0.943 | 2.11 | 0.490899552 | 7.54E-05 | TRUE |
| Zbp1 | 0.971 | 2.38 | 0.514614181 | 2.45E-06 | TRUE |
| Socs1 | -1.36 | -1.32 | 0.141732614 | 0.00574272 | TRUE |
| Ms4a6b | 3.22 | 2.02 | 0.078159553 | 0.0044865 | TRUE |
| Lgals3bp | 0.804 | 1.95 | 0.709372103 | 0.0044865 | TRUE |
| Epsti1 | 1.79 | 1.72 | 0.070200529 | 0.0044865 | TRUE |
| Ffar2 | 1.36 | 1.38 | 0.120999545 | 0.0044865 | TRUE |
| 4632428N05Rik | 1.28 | 1.58 | 0.323859934 | 0.004262175 | TRUE |
| Phf11a | 1.52 | 1.98 | 0.310827302 | 0.003181964 | TRUE |
| Gp49a | 1.04 | 1.62 | 0.386641463 | 0.003181964 | TRUE |
| Gskip | 0.645 | 1.72 | 0.698543226 | 0.001453626 | TRUE |
| Ly6a | 0.412 | 1.67 | 0.833704733 | 0.000830501 | TRUE |
| Slfn2 | 0.267 | 1.6 | 0.919977774 | 0.000830501 | TRUE |
| Anxa2 | 0.693 | 1.81 | 0.702267971 | 0.000608882 | TRUE |
| Trafd1 | 0.993 | 1.81 | 0.469251276 | 0.000608882 | TRUE |
| Lpcat2 | -0.773 | -1.56 | 0.515901437 | 0.000608882 | TRUE |

TABLE 5-continued (IL-33)

| | gp.IL25.coeff | gp.IL33.coeff | gp.IL25.pvalue.adj | gp.IL33.pvalue.adj | candidate |
|---|---|---|---|---|---|
| Cirbp | −1.41 | −1.67 | 0.104860941 | 0.000608882 | TRUE |
| Gbp6 | 0.949 | 1.87 | 0.490899552 | 0.000232102 | TRUE |
| Trip13 | −1.91 | −2.7 | 0.539011346 | 0.087578938 | TRUE |
| AI593442 | −2.55 | −3.15 | 0.366414849 | 0.087571546 | TRUE |
| Vdr | −0.748 | 2.04 | 0.912852298 | 0.08751053 | TRUE |
| Oas1a | 0.0294 | 2.09 | 1 | 0.073479685 | TRUE |
| Gm12250 | 3.54 | 3.39 | 0.141732614 | 0.058846186 | TRUE |
| Fbxl21 | 12.2 | −2.6 | 1 | 0.053838 | TRUE |
| Tango6 | −1.32 | −2.16 | 0.515901437 | 0.043629198 | TRUE |
| Bmp2 | −0.856 | −2.03 | 0.776399425 | 0.038648412 | TRUE |
| Dhx58 | 2.3 | 2.39 | 0.197933824 | 0.024040868 | TRUE |
| AA467197 | −0.724 | 2.99 | 0.89766196 | 0.013833375 | TRUE |
| Rab7l1 | 1.18 | 2.2 | 0.565041855 | 0.008507733 | TRUE |
| Isg15 | 2.03 | 3.16 | 0.330584211 | 0.007987729 | TRUE |
| Ctla4 | 1.48 | 2.65 | 0.477699281 | 0.007987729 | TRUE |
| Isg20 | 1.54 | 2.26 | 0.351795037 | 0.007987729 | TRUE |
| Rtp4 | 0.866 | 2.55 | 0.836409396 | 0.006043579 | TRUE |
| Ms4a4b | 3.49 | 2.44 | 0.070200529 | 0.004529229 | TRUE |
| Dkk3 | −0.0269 | 0.959 | 1 | 0.099761925 | TRUE |
| Ddrgk1 | −0.21 | −0.935 | 0.931580949 | 0.099761925 | TRUE |
| Commd10 | −0.867 | −1.3 | 0.609622661 | 0.099574984 | TRUE |
| Tap2 | 0.406 | 1.07 | 0.867316214 | 0.097630755 | TRUE |
| Plac8 | 0.268 | 1.62 | 0.951245067 | 0.096828892 | TRUE |
| 1700113H08Rik | −0.86 | −1.32 | 0.655772517 | 0.096828892 | TRUE |
| Nsmaf | 1.41 | 0.914 | 0.129872368 | 0.09630258 | TRUE |
| Mrpl52 | 0.158 | 0.944 | 0.961345695 | 0.095769519 | TRUE |
| Gpr108 | 0.205 | 0.909 | 0.937163286 | 0.09321466 | TRUE |
| Gigyf1 | −0.844 | −0.966 | 0.454729268 | 0.09321466 | TRUE |
| Plekha5 | −1.01 | −1.23 | 0.530484418 | 0.092360521 | TRUE |
| AW112010 | 0.787 | 0.998 | 0.587991809 | 0.090316471 | TRUE |
| C1qbp | −0.742 | −1.08 | 0.620445671 | 0.090316471 | TRUE |
| Abtb2 | 0.292 | 1.34 | 0.950836855 | 0.090025164 | TRUE |
| Ifngr2 | −0.761 | −0.881 | 0.520644716 | 0.090025164 | TRUE |
| Fhl2 | −1.07 | −0.933 | 0.323945367 | 0.090025164 | TRUE |
| Idh2 | −0.56 | −1.43 | 0.825779497 | 0.090025164 | TRUE |
| Mrps18a | −1.24 | −1.11 | 0.301448306 | 0.089129799 | TRUE |
| Adsl | −1.77 | −0.98 | 0.120999545 | 0.088826678 | TRUE |
| Bcl3 | 1.33 | 1.42 | 0.428883907 | 0.088823636 | TRUE |
| Tradd | 0.964 | 1.29 | 0.534202775 | 0.088823636 | TRUE |
| Itgae | −0.182 | 1.21 | 0.968373267 | 0.088823636 | TRUE |
| Sesn3 | 0.328 | 1.18 | 0.919887997 | 0.088823636 | TRUE |
| Ccng1 | 0.622 | 0.916 | 0.65223303 | 0.088823636 | TRUE |
| Trim30d | 0.527 | 1.14 | 0.825648863 | 0.087564103 | TRUE |
| Ssr3 | 0.609 | 0.999 | 0.712259411 | 0.087564103 | TRUE |
| Phc3 | 0.476 | 0.936 | 0.766387836 | 0.087564103 | TRUE |
| P1xdc2 | −0.906 | −0.903 | 0.419753898 | 0.087564103 | TRUE |
| Sptssa | −0.974 | −0.952 | 0.412315669 | 0.087564103 | TRUE |
| Mrpl53 | −1.87 | −1.26 | 0.120999545 | 0.087564103 | TRUE |
| Mybbp1a | −0.514 | −0.978 | 0.750905063 | 0.084638936 | TRUE |
| Ccdc142 | −1.86 | −1.56 | 0.199126849 | 0.084620819 | TRUE |
| Dhx37 | −0.288 | −0.889 | 0.884634944 | 0.084602571 | TRUE |
| Ccr2 | −1.53 | −1.11 | 0.151175543 | 0.084602571 | TRUE |
| Dock10 | −0.792 | −0.886 | 0.474128889 | 0.083878043 | TRUE |
| Ccdc50 | 1.05 | 0.948 | 0.345810831 | 0.082877891 | TRUE |
| Paxip1 | −1.15 | −0.998 | 0.275200622 | 0.082877891 | TRUE |
| Sntb1 | 1.29 | 1.19 | 0.389063672 | 0.082472426 | TRUE |
| Myo1f | 0.897 | 1.04 | 0.485993669 | 0.082472426 | TRUE |
| H2-T10 | 0.799 | 0.906 | 0.475558017 | 0.080056506 | TRUE |
| Asph | −1.27 | −1.56 | 0.523995802 | 0.080056506 | TRUE |
| Tpm4 | 0.311 | 0.969 | 0.8973 | 0.079984045 | TRUE |
| Zfp110 | −0.396 | −1.24 | 0.885254421 | 0.079984045 | TRUE |
| Lat2 | −0.0259 | 1.05 | 1 | 0.079571887 | TRUE |
| Npnt | 0.056 | 0.949 | 1 | 0.079571887 | TRUE |
| Exosc4 | −0.31 | −0.925 | 0.872264615 | 0.078812281 | TRUE |
| Cox10 | 0.786 | 0.894 | 0.485993669 | 0.077743168 | TRUE |
| Rnf125 | 1.65 | 1.06 | 0.104860941 | 0.076665862 | TRUE |
| Zcchc10 | −1.82 | −0.914 | 0.02171466 | 0.076665862 | TRUE |
| Mrpl40 | −0.837 | −1.08 | 0.518865549 | 0.076564981 | TRUE |
| Gucd1 | −0.0721 | 1.09 | 1 | 0.076166163 | TRUE |
| Ifi35 | 0.307 | 0.95 | 0.894717311 | 0.076166163 | TRUE |
| Bcl2a1d | 0.357 | 0.97 | 0.845361347 | 0.07535918 | TRUE |
| Mlec | 0.715 | 0.999 | 0.591442924 | 0.073543412 | TRUE |
| Mfsd1 | 1.25 | 1.05 | 0.241118045 | 0.072351462 | TRUE |
| Myg1 | −1.33 | −1.26 | 0.328922287 | 0.071926429 | TRUE |
| Il13 | 1.61 | 1.57 | 0.247109843 | 0.0699894 | TRUE |
| Sdc4 | 0.206 | −0.924 | 0.936010617 | 0.069106573 | TRUE |

TABLE 5-continued (IL-33)

| | gp.IL25.coeff | gp.IL33.coeff | gp.IL25.pvalue.adj | gp.IL33.pvalue.adj | candidate |
|---|---|---|---|---|---|
| Cybrd1 | −0.158 | −1.22 | 0.96501833 | 0.069023077 | TRUE |
| Sema4a | −0.348 | −0.903 | 0.833335843 | 0.068854041 | TRUE |
| Dennd5a | 0.929 | 0.993 | 0.434407143 | 0.068768484 | TRUE |
| Ap3d1 | 0.719 | 0.94 | 0.546182609 | 0.067943704 | TRUE |
| Gba | −0.05 | 0.976 | 1 | 0.067482893 | TRUE |
| Atxn7l3b | 0.557 | 0.957 | 0.702796359 | 0.067482893 | TRUE |
| Socs3 | 1.02 | 1.44 | 0.566715789 | 0.06654975 | TRUE |
| Fus | −0.388 | −0.954 | 0.821454766 | 0.06654975 | TRUE |
| Ddx58 | 0.528 | 0.912 | 0.690537811 | 0.066354958 | TRUE |
| Neu3 | −2.64 | −1.92 | 0.196715769 | 0.066354958 | TRUE |
| Dcaf12 | 0.717 | 0.975 | 0.567597535 | 0.066056553 | TRUE |
| Arf5 | 0.592 | 0.972 | 0.690537811 | 0.066056553 | TRUE |
| Med16 | −0.61 | −0.941 | 0.652753822 | 0.066056553 | TRUE |
| Mkl2 | −1.12 | −0.923 | 0.233085621 | 0.062927532 | TRUE |
| Chst11 | −0.0352 | 1.25 | 1 | 0.062811 | TRUE |
| Mxd1 | 0.448 | 1.05 | 0.804221275 | 0.062811 | TRUE |
| Brix1 | −0.00742 | −1.21 | 1 | 0.062059956 | TRUE |
| Asl | 1.17 | 1.31 | 0.390731792 | 0.061840946 | TRUE |
| Sema4d | 0.548 | 1.28 | 0.806269565 | 0.061840946 | TRUE |
| Gbp4 | 0.318 | 0.935 | 0.865457689 | 0.061840946 | TRUE |
| Dhx35 | −1.63 | −1.51 | 0.295215584 | 0.061840946 | TRUE |
| Lamp2 | 0.692 | 0.996 | 0.591211682 | 0.061740826 | TRUE |
| Rdh1 | −2.49 | −1.91 | 0.082137462 | 0.061611843 | TRUE |
| Sdccag3 | 0.312 | 1.08 | 0.907323767 | 0.060235417 | TRUE |
| Inpp1 | 1.79 | 1.29 | 0.121470313 | 0.058846186 | TRUE |
| Fosb | 0.156 | −0.948 | 0.951245067 | 0.058846186 | TRUE |
| Lcmt2 | −2.32 | −1.12 | 0.0583245 | 0.058832406 | TRUE |
| Sp100 | 0.451 | 1.07 | 0.812545277 | 0.058538143 | TRUE |
| Rab8b | 1.5 | 1.03 | 0.157258763 | 0.057100909 | TRUE |
| Nol9 | −0.775 | −1.02 | 0.510829638 | 0.057100909 | TRUE |
| Mtfmt | −2.15 | −1.57 | 0.089521326 | 0.057100909 | TRUE |
| Hpcal1 | −0.169 | 1.26 | 0.970832752 | 0.055861324 | TRUE |
| Ecm1 | −0.0192 | 1.16 | 1 | 0.055861324 | TRUE |
| Usp36 | −0.645 | −1.09 | 0.670090504 | 0.055861324 | TRUE |
| Lsm6 | −0.616 | −1.12 | 0.768357283 | 0.055861324 | TRUE |
| Soat1 | 0.339 | 1.07 | 0.911016041 | 0.0556326 | TRUE |
| Foxo3 | 2.06 | 1.17 | 0.308917786 | 0.055010352 | TRUE |
| Gnai2 | 0.501 | 1.04 | 0.772683069 | 0.055010352 | TRUE |
| Cblb | 1.08 | 0.969 | 0.290740873 | 0.055010352 | TRUE |
| Smn1 | −1.53 | −1.01 | 0.120999545 | 0.05365299 | TRUE |
| Zc3h12a | −1.14 | −1.12 | 0.429651792 | 0.051606373 | TRUE |
| Tmem33 | 1.18 | 1.08 | 0.310827302 | 0.051407813 | TRUE |
| Inpp4b | −0.752 | −0.999 | 0.520644716 | 0.050799524 | TRUE |
| Atp8b4 | 1 | 1.07 | 0.361882783 | 0.05011516 | TRUE |
| Picalm | 1.79 | 1 | 0.02171466 | 0.049903316 | TRUE |
| Gnl3l | −0.617 | −1.25 | 0.830748338 | 0.049903316 | TRUE |
| Igsf5 | −0.93 | −1.13 | 0.474128889 | 0.04898773 | TRUE |
| Morc3 | 0.662 | 1.05 | 0.65106874 | 0.048717538 | TRUE |
| Tmem229b | 0.199 | 1.01 | 0.942597451 | 0.047806967 | TRUE |
| Fam118a | −0.764 | −0.991 | 0.520644716 | 0.0473575 | TRUE |
| Ndufaf3 | 1.45 | 1.52 | 0.361471564 | 0.047271168 | TRUE |
| Lxn | 0.065 | 1.29 | 1 | 0.047271168 | TRUE |
| Mier3 | −0.901 | −1.41 | 0.591211682 | 0.047271168 | TRUE |
| Syt11 | 0.291 | 0.979 | 0.888359339 | 0.046955301 | TRUE |
| Eva1b | 0.99 | 1.29 | 0.537267316 | 0.045073674 | TRUE |
| Mplkip | −0.607 | −1.13 | 0.702267971 | 0.045073674 | TRUE |
| Nol6 | −1.65 | −1.23 | 0.22835479 | 0.045073674 | TRUE |
| Krit1 | 0.612 | 1.04 | 0.661645455 | 0.043629198 | TRUE |
| E030030106Rik | −0.87 | −1.01 | 0.438085243 | 0.043629198 | TRUE |
| Cap1 | 1.28 | 1.24 | 0.301448306 | 0.04245761 | TRUE |
| Mgat5 | 1.02 | 1.08 | 0.345290127 | 0.04245761 | TRUE |
| Ctsw | −0.0379 | 1.07 | 1 | 0.04245761 | TRUE |
| Dgka | −0.0503 | 1.02 | 1 | 0.04245761 | TRUE |
| Pin4 | 0.928 | 1.28 | 0.525537288 | 0.040406717 | TRUE |
| St3gal6 | −0.764 | −1.32 | 0.661645455 | 0.040094544 | TRUE |
| Gbp9 | 0.745 | 1.12 | 0.585941803 | 0.039206866 | TRUE |
| Pyhin1 | 0.623 | 1.04 | 0.652753822 | 0.039206866 | TRUE |
| Zfp825 | −1.4 | −1.02 | 0.104860941 | 0.039206866 | TRUE |
| Pml | 1.04 | 1.2 | 0.449297403 | 0.038648412 | TRUE |
| Tmem176a | −0.146 | −1 | 0.954115055 | 0.038648412 | TRUE |
| Xrcc3 | −1.4 | −1.02 | 0.120999545 | 0.038648412 | TRUE |
| Nbn | −0.499 | −1.39 | 0.807775803 | 0.038648412 | TRUE |
| Tnfsf10 | −1.18 | −1.88 | 0.576188312 | 0.038648412 | TRUE |
| Extl3 | −0.16 | −1.19 | 0.955090377 | 0.038491076 | TRUE |
| Irf4 | 1.11 | 1.58 | 0.522128324 | 0.035382894 | TRUE |
| Rab33b | −1.3 | −1.1 | 0.306897549 | 0.035379257 | TRUE |

TABLE 5-continued

| (IL-33) | | | | | |
|---|---|---|---|---|---|
| | gp.IL25.coeff | gp.IL33.coeff | gp.IL25.pvalue.adj | gp.IL33.pvalue.adj | candidate |
| Ogfr | 0.578 | 1.12 | 0.715395433 | 0.035371826 | TRUE |
| Gal3st3 | −1.01 | −1.08 | 0.353145297 | 0.035371826 | TRUE |
| Herc6 | 0.579 | 1.21 | 0.726987067 | 0.035100265 | TRUE |
| Chordc1 | 1.4 | 1.09 | 0.129872368 | 0.035100265 | TRUE |
| Adrbk1 | 0.798 | 1.08 | 0.522849808 | 0.035100265 | TRUE |
| Nrip1 | 0.668 | 1.07 | 0.620445671 | 0.035100265 | TRUE |
| Nfil3 | 2.04 | 1.77 | 0.138378795 | 0.034940318 | TRUE |
| Chdh | −0.136 | 1.07 | 0.965100557 | 0.03366614 | TRUE |
| Zfc3h1 | 0.466 | 1.14 | 0.797121248 | 0.032527125 | TRUE |
| H2-T9 | 0.437 | 1.1 | 0.803710077 | 0.032527125 | TRUE |
| Cpsf7 | 0.986 | 1.13 | 0.3988 | 0.032117643 | TRUE |
| Ube2h | 0.767 | 1.05 | 0.519871486 | 0.03194388 | TRUE |
| Taf1d | 1.28 | 1.1 | 0.219781709 | 0.030754234 | TRUE |
| Tap1 | 0.561 | 1.17 | 0.740108759 | 0.030449361 | TRUE |
| Socs2 | −0.923 | −1.33 | 0.486512948 | 0.030449361 | TRUE |
| Mgat1 | 1.24 | 1.21 | 0.247109843 | 0.0293118 | TRUE |
| Ttc19 | 0.891 | 1.44 | 0.526731138 | 0.026842958 | TRUE |
| Hsph1 | 0.237 | 1.26 | 0.943138893 | 0.026842958 | TRUE |
| Naa60 | 0.241 | 1.11 | 0.921741321 | 0.026842958 | TRUE |
| Stat1 | 1.88 | 1.23 | 0.070200529 | 0.026525447 | TRUE |
| Lgals3 | 0.303 | 1.4 | 0.915235942 | 0.025727894 | TRUE |
| Mrp63 | 1.09 | 1.21 | 0.330310435 | 0.025727894 | TRUE |
| Slc25a24 | 0.607 | 1.33 | 0.709372103 | 0.025383081 | TRUE |
| Arhgap1 | 1.34 | 1.12 | 0.141732614 | 0.024367046 | TRUE |
| Nipal1 | 1.61 | 1.74 | 0.193208952 | 0.024094167 | TRUE |
| Ifrd2 | −1.53 | −1.74 | 0.389063672 | 0.024094167 | TRUE |
| Marf1 | 3.17 | 1.15 | 0.055547143 | 0.023928 | TRUE |
| Kit | −0.406 | −1.23 | 0.845361347 | 0.022476058 | TRUE |
| Ppp1r15a | 0.186 | −1.09 | 0.941038405 | 0.0224325 | TRUE |
| Cd247 | 1.16 | 1.52 | 0.465994716 | 0.021571455 | TRUE |
| Trp53inp1 | 1.28 | 1.16 | 0.193208952 | 0.021571455 | TRUE |
| Pfas | −0.546 | −1.41 | 0.754449345 | 0.021217406 | TRUE |
| Il2rb | 0.699 | 1.27 | 0.658568807 | 0.020968484 | TRUE |
| Trim30a | 1.17 | 1.18 | 0.290740873 | 0.020968484 | TRUE |
| Tnfrsf18 | −1.25 | −1.12 | 0.172422353 | 0.018814355 | TRUE |
| Amd1 | −0.74 | −1.75 | 0.655540415 | 0.018814355 | TRUE |
| Crlf2 | 0.355 | 1.16 | 0.851703739 | 0.0187436 | TRUE |
| Ttc39b | 0.546 | 1.16 | 0.713471805 | 0.017643539 | TRUE |
| 1700017B05Rik | −1.49 | −1.5 | 0.344202381 | 0.01743617 | TRUE |
| Inpp5b | 0.937 | 1.22 | 0.429774757 | 0.016798291 | TRUE |
| Rilpl2 | 1.4 | 1.43 | 0.207349054 | 0.016362529 | TRUE |
| Glrx | 0.346 | 1.26 | 0.887397708 | 0.016362529 | TRUE |
| Sbno2 | 1.09 | 1.2 | 0.323859934 | 0.016362529 | TRUE |
| Omd | −1.12 | −1.13 | 0.241118045 | 0.016304598 | TRUE |
| Ddx20 | −1.24 | −1.92 | 0.547870673 | 0.016173556 | TRUE |
| Cst7 | −0.0555 | 1.5 | 1 | 0.016039238 | TRUE |
| Myo1g | 0.257 | 1.31 | 0.933509791 | 0.015333608 | TRUE |
| Map2k4 | 1.89 | 1.64 | 0.120999545 | 0.015300115 | TRUE |
| Serinc5 | 0.779 | 1.44 | 0.600465909 | 0.015300115 | TRUE |
| Mov10 | 1.08 | 1.45 | 0.494819799 | 0.01411752 | TRUE |
| Tmem209 | −0.847 | −1.27 | 0.477990963 | 0.014065784 | TRUE |
| H2-T22 | 0.0651 | 1.27 | 0.997500376 | 0.01339631 | TRUE |
| Impact | −1.46 | −1.54 | 0.193208952 | 0.013331314 | TRUE |
| Parp3 | 0.335 | 1.21 | 0.886033624 | 0.012419152 | TRUE |
| Trim12c | 0.974 | 1.16 | 0.330584211 | 0.012419152 | TRUE |
| Pen1 | −0.785 | −1.16 | 0.490743021 | 0.012419152 | TRUE |
| Parp14 | 0.934 | 1.21 | 0.443178659 | 0.01121625 | TRUE |
| Trim34a | 0.632 | 1.29 | 0.684588556 | 0.010822818 | TRUE |
| Pigv | −2.73 | −1.36 | 0.135162911 | 0.010473173 | TRUE |
| Usp18 | 1.1 | 1.6 | 0.507670267 | 0.009898786 | TRUE |
| Pde4b | 0.735 | 1.24 | 0.575491757 | 0.009898786 | TRUE |
| Pydc4 | 1.52 | 1.37 | 0.172422353 | 0.009708492 | TRUE |
| Samd91 | 0.773 | 1.2 | 0.515901437 | 0.009708492 | TRUE |
| Rdh13 | −1.37 | −1.75 | 0.301448306 | 0.009708492 | TRUE |
| Lancl1 | −1.11 | −1.58 | 0.36889 | 0.009700122 | TRUE |
| S1c44a2 | 0.294 | 1.22 | 0.890722932 | 0.009602684 | TRUE |
| Gga1 | 0.739 | 1.33 | 0.572314255 | 0.009070887 | TRUE |
| Endod1 | 0.398 | 1.51 | 0.866595452 | 0.008507733 | TRUE |
| Parp10 | 0.371 | 1.34 | 0.877516699 | 0.008507733 | TRUE |
| Stab1 | 1.24 | 1.65 | 0.349947 | 0.007987729 | TRUE |
| Irf7 | 0.423 | 1.43 | 0.866595452 | 0.007987729 | TRUE |
| Vmp1 | 1.49 | 1.4 | 0.182664643 | 0.007987729 | TRUE |
| Pdcd1 | 1.04 | 1.35 | 0.438085243 | 0.007987729 | TRUE |
| Tmem176b | −0.422 | −1.23 | 0.794836397 | 0.007987729 | TRUE |
| Ahcy12 | −1.01 | −1.24 | 0.323859934 | 0.007987729 | TRUE |
| AI836003 | −0.781 | −1.26 | 0.520644716 | 0.007987729 | TRUE |

TABLE 5-continued (IL-33)

| | gp.IL25.coeff | gp.IL33.coeff | gp.IL25.pvalue.adj | gp.IL33.pvalue.adj | candidate |
|---|---|---|---|---|---|
| Nop56 | −0.619 | −1.41 | 0.679264486 | 0.007987729 | TRUE |
| Ppif | −1.14 | −1.91 | 0.452378393 | 0.007987729 | TRUE |
| Il5 | 1.4 | 1.34 | 0.141732614 | 0.007937654 | TRUE |
| 0610031J06Rik | 0.555 | 1.33 | 0.726987067 | 0.00762705 | TRUE |
| Csf1 | −1.01 | −1.61 | 0.502957688 | 0.006669122 | TRUE |
| Sipa1 | 1.56 | 1.34 | 0.070200529 | 0.006605125 | TRUE |
| Tet3 | 1.62 | 1.32 | 0.05518395 | 0.006605125 | TRUE |
| Bcl6 | 1.29 | 1.98 | 0.445256278 | 0.006043579 | TRUE |
| Gng2 | 1.06 | 1.35 | 0.323945367 | 0.006043579 | TRUE |
| Arhgap26 | 0.821 | 1.3 | 0.463235501 | 0.006043579 | TRUE |
| Nlrc5 | 0.93 | 1.3 | 0.387677282 | 0.005815833 | TRUE |
| Zfand6 | 0.659 | 1.38 | 0.65223303 | 0.005797938 | TRUE |
| Grn | −0.326 | 1.55 | 0.904752946 | 0.005346413 | TRUE |
| Phf11b | 1.38 | 1.89 | 0.368386927 | 0.005110709 | TRUE |
| Acot7 | 0.807 | 1.78 | 0.690230769 | 0.004649645 | TRUE |
| Npc2 | 0.143 | 1.53 | 0.971845693 | 0.0044865 | TRUE |

To compare plates and droplets, Applicants took as the null set all genes (11,132 genes) detected in both Group A from droplet-based data and in plates. For the differentially expressed genes, Applicants used those genes that met the "candidate" selection requirements in each group, intersected with the null set (for IL-25, 1,166 genes in Group A and 35 genes in plates, with 17 in the intersection; for IL-33, 1,489 genes in Group A and 35 in plates, with 24 in the intersection) and computed Fisher's exact test to determine significance.

Figure 8A:
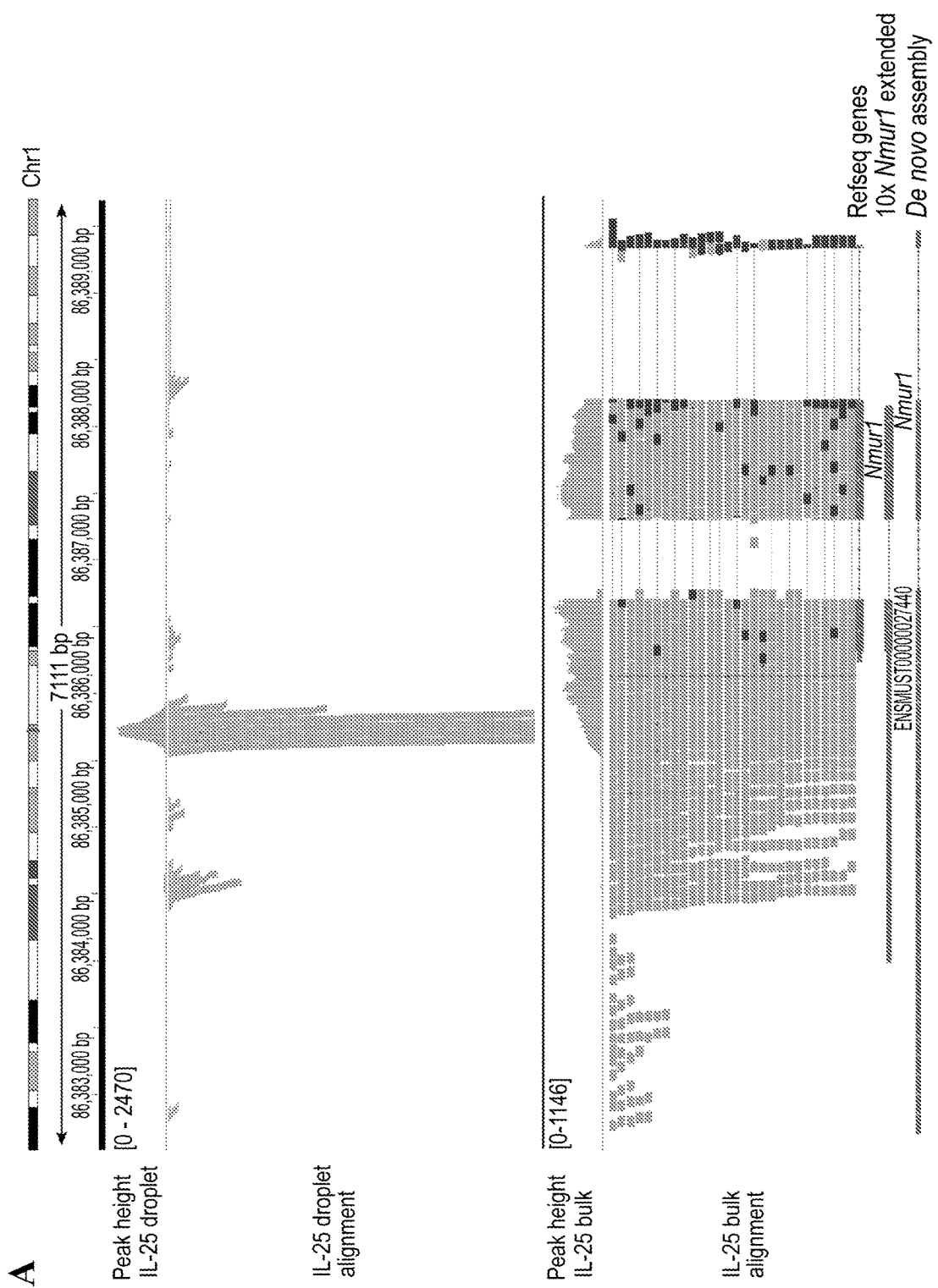
FIG. 8 illustrates that accurate detection of Nmur1 from massively parallel 3' end scRNA-seq requires cell type specific annotation. (a) Reannotation of the Nmur1 locus by RNA-Seq and assembly. Shown is a window of ~7Kb around the annotated Nmur1 locus on chromosome 1 (top) along with either read alignments to that region from either massively parallel droplet based 3' scRNA-seq (top, 55nt reads) or from population (bulk) RNA-seq of ILCs (bottom, 75nt reads). The Refseq annotation of Nmur1 (top track) does not extend to the 3' end of the transcript, as defined by either the scRNA-seq reads (10× Nmur1 extended; middle track) or by a transcriptome reassembly from bulk RNA-Seq (StringTie reassembled; bottom track). (b,c) Corrected annotation recovers Nmur1 expression (*=P<0.0001, GLM binomial test). (b) Histogram shows the distribution of expression levels of Nmur1 in single cells based on droplet scRNA-seq data when expression was calculated by aligning reads with the original RefSeq annotation (left), the scRNA-seq read based extended annotation (middle) or the reassembled transcript annotation from bulk RNA-Seq (right). (c) Nmur1 induction by IL-25. Shown is the proportion of cells expressing Nmur1 (y axis) across each of the three treatments when using the updated annotation.

Reannotation of the 3' UTR of Nmur1. Initially, Nmur1 had essentially no detected expression in the droplet-based scRNA-seq data, though many reads align to a region just downstream of the Nmur1 3' UTR annotation (FIG. 8a). To explore the basis of this discrepancy, Applicants aligned long (75 bp) paired-end reads from full-length RNA-seq of population samples that included cells from all three stimulation conditions (only those from IL-25 shown). Many read alignments bridge the annotated Nmur1 transcript and the region downstream where droplet-based 3' reads align (FIG. 8a), evidence that Nmur1 has isoforms longer than the annotated transcript. Applicants reannotated the transcriptome, moving the 3' end from 86,386,242 to 86,384,000, and realigned the droplet-based scRNA-seq data, resulting in a robust increase in frequency of detection of Nmur1. All droplet-based scRNA-seq data shown herein was aligned to the reannotated transcriptome.

Results

To better define the transcriptional landscape of lung-resident ILCs, Applicants analyzed more than 9,000 high quality, droplet-based scRNA-seq profiles of IL-7Rα+ CD90+ Lineage-lung-resident ILCs at both steady state and after in vivo activation with either IL-25 or IL-33 (FIG. 5a-c, Methods). Applicants scored cells based on their expression of ILC subset-specific signature genes and classified them as ILC1, ILC2, ILC3, "mixed, or, if no score was sufficiently high, "none" (FIG. 1a, FIG. 5d, e, Table 2, Methods). While ILCs with a mixed profile could in principle represent a transient or plastic transcriptional state, Applicants could not exclude that they represent doublets, as their frequency (2-3.4%) is comparable to the expected doublet rate (3-4% given the number of cells loaded). In all conditions, most cells were classified as ILC2 regardless of condition, with less than 9% of cells classified as any other type (FIG. 1a). Cell classifications were supported by the expression of key signature genes (e.g., Tbx21, Il1rl1, Rorc), with those classified as ILC2s preferentially expressing Gata3 and Il1rl1 (ST2, IL-33R), and up-regulating Il5 and Il13 upon alarmin stimulation (FIG. 1b). Alarmins did not induce dramatic changes in the relative proportions of different types of ILCs, although there is a statistically significant association between condition and ILC type ($\chi^2$ test, $p<2.2\times10^{-16}$), with modestly increased proportions of ILC2s in IL-33 treated mice and ILC3s in IL-25 treated mice (FIG. 1a).

Rather, the most salient effect of treatment with alarmins in vivo was the induction of unique gene expression programs, as suggested by the relationship between cells from different treatment conditions, independent of experimental batch, in plots based on principle components analysis (PCA) (FIG. 1c, FIG. 5f). Activation by either alarmin resulted in up regulation of several genes associated with ILC2-activation, including Il5, Klrg1, and Arg1, a metabolic regulator of ILC2 function (FIG. 1d). Other genes, such as Areg, were preferentially induced by IL-25 treatment and not IL-33 (or vice versa).

Applicants identified transcriptionally distinct groups of ILCs across all conditions by applying a nearest-neighbor-graph based clustering algorithm on the significant principle components of gene expression, which Applicants then visualized post hoc in two dimensions in tSNE plots (FIG. 1e, Methods). The seven clusters, ranging in size from 275 to 1,799 cells, showed high expression of genes that encode the proteins used for isolating ILCs (Ptprc, Il7r, Thy1) and did not express key marker genes of other cell types, with the exception of CD3 genes (for simplicity Cd3d is shown, clusters 4 and 6), which has previously been observed at the mRNA level in ILCs (FIG. 5g)[7,17]. Supporting our supervised ILC-type scoring scheme, ILC1s, ILC2s, and ILC3s largely partitioned into transcriptionally distinct clusters by this unsupervised clustering (FIG. 1e, f, FIG. 5h, Methods). In most clusters (clusters 1, 2, 3, 5, and 7, which contain 8,422 of the 9,138 cells), 96% of cells are ILC2s, while clusters 4 (354 cells) and 6 (362 cells) contain ILC3s (cluster 4), ILC1s (cluster 6), or ILCs of mixed profile (FIG. 1f, FIG. 5h). Cluster assignment is also strongly associated with treatment condition ($\chi^2$ test, $p<2.2\times10^{-16}$): approximately 90% of the cells in clusters 1 and 2 are IL-33 activated ILCs, at least two thirds of cells in clusters 5 and 7 are IL-25 activated ILCs, while control ILC2s make up three quarters of cluster 3 (FIG. 1g, FIG. 5i).

Figure 6:
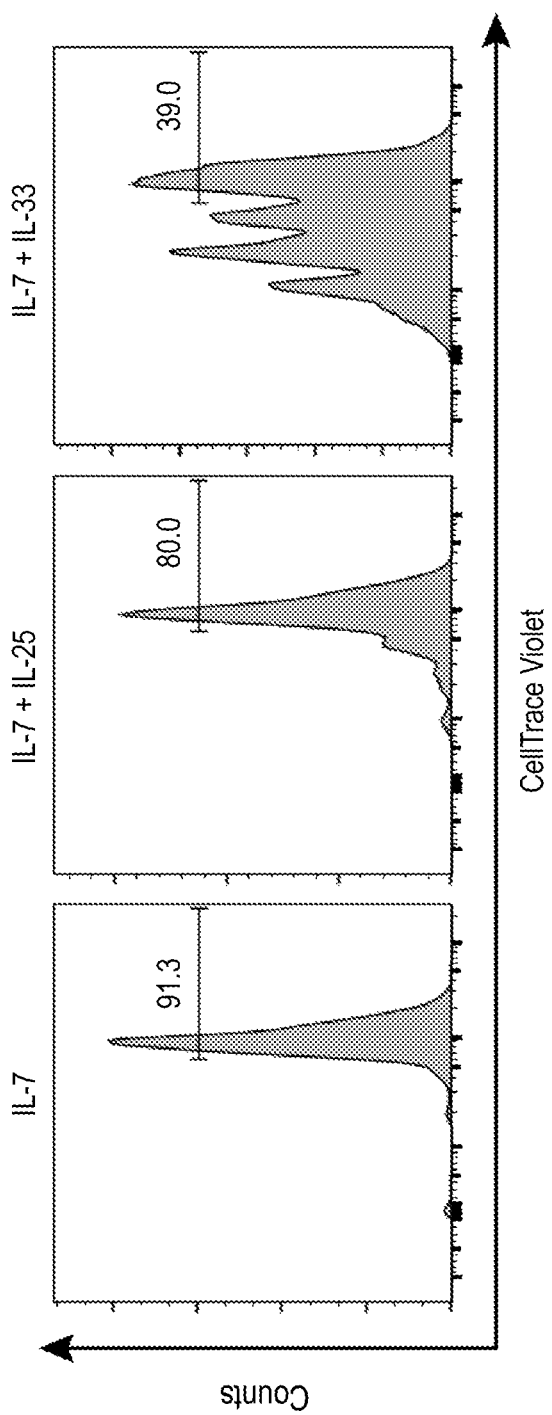
FIG. 6 illustrates proportions of non-proliferating ILCs. ILCs were labeled with CellTrace Violet and cultured in vitro under the indicated conditions. After 3 days, proliferation was analyzed by flow cytometric analysis of CellTrace Violet dilution. The frequency of non-proliferating ILCs is indicated. Data are representative of two individual experiments.

Observing that activated ILCs express on average 1.6 times (IL-25 activated) to 2.3 times (IL-33 activated) the number of genes of resting ILCs (FIG. 5c), Applicants scored cells according to a proliferative gene signature containing cell-cycle markers (Methods, Table 3)[8,9]. IL-33-activated ILC2s in cluster 1 scored particularly, significantly highly relative to all other clusters (Student's t-test, p<4.9× $10^{-7}$) (FIG. 1h). Consistent with this finding, IL-33 induced more robust proliferation of ILCs in vitro than did IL-25 (FIG. 6).

Applicants hypothesized that by identifying genes that are differentially expressed across clusters, Applicants could uncover novel molecular and regulatory mechanisms that control different ILC responses in vivo. Because cells in different clusters vary in global properties, such as proliferation, that affect gene counts, Applicants fit gene counts to mixtures of generalized linear mode is, which included covariates to account for the numbers of genes and UMIs (Unique Molecular Identifiers) per cell (Methods). In this way, Applicants identified genes that are significantly differentially expressed across clusters, groups of clusters, or conditions.

Representative highly ranked genes identified by this method include both those with known roles in ILC biology, as well as many novel genes (FIG. 1i). Among known genes, some, like Il13 and Klrg1, are highly expressed in clusters where alarmin-activated ILCs (clusters 1, 2, 5, 7) are predominant. In contrast, other genes are specific to certain alarmin-activated ILC clusters. For example, Csf2, which encodes GM-CSF, is expressed by ILCs in cluster 5 but not cluster 7, though cells from IL-25-treated mice are the predominant members of both clusters. Similarly, Ctla4 was induced by both IL-25 and IL-33, but only in some subsets of cells from these conditions (cluster 7 for IL-25, cluster 2 for IL-33) (FIG. 1i). Other genes are preferentially expressed in cells derived a single condition, regardless of cluster. Areg, for example, is highly expressed by cells from IL-25-dominant clusters (5 and 7), and Tff1 is preferentially expressed by ILCs in IL-33-dominant clusters (1 and 2). Finally, genes such as the hyalouronic acid receptor Stab2 and the lysophospholipid transferase Lpcat2, are downregulated in alarmin activated ILCs, with the exception of cluster 5, where expression is sustained (FIG. 1i). Taken together, these results suggest that not only do distinct subsets or functional states exist within defined ILC subsets, but also that IL-33 and IL-25 differentially regulate these transcriptional states.

The large number of cells profiled by massively parallel scRNA-seq using droplet technologies provides an extensive view of gene expression across a broad sample of cells, allowing us to identify variations within and between cell populations. However, the complexity, or number of distinct transcripts captured per cell is sometimes lower than in full-length protocols applied to single cells separated by flow cytometry into wells[20,21]. Depth of coverage is potentially a particular challenge in very small cells, like ILCs, that have lower RNA content[12]. Nevertheless, studies in other systems, such as the retina, have shown that sequencing large numbers of cells, even at shallow coverage, can readily classify cells and identify markers, as compared to smaller numbers of cells analyzed at greater depth[15]. To explore the possible impact of this on detection of genes that may explain cell-to-cell differences in our case, Applicants complemented our droplet based survey with an analysis of single ILCs using a modified version of the SMART-Seq2 protocol[21], optimized for performance on small cells, including T cells and ILCs (Methods).

Using this alternative method, Applicants analyzed 684 high-quality lung-resident ILC scRNA-seq profiles from mice treated with IL-33, IL-25, or PBS (FIG. 7a). The majority of these cells were classified as ILC2 by their gene signature score, consistent with our droplet-based atlas analysis (FIGS. 1, 2a, FIG. 7b-c, Table 2). Following PCA on 270 profiles from one batch, Applicants analyzed the genes associated with each of the top nine principle components (FIG. 2a), and tested those genes for statistically significant differential expression between IL-25 and IL-33 conditions. Applicants also tested all genes expressed in the full data set for differential expression across conditions using a model that accounts for the significant batch effect associated with the plates (Methods, Table 4,5). The genes identified as significantly associated with a condition in this analysis have a significant overlap with those identified in the droplet data (e.g., Lpcat2, Dgat2, Anxa2) (hypergeometric test, P<1.4×$10^{-8}$) (FIG. 1i, 2a). Of the genes specifically identified by plate-based scRNA-seq, the neuropeptide receptor Nmur1 (Gpr66, FM-3) stood out as being significantly associated with IL-25 compared to either PBS or IL-33 treated ILCs (FIG. 2a).

Applicants next explored why Nmur1 was not identified as a differentially expressed gene in our droplet-based scRNA-seq data set. In large part, the culprit is the lack of correct annotation of its 3' end, not its lack of detection in the libraries. Naïve inspection of our cells suggested that there is essentially no expression of Nmur1 in the droplet-based profiles. However, alignments of long reads from population RNA-seq controls, show that Nmur1's current annotated 3' end is incorrect (FIG. 8a, Methods), and the correct 3' end is at least 2.2 kb away. Thus, an automated pipeline would never recover its presence in a 3' end library such as those generated by droplets (FIG. 8a,b). Indeed, once Applicants used a corrected Nmur1 annotation based on a population (bulk) full-length RNA-seq of all ILCs, it was discovered as a top differentially expressed gene in the scRNA-Seq droplet-based data set, with statistically significant up regulation in IL-25 activated cells (GLM binomial test, P<0.0001) (FIG. 8a-c, Methods). Thus, while massively parallel methods may have lower complexity due to experimental limitations, our analysis suggests informatics limitations in the quality of annotations can be another major cause of false negatives. Fortunately, these can be addressed by generating a data-driven annotation from a full-length, bulk population library of the same cell population analyzed by scRNA-seq. Overall, Applicants concluded that both droplet and plate data supported the differential expression of Nmur1 as well as the same global trends in the data, and Applicants used a reannotated transcriptome for all droplet based data.

While Nmur1 has been shown to modulate inflammatory responses[22], its function on ILCs is unknown, prompting us to further investigate Nmur1 expression in ILCs and other relevant cell types. Applicants began by comparing the expression of Nmur1 to Vipr2, another neuropeptide receptor known to impact ILC2 function[23,24]. While both receptors were preferentially expressed by ILC2s compared to other ILC types, IL-25 activation increased the frequency of Nmur1-expressing ILCs compared to control, while IL-33 did not (GLM binomial test, p<3.4×$10^{-6}$) (FIG. 2b, Methods). In contrast, Vipr2 expression was not significantly increased after activation by either alarmin, after taking into account the number of genes detected in each condition (FIG. 2b, Methods). Applicants then assayed whether lung-resident ILCs expressed Nmur2, the other known receptor for NMU, and did not detect expression by qPCR (FIG. 2c)[25,26]. Finally, Applicants confirmed by several lines of evidence that Nmur1 is preferentially expressed on ST2$^+$ ILC2s: (1) Applicants did not detect significant Nmur1 expression by qPCR on other relevant lung resident immune populations, including CD4 T cells (FIG. 2d); (2) In mice heterozygous for a LacZ reporter gene knocked into the Nmur1 locus, LacZ activity was readily detectable in ST2+ ILCs, but not in ST2− ILCs or in T cells (FIG. 2e); (3) Only minimal (albeit detectable) expression of Nmur1 was observed on lung-resident CD4 T cells after induction of airway inflammation with house dust mite extract (HDM) and on in vitro differentiated Th2 cells, even after stimulation with alarmins (FIG. 2f, FIG. 9). Indeed, the relative expression on CD4 T cells was three orders of magnitude lower than that observed in ILC2s.

Since Nmur1 was preferentially expressed by IL-25-activated ILC2s, Applicants next investigated whether the neuropeptide NMU had any effect on cytokine production by ILCs in vitro either alone or in conjunction with alarmins. NMU alone induced modest upregulation of Il5 and Il13 in ILCs cultured in vitro (FIG. 3a). The modest induction of Il5 and Il13 was specific to ILCs and was not observed in Th2 cells cultured with NMU (FIG. 10a). The NMU-induced changes in Il5 and Il13 expression in ILCs were far lower than those observed in response to IL-25 and IL-33, prompting us to examine if NMU could modulate ILC responses to these alarmins. Applicants therefore stimulated ILCs in vitro with IL-25 or IL-33 either alone or in conjunction with NMU. NMU markedly increased expression of Il5 and Il13 in response to IL-25 by at least 3.6 fold for mRNA levels and at least 8 fold for protein levels (FIG. 3b), while its combination with IL-33 did not significantly alter Il5 and Il13 levels (FIG. 10b). These results demonstrate that NMU selectively synergizes with IL-25 to promote type-2 cytokine production by ILCs.

The synergy between IL-25 and NMU was even more striking in vivo, where treatment with NMU alone had little effect, while NMU dramatically enhanced the airway inflammation induced by IL-25 but not IL-33. Specifically, in vivo, treatment with NMU alone did not cause a significant increase in the expression of Il5 or Il13 mRNA in lung tissue, and only trace quantities of IL-5 protein were detectable in the bronchoalveolar lavage fluid (BALF) (FIG. 10c-e). The frequency of eosinophils in lung parenchyma did not increase following treatment with NMU, and there was only a mild increase in BALF eosinophils (FIG. 10f,g). While IL-25 alone modestly induced expression of IL-5 and IL-13 in the lung and BALF at the dose Applicants administered, the combination of NMU+IL-25 strongly increased IL-5 and IL-13 expression in the lung, and both cytokines were increased in BALF by more than 12-fold (FIG. 3c,d). Moreover, co-administration of IL-25 and NMU resulted in significant eosinophilia in both lung parenchyma and the BALF (FIG. 3e,f) and markedly enhanced histopathological signs of allergic inflammation, with increased perivascular and peribronchial infiltrates (FIG. 3g). Mice treated with both NMU+IL-25 had significantly increased lung resistance after inhaled methacholine challenge, demonstrating physiologically significant airway hyper-reactivity (FIG. 3h). In contrast, NMU had little impact on IL-33-induced lung inflammation, as the combination of IL-33 and NMU only modestly increased IL-5 expression and did not significantly enhance IL-13 expression, parenchymal eosinophilia, or airway hyper-reactivity (FIG. 11). Therefore, co-treatment with NMU specifically amplified IL-25-induced type 2 airway inflammation, converting a non-pathologic dose of IL-25 into one that resulted in a pathologic inflammatory response.

To further characterize how NMU and IL-25 synergize to induce inflammatory ILC2s, Applicants performed scRNA-seq of more than 7,000 lung-resident ILCs after in vivo treatment with NMU alone or in combination with IL-25. Applicants then combine these profiles together with 6,335 of the previously generated profiles of cells isolated from control or IL-25 treated mice. Applicants analyzed the relation between the cells' profiles according to the top 30 significant PCs (FIG. 4a). ILCs from mice treated with NMU alone largely localized with those from control mice, as visualized in the tSNE plot, consistent with the minimal in vivo impact of NMU alone (FIG. 4a, FIG. 10d-g). In contrast, ILCs from mice co-treated with NMU+IL-25 expressed significantly more genes and were distinctly localized, independent of batch effect, compared to the other three conditions (FIG. 12a,b). To better characterize the population substructure, Applicants partitioned ILCs into nine clusters that show a strong, significant association with treatment condition (FIG. 4b, Methods, $\chi^2$ test, $p<2.2\times10^{-16}$). Four of the clusters (5, 6, 8 and 9) consisted almost exclusively of IL-25- or NMU+IL-25 activated cells, though in different proportions. Whereas the majority (60% of 1262 cells) of cluster 6 is IL-25 activated (with a minority from mice co-treated with NMU+IL-25), in clusters 5, 8, and 9, the majority of cells (85% of 2242 cells in clusters 8 and 9, ~70% of 622 cells in cluster 5) are from mice co-treated with NMU+IL-25, with the remainder from IL-25 treated mice (FIG. 4b-c, FIG. 12c). This suggests that the combination of NMU+IL-25 expands three transcriptionally distinct populations of ILCs that are already present at lower numbers in mice treated with IL-25 alone.

Applicants therefore tested if these populations expanded due to increased proliferation in vivo. While IL-25 alone did not induce marked proliferation of ILC2s, mice treated with NMU+IL-25 had approximately twice as many Ki67+ ILCs (FIG. 4d), and an increased frequency of ILCs (FIG. 4e). Furthermore, NMU+IL-25 activated cells had a bimodal distribution of proliferative signature scores, with a subset of cells with high proliferation scores, compared to cells from the other conditions, which had generally low scores (FIG. 4f). Cluster 8 had a particularly high proportion of proliferative cells, compared with clusters 5 and 9 (Student's t-test, $P<8.6\times10^{-253}$), suggesting that only distinct subsets of ILCs may proliferate in response to NMU+IL-25 (FIG. 12d). Together these results suggest that while IL-25 activated ILC2s, the interaction with NMU promoted the proliferation and expansion of specific subpopulations of inflammatory ILCs.

Applicants also considered the possibility that NMU amplified IL-25-initiated ILC responses via a positive feedback circuit in which NMU up-regulated IL-17RB, the unique receptor chain for IL-25. Indeed, the combination of NMU+IL-25 increased the frequency of IL-17RB+ ILCs by flow cytometry, compared to IL-25 treatment alone (FIG. 4g), and expression of Il17rb mRNA in the lungs of mice co-treated with NMU+IL-25 was also increased by qPCR (FIG. 4h). Finally, single cell profiles from NMU+IL-25 treated mice show a significantly increased frequency of Il17rb expressing ILCs compared to other conditions (FIG. 4i, GLM binomial test, $P<2.2\times10^{-5}$, Methods).

Since the combination of IL-25 and NMU synergistically induced allergic lung inflammation in vivo, Applicants hypothesized that by identifying genes whose expression was specifically modified by the combination treatment, Applicants could generate a signature characterizing inflammatory ILC2s. Applicants tested genes for expression patterns showing a significant interaction between the NMU and IL-25 treatments, as well as for overall expression differentiating the NMU+IL-25 treatment condition from either IL-25 or NMU alone, or control (Methods). To increase our power to detect functionally relevant genes, Applicants also included a focused analysis of differential expression comparing the cells in clusters 8 and 9 (where most cells are from NMU+IL-25 mice, and hence likely highly inflammatory) with the cells in cluster 6 (where most cells are from mice treated only with IL-25). Applicants ranked genes by statistical significance and strength of effect according to each test, excluded those associated with our proliferative signature, and finally selected a representative group of 41 top-ranked genes, which Applicants refer to as an inflammatory ILC2 signature (FIG. 4j, Methods, Table 6).

This signature includes both established regulators of ILC function (e.g., Areg and Il5), as well as a number of genes not previously known to play a role in ILCs, including transcription factors such as Nr4a1 (Nurr77), cell surface receptors such as Tnfrsf8 (CD30), and soluble mediators such as Tff1 (FIG. 4j). The signature genes demonstrated several distinct expression patterns based on how expression in the combination treatment (NMU+IL-25) compared to that in the sum of the individual treatment effects (NMU or IL-25 separately). One subset of genes, including Il1r2 and Tnfrsf8, was strongly, and for some genes (e.g., Anxa2) non-additively, up regulated by the combination treatment (FIG. 4j). A second subset consisted of genes, including Zfp36l1, Dgat2, and Csf2, where the interaction between treatments led to a change in the direction of regulation; whereas a gene was up-regulated following activation with IL-25 and/or NMU, it was down-regulated after combination treatment. Finally, a few genes (e.g., Lpcat2 and Fosb) were highly expressed at both steady state and in single-treatment conditions, but were down-regulated after activation with NMU+IL-25.

Next, Applicants scored each cell by the inflammatory ILC2 signature, with genes contributing positively to the score if they are up-regulated in NMU+IL-25 relative to IL-25, and negatively otherwise. Certain signature genes, such as Anxa2 and Ltb, that strongly correlate or anti correlate with the signature scores are good single-gene indicators of pro-inflammatory ILCs (FIG. 4k). As expected, all high-scoring cells were discretely localized when visualized (FIG. 4l). Whereas only some cells from NMU+IL-25 treated mice score highly for the proliferative signature (FIG. 4f), all of them score highly for the inflammatory ILC2 signature (FIG. 4m). Indeed, while only cluster 8 has a pronounced proliferative signal, cells in clusters 5, 8, 9 all have similarly high scores for the inflammatory ILC2 signature, indicating that this signature captures cells that are inflammatory regardless of proliferative state (FIG. 12d,e). IL-33 has previously been shown to induce airway inflammation[27]. Applicants also scored cells from IL-33 treated mice, which were not used to develop the inflammatory signature, and observed that these cells scored highly, relative to cells in IL-25 and control, indicating that the signature captures a general transcriptional state present in ILCs under inflammatory conditions (Student's t-test, $P<2.2\times10^{-16}$).

Further analysis by cluster of expression of our signature genes suggested that activated and inflammatory ILC2s were transcriptionally heterogeneous. While expression of genes known to be involved in ILC2 activation, such as Klrg1 or IL-13, were highly expressed in all clusters principally composed of cells from mice treated with NMU+IL-25 or IL-25 alone (5, 6, 8, 9), Applicants also observed distinct transcriptional patterns between these clusters (FIG. 12f). In particular, regardless of their condition of origin, cells from cluster 5 uniquely express 114, and express only low levels of Il1rl1 and Il5, in contrast to cells in clusters 6, 8, and 9 (FIG. 12f). This cluster also had particularly robust expression of Klrg1, suggesting that these cells may be similar to previously described IL-25-induced inflammatory ILC populations[6].

While many of our signature genes have not been previously identified to modulate ILC2 function, several of them have been linked to allergic airway inflammation both in mice and humans. For instance, compared to controls, mice lacking Tnfrsf8 (CD30) and Anxa2 have been reported to have reduced airway inflammation in mouse models of asthma[28,29]. Additionally, Tnfrsf8, Anxa2, and Il1r2, are overexpressed in patients with allergic asthma[30-32]. Other reports showed that in vivo blockade of the OX40 pathway (Tnfrsf4) reduced inflammation in mouse models of allergic airway inflammation[33]. Deletion of Nr4a1, which is down-regulated in our inflammatory ILCs, exacerbates mouse models of airway inflammation, suggesting that this gene may have a functional role in limiting inflammatory ILC responses[34]. Similarly, Areg, which is known to promote epithelial cell survival and proliferation[2], is upregulated in IL-25 activated ILCs but relatively down-regulated in our inflammatory population. Finally, Nmur1 is also most highly expressed in IL-25 activated ILCs, suggesting that NMU/Nmur1 signaling initiates an inflammatory program in IL-25-activated ILC2s, potentially switching activated, tissue protective ILCs into tissue inflammatory cells.

In conclusion, Applicants used scRNA-seq of thousands of cells to establish the transcriptional landscape of lung-resident ILCs under homeostatic and inflammatory conditions, and identified Nmur1 as a specific modulator of IL-25 driven ILC2 responses. NMU-deficient mice were previously reported to develop attenuated airway eosinophilia after allergic sensitization[22], but the underlying mechanism was not clear. IL-25 is elevated in steroid-naïve Th2-high asthmatics, and asthmatics with elevated IL-25 have both more severe airway hyperreactivity and an improved response to inhaled corticosteroids, highlighting the role of this cytokine in promoting a common and potentially severe disease subtype[9]. IL-25 also plays an important role in post-viral asthma exacerbations[35]. Our findings raise the question of whether NMU plays a role in potentiating airway inflammation in these clinical contexts. While IL-25 is expressed by airway epithelial cells, recent data have also highlighted chemosensory cells as key producers of IL-25 in the intestine[36-38], and such cells may also play important roles in modulating lung and gut immune responses[39,40]. The data indicate that NMU is expressed both in the trachea as well as in neurons from thoracic dorsal root ganglia (data not shown), suggesting that the coordinated action of chemosensory cells and neurons could represent a pathway that induces tissue-based type 2 immune responses via ILCs. Given the importance of smooth muscle contraction in the clinical manifestations of many allergic diseases, it is intriguing that NMU can both promote smooth muscle contraction[41] and also modulate ILC function. This, in turn, might suggest that neuronal activation following inhalation of noxious substances or allergens could induce both smooth muscle contraction and the development of type 2 inflammation against the provoking substance, thus simultaneously promoting physical expulsion and immunity to the stimulus. Taken together, the findings demonstrate a novel neuro-immune molecular circuit that plays an important role in exacerbating mucosal allergic inflammation in vivo.

REFERENCES

1 Neill, D. R. et al. Nuocytes represent a new innate effector leukocyte that mediates type-2 immunity. Nature 464, 1367-1370, doi:10.1038/nature08900 (2010).

2 Monticelli, L. A. et al. Innate lymphoid cells promote lung-tissue homeostasis after infection with influenza virus. Nature immunology 12, 1045-1054, doi:10.1031/ni.2131 (2011).
3 Chang, Y. J. et al. Innate lymphoid cells mediate influenza-induced airway hyper reactivity independently of adaptive immunity. Nature immunology 12, 631-638, doi: 10.1038/ni.2045 (2011).
4 Moro, K. et al. Innate production of T(h)2 cytokines by adipose tissue-associated c-Kit(+)Sca-1(+) lymphoid cells. Nature 463, 540-544, doi:10.1038/nature08636 (2010).
5 Halim, T. Y. et al. Group 2 innate lymphoid cells are critical for the initiation of adaptive T helper 2 cell-mediated allergic lung inflammation. Immunity 40, 425-435, doi:10.1016/j.immuni.2014.01.011 (2014).
6 Huang, Y. et al. IL-25-responsive, lineage-negative KLRG1(415 hi) cells are multipotential 'inflammatory' type 2 innate lymphoid cells. Nature immunology 16, 161-169, doi:10.1038/ni.3078 (2015).
7 Bjorklund, A. K. et al. The heterogeneity of human CD127(+) innate lymphoid cells revealed by single-cell RNA sequencing. Nature immunology 17, 451-460, doi: 10.1038/ni.3368 (2016).
8 Salimi, M. et al. A role for IL-25 and IL-33-driven type-2 innate lymphoid cells in atopic dermatitis. The Journal of experimental medicine 210, 2939-2950, doi:10.1084/jem.20130351 (2013).
9 Cheng, D. et al. Epithelial interleukin-25 is a key mediator in Th2-high, corticosteroid responsive asthma. American journal of respiratory and critical care medicine 190, 639-648, doi:10.1164/rccm.201403-05050C (2014).
10 Gudbjartsson, D. F. et al. Sequence variants affecting eosinophil numbers associate with asthma and myocardial infarction. Nature genetics 41, 342-347, doi:10.1038/ng.323 (2009).
11 Tanay, A. & Regev, A. Scaling single-cell genomics from phenomenology to mechanism. Nature 541, 331-338, doi:10.1038/nature21350 (2017).
12 Wagner, A., Regev, A. & Yosef, N. Revealing the vectors of cellular identity with single433 cell genomics. Nat Biotechnol 34, 1145-1160, doi:10.1038/nbt.3711 (2016).
13 Gaublomme, J. T. et al. Single-Cell Genomics Unveils Critical Regulators of Th17 Cell Pathogenicity. Cell 163, 1400-1412, doi:10.1016/j.cell.2015.11.009 (2015).
14 Habib, N. et al. Div-Seq: Single-nucleus RNA-Seq reveals dynamics of rare adult newborn neurons. Science 353, 925-928, doi:10.1126/science.aad7038 (2016).
15 Shekhar, K. et al. Comprehensive Classification of Retinal Bipolar Neurons by Single-Cell Transcriptomics. Cell 166, 1308-1323 e1330, doi:10.1016/j.cell.2016.07.054 (2016).
16 Gury-BenAri, M. et al. The Spectrum and Regulatory Landscape of Intestinal Innate Lymphoid Cells Are Shaped by the Microbiome. Cell 166, 1231-1246 e1213, doi:10.1016/j.cell.2016.07.043 (2016).
17 Robinette, M. L. et al. Transcriptional programs define molecular characteristics of innate lymphoid cell classes and subsets. Nature immunology 16, 306-317, doi: 10.1038/ni.3094 (2015).
18 Kowalczyk, M. S. et al. Single-cell RNA-seq reveals changes in cell cycle and differentiation programs upon aging of hematopoietic stem cells. Genome Res 25, 1860-1872, doi:10.1101/gr.192237.115 (2015).
19 Tirosh, I. et al. Dissecting the multicellular ecosystem of metastatic melanoma by single cell RNA-seq. Science 352, 189-196, doi:10.1126/science.aad0501 (2016).
20 Zheng, G. X. et al. Massively parallel digital transcriptional profiling of single cells. Nature communications 8, 14049, doi:10.1038/ncomms14049 (2017).
21 Picelli, S. et al. Smart-seq2 for sensitive full-length transcriptome profiling in single cells. Nature methods 10, 1096-1098, doi:10.1038/nmeth.2639 (2013).
22 Moriyama, M. et al. The neuropeptide neuromedin U activates eosinophils and is involved in allergen-induced eosinophilia. American journal of physiology. Lung cellular and molecular physiology 290, L971-977, doi: 10.1152/ajplung.00345.2005 (2006).
23 Nussbaum, J. C. et al. Type 2 innate lymphoid cells control eosinophil homeostasis. Nature 502, 245-248, doi:10.1038/nature12526 (2013).
24 Talbot, S. et al. Silencing Nociceptor Neurons Reduces Allergic Airway Inflammation. Neuron 87, 341-354, doi: 10.1016/j.neuron.2015.06.007 (2015).
25 Hedrick, J. A. et al. Identification of a human gastrointestinal tract and immune system receptor for the peptide neuromedin U. Molecular pharmacology 58, 870-875 (2000).
26 Szekeres, P. G. et al. Neuromedin U is a potent agonist at the orphan G protein-coupled receptor FM3. The Journal of biological chemistry 275, 20247-20250, doi: 10.1074/jbc.C000244200 (2000).
27 Bartemes, K. R. et al. IL-33-responsive lineage-CD25+CD44(hi) lymphoid cells mediate innate type 2 immunity and allergic inflammation in the lungs. Journal of immunology 188, 1503-1513, doi:10.4049/jimmunol.1102832 (2012).
28 Polte, T., Behrendt, A. K. & Hansen, G. Direct evidence for a critical role of CD30 in the development of allergic asthma. The Journal of allergy and clinical immunology 118, 942-948, doi:10.1016/j.jaci.2006.07.014 (2006).
29 Schuliga, M. et al. Plasminogen-stimulated inflammatory cytokine production by airway smooth muscle cells is regulated by annexin A2. Am J Respir Cell Mol Biol 49, 751-758, doi:10.1165/rcmb.2012-04040C (2013).
30 Heshmat, N. M. & El-Hadidi, E. S. Soluble CD30 serum levels in atopic dermatitis and bronchial asthma and its relationship with disease severity in pediatric age. Pediatr Allergy Immunol 17, 297-303, doi:10.1111/j.1399-3038.2006.00405.x (2006).
31 Katsunuma, T. et al. Analysis of gene expressions of T cells from children with acute exacerbations of asthma. Int Arch Allergy Immunol 134, 29-33, doi:10.1159/000077530 (2004).
32 Sekigawa, T. et al. Gene-expression profiles 482 in human nasal polyp tissues and identification of genetic susceptibility in aspirin-intolerant asthma. Clinical and experimental allergy: journal of the British Society for Allergy and Clinical Immunology 39, 972-981, doi: 10.1111/j.1365-2222.2009.03229.x (2009).
33 Burrows, K. E. et al. OX40 blockade inhibits house dust mite driven allergic lung inflammation in mice and in vitro allergic responses in humans. European journal of immunology 45, 1116-1128, doi:10.1002/eji.201445163 (2015).
34 Kurakula, K. et al. Nuclear Receptor Nur77 Attenuates Airway Inflammation in Mice by Suppressing NF-kappaB Activity in Lung Epithelial Cells. Journal of immunology 195, 1388-1398, doi:10.4049/jimmunol.1401714 (2015).
35 Beale, J. et al. Rhinovirus-induced IL-25 in asthma exacerbation drives type 2 immunity and allergic pulmonary inflammation. Sci Transl Med 6, 256ra134, doi: 10.1126/scitranslmed.3009124 (2014).

36 von Moltke, J., Ji, M., Liang, H. E. & Locksley, R. M. Tuft-cell-derived IL-25 regulates an intestinal ILC2-epithelial response circuit. Nature 529, 221-225, doi: 10.1038/nature16161 (2016).

37 Gerbe, F. et al. Intestinal epithelial tuft cells initiate type 2 mucosal immunity to helminth parasites. Nature 529, 226-230, doi:10.1038/nature16527 (2016).

38 Howitt, M. R. et al. Tuft cells, taste-chemosensory cells, orchestrate parasite type 2 immunity in the gut. Science 351, 1329-1333, doi:10.1126/science.aaf1648 (2016).

39 Gu, X. et al. Chemosensory functions for pulmonary neuroendocrine cells. Am J Respir Cell Mol Biol 50, 637-646, doi: 10.1165/rcmb.2013-0199OC (2014).

40 Branchfield, K. et al. Pulmonary neuroendocrine cells function as airway sensors to control lung immune response. Science 351, 707-710, doi:10.1126/science.aad7969 (2016).

41 Prendergast, C. E., Morton, M. F., Figueroa, K. W., Wu, X. & Shankley, N. P. Species508 dependent smooth muscle contraction to Neuromedin U and determination of the receptor subtypes mediating contraction using NMU1 receptor knockout mice. British journal of pharmacology 147, 886-896, doi:10.1038/sj.bjp.0706677 (2006).

42 Singer, M. et al. A Distinct Gene Module for Dysfunction Uncoupled from Activation in Tumor-Infiltrating T Cells. Cell 166, 1500-1511 e1509, doi:10.1016/j.cell.2016.08.052 (2016).

43 Jager, A., Dardalhon, V., Sobel, R. A., Bettelli, E. & Kuchroo, V. K. Th1, Th17, and Th9 effector cells induce experimental autoimmune encephalomyelitis with different pathological phenotypes. Journal of immunology 183, 7169-7177, doi:10.4049/jimmunol.0901906 (2009).

44 Satija, R., Farrell, J. A., Gennert, D., Schier, A. F. & Regev, A. Spatial reconstruction of single-cell gene expression data. Nat Biotechnol 33, 495-502, doi: 10.1038/nbt.3192 (2015).

45 Zeileis, A., Kleiber, C. & Jackman, S. Regression Models for Count Data in R. Journal of Statistical Software 27, doi:10.18637/jss.v027.i08 (2008).

46 Jackman, S. pscl: Classes and Methods for R Developed in the Political Science Computational Laboratory, Stanford University. Department of Political Science, Stanford University. Stanford, California. R package version 1.4.9. (2015).

47 Bray, N. L., Pimentel, H., Melsted, P. & Pachter, L. Near-optimal probabilistic RNA-seq quantification. Nat Biotechnol 34, 525-527, doi:10.1038/nbt.3519 (2016).

48 Soneson, C., Love, M. I. & Robinson, M. D. Differential analyses for RNA-seq: transcript-level estimates improve gene-level inferences [version 2; referees: 2 approved]. F1000Research 4, doi:10.12688/f1000research.7563.2 (2016).

Example 2—Further Experiments and Analysis

Methods

Mice and in vivo ILC activation. C57Bl/6J mice were purchased from the Jackson Laboratory. Nmur1-LacZ reporter mice with a LacZ cassette knocked into the Nmur1 locus were rederived from Nmur1$^{tm1.1(KOMP)Vleg}$ sperm obtained from the trans-NIH Knock-Out Mouse Project (KOMP) Repository. NMU-deficient mice (NMU-KO) were rederived from B6.129S2-Nmu<tm1Mko> embryos from the RIKEN BioResource Center. For experiments with Nmur1-LacZ (Nmur1-KO) and NMU-KO mice, littermates that were either homozygous or heterozygous for the wild type allele were used as controls. Mice were housed under specific-pathogen-free conditions. For experiments, mice were matched for sex and age, and most mice were 6-10 weeks old. Where indicated, mice were anesthetized with Isoflurane and treated intranasally with the indicated stimuli (500 ng IL-25, 500 ng IL-33, or 20 µg Neuromedin U) daily for three consecutive days. The total administered volume was 20 µl for all conditions. Mice were randomly assigned to treatment groups after matching for sex and age. Airway inflammation was also induced with house dust mite (HDM) extract (Greer Laboratories). Mice were treated intranasally with 10 µg HDM on day 0, 7, 8, and 9, prior to sacrifice on day 10. All experiments were conducted in accordance with animal protocols approved by the Harvard Medical Area Standing Committee on Animals or BWH IACUC.

Flow cytometry. For flow cytometric analysis CD3ε (clone: 145-2C11), CD4 (clone: RM4-5), CD8a (clone: 53-6.7), CD11b (clone: M1/70), CD11c (clone: N418), CD19 (clone: 6D5), CD30 (Tnfrsf8; clone: mCD30.1), CD45 (clone: 30-F11), CD47 (clone: miap301), CD48 (clone: HM48-1), CD81 (clone: Eat-2), CD90.2 (clone: 30-H12), CD127 (clone: A7R34), CD152 (CTLA-4; clone: UC10-4B9), I-A/I-E (clone: M5/114.15.2), IL-5 (clone: TRFKS), KLRG1 (clone: 2F1/KLRG1), NK1.1 (clone: PK136), Sema4A (clone: 5E3/SEMA4A), ST2 (clone: DIH9), TCRβ (clone: H57-597) and TCRγδ (clone: GL3) were purchased from BioLegend. 7AAD was obtained from BD Pharmingen, CD121b (IL1r2; clone: 4E2), Batf (clone: S39-1060) and Siglec-F (clone: E50-2440) from BD Biosciences and CD85k (gp49; clone: H1.1), Fixable Viability Dye eFluor 506, Galectin-3 (Lgals3; clone: eBioM3/38), IL-13 (clone: eBio13A), IL17RB (IL-25R; clone: Munc33), Ki-67 (clone: SolA15) and Nur77 (Nr4a1) (clone: 12.14) from eBioscience. Cells were stained on ice with antibodies for surface molecules and the live/dead marker 7AAD and analyzed on a LSRFortessa (BD Biosciences). Intracellular cytokine staining was performed after incubation for 5 hr with 1 µM ionomycin (Sigma-Aldrich), 50 ng/ml phorbol 12-myristate 13-acetate (Sigma-Aldrich) and GolgiStop (BD Biosciences). Cells were then fixed and stained using the BD Cytofix/Cytoperm buffer set (BD Biosciences) per manufacturer's instructions. Proliferation was assessed by Ki-67 staining after cell fixation and permeabilization using the Foxp3/Transcription Factor Staining Buffer Set (eBioscience). Different cell types were identified by the following gating strategies: ST2$^+$ ILCs (7AAD$^-$ CD45$^+$ CD4$^-$ Lineage$^-$ CD90.2$^+$ CD127$^+$ ST2$^+$), T cells (7AAD$^-$ CD45$^+$ CD4$^+$), B cells (7AAD$^-$ CD45$^+$ CD19$^-$), eosinophils (7AAD$^-$ CD45$^-$ CD11b$^-$ CD 11 c$^{low}$ Siglec-F$^+$ SSC$^{high}$), neutrophils (7AAD$^-$ CD45$^+$ CD11c$^{low}$ CD11b$^+$ Ly6G$^+$ CD11b$^+$), alveolar macrophages (7AAD$^-$ CD45$^+$ CD11 c$^{high}$ CD 11b$^{intermediate}$) and CD45$^-$ cells (7AAD$^-$ CD45$^-$).

Lung analysis. Mice were sacrificed and perfused with cold PBS. Where indicated, after perfusion, broncho-alveolar lavage (BAL) was obtained by injecting 1.5 ml cold PBS into the lungs via a secured tracheal cannula. BALF was centrifuged, and the supernatant was used for analyzing cytokine levels and the cell pellet was resuspended, counted, and used for flow cytometry. Following BAL, lung lobes were dissected. The post-caval lobe was fixed in buffered formalin for histological analysis. Single cell suspensions of the remaining lung parenchymal tissue were prepared with the GentleMACS lung dissociation kit (Miltenyi Biotec) according to the manufacturer's instructions. Where indicated, cells were diluted in 10% Trypan Blue and viable cells counted using a hemocytometer.

Fluorescence-activated cell sorting of innate lymphoid cells. After dissociation, single cell suspensions were incubated with CD90.2 MicroBeads (Miltenyi Biotec) on ice and enriched for CD90.2$^+$ cells by magnetic separation using LS columns according to the manufacturer's protocol. CD90.2$^-$ lung cells were then stained on ice with antibodies for sorting. ILCs were defined as 7AAD$^-$ CD45$^+$ CD90.2$^+$ CD127$^+$ Lineage (CD11b, CD 11c, CD19, NK1.1, CD3ε, CD4, CD8a, TCRβ, TCRγδ)$^-$ cells and sorted on a BD FACS Aria (BD Biosciences).

RNA-Seq. For population (bulk) RNA-seq, sorted ILCs were lysed with RLT Plus buffer and RNA was extracted using the RNeasy Plus Mini Kit (Qiagen). Full-length RNA-seq libraries were prepared as previously described[45] and paired-end sequenced (75 bp×2) with a 150 cycle Nextseq 500 high output V2 kit.

For droplet-based 3' end massively parallel single-cell RNA sequencing (scRNA-seq), sorted ILCs were encapsulated into droplets, and libraries were prepared using Chromium™ Single Cell 3' Reagent Kits v2 according to manufacturer's protocol (10× Genomics). The generated scRNA-seq libraries were sequenced using a 75 cycle Nextseq 500 high output V2 kit.

For full-length scRNA-Seq, single ILCs were sorted into 96-well plates containing 5 µl TCL Buffer (QIAGEN) with 1% 2-Mercaptoethanol, centrifuged and frozen at −80° C. SMART-Seq2 protocol was carried out as previously described[21] with minor modifications in the reverse transcription step. cDNA was amplified with 22 cycles and tagmented with one-eighth of the standard Illumina NexteraXT reaction volume. Single-cell libraries were pooled and paired-end sequenced (38 bp×2) with a 75 cycle Nextseq 500 high output V2 kit.

All RNA-Seq data represent pooled data from at least two distinct biological replicates.

ILC in vitro culture. For in vitro experiments 5,000 ILCs/well were cultured in a 96 well round bottom plate with 20 ng/ml IL-7 (R&D Systems), 200 ng/ml IL-25 (R&D Systems) or 20 ng/ml, 2 ng/ml or 0.2 ng/ml IL-33 (BioLegend) with or without 1 µg/ml Neuromedin U (US Biological). In some cases purified CD90.2$^+$ lung cells were first labeled with CellTrace Violet (Thermo Fisher Scientific), then sorted as described above, and cultured for 3 days under the indicated conditions.

Histology. Following paraffin embedding, sections of the formalin-fixed lung lobe were stained by H&E staining. Tissue sections were scored by a histopathologist in a blinded manner for severity of lung inflammation according to the following scoring system: 0=normal, 1=very mild, 2=mild, 3=moderate or 4=severe.

Methacholine challenge. Airway hyperresponsiveness was determined as previously described[28] using a flexiVent rodent ventilator (SciReq).

LacZ reporter assay. The Nmur1 null allele contains a LacZ reporter cassette. Single cell suspensions of lung cells from Nmur1-LacZ$^{+/-}$ mice were stained with the FluoReporter lacZ flow cytometry kit (Thermo Fisher Scientific) according to the manufacturer's protocol. Immediately after fluorescein di-V-galactoside (FDG) loading was stopped with 1.8 ml ice-cold medium, cells were stained with 7AAD and antibodies against surface markers and analyzed by flow cytometry.

Quantitative real-time PCR. RNA was isolated using RNeasy Plus Mini Kit (Qiagen) and reverse transcribed to cDNA with iScript cDNA Synthesis Kit (Bio-Rad). Gene expression was analyzed by quantitative real-time PCR on a ViiA7 System (Thermo Fisher Scientific) using TaqMan Fast Advanced Master Mix (Thermo Fisher Scientific) with the following primer/probe sets: Il5 (Mm00439646_m1), Il13 (Mm00434204_m1), Il17rb (Mm00444709_m1), Nmur1 (Mm04207994_m1), Nmur2 (Mm00600704_m1), Nmu (Mm00479868_m1) and Actb (Applied Biosystems). Expression values were calculated relative to Actb detected in the same sample by duplex qPCR.

Cytokine quantification. Cytokine concentrations in BAL fluid, lung and supernatant of in vitro ILC cultures were analyzed by the LegendPlex Mouse Th Cytokine Panel (13-plex) (BioLegend) according to the manufacturer's instructions and analyzed on a FACS Calibur (BD Biosciences).

T cell in vitro culture. CD4$^+$ T cells were isolated as described previously[46] and sorted for naive T cells (CD4$^-$ CD62L$^+$ CD44$^{low}$) on a FACS Aria. Naive T cells were cultured in the presence of plate-bound anti-CD3 (1 µg/ml; Bio X Cell) and anti-CD28 (1 µg/ml; Bio X Cell) antibodies. Th2 cells were generated by addition of 20 ng/ml IL-4 (Miltenyi Biotec) and 20 ng/ml anti-IFNγ (Bio X Cell) antibody. On day 3 of in vitro differentiation, PBS, 200 ng/ml IL-33 (BioLegend) or 100 ng/ml IL-25 (R&D Systems) were added to the T cell culture either with or without 1 µg/ml NMU (US Biological). After 2 additional days, RNA was isolated.

Nodose/jugular and dorsal root ganglion isolation and cultures. Nodose/jugular ganglion and dorsal root ganglia (DRG) were dissected from mice and dissociated in 1 mg/mL Collagenase A with 3 mg/ml dispase II (Roche Applied Sciences) in HEPES buffered saline (Sigma) for 60 minutes at 37° C. For some experiments, cells were then lysed in RLT Plus buffer and RNA was isolated using the RNeasy Plus Mini Kit (Qiagen). For the purposes of cell culture, the DRG cell suspension was then triturated with glass pasteur pipettes of decreasing size, followed by centrifugation over a 12% BSA (Sigma) gradient. After centrifugation, the top layer of neuronal debris was discarded and the DRG pellet was resuspended in neurobasal (NB) media containing B-27 and penicillin/streptomycin (Life Technologies). DRGs were then plated on laminin-coated 96-well culture dishes in NB media with B27, 50 ng/ml nerve growth factor (NGF) and penicillin/streptomycin. The next day the cells were washed with PBS prior to addition of fresh NB media containing B-27, NGF and penicillin/streptomycin. DRG cultures were stimulated with 200 ng/ml IL-13 for 30 minutes, at which time RNA was isolated for qPCR analyses.

Immunofluorescence Microscopy. Mice were perfused with 37° C. PBS via the heart. The lungs were extracted and inflated via the trachea with 4% low melting agarose (16520-100; Invitrogen) and fixed in 4% PFA on ice for 1 hour. The lungs were embedded in agarose for vibratome cutting (Leica). 100 µm lung slices were blocked first with the mouse on mouse blocking reagent (Vector Laboratories) and subsequently with 5% goat and donkey serum (Jackson ImmunoResearch) in PBS/0.1% Triton-X-100. Tissue was stained for rat anti-CD3ε (17A2; BioLegend), hamster anti-KLRG1 (2F1; eBioscience) and mouse anti-SNAP25 (SMI81; BioLegend) overnight at 4° C. shaking. After washing in PBS, tissues were incubated at room temperature for 1 h in PBS/0.1% Triton-X-100 containing goat anti-rat-AF555, goat anti-hamster-AF647, or goat anti-mouse IgG1-AF488 (all ThermoFisher Scientific) and then washed again. Images were acquired with an inverted Nikon Eclipse Ti microscope (Nikon). Z-stacks were acquired and converted into all-in-focus images using the Extended Depth of Focus (EDF) plug-in (NIS-Elements). Distances of KLRG1$^-$ CD3ε⁻ cells to the closest SNAP-25⁺ nerve fiber were measured using the NIS-Elements software.

Statistical analysis of functional data. No data were excluded from analysis. Prism 7 (GraphPad Software) was used to perform two-tailed t-test and ordinary one-way or two-way ANOVA with Tukey's multiple comparisons test on datasets for which statistical significance is indicated (except the RNA-sequencing data). All figures of functional data show mean±SEM.

P values in transcriptomic analysis. For certain types of numeric computations, the smallest P value that R can report is "<$2.2 \times 10^{-16}$".

Analysis of droplet-based scRNA-Seq data: Initial QC. Gene counts were obtained by aligning reads to the mm10 genome using CellRanger software (v1.2 for data from alarmin-treated and NMU-treated mice, v1.3 for data from HDM-treated mice) (10× Genomics), with the genome reannotated at the 3' end of Nmur1 (see main text). To remove doublets and poor-quality cells, cells were excluded from subsequent analysis if they were outliers in their sample of origin in terms of number of genes, number of UMIs, and percentage of mitochondrial genes (FIG. 18b,c). The number of UMIs per cell and number of genes expressed per cell are tightly correlated with condition (FIG. 18c), likely due to the effect of proliferation on transcript numbers. Sample-specific cutoffs ranged from 626-2,483 genes per cell for a PBS treated sample to 1,502-5,260 genes per cell for an IL-33 treated sample. At least 92% of cells were retained for each sample.

To further estimate and remove technical variability from the overall increased variability across replicates in Group C (defined below), additional QC measures were taken (FIG. 27a,b). UMI and gene saturation were estimated independently for each cell by subsampling a fraction of the total number of reads, with replacement, across a range of fractions (0.02 to 0.98, in 0.02 increments). For each subsample, Applicants calculated the number of UMIs and transcripts detected. The sampling procedure was repeated 10 times, and the values were used to estimate saturation limits for UMI/genes by nonlinear fitting of the following saturation function: y=ax/(b+x)+c. Cells were removed if they were outliers with respect to estimated saturation for either genes or UMIs. Cells were also removed if they were outliers in terms of the ratio or relative difference of the total number of UMIs with the number of unique UMIs. After all QC, 73-83% of cells in each of these samples were retained.

Parts of the subsequent analysis utilized the R package Seurat[47], version 1.4.0.7, which includes sparse matrix support for large datasets. To normalize gene counts while accounting for widely varying UMI counts among conditions, Applicants used a scaling factor reflecting the expected number of UMIs in each condition. Let $w_{c,i}$ be the mean number of UMIs per cell in condition c, batch i. Seurat's LogNormalize( ) function was called on cells from condition c with the scale factor argument set to:

$$10{,}000 \times (w_{c,i}/\mathrm{mean}_i(w_{control,i}))$$

Applicants refer to the output values as log TPX (as opposed to the default log TPM).

The 63,152 high-quality cell profiles were combined into three (non-exclusive) groups.

Group A (24,187 cells): cells stimulated with PBS (9,623 cells), IL-25 (6,849 cells), or IL-33 (7,715 cells).

Group B (35,542 cells): cells stimulated with PBS (9,623 cells), NMU (9,698 cells), IL-25 (6,849 cells), or IL-25+ NMU (9,372 cells).

Group C (21,895 cells: cells from WT mice stimulated with PBS (5,393 cells) or HDM (6,280 cells), as well as Nmur1-KO mice stimulated with PBS (4,191 cells) or HDM (6,031 cells).

To verify that the dataset consists of ILCs, Applicants checked the raw counts for the expression of major markers of other immune cell groups (FIG. 18j). For subsequent analysis, genes expressed in less than 0.1% of cells were excluded.

Analysis of droplet-based scRNA-Seq samples: Signature scores. Applicants calculated signature scores as the log of the geometric mean of the TPX values for the genes in the signature. That is, let S be a set of m genes defining a signature, and for any gene g in S and a given cell, let $x_g$ be the expression of g in the cell in TPX. Then the signature score for that cell is calculated as $$\log(\Pi_g(x_g+1)^{1/m})$$

which is equivalent to the arithmetic mean of the log TPX values. Actual expression values, rather than centered or z-scored expression values were used. For several of our signatures, centering (or z-scoring) expression values before computing signatures leads to misleading scores that are close to 0 across the whole dataset, though the corresponding gene expression is high. This is in part due to ILC2s composing the majority of the cells, and hence genes that are highly expressed by ILC2s lack sufficient variance over the data set to be useful in a mean-centered signature.

Applicants also did not replace these scores with a statistical comparison of them to randomized signatures selected from a null distribution (in contrast to Applicants other studies[20,45]). Due to the varying proliferative responses in the cells, it is difficult to find a true null set of signatures, even after matching genes for dataset-wide mean and variance profiles. Signature scores are thus calculated in a way that is independent of the expression levels of unrelated genes in the same cell, and may be interpreted as similar to, though less noisy than, single-gene expression values.

The ILC subset signatures (ILC1, 2, 3 as used in FIGS. 13c, 17b, FIGS. 18d-g,k, 20b-e, 27c-e) were curated based on established markers for ILC subsets. The proliferation signature was created by combining Applicants previously published gene signatures[19,20] that define G1-S and G2-M phases. For both ILC subset and proliferative signatures, all genes contribute positively to the signature score. For the inflammatory ILC2 signature, differentially expressed genes contribute positively to the score if they are up-regulated in ILC2s from WT mice after HDM stimulation relative to PBS, and negatively otherwise.

Analysis of droplet-based scRNA-Seq samples: Assigning ILC type. ILC signatures were used to assign each cell to one of the following categories: ILC1, ILC2, ILC3, "mixed" (scoring highly for multiple ILC types), and "none" (not scoring highly for any ILC type). The frequency of mixed type ILCs (2.6%) is comparable to the expected doublet rate (3-4%). Based upon the dip in the bimodal distributions of ILC subset signature scores (FIG. 18d, 20b, 27c,d), the minimum score for assignment to a given category was set to 0.08. To be uniquely assigned to a category, the ratio of the highest score to the next highest score was required to be at least 1.25. The analysis is not sensitive to the specific ratio threshold choice of 1.25; that selection was made to balance the trade-off between the purity of the transcriptional profile of cells assigned to one of the three ILC subtype populations, and the number of cells called as mixed.

To test the strength of association between ILC type and treatment conditions, Applicants used the R package nnet, version 7.3-12, to do a multinomial logistic regression on the ILC type, with replicate and condition as predictors.

Analysis of droplet-based scRNA-Seq samples: PCA, clustering, and tSNE. Variable genes were then selected using the MeanVarPlot function in Seurat with the x.low-.cutoff and y.cutoff parameters set to 0.05 and 0.7, respectively, resulting in gene sets of size 774 (Group A), 723 (Group B), and 475 (Group C). PCAFast was run on mean-centered variable genes to compute a limited number of PCs. To select the number of PCs to include for subsequent analysis, Applicants estimated the number of eigenvalues larger than would be predicted by a null distribution for random matrices (Marchenko-Pastur law), and also assessed the decrease in marginal proportion of variance explained with larger PCs. The top 22 (Groups A, B) and 13 (Group C) PCs were included for subsequent analysis. Applicants confirmed that the resulting analyses were not particularly sensitive to this exact choice.

The cells were clustered via Seurat's FindClusters function, which optimizes a modularity function on a k-nearest-neighbor graph computed from the top eigenvectors. After a range of cluster resolution parameters were tested, 0.6 (Groups A and B) and 0.5 (Group C) were selected because the resulting clusters captured major, condition-related divisions, known subgroups, and statistically validated transcriptional distinctions of interest, while avoiding subdivisions of relatively uniform parts of the data.

To visualize the data, tSNE plots were created by calling Seurat's RunTSNE function, with the dims.use parameter set to the selected number of significant PCs and the do.fast parameter set to TRUE. A number of perplexity parameter choices were evaluated before selecting 100 (Group A) and 50 (Groups B and C). These perplexity settings produced tSNE plots that reflected the cluster structure found independently of tSNE, without introducing extreme artifacts. TSNE plots of cells separated by batch indicate that experimental batches appear to have a relatively minor impact on the PCA and clustering (FIG. 18h, 26b, 27b).

Analysis of droplet-based scRNA-Seq samples: Differential gene expression. To avoid spurious results due to cells in different conditions or clusters having vastly different amounts of mRNA, differential expression (DE) analysis accounted for the varying number of transcripts and genes in each condition. Applicants fit raw counts to a mixture of generalized linear models that include covariates for the log of the number of UMIs in a cell, as well as a factor for the batch. Specifically, Applicants fit a zero-inflated negative binomial model using the zeroinfl function[48] from the pscl R package[49], version 1.4.9. The zero-inflated negative binomial model combines a count component and a point mass at zero, which is relevant for scRNA-Seq data where zero values are significantly inflated due to the technology not capturing expressed genes, particularly those with low expression[11]. The model requires a substantial amount of data to fit, making it well suited to data generated by massively-parallel methods. As an alternative to the zero-inflated negative binomial, Applicants also performed a logistic regression by fitting a generalized linear model using the binomial family with a logit link, with the same covariates.

DE tests included the following models: (1) a cluster-based model with indicator coefficients for each cluster except the reference PBS-dominated cluster (Groups A, B, and C); (2) a condition-wide model with indicator coefficients for each condition (with the control condition as reference) (Groups A, B, and C); and (3) a direct comparison of IL-25 vs. IL-33, with IL-33 as reference (Group A); (4) a condition-based model with indicator coefficients for NMU and IL-25, and an additional interaction term (with the control condition as reference) to detect non-additive effects (Group B); (5) a direct comparison between IL-25+NMU and IL-25, with IL-25 as reference (Group B). In Group C, Applicants restricted the DE analysis to the cells transcriptionally classified as ILC2s, in order to identify difference in these particular cells, without the analysis being driven by the change in relative proportions of ILC1s and ILC3s compared to ILC2s after HDM treatment.

Many cell-cycle genes and ribosomal protein genes are differentially expressed across conditions and clusters, particularly if there is a difference in proliferation. To detect other differentially expressed genes as well, before ranking DE results, Applicants removed ribosomal protein genes and (in all cases except Group C, where it was not needed), the genes in the proliferation signature.

DE tests report coefficients and associated p-values for each variable of interest (e.g., cluster or condition), separately for each model component. To rank the results for any given model, Applicants created a list of differentially expressed candidate genes that are detected in at least 10% (15% for Group C) of the cells in one of the groups in the model and have a coefficient for a term of interest with absolute value at least 0.5 (0.75 for Group C) and corresponding FDR-adjusted p-value $<1\times10^{-20}$ for condition-wide DE, $<1\times10^{-6}$ for cluster DE, for at least one component. Applicants ranked these candidates by lowest p-value and also by largest absolute value of coefficient. The top 25 (5 and 3 for cluster models in Groups A-B and C, respectively) genes according to each ranking were reported, with a minimum of 1-2 genes, if available, selected from each of the set of candidates with positive coefficients and the set with negative coefficients. These genes are reported according to the condition or cluster for which they were ranked highly, and the sign reported is "plus" ("minus") if that condition or cluster has a higher (lower) expression by both fraction of cells expressing and level of expression than the reference, or if these are discordant then the sign is reported as "NA".

Applicants curated a representative selection from the highest-ranked results to represent, in FIG. 13f, common, distinctive patterns across clusters in Group A, and, in FIG. 16h, patterns that distinguish IL-25+NMU from the other conditions in Group B and highlight non-linear interactions between NMU and IL-25. To create the inflammatory ILC2 signature (FIG. 17c-e), Applicants used the top-ranked genes differentially expressed between HDM and PBS treatments in ILC2s only in WT mice, as well as those differentially expressed in HDM- and ILC2-dominated clusters (5 and 6) in this dataset. The signature genes are reported with the sign positive if the respective condition or cluster has higher expression than the reference for that model.

To more broadly compare differentially expressed genes between HDM and IL-25+NMU datasets, Applicants constructed one gene set for IL-25+NMU by taking the top differentially expressed genes for all models and comparisons in Group B in which there is a coefficient for the condition IL-25+NMU or a coefficient for a group or cluster to which IL-25+NMU-treated cells contribute significantly (clusters 2, 6-11). Applicants then performed the analogous procedure in the HDM data (including clusters 1-2 and 4-7). Using as the null set the 12,719 genes shared between Groups B and C, Applicants used Fisher's exact test to determine the significance of the overlap of 23 genes between the 156 genes in the IL-25+NMU gene set (151 of which are in the null set) and 85 from the HDM data (all of which are in the null set) ($P<1.64\times10^{-25}$).

Analysis of SMART-Seq2 plate-based scRNA-Seq data. Reads were aligned to mm10 using Kallisto[50] quant, version 0.42.3. The R package tximport[51], version 1.2.0, was used to convert the output to gene counts and traditional TPM values. Because of the variability in read counts per cell across plates, even from the same condition, as well as in the number of genes per cell across conditions, QC was performed for each of eight plates individually in order to remove cells that were outliers with respect to either measure (FIG. 20a). Out of 752 cells, 606 cells met QC criteria (234 from control, 152 from IL-25 treated mice, and 220 from IL-33 treated mice), and the number of genes per cell in this set ranged from 1,625 to 6,375. Genes that were not expressed with log(TPM)>2.5 in at least two cells were removed from further analysis. Subsequent analysis proceeded analogously to the droplet-based RNA-seq analysis, with parameter settings that reflected both the wider dynamic range of expression and much smaller cell numbers. The minimum ILC signature score required in ILC type assignment was 0.3. Variable genes were identified by running MeanVarPlot with x.low.cutoff=0.1, y.cutoff=1.5, and x.high.cutoff=10, resulting in a set of 519 genes. PCA was performed on the mean-centered expression of variable genes, with 9 PCs chosen for the subsequent clustering analysis (resolution parameter 0.6). RuntSNE was called with the default perplexity value of 30.

The DE analysis for plate-based data followed the structure of the droplet-based analysis but used only logistic regression, with both a condition-based model and a cluster-based model. To rank the results for each model, Applicants created a list of differentially expressed candidate genes that are detected in at least 30% of the cells in one of the groups in the model and have a coefficient for a term of interest with an absolute value at least 1.0 (for condition-based models) or 1.5 (for cluster models) and corresponding FDR-adjusted p-values $<1\times10^{-4}$ (for condition-based models) or $<1\times10^{-5}$ (for cluster models). Applicants ranked the candidates by lowest p-value and by largest absolute value of coefficient. The top 40 genes (for condition model) or 3 genes (for cluster model) according to each ranking were reported, with a minimum of 10 genes (for condition model) or 1 gene (for cluster model), if available, selected from each of the set of candidates with positive coefficients and the set with negative coefficients. To create the plot in FIG. 14c, Applicants took a high-ranked illustrative subset of these genes.

To compare plates and droplets, Applicants took as the null set all genes (11,117 genes) detected in both Group A from droplet-based data and in plates. For the PCA comparison, Applicants took the union of the highest and lowest 10 (Group A) or 20 (plates) genes for the PCs used in each analysis (141 genes from droplet-based data, 202 genes from plate-based data, 66 genes in the intersection), and used Fisher's exact test to determine significance ($P<3.74\times10^{-80}$). For the comparison of differentially expressed genes, Applicants used the previously computed sets of top-ranked DE genes for Group A (219 genes) and for the plate data (72 genes), and again used Fisher's exact test to determine significance of the overlap ($P<3.91\times10^{-25}$).

Reannotation of the 3' UTR of Nmur1. Initially, Nmur1 had essentially no detected expression in the droplet-based scRNA-seq data, though many reads align to a region just downstream of the Nmur1 3' UTR annotation (FIG. 21b). To explore the basis of this discrepancy, Applicants aligned long (75 bp) paired-end reads from full-length RNA-seq of population samples that included cells from all three stimulation conditions (only those from IL-25 shown). Many read alignments bridge the annotated Nmur1 transcript and the region downstream where droplet-based 3' reads align (FIG. 21b), evidence that Nmur1 has isoforms longer than the annotated transcript. Applicants reannotated the transcriptome, moving the 3' end from 86,386,242 to 86,384,000, and realigned the droplet-based scRNA-seq data, resulting in a robust increase in frequency of detection of Nmur1. All droplet-based scRNA-seq data shown in this manuscript was aligned to this reannotated transcriptome.

Data availability. The data discussed in this application have been deposited in NCBI's Gene Expression Omnibus and are accessible through GEO Series accession number GSE102299.

Results

Given the increased prevalence of allergy and asthma, identifying the molecular pathways that modulate the response of type 2 innate lymphoid cells (ILC2s) to alarmins is an important area of inquiry. Damaged or stressed epithelial cells produce alarmin cytokines, such as IL-25 and IL-33, which activate ILC2s[1-5]. Activated ILC2s initiate allergic tissue inflammation at mucosal surfaces, in part by rapidly producing effector cytokines, such as IL-5 and IL-13[6-8]. ILC2s also maintain tissue homeostasis by promoting epithelial cell proliferation, survival, and barrier integrity[9]. However, the factors that balance homeostatic and inflammatory ILC2 responses are unknown, as is whether distinct ILC2 subsets mediate these effects.

It is challenging to distinguish homeostatic from pro-inflammatory ILC2s, since there are few known markers of these functional states. Single-cell genomics, especially scRNA-seq[10,11], can identify such diversity, both when changes in cell states are continuous across a population[12] and when there are discrete sub-populations of varying sizes, including in intestinal ILCs[13-15].

Alarmins Induce Heterogeneity in ILC2s

To define the transcriptional landscape of lung-resident ILCs, Applicants collected 24,187 high quality, droplet-based scRNA-seq profiles of IL-7Rα+ CD90+ Lineage− ILCs at steady state and after in vivo activation by IL-25 or IL-33 (FIG. 13a, FIG. 18a-c). Applicants scored cells based on expression of ILC subset-specific signature genes (after condition-specific normalization, Methods), and classified cells as ILC1, ILC2, ILC3, "mixed," or "none" if no score was sufficiently high (FIG. 18d-f, Methods). Mixed profile ILCs could either represent a transient or plastic transcriptional state or cell doublets. Expression of key signature genes (e.g., Tbx21, Il1rl1, Rorc) supported our cell classification (FIG. 18g). ILC2s composed greater than 94% of cells in all conditions; IL-33 increased their proportion further, whereas IL-25 increased the proportion of ILC3s (FIG. 18e) (multinomial logistic, IL-33: $P<2.2\times10^{-16}$, IL-25: $P<8.4\times10^{-8}$).

Alarmin treatment induced unique gene expression programs, as suggested by the relationship between the expression profiles of cells from different treatment conditions, independent of experimental batch (FIG. 13a, FIG. 18h). IL-25 and IL-33 both up-regulated genes associated with ILC2 activation, including Il5, Klrg1, and Arg1, while other genes, (e.g., Areg), were preferentially induced by one alarmin but not the other (FIG. 18i)[2,16].

Applicants partitioned transcriptionally distinct ILCs into eleven clusters (FIG. 13b). All clusters highly expressed key marker genes of ILCs, while markers of other cell types were minimally expressed, except for CD3 genes (Extended Data FIG. 13j; Cd3d), which have previously been observed at the mRNA level in ILCs[17,18]. ILC1s, ILC2s, and ILC3s largely partitioned into distinct clusters. ILC1s composed ~50% of cluster 1 (392 cells; 56% of ILC1 s), ILC3s and mixed ILCs each made up ~25% of cluster 2 (926 cells; 64% of ILC3s), and the remaining clusters (22,869 cells) were predominantly composed of ILC2s, particularly clusters 3-5 and 8-11 (FIG. 13c, FIG. 18k). Cluster assignment is strongly associated with treatment ($\chi^2$ test, P<2.2×10$^{-16}$): most cells in clusters 7 and 9-11 are IL-33-activated ILCs, while cells in clusters 5 and 8 are primarily IL-25-activated ILCs, and control ILC2s comprise ~90% of clusters 3 and 4 (FIG. 13d, FIG. 18l).

Alarmin-activated ILCs express 1.5-2.5 fold more genes than do resting ILCs, partly due to proliferation, particularly among IL-33-activated ILC2s (FIG. 18c). Clusters 7 and 11, enriched with such cells, scored highly for a proliferative gene signature (t-test, P<2.2×10$^{-16}$) (FIG. 13e)[19,20]. Consistent with this, IL-33 induced more robust proliferation of ILCs in vitro than did IL-25 (FIG. 19).

To uncover novel molecular cues that regulate ILC responses, Applicants identified genes differentially expressed across clusters by fitting gene counts to generalized linear models that account for variation in both dropout rates and proliferation (Methods). Highly differentially expressed genes include both those with known and novel roles in ILC biology (FIG. 13f). Among known genes, Arg1, Il13, and Klrg1 are highly expressed in clusters where alarmin-activated ILC2s are predominant. Other genes discriminate between cells activated by a single alarmin. For example, clusters 5 and 8 both consist predominantly of IL-25-activated ILC2s, yet Ms4a4b is expressed only in cluster 8. Similarly, Ctla4 was induced only in certain clusters of IL-25- or IL-33-activated cells (FIG. 13f).

Applicants validated the expression patterns at the protein level for a number of genes using flow cytometry (FIG. 18m). As predicted, KLRG1, gp49 (Lilrb4a), and BATF were upregulated after activation by IL-25 and IL-33. Expression of Semaphorin 4a (Sema4a) was reduced in IL-33-activated ILCs, mirroring the lower expression in IL-33-dominant scRNA-seq clusters. Finally, consistent with the scRNA-seq data, only a subset of ILCs upregulated CTLA4 or MHC Class II after alarmin activation. These results suggest that distinct functional states exist within defined ILC subsets, and that IL-33 and IL-25 differentially regulate these states.

Studies in other systems have shown that analysis of large cell numbers, even at shallow coverage, can readily identify markers of transcriptional states[14,21]. However, the number of distinct transcripts per cell in droplet-based scRNA-seq may be lower than in full-length protocols[22,23]. To explore the possible impact of these differences, Applicants complemented their droplet-based survey with an analysis using a plate-based full-length protocol[23].

Applicants analyzed 606 high-quality full-length scRNA-seq profiles of ILCs from PBS-, IL-25-, or IL-33-treated mice (FIG. 14a, FIG. 20a). Most cells were classified as ILC2s, consistent with the droplet-based atlas (FIG. 20b-e). The two data sets were highly concordant in terms of the similarity of expression profiles (FIG. 21a), clustering (FIG. 13a,b vs. 14a,b), and top genes identified by PCA or differential expression analysis (e.g., Lpcat2, Anxa2, Lgals3 bp, Ms4a4b) (Fisher's exact test, P<3.74×10$^{-80}$, for PCA genes) (FIG. 13f, 14c).

Figure 21D:
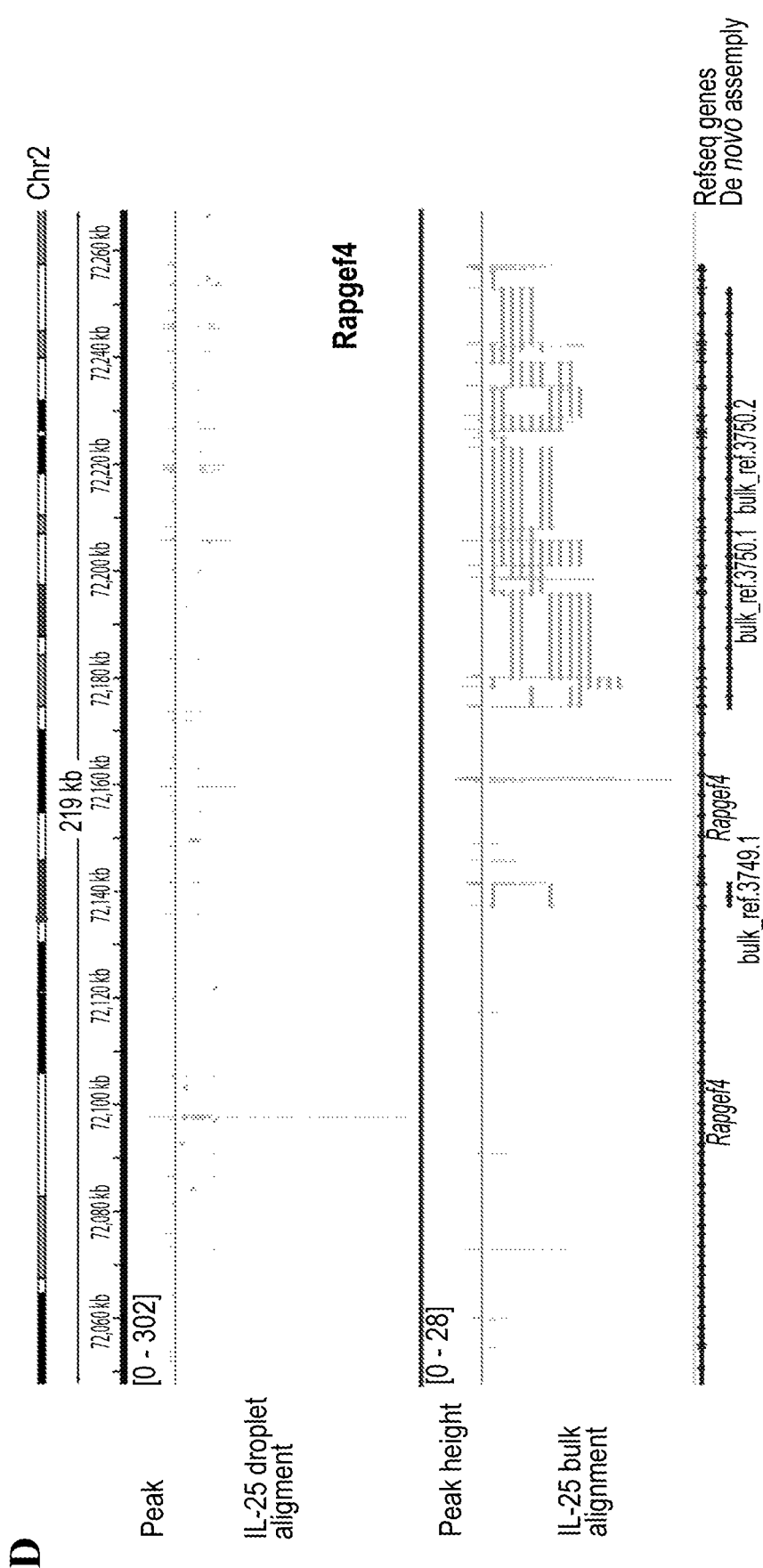

Of the differentially expressed genes in plate-based scRNA-seq, Nmur1 (GPR66, FM-3) was highly expressed in ILC2s at steady state and after IL-25 stimulation, but down-regulated by IL-33 (FIG. 14c), and yet was essentially absent in the initial droplet-based scRNA-seq analysis (FIG. 21a). Alignment of bulk, full-length RNA-seq indicated that the Nmur1 transcript extends to a different 3' end in lung ILCs than is annotated in the reference transcriptome (FIG. 21b). Upon correcting the Nmur1 annotation, Nmur1 was recovered in the droplet-based data (FIG. 21c). In contrast, Rapgef4, another of the few differentially expressed genes absent in the droplet-based data, has an annotated 3' end consistent with the bulk RNA-seq, indicating that technical issues other than transcriptome annotation also contribute to discrepancies (FIG. 21d). Overall, however, both droplet and plate data supported the same global trends, including the differential expression of Nmur1.

ILC2-Specific Expression of Nmur1

Nmur1 is a receptor for the neuropeptide Neuromedin U (NMU), and NMU/Nmur1 signaling modulates inflammatory responses[24], although the role of this pathway in ILCs was unknown. Applicants found that Nmur1 expression was largely specific to ILCs, compared to other lung-resident cell populations. It was highly expressed in ST2$^+$ ILCs both at steady state and after induction of airway inflammation with house dust mite (HDM) extract (FIG. 14d). In either setting, the only non-ILC population with detectable Nmur1 expression was CD4$^+$ T cells, which expressed very low levels both after HDM-challenge in vivo, as well after Th2-differentiation in vitro (FIG. 14d, FIG. 22a). Nmur2, the other known receptor for NMU, was not detectably expressed in lung-resident cells, including ILCs, but was expressed in the CNS, as previously reported (FIG. 22b)[25-27].

Applicants assessed Nmur1 protein expression by flow cytometry of cells from heterozygous Nmur1-LacZ reporter mice. Approximately 40% of ST2$^+$ ILCs expressed Nmur1 (FIG. 14e, FIG. 22c). Only ILC2s had significant specific staining, although several myeloid cell types demonstrated non-specific staining independent of the reporter allele (FIG. 22d). Treatment in vivo with IL-25 did not alter the frequency of Nmur1$^+$ ILCs, whereas IL-33 markedly reduced their frequency (FIG. 14f). Regardless of alarmin treatment, Nmur1 was predominantly expressed by ST2$^-$ ILCs and did not correlate with expression of IL-17RB, the receptor for IL-25 (FIG. 22e).

ILCs express several neuropeptide receptors in addition to Nmur1[28,29], raising the possibility that neurons communicate directly to ILCs. Immunofluorescence microscopy showed that ~70% CD3$^-$ KLRG1$^-$ cells are within 10 μm of SNAP-25$^+$ nerve fibers (FIG. 23a). The nodose/jugular ganglion and thoracic dorsal root ganglia (DRG) both contain sensory afferent neurons innervating the lung[28,30], and neurons in the DRG, though not in the nodose/jugular ganglion, express Nmu (FIG. 23b). Additionally, IL-13 induced upregulation of Nmu in cultured DRG neurons, suggesting ILCs may also communicate to neurons (FIG. 23c).

NMU Amplifies IL-25-Driven Inflammation

Applicants next investigated whether NMU affected ILC production of type 2 cytokines in vitro. While NMU did not affect cytokine expression by Th2 cells (FIG. 24a) and only mildly upregulated Il5 and Il13 in cultured ILC2s, NMU dramatically increased their mRNA and protein expression when combined with IL-25, suggesting NMU modulates ILC2 responses to alarmins (FIG. 15a,b, FIG. 24b). The combination of IL-33+NMU also increased Il5 and Il13 expression, but to a lesser extent than IL-25+NMU (FIG. 24c).

The synergy between IL-25 and NMU was even more striking in vivo. NMU alone did not increase expression of Il5 or Il13 mRNA in lung tissue, and only trace quantities of IL-5 protein were detectable in the bronchoalveolar lavage fluid (BALF), consistent with a small increase in BALF eosinophils (FIG. 24d-h). IL-25 modestly induced expression of IL-5 and IL-13 in the lung and BALF, while the combination of IL-25+NMU strongly increased their expression (FIG. 15c, FIG. 24i). Moreover, IL-25+NMU increased lung and BALF eosinophilia, and markedly enhanced histopathologic evidence of inflammation (FIG. 15d,e, FIG. 24j). Finally, IL-25+NMU induced significant airway hyper-reactivity (FIG. 15f). In summary, NMU converted a non-pathologic dose of IL-25 into a pathologic one.

To understand the role of endogenous NMU in ILC function, Applicants analyzed ILCs in NMU-deficient (NMU-KO) mice. At steady state, both the overall frequency of ILCs and ILC expression of KLRG1, ST2, IL-5, and IL-13 were unchanged in NMU-KO mice versus WT (FIG. 25a-c). After challenge with HDM, total cell numbers and eosinophil frequencies in BALF were similar in WT and NMU-KO mice (FIG. 25d). However, the frequency of ST2$^+$ ILCs after HDM challenge was reduced in NMU-KO mice, compared to WT (FIG. 15g), and a lower percentage of ILCs expressed IL-5 and IL-13 ex vivo (FIG. 15h). The frequency of lung-infiltrating CD4$^-$ T cells was higher in NMU-KO mice, while the frequency of T cells expressing type 2 cytokines ex vivo was unchanged, suggesting potential adaptive immune compensation that could explain the similar degree of BALF eosinophilia (FIG. 25e,f). Overall, the reduced frequency of ILC2s expressing effector cytokines after allergen challenge in NMU-KO mice indicates that NMU promotes ILC activation and effector function.

IL-25+NMU Expands Inflammatory ILC2s

To characterize how IL-25+NMU synergistically promote allergic inflammation, Applicants profiled lung-resident ILCs by scRNA-seq after in vivo treatment with NMU alone or in combination with IL-25 (FIG. 16a, FIG. 26a,b). NMU-treated ILCs were transcriptionally similar to control ILCs, consistent with the minimal in vivo impact of NMU alone (FIG. 16a), whereas the expression profiles of IL-25+NMU-treated ILCs were distinct from those of IL-25- and NMU-treated ILCs, and comparable to those of IL-33-activated ILCs (FIG. 26c). Combined analysis of profiles from PBS-, NMU-, IL-25-, and IL-25+NMU-treated ILCs partitioned them into eleven clusters (FIG. 16b). There was a significant association between cluster and treatment ($\chi^2$ test, P<2.2×10$^{-16}$). Five clusters (6 and 8-11) consisted almost exclusively of IL-25- or IL-25+NMU-activated cells (FIG. 26d,e), suggesting that IL-25+NMU expands transcriptionally distinct subsets of ILCs present at lower numbers in IL-25-treated mice.

One mechanism by which IL-25 and NMU synergized was by inducing proliferation in distinct subpopulations of ILCs. Mice treated with IL-25+NMU had increased ILC frequencies and approximately twice as many Ki67$^+$ ILCs as IL-25-treated mice, indicating significant proliferation (FIG. 16c, FIG. 26f). IL-25+NMU-activated cells had bimodally distributed proliferative signature scores (FIG. 16d), with cells in IL-25+NMU-dominated cluster 11 scoring higher than cells in other clusters (t-test, P<2.2×10$^{-16}$, FIG. 26g).

Another mechanism by which NMU could amplify IL-25-initiated ILC responses was by up-regulating IL-17RB on ILCs. Compared to IL-25 alone, IL-25+NMU increased the frequency of IL-17RB$^+$ ILCs by flow cytometry and upregulated the expression of Il17rb mRNA in the lung by qPCR (FIG. 16e, FIG. 26h). The frequency of Il17rb-expressing ILCs was also increased in the scRNA-seq profiles from IL-25+NMU-treated mice (FIG. 16f, GLM binomial test, P<2.73×10$^{-10}$). Finally, IL-17RB$^+$ ILC frequency after HDM-challenge was reduced in NMU-KO versus WT mice (FIG. 16g), suggesting that NMU potentiates ILC responsiveness to IL-25 following both allergen challenge and alarmin stimulation.

Applicants analyzed differential gene expression between IL-25+NMU and other conditions, focusing on genes with a non-additive pattern of expression. One subset of such genes, including Il1r2, Tnfrsf8 (CD30), and Mt1, was strongly up-regulated specifically by IL-25+NMU (FIG. 16h). A second subset, including Zfp36l1 and Csf2, was down-regulated by IL-25+NMU, even though it was up-regulated after treatment with IL-25 and/or NMU alone. Finally, a few genes (e.g., Btg2 and Fosb) were expressed at steady state and in single-treatment conditions at similar levels, but were down-regulated by IL-25+NMU. Applicants validated these expression patterns for several representative genes by flow cytometry. Consistent with the scRNA-seq data, both CD30 and IL-1R2 were up-regulated only by IL-25+NMU; Galectin-3 (Lgals3) and gp49 (Lilrb4a) were up-regulated by either NMU or IL-25 alone and further induced by IL-25+NMU; and Nr4a1 expression was highest in response to IL-25 alone (FIG. 26i).

Several of these genes have been previously linked to allergic airway inflammation in both mice and humans. Mice lacking Tnfrsf8 and Anxa2 have reduced airway inflammation in asthma models[31,32]. Tnfrsf8, Anxa2, and Il1r2 are overexpressed in allergic asthmatics[33-35]. Deletion of Nr4a1, which is down-regulated by IL-25+NMU, exacerbates airway inflammation in mice, suggesting a potential role in limiting inflammatory ILC responses[36].

Cluster-based analysis of differentially expressed genes further highlighted that ILCs from IL-25+NMU-treated mice were transcriptionally heterogeneous (FIG. 16b, FIG. 26j). Some genes, such as Il13, were highly expressed in all clusters principally composed of IL-25+NMU- or IL-25-treated ILC2s (clusters 6-11), while other genes were specific to certain clusters. For example, Ifitm3 was highly expressed in ILCs in cluster 10, whereas ILCs in cluster 7, which were also expanded by IL-25+NMU, co-expressed key antigen presentation genes, including MHC Class II (e.g., H2-Ab1) and the invariant chain (Cd74). IL-25+NMU also increased the frequency of a population of MHC-II$^{Hi}$ ILCs by flow cytometry (FIG. 26i). Cluster 8 primarily consisted of IL-25- or IL-25+NMU-treated ILCs that expressed Klrg1, Il13, and Il4, as well as some Il17a, but little Il1rl1 and Il5, similar to previous reports of an IL-25-induced KLRG1$^{hi}$ ST2$^-$ inflammatory ILC2 (iILC2) population[2]. Cluster-8 ILCs also expressed Nmur1, as did cells in IL-25 predominant cluster 6, suggesting these two subsets are preferentially NMU-responsive. Nmur1 was expressed by flow cytometry on IL-25-treated ILCs, including iILC2s (FIG. 26k). While both IL-25+NMU and IL-33 down-regulated Nmur1 on ILC2s, IL-25+NMU uniquely expanded iILC2s, suggesting that NMU/Nmur1-signaling preferentially modulates the activation and/or expansion of certain IL-25-induced iILC2 subsets (FIG. 26l,m).

Nmur1 Promotes ILC2 Activation by HDM

To further characterize the impact of Nmur1-signaling on ILCs, Applicants challenged WT and Nmur1-KO mice with HDM and profiled lung-resident ILCs by scRNA-seq. Analysis of 21,895 high-quality profiles largely clustered them by in vivo treatment, regardless of genotype or batch (FIG. 17a, FIG. 27a,b). In Nmur1-KO mice, ILC2 frequency was markedly reduced after HDM challenge compared to PBS (76% vs. 91%; multinomial logistic, P<2.2×10$^{-6}$), exaggerating a trend also seen in WT mice (87% vs. 94%, multinomial logistic, P<2.2×10$^{-16}$), which is consistent with the reduced frequency of ST2+ ILCs in NMU-KO mice after HDM challenge (FIG. 17b, FIG. 27c,d). While IL-25+NMU and IL-33 induced robust proliferation and increased ILC2 frequency, HDM challenge only induced a high proliferation score in the cells of one small cluster (cluster 6, 210 cells) (FIG. 13e, FIG. 18e, 27e-h). This minimal induction of proliferation, in conjunction with an increase in ILC1s and ILC3s, may be related to the observed reduction in ILC2 frequency after HDM challenge.

Based on genes differentially expressed between HDM- and PBS-treated WT ILC2s, Applicants defined an inflammatory ILC2 signature (FIG. 17c-e). ILCs from IL-25+ NMU-treated mice scored highly for this inflammatory signature, suggesting that it identifies inflammatory ILC2s independent of the model of airway inflammation (FIG. 17d,e). Differentially expressed genes in ILC2s from HDM-treated mice significantly overlapped with those in ILCs from IL-25+NMU-treated mice (Fisher's exact test, $P<1.64\times10^{-25}$) (FIG. 16h). Finally, Nmur1-KO ILC2s had a lower average inflammatory score than WT ILC2s after HDM challenge (t-test, $P<4.9\times10^{-15}$), consistent with NMU/Nmur1-signaling promoting ILC2 responses in vivo (FIG. 17e).

DISCUSSION

Applicants used massively parallel droplet-based scRNA-seq to establish the transcriptional landscape of lung-resident ILCs under homeostatic and inflammatory conditions, and identified Nmur1 as a modulator of alarmin- and allergen-driven ILC2 responses. NMU-KO mice were previously reported to develop attenuated airway inflammation after allergic sensitization[24], but the underlying mechanism was unclear. NMU expression in bronchial brushing samples from asthmatic patients correlates with disease severity, which our data suggests could be related to NMU's impact on ILC function[37]. Functional analysis and scRNA-seq-based approaches both demonstrate that, in the absence of NMU/Nmur1-signaling, ILC2s are decreased in frequency and have impaired effector function after allergen challenge. Although the inflammatory signature score of allergen-challenged Nmur1-deficient ILC2s is significantly decreased compared to allergen-challenged WT ILC2s, it is still increased compared to PBS-treated controls, suggesting that other factors, in addition to NMU, contribute to ILC activation in this context.

The findings raise the question of whether NMU potentiates airway inflammation when high levels of alarmins, such as IL-25, are present, as is the case, for example, in steroid-naïve Th2-high asthma or post-viral asthma exacerbations[1,38]. While airway epithelial cells up-regulate IL-25 in response to stress, chemosensory cells, which are found in both the intestine and trachea, constitutively produce IL-25 and modulate mucosal immune responses[39-43]. The observation that NMU is expressed by neurons from thoracic DRG suggests that the coordinated action of neurons and chemosensory cells could promote tissue-based, ILC-dependent, type 2 immune responses. Given the importance of smooth muscle contraction in the clinical manifestations of allergic diseases, it is intriguing that NMU can induce both smooth muscle contraction[44] and ILC2-driven inflammation. Neuronal activation following inhalation of noxious substances or allergens could potentially trigger both processes, simultaneously promoting physical expulsion and allergic immunity to the provoking stimulus. Taken together, Applicants findings demonstrate a novel neuro-immune pathway that exacerbates mucosal allergic inflammation in vivo.

REFERENCES

1 Cheng, D. et al. Epithelial interleukin-25 is a key mediator in Th2-high, corticosteroid-responsive asthma. *American journal of respiratory and critical care medicine* 190, 639-648, doi:10.1164/rccm.201403-05050C (2014).

2 Huang, Y. et al. IL-25-responsive, lineage-negative KLRG1(hi) cells are multipotential 'inflammatory' type 2 innate lymphoid cells. *Nature immunology* 16, 161-169, doi:10.1038/ni.3078 (2015).

3 Gudbjartsson, D. F. et al. Sequence variants affecting eosinophil numbers associate with asthma and myocardial infarction. *Nature genetics* 41, 342-347, doi:10.1038/ng.323 (2009).

4 Halim, T. Y. et al. Group 2 innate lymphoid cells are critical for the initiation of adaptive T helper 2 cell-mediated allergic lung inflammation. *Immunity* 40, 425-435, doi:10.1016/j.immuni.2014.01.011 (2014).

5 Salimi, M. et al. A role for IL-25 and IL-33-driven type-2 innate lymphoid cells in atopic dermatitis. *The Journal of experimental medicine* 210, 2939-2950, doi:10.1084/jem.20130351 (2013).

6 Moro, K. et al. Innate production of T(H)2 cytokines by adipose tissue-associated c-Kit(+)Sca-1(+) lymphoid cells. *Nature* 463, 540-544, doi:10.1038/nature08636 (2010).

7 Neill, D. R. et al. Nuocytes represent a new innate effector leukocyte that mediates type-2 immunity. *Nature* 464, 1367-1370, doi:10.1038/nature08900 (2010).

8 Chang, Y. J. et al. Innate lymphoid cells mediate influenza-induced airway hyper-reactivity independently of adaptive immunity. *Nature immunology* 12, 631-638, doi: 10.1038/ni.2045 (2011).

9 Monticelli, L. A. et al. Innate lymphoid cells promote lung-tissue homeostasis after infection with influenza virus. *Nature immunology* 12, 1045-1054, doi:10.1031/ni.2131 (2011).

10 Tanay, A. & Regev, A. Scaling single-cell genomics from phenomenology to mechanism. *Nature* 541, 331-338, doi:10.1038/nature21350 (2017).

11 Wagner, A., Regev, A. & Yosef, N. Revealing the vectors of cellular identity with single-cell genomics. *Nat Biotechnol* 34, 1145-1160, doi:10.1038/nbt.3711 (2016).

12 Gaublomme, J. T. et al. Single-Cell Genomics Unveils Critical Regulators of Th17 Cell Pathogenicity. *Cell* 163, 1400-1412, doi:10.1016/j.cell.2015.11.009 (2015).

13 Habib, N. et al. Div-Seq: Single-nucleus RNA-Seq reveals dynamics of rare adult newborn neurons. *Science* 353, 925-928, doi:10.1126/science.aad7038 (2016).

14 Shekhar, K. et al. Comprehensive Classification of Retinal Bipolar Neurons by Single-Cell Transcriptomics. *Cell* 166, 1308-1323 e1330, doi:10.1016/j.cell.2016.07.054 (2016).

15 Gury-BenAri, M. et al. The Spectrum and Regulatory Landscape of Intestinal Innate Lymphoid Cells Are Shaped by the Microbiome. *Cell* 166, 1231-1246 e1213, doi:10.1016/j.cell.2016.07.043 (2016).

16 Monticelli, L. A. et al. Arginase 1 is an innate lymphoid-cell-intrinsic metabolic checkpoint controlling type 2 inflammation. *Nature immunology* 17, 656-665, doi: 10.1038/ni.3421 (2016).

17 Robinette, M. L. et al. Transcriptional programs define molecular characteristics of innate lymphoid cell classes and subsets. *Nature immunology* 16, 306-317, doi:10.1038/ni.3094 (2015).

18 Bjorklund, A. K. et al. The heterogeneity of human CD127(+) innate lymphoid cells revealed by single-cell RNA sequencing. *Nature immunology* 17, 451-460, doi:10.1038/ni.3368 (2016).

19 Kowalczyk, M. S. et al. Single-cell RNA-seq reveals changes in cell cycle and differentiation programs upon aging of hematopoietic stem cells. *Genome Res* 25, 1860-1872, doi:10.1101/gr.192237.115 (2015).

20 Tirosh, I. et al. Dissecting the multicellular ecosystem of metastatic melanoma by single-cell RNA-seq. *Science* 352, 189-196, doi:10.1126/science.aad0501 (2016).

21 Dixit, A. et al. Perturb-Seq: Dissecting Molecular Circuits with Scalable Single-Cell RNA Profiling of Pooled Genetic Screens. *Cell* 167, 1853-1866 e1817, doi:10.1016/j.cell.2016.11.038 (2016).

22 Zheng, G. X. et al. Massively parallel digital transcriptional profiling of single cells. *Nature communications* 8, 14049, doi:10.1038/ncomms14049 (2017).

23 Picelli, S. et al. Smart-seq2 for sensitive full-length transcriptome profiling in single cells. *Nature methods* 10, 1096-1098, doi: 10.1038/nmeth.2639 (2013).

24 Moriyama, M. et al. The neuropeptide neuromedin U activates eosinophils and is involved in allergen-induced eosinophilia. American journal of physiology. *Lung cellular and molecular physiology* 290, L971-977, doi:10.1152/ajplung.00345.2005 (2006).

25 Hedrick, J. A. et al. Identification of a human gastrointestinal tract and immune system receptor for the peptide neuromedin U. *Molecular pharmacology* 58, 870-875 (2000).

26 Szekeres, P. G. et al. Neuromedin U is a potent agonist at the orphan G protein-coupled receptor FM3. *The Journal of biological chemistry* 275, 20247-20250, doi:10.1074/jbc.C000244200 (2000).

27 Shan, L. et al. Identification of a novel neuromedin U receptor subtype expressed in the central nervous system. *The Journal of biological chemistry* 275, 39482-39486, doi:10.1074/jbc.C000522200 (2000).

28 Talbot, S. et al. Silencing Nociceptor Neurons Reduces Allergic Airway Inflammation. *Neuron* 87, 341-354, doi:10.1016/j.neuron.2015.06.007 (2015).

29 Nussbaum, J. C. et al. Type 2 innate lymphoid cells control eosinophil homeostasis. *Nature* 502, 245-248, doi:10.1038/nature12526 (2013).

30 Audrit, K. J., Delventhal, L., Aydin, O. & Nassenstein, C. The nervous system of airways and its remodeling in inflammatory lung diseases. *Cell and tissue research* 367, 571-590, doi:10.1007/s00441-016-2559-7 (2017).

31 Polte, T., Behrendt, A. K. & Hansen, G. Direct evidence for a critical role of CD30 in the development of allergic asthma. *The Journal of allergy and clinical immunology* 118, 942-948, doi:10.1016/j.jaci.2006.07.014 (2006).

32 Schuliga, M. et al. Plasminogen-stimulated inflammatory cytokine production by airway smooth muscle cells is regulated by annexin A2. *Am J Respir Cell Mol Biol* 49, 751-758, doi:10.1165/rcmb.2012-04040C (2013).

33 Heshmat, N. M. & El-Hadidi, E. S. Soluble CD30 serum levels in atopic dermatitis and bronchial asthma and its relationship with disease severity in pediatric age. *Pediatr Allergy Immunol* 17, 297-303, doi:10.1111/j.1399-3038.2006.00405.x (2006).

34 Katsunuma, T. et al. Analysis of gene expressions of T cells from children with acute exacerbations of asthma. *Int Arch Allergy Immunol* 134, 29-33, doi:10.1159/000077530 (2004).

35 Sekigawa, T. et al. Gene-expression profiles in human nasal polyp tissues and identification of genetic susceptibility in aspirin-intolerant asthma. *Clinical and experimental allergy: journal of the British Society for Allergy and Clinical Immunology* 39, 972-981, doi:10.1111/j.1365-2222.2009.03229.x (2009).

36 Kurakula, K. et al. Nuclear Receptor Nur77 Attenuates Airway Inflammation in Mice by Suppressing NF-kappaB Activity in Lung Epithelial Cells. *Journal of immunology* 195, 1388-1398, doi:10.4049/jimmunol.1401714 (2015).

37 Modena, B. D. et al. Gene Expression Correlated with Severe Asthma Characteristics Reveals Heterogeneous Mechanisms of Severe Disease. *American journal of respiratory and critical care medicine* 195, 1449-1463, doi:10.1164/rccm.201607-14070C (2017).

38 Beale, J. et al. Rhinovirus-induced IL-25 in asthma exacerbation drives type 2 immunity and allergic pulmonary inflammation. *Sci Transl Med* 6, 256ra134, doi:10.1126/scitranslmed.3009124 (2014).

39 von Moltke, J., Ji, M., Liang, H. E. & Locksley, R. M. Tuft-cell-derived IL-25 regulates an intestinal ILC2-epithelial response circuit. *Nature* 529, 221-225, doi:10.1038/nature16161 (2016).

40 Gerbe, F. et al. Intestinal epithelial tuft cells initiate type 2 mucosal immunity to helminth parasites. *Nature* 529, 226-230, doi:10.1038/nature16527 (2016).

41 Howitt, M. R. et al. Tuft cells, taste-chemosensory cells, orchestrate parasite type 2 immunity in the gut. *Science* 351, 1329-1333, doi:10.1126/science.aaf1648 (2016).

42 Gu, X. et al. Chemosensory functions for pulmonary neuroendocrine cells. *Am J Respir Cell Mol Biol* 50, 637-646, doi:10.1165/rcmb.2013-01990C (2014).

43 Branchfield, K. et al. Pulmonary neuroendocrine cells function as airway sensors to control lung immune response. *Science* 351, 707-710, doi: 10.1126/science.aad7969 (2016).

44 Prendergast, C. E., Morton, M. F., Figueroa, K. W., Wu, X. & Shankley, N. P. Species-dependent smooth muscle contraction to Neuromedin U and determination of the receptor subtypes mediating contraction using NMU1 receptor knockout mice. *British journal of pharmacology* 147, 886-896, doi:10.1038/sj.bjp.0706677 (2006).

45 Singer, M. et al. A Distinct Gene Module for Dysfunction Uncoupled from Activation in Tumor-Infiltrating T Cells. *Cell* 166, 1500-1511 e1509, doi:10.1016/j.cell.2016.08.052 (2016).

46 Jager, A., Dardalhon, V., Sobel, R. A., Bettelli, E. & Kuchroo, V. K. Th1, Th17, and Th9 effector cells induce experimental autoimmune encephalomyelitis with different pathological phenotypes. *Journal of immunology* 183, 7169-7177, doi:10.4049/jimmunol.0901906 (2009).

47 Satija, R., Farrell, J. A., Gennert, D., Schier, A. F. & Regev, A. Spatial reconstruction of single-cell gene expression data. *Nat Biotechnol* 33, 495-502, doi:10.1038/nbt.3192 (2015).

48 Zeileis, A., Kleiber, C. & Jackman, S. Regression Models for Count Data in R. *Journal of Statistical Software* 27, doi:10.18637/jss.v027.i08 (2008).

49 Jackman, S. pscl: Classes and Methods for R Developed in the Political Science Computational Laboratory, Stanford University. Department of Political Science, Stanford University. Stanford, California. R package version 1.4.9. (2015).

50 Bray, N. L., Pimentel, H., Melsted, P. & Pachter, L. Near-optimal probabilistic RNA-seq quantification. *Nat Biotechnol* 34, 525-527, doi:10.1038/nbt.3519 (2016).

51 Soneson, C., Love, M. I. & Robinson, M. D. Differential analyses for RNA-seq: transcript-level estimates improve gene-level inferences [version 2; referees: 2 approved]. *F1000Research* 4, doi:10.12688/f1000research.7563.2 (2016).

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of treating a subject suffering from lung cancer, comprising administering to the lungs of the subject an amount of Interleukin-25 (IL-25) as set forth in SEQ ID NO: 3 and an agonist of Neuromedin-U receptor 1 (NMUR1) sufficient to induce an innate lymphoid cell (ILC) Type 2 inflammatory response in the lungs of the subject, wherein the agonist of NMUR1 is Neuromedin U (NMU) as set forth in SEQ ID NO: 2, or a peptide selected from the group consisting of SEQ ID NOS: 4-68.

2. The method according to claim 1, wherein the subject is treated for a drug resistant lung cancer.

3. The method according to claim 2, wherein the drug resistant lung cancer is resistant to an immunotherapy targeting the adaptive immune system.

4. The method according to claim 3, wherein the immunotherapy is a check point inhibitor.

5. The method according to claim 1, wherein expression is reduced of one or more genes or polypeptides selected from the group consisting of:

Nmur1, Dgat2, Calca, Ccl5, Btg1, Nr4a1, Klf3, Klf4, Csf2, Stab2, Sdc4, Ccr2, Fosb, Zfp36l1, Lpcat2 and Ltb;

Nmur1, Dgat2, Calca, Ccl5, Btg1, Klf3, Klf4, Csf2, Stab2, Sdc4, Ccr2, Fosb, Zfp36l1, Lpcat2 and Ltb; or Nmur1, Calca, Ccl5, Csf2, Stab2, Sdc4, Ccr2 and Ltb.

6. The method according to claim 1, wherein activity is inhibited of one or more genes or polypeptides selected from the group consisting of:

Nmur1, Dgat2, Calca, Ccl5, Btg1, Nr4a1, Klf3, Klf4, Csf2, Stab2, Sdc4, Ccr2, Fosb, Zfp36l1, Lpcat2 and Ltb;

Nmur1, Dgat2, Calca, Ccl5, Btg1, Klf3, Klf4, Csf2, Stab2, Sdc4, Ccr2, Fosb, Zfp36l1, Lpcat2 and Ltb; or Nmur1, Calca, Ccl5, Csf2, Stab2, Sdc4, Ccr2 and Ltb.

7. The method according to claim 1, wherein administering to the subject's lungs is by aerosol inhalation.

8. The method according to claim 1, wherein administering to the subject's lungs is through a mucosal surface.

9. The method according to claim 1, wherein administering to the subject's lungs is directly through a nasal passage or trachea.

* * * * *

SEQUENCE LISTING

```
<160> NUMBER OF SEQ ID NOS: 70

<210> SEQ ID NO 1
<211> LENGTH: 426
<212> TYPE: PRT
<213> ORGANISM: Homo sapiens

<400> SEQUENCE: 1

Met Thr Pro Leu Cys Leu Asn Cys Ser Val Leu Pro Gly Asp Leu Tyr
1               5                   10                  15

Pro Gly Gly Ala Arg Asn Pro Met Ala Cys Asn Gly Ser Ala Ala Arg
            20                  25                  30

Gly His Phe Asp Pro Glu Asp Leu Asn Leu Thr Asp Glu Ala Leu Arg
        35                  40                  45

Leu Lys Tyr Leu Gly Pro Gln Gln Thr Glu Leu Phe Met Pro Ile Cys
    50                  55                  60

Ala Thr Tyr Leu Leu Ile Phe Val Val Gly Ala Val Gly Asn Gly Leu
65                  70                  75                  80

Thr Cys Leu Val Ile Leu Arg His Lys Ala Met Arg Thr Pro Thr Asn
                85                  90                  95

Tyr Tyr Leu Phe Ser Leu Ala Val Ser Asp Leu Leu Val Leu Leu Val
            100                 105                 110

Gly Leu Pro Leu Glu Leu Tyr Glu Met Trp His Asn Tyr Pro Phe Leu
        115                 120                 125

Leu Gly Val Gly Gly Cys Tyr Phe Arg Thr Leu Leu Phe Glu Met Val
    130                 135                 140

Cys Leu Ala Ser Val Leu Asn Val Thr Ala Leu Ser Val Glu Arg Tyr
145                 150                 155                 160

Val Ala Val Val His Pro Leu Gln Ala Arg Ser Met Val Thr Arg Ala
                165                 170                 175

His Val Arg Arg Val Leu Gly Ala Val Trp Gly Leu Ala Met Leu Cys
            180                 185                 190

Ser Leu Pro Asn Thr Ser Leu His Gly Ile Arg Gln Leu His Val Pro
        195                 200                 205

Cys Arg Gly Pro Val Pro Asp Ser Ala Val Cys Met Leu Val Arg Pro
    210                 215                 220

Arg Ala Leu Tyr Asn Met Val Val Gln Thr Thr Ala Leu Leu Phe Phe
225                 230                 235                 240

Cys Leu Pro Met Ala Ile Met Ser Val Leu Tyr Leu Leu Ile Gly Leu
                245                 250                 255

Arg Leu Arg Arg Glu Arg Leu Leu Met Gln Glu Ala Lys Gly Arg
            260                 265                 270

Gly Ser Ala Ala Ala Arg Ser Arg Tyr Thr Cys Arg Leu Gln Gln His
```

```
                275                 280                 285
Asp Arg Gly Arg Arg Gln Val Thr Lys Met Leu Phe Val Leu Val Val
        290                 295                 300
Val Phe Gly Ile Cys Trp Ala Pro Phe His Ala Asp Arg Val Met Trp
305                 310                 315                 320
Ser Val Val Ser Gln Trp Thr Asp Gly Leu His Leu Ala Phe Gln His
                325                 330                 335
Val His Val Ile Ser Gly Ile Phe Phe Tyr Leu Gly Ser Ala Ala Asn
            340                 345                 350
Pro Val Leu Tyr Ser Leu Met Ser Ser Arg Phe Arg Glu Thr Phe Gln
                355                 360                 365
Glu Ala Leu Cys Leu Gly Ala Cys Cys His Arg Leu Arg Pro Arg His
        370                 375                 380
Ser Ser His Ser Leu Ser Arg Met Thr Thr Gly Ser Thr Leu Cys Asp
385                 390                 395                 400
Val Gly Ser Leu Gly Ser Trp Val His Pro Leu Ala Gly Asn Asp Gly
                405                 410                 415
Pro Glu Ala Gln Gln Glu Thr Asp Pro Ser
            420                 425

<210> SEQ ID NO 2
<211> LENGTH: 174
<212> TYPE: PRT
<213> ORGANISM: Homo sapiens

<400> SEQUENCE: 2

Met Leu Arg Thr Glu Ser Cys Arg Pro Arg Ser Pro Ala Gly Gln Val
1               5                   10                  15
Ala Ala Ala Ser Pro Leu Leu Leu Leu Leu Leu Leu Ala Trp Cys
            20                  25                  30
Ala Gly Ala Cys Arg Gly Ala Pro Ile Leu Pro Gln Gly Leu Gln Pro
        35                  40                  45
Glu Gln Gln Leu Gln Leu Trp Asn Glu Ile Asp Asp Thr Cys Ser Ser
    50                  55                  60
Phe Leu Ser Ile Asp Ser Gln Pro Gln Ala Ser Asn Ala Leu Glu Glu
65                  70                  75                  80
Leu Cys Phe Met Ile Met Gly Met Leu Pro Lys Pro Gln Glu Gln Asp
                85                  90                  95
Glu Lys Asp Asn Thr Lys Arg Phe Leu Phe His Tyr Ser Lys Thr Gln
            100                 105                 110
Lys Leu Gly Lys Ser Asn Val Val Ser Ser Val Val His Pro Leu Leu
        115                 120                 125
Gln Leu Val Pro His Leu His Glu Arg Arg Met Lys Arg Phe Arg Val
    130                 135                 140
Asp Glu Glu Phe Gln Ser Pro Phe Ala Ser Gln Ser Arg Gly Tyr Phe
145                 150                 155                 160
Leu Phe Arg Pro Arg Asn Gly Arg Arg Ser Ala Gly Phe Ile
                165                 170

<210> SEQ ID NO 3
<211> LENGTH: 177
<212> TYPE: PRT
<213> ORGANISM: Homo sapiens

<400> SEQUENCE: 3

Met Arg Glu Arg Pro Arg Leu Gly Glu Asp Ser Ser Leu Ile Ser Leu
```

```
                1               5                   10                  15
            Phe Leu Gln Val Val Ala Phe Leu Ala Met Val Met Gly Thr His Thr
                                20                  25                  30

Tyr Ser His Trp Pro Ser Cys Cys Pro Ser Lys Gly Gln Asp Thr Ser
                        35                  40                  45

Glu Glu Leu Leu Arg Trp Ser Thr Val Pro Val Pro Pro Leu Glu Pro
                    50                  55                  60

Ala Arg Pro Asn Arg His Pro Glu Ser Cys Arg Ala Ser Glu Asp Gly
             65                  70                  75                  80

Pro Leu Asn Ser Arg Ala Ile Ser Pro Trp Arg Tyr Glu Leu Asp Arg
                            85                  90                  95

Asp Leu Asn Arg Leu Pro Gln Asp Leu Tyr His Ala Arg Cys Leu Cys
                        100                 105                 110

Pro His Cys Val Ser Leu Gln Thr Gly Ser His Met Asp Pro Arg Gly
                    115                 120                 125

Asn Ser Glu Leu Leu Tyr His Asn Gln Thr Val Phe Tyr Arg Arg Pro
            130                 135                 140

Cys His Gly Glu Lys Gly Thr His Lys Gly Tyr Cys Leu Glu Arg Arg
            145                 150                 155                 160

Leu Tyr Arg Val Ser Leu Ala Cys Val Cys Val Arg Pro Arg Val Met
                            165                 170                 175

Gly

<210> SEQ ID NO 4
<211> LENGTH: 25
<212> TYPE: PRT
<213> ORGANISM: Homo sapiens

<400> SEQUENCE: 4

Phe Arg Val Asp Glu Glu Phe Gln Ser Pro Phe Ala Ser Gln Ser Arg
1               5                   10                  15

Gly Tyr Phe Leu Phe Arg Pro Arg Asn
            20                  25

<210> SEQ ID NO 5
<211> LENGTH: 25
<212> TYPE: PRT
<213> ORGANISM: Homo sapiens
<220> FEATURE:
<221> NAME/KEY: VARIANT
<222> LOCATION: (1)..(1)
<223> OTHER INFORMATION: (PEG)2   40 kDa

<400> SEQUENCE: 5

Phe Arg Val Asp Glu Glu Phe Gln Ser Pro Phe Ala Ser Gln Ser Arg
1               5                   10                  15

Gly Tyr Phe Leu Phe Arg Pro Arg Asn
            20                  25

<210> SEQ ID NO 6
<211> LENGTH: 25
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION

<400> SEQUENCE: 6

Phe Arg Val Asp Glu Glu Phe Gln Ser Pro Phe Ala Ser Gln Ser Arg
```

```
                1               5                   10                  15

Gly Tyr Phe Leu Phe Arg Pro Arg Asn
                20                  25

<210> SEQ ID NO 7
<211> LENGTH: 9
<212> TYPE: PRT
<213> ORGANISM: Homo sapiens

<400> SEQUENCE: 7

Gly Tyr Phe Leu Phe Arg Pro Arg Asn
1               5

<210> SEQ ID NO 8
<211> LENGTH: 25
<212> TYPE: PRT
<213> ORGANISM: Homo sapiens

<400> SEQUENCE: 8

Phe Arg Val Asp Glu Glu Phe Gln Ser Pro Phe Ala Ser Gln Ser Arg
1               5                   10                  15

Pro Tyr Phe Leu Phe Arg Pro Arg Asn
                20                  25

<210> SEQ ID NO 9
<211> LENGTH: 25
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION

<400> SEQUENCE: 9

Phe Arg Val Asp Glu Glu Phe Gln Ser Pro Phe Ala Ser Gln Ser Arg
1               5                   10                  15

Pro Tyr Phe Leu Phe Arg Pro Arg Asn
                20                  25

<210> SEQ ID NO 10
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION

<400> SEQUENCE: 10

Cys Gly Tyr Phe Leu Phe Arg Pro Arg Asn
1               5                   10

<210> SEQ ID NO 11
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (1)..(1)
<223> OTHER INFORMATION: Cys(N-ethylmaleimidyl)

<400> SEQUENCE: 11
```

Cys Gly Tyr Phe Leu Phe Arg Pro Arg Asn
1               5                   10

<210> SEQ ID NO 12
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (1)..(1)
<223> OTHER INFORMATION: Cys(PEG)2 40 kDa

<400> SEQUENCE: 12

Cys Gly Tyr Phe Leu Phe Arg Pro Arg Asn
1               5                   10

<210> SEQ ID NO 13
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (1)..(1)
<223> OTHER INFORMATION: Cys(Cholesteroyl)

<400> SEQUENCE: 13

Cys Gly Tyr Phe Leu Phe Arg Pro Arg Asn
1               5                   10

<210> SEQ ID NO 14
<211> LENGTH: 26
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION

<400> SEQUENCE: 14

Cys Phe Arg Val Asp Glu Glu Phe Gln Ser Pro Phe Ala Ser Gln Ser
1               5                   10                  15

Arg Gly Tyr Phe Leu Phe Arg Pro Arg Asn
            20                  25

<210> SEQ ID NO 15
<211> LENGTH: 26
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (1)..(1)
<223> OTHER INFORMATION: Cys(N-ethylmaleimidyl)

<400> SEQUENCE: 15

Cys Phe Arg Val Asp Glu Glu Phe Gln Ser Pro Phe Ala Ser Gln Ser
1               5                   10                  15

Arg Gly Tyr Phe Leu Phe Arg Pro Arg Asn

```
                        20                  25

<210> SEQ ID NO 16
<211> LENGTH: 26
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (1)..(1)
<223> OTHER INFORMATION: Cys(PEG)2  40 kDa

<400> SEQUENCE: 16

Cys Phe Arg Val Asp Glu Glu Phe Gln Ser Pro Phe Ala Ser Gln Ser
1               5                   10                  15

Arg Gly Tyr Phe Leu Phe Arg Pro Arg Asn
            20                  25

<210> SEQ ID NO 17
<211> LENGTH: 26
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (1)..(1)
<223> OTHER INFORMATION: Cys(PEG)2 40 kDa

<400> SEQUENCE: 17

Cys Phe Arg Val Asp Glu Glu Phe Gln Ser Pro Phe Ala Ser Gln Ser
1               5                   10                  15

Arg Gly Tyr Phe Leu Phe Arg Pro Arg Asn
            20                  25

<210> SEQ ID NO 18
<211> LENGTH: 26
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (1)..(1)
<223> OTHER INFORMATION: Cys(Cholesteroyl)

<400> SEQUENCE: 18

Cys Phe Arg Val Asp Glu Glu Phe Gln Ser Pro Phe Ala Ser Gln Ser
1               5                   10                  15

Arg Gly Tyr Phe Leu Phe Arg Pro Arg Asn
            20                  25

<210> SEQ ID NO 19
<211> LENGTH: 26
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
```

-continued

```
<222> LOCATION: (1)..(1)
<223> OTHER INFORMATION: Cys(PEG) 20 kDa

<400> SEQUENCE: 19

Cys Phe Arg Val Asp Glu Glu Phe Gln Ser Pro Phe Ala Ser Gln Ser
1               5                   10                  15

Arg Gly Tyr Phe Leu Phe Arg Pro Arg Asn
            20                  25

<210> SEQ ID NO 20
<211> LENGTH: 26
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (1)..(1)
<223> OTHER INFORMATION: Cys(PEG)2 20 kDa

<400> SEQUENCE: 20

Cys Phe Arg Val Asp Glu Glu Phe Gln Ser Pro Phe Ala Ser Gln Ser
1               5                   10                  15

Arg Gly Tyr Phe Leu Phe Arg Pro Arg Asn
            20                  25

<210> SEQ ID NO 21
<211> LENGTH: 26
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (21)..(21)
<223> OTHER INFORMATION: D-Alanine

<400> SEQUENCE: 21

Cys Phe Arg Val Asp Glu Glu Phe Gln Ser Pro Phe Ala Ser Gln Ser
1               5                   10                  15

Arg Gly Tyr Phe Ala Trp Arg Pro Arg Asn
            20                  25

<210> SEQ ID NO 22
<211> LENGTH: 26
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (1)..(1)
<223> OTHER INFORMATION: Cys(N-ethylmaleimidyl)
<220> FEATURE:
<221> NAME/KEY: VARIANT
<222> LOCATION: (21)..(21)
<223> OTHER INFORMATION: D-Alanine

<400> SEQUENCE: 22

Cys Phe Arg Val Asp Glu Glu Phe Gln Ser Pro Phe Ala Ser Gln Ser
1               5                   10                  15

Arg Gly Tyr Phe Ala Trp Arg Pro Arg Asn
```

```
<210> SEQ ID NO 23
<211> LENGTH: 26
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (1)..(1)
<223> OTHER INFORMATION: Cys(PEG)2 40 kDa
<220> FEATURE:
<221> NAME/KEY: VARIANT
<222> LOCATION: (21)..(21)
<223> OTHER INFORMATION: D-Alanine

<400> SEQUENCE: 23

Cys Phe Arg Val Asp Glu Glu Phe Gln Ser Pro Phe Ala Ser Gln Ser
1               5                   10                  15

Arg Gly Tyr Phe Ala Trp Arg Pro Arg Asn
            20                  25

<210> SEQ ID NO 24
<211> LENGTH: 9
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: X at position 2 = 1-amino-4,7,10-trioxa-13-
      tridecanamine succinimic acid

<400> SEQUENCE: 24

Cys Xaa Phe Leu Phe Arg Pro Arg Asn
1               5

<210> SEQ ID NO 25
<211> LENGTH: 9
<212> TYPE: PRT
<213> ORGANISM: Homo sapiens
<220> FEATURE:
<221> NAME/KEY: VARIANT
<222> LOCATION: (1)..(1)
<223> OTHER INFORMATION: Cys(N-ethylmaleimidyl)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: X at position 2 = 1-amino-4,7,10-trioxa-13-
      tridecanamine succinimic acid

<400> SEQUENCE: 25

Cys Xaa Phe Leu Phe Arg Pro Arg Asn
1               5

<210> SEQ ID NO 26
<211> LENGTH: 9
<212> TYPE: PRT
<213> ORGANISM: Homo sapiens
<220> FEATURE:
<221> NAME/KEY: VARIANT
```

```
<222> LOCATION: (1)..(1)
<223> OTHER INFORMATION: Cys(PEG)2 40 kDa
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: N at position 2 = 1-amino-4,7,10-trioxa-13-
      tridecanamine succinimic acid
<220> FEATURE:
<221> NAME/KEY: MISC_FEATURE
<222> LOCATION: (2)..(2)
<223> OTHER INFORMATION: X at position 2 = 1-amino-4,7,10-trioxa-13-
      tridecanamine succinimic acid

<400> SEQUENCE: 26

Cys Xaa Phe Leu Phe Arg Pro Arg Asn
1               5

<210> SEQ ID NO 27
<211> LENGTH: 15
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION

<400> SEQUENCE: 27

Cys Ala Ser Gln Ser Arg Gly Tyr Phe Leu Phe Arg Pro Arg Asn
1               5                   10                  15

<210> SEQ ID NO 28
<211> LENGTH: 15
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (1)..(1)
<223> OTHER INFORMATION: Cys(N-ethylmaleimidyl

<400> SEQUENCE: 28

Cys Ala Ser Gln Ser Arg Gly Tyr Phe Leu Phe Arg Pro Arg Asn
1               5                   10                  15

<210> SEQ ID NO 29
<211> LENGTH: 15
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (1)..(1)
<223> OTHER INFORMATION: Cys(PEG)2 40 kDa

<400> SEQUENCE: 29

Cys Ala Ser Gln Ser Arg Gly Tyr Phe Leu Phe Arg Pro Arg Asn
1               5                   10                  15

<210> SEQ ID NO 30
<211> LENGTH: 20
<212> TYPE: PRT
```

```
<213> ORGANISM: Homo sapiens
<220> FEATURE:
<221> NAME/KEY: MOD_RES
<222> LOCATION: (1)..(1)
<223> OTHER INFORMATION: ACETYLATION

<400> SEQUENCE: 30

Cys Phe Gln Ser Pro Phe Ala Ser Gln Ser Arg Gly Tyr Phe Leu Phe
1               5                   10                  15

Arg Pro Arg Asn
            20

<210> SEQ ID NO 31
<211> LENGTH: 20
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (1)..(1)
<223> OTHER INFORMATION: Cys(N-ethylmaleimidyl)

<400> SEQUENCE: 31

Cys Phe Gln Ser Pro Phe Ala Ser Gln Ser Arg Gly Tyr Phe Leu Phe
1               5                   10                  15

Arg Pro Arg Asn
            20

<210> SEQ ID NO 32
<211> LENGTH: 20
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (1)..(1)
<223> OTHER INFORMATION: Cys(PEG)2 40 kDa

<400> SEQUENCE: 32

Cys Phe Gln Ser Pro Phe Ala Ser Gln Ser Arg Gly Tyr Phe Leu Phe
1               5                   10                  15

Arg Pro Arg Asn
            20

<210> SEQ ID NO 33
<211> LENGTH: 27
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION

<400> SEQUENCE: 33

Cys Cys Phe Arg Val Asp Glu Glu Phe Gln Ser Pro Phe Ala Ser Gln
1               5                   10                  15

Ser Arg Gly Tyr Phe Leu Phe Arg Pro Arg Asn
            20                  25

<210> SEQ ID NO 34
<211> LENGTH: 27
```

```
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (1)..(1)
<223> OTHER INFORMATION: Cys(N-ethylmaleimidyl)
<220> FEATURE:
<221> NAME/KEY: VARIANT
<222> LOCATION: (2)..(2)
<223> OTHER INFORMATION: Cys(N-ethylmaleimidyl)

<400> SEQUENCE: 34

Cys Cys Phe Arg Val Asp Glu Glu Phe Gln Ser Pro Phe Ala Ser Gln
1               5                   10                  15

Ser Arg Gly Tyr Phe Leu Phe Arg Pro Arg Asn
            20                  25

<210> SEQ ID NO 35
<211> LENGTH: 27
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (1)..(1)
<223> OTHER INFORMATION: Cys(PEG) 20 kDa
<220> FEATURE:
<221> NAME/KEY: VARIANT
<222> LOCATION: (2)..(2)
<223> OTHER INFORMATION: Cys(PEG)20 kDa

<400> SEQUENCE: 35

Cys Cys Phe Arg Val Asp Glu Glu Phe Gln Ser Pro Phe Ala Ser Gln
1               5                   10                  15

Ser Arg Gly Tyr Phe Leu Phe Arg Pro Arg Asn
            20                  25

<210> SEQ ID NO 36
<211> LENGTH: 26
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Palmitoyl-Cysteine

<400> SEQUENCE: 36

Cys Phe Arg Val Asp Glu Glu Phe Gln Ser Pro Phe Ala Ser Gln Ser
1               5                   10                  15

Arg Gly Tyr Phe Leu Phe Arg Pro Arg Asn
            20                  25

<210> SEQ ID NO 37
<211> LENGTH: 26
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Palmitoyl Cysteine
<220> FEATURE:
<221> NAME/KEY: VARIANT
<222> LOCATION: (1)..(1)
```

<223> OTHER INFORMATION: Cys(N-ethylmaleimidyl)

<400> SEQUENCE: 37

Cys Phe Arg Val Asp Glu Glu Phe Gln Ser Pro Phe Ala Ser Gln Ser
1               5                   10                  15

Arg Gly Tyr Phe Leu Phe Arg Pro Arg Asn
            20                  25

<210> SEQ ID NO 38
<211> LENGTH: 26
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Palmitoyl Cysteine
<220> FEATURE:
<221> NAME/KEY: VARIANT
<222> LOCATION: (1)..(1)
<223> OTHER INFORMATION: Cys(PEG)2 40 kDa

<400> SEQUENCE: 38

Cys Phe Arg Val Asp Glu Glu Phe Gln Ser Pro Phe Ala Ser Gln Ser
1               5                   10                  15

Arg Gly Tyr Phe Leu Phe Arg Pro Arg Asn
            20                  25

<210> SEQ ID NO 39
<211> LENGTH: 26
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (1)..(1)
<223> OTHER INFORMATION: Cys(PEG) 40 kDa

<400> SEQUENCE: 39

Cys Phe Arg Val Asp Glu Glu Phe Gln Ser Pro Phe Ala Ser Gln Ser
1               5                   10                  15

Arg Gly Tyr Phe Leu Phe Arg Pro Arg Asn
            20                  25

<210> SEQ ID NO 40
<211> LENGTH: 11
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: X at position 2 = 1-amino-4,7,10-trioxa-13-
      tridecanamine succinimic acid

<400> SEQUENCE: 40

Cys Xaa Gly Tyr Phe Leu Phe Arg Pro Arg Asn
1               5                   10

<210> SEQ ID NO 41
<211> LENGTH: 11
<212> TYPE: PRT
<213> ORGANISM: Homo sapiens

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (1)..(1)
<223> OTHER INFORMATION: Cys(N-ethylmaleimidyl)
<220> FEATURE:
<221> NAME/KEY: MISC_FEATURE
<222> LOCATION: (2)..(2)
<223> OTHER INFORMATION: X at position 2 = 1-amino-4,7,10-trioxa-13-
      tridecanamine succinimic acid

<400> SEQUENCE: 41

Cys Xaa Gly Tyr Phe Leu Phe Arg Pro Arg Asn
1               5                   10

<210> SEQ ID NO 42
<211> LENGTH: 11
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (1)..(1)
<223> OTHER INFORMATION: Cys(PEG)2 40 kDa
<220> FEATURE:
<221> NAME/KEY: MISC_FEATURE
<222> LOCATION: (2)..(2)
<223> OTHER INFORMATION: X at position 2 = 1-amino-4,7,10-trioxa-13-
      tridecanamine succinimic acid

<400> SEQUENCE: 42

Cys Xaa Gly Tyr Phe Leu Phe Arg Pro Arg Asn
1               5                   10

<210> SEQ ID NO 43
<211> LENGTH: 26
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (1)..(1)
<223> OTHER INFORMATION: Cys(N-ethylmaleimidyl)

<400> SEQUENCE: 43

Cys Phe Arg Val Asp Glu Glu Phe Gln Ser Pro Phe Ala Ser Gln Ser
1               5                   10                  15

Arg Pro Tyr Phe Leu Phe Arg Pro Arg Asn
            20                  25

<210> SEQ ID NO 44
<211> LENGTH: 26
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (1)..(1)
<223> OTHER INFORMATION: Cys(PEG)2 40 kDa
```

```
<400> SEQUENCE: 44

Cys Phe Arg Val Asp Glu Glu Phe Gln Ser Pro Phe Ala Ser Gln Ser
1               5                   10                  15

Arg Pro Tyr Phe Leu Phe Arg Pro Arg Asn
            20                  25

<210> SEQ ID NO 45
<211> LENGTH: 7
<212> TYPE: PRT
<213> ORGANISM: Homo sapiens

<400> SEQUENCE: 45

Tyr Phe Trp Arg Pro Arg Asn
1               5

<210> SEQ ID NO 46
<211> LENGTH: 8
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: L at position 3 is D-Leucine

<400> SEQUENCE: 46

Tyr Phe Leu Trp Arg Pro Arg Asn
1               5

<210> SEQ ID NO 47
<211> LENGTH: 8
<212> TYPE: PRT
<213> ORGANISM: Homo sapiens

<400> SEQUENCE: 47

Tyr Phe Gly Trp Arg Pro Arg Asn
1               5

<210> SEQ ID NO 48
<211> LENGTH: 8
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: A at position 3 is D-Alanine

<400> SEQUENCE: 48

Tyr Phe Ala Trp Arg Pro Arg Asn
1               5

<210> SEQ ID NO 49
<211> LENGTH: 7
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: L at position 2 is D-Leucine

<400> SEQUENCE: 49

Phe Leu Trp Arg Pro Arg Asn
1               5
```

```
<210> SEQ ID NO 50
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION

<400> SEQUENCE: 50

Phe Phe Arg Pro Arg Asn
1               5

<210> SEQ ID NO 51
<211> LENGTH: 24
<212> TYPE: PRT
<213> ORGANISM: Homo sapiens

<400> SEQUENCE: 51

Phe Arg Val Asp Glu Glu Phe Gln Ser Pro Phe Ala Ser Gln Ser Arg
1               5                   10                  15

Gly Tyr Phe Trp Arg Pro Arg Asn
            20

<210> SEQ ID NO 52
<211> LENGTH: 25
<212> TYPE: PRT
<213> ORGANISM: Homo sapiens
<220> FEATURE:
<221> NAME/KEY: MISC_FEATURE
<222> LOCATION: (20)..(20)
<223> OTHER INFORMATION: L at position 20 is D-Leucine

<400> SEQUENCE: 52

Phe Arg Val Asp Glu Glu Phe Gln Ser Pro Phe Ala Ser Gln Ser Arg
1               5                   10                  15

Gly Tyr Phe Leu Trp Arg Pro Arg Asn
            20                  25

<210> SEQ ID NO 53
<211> LENGTH: 8
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: X at position 7 is Homoarginine

<400> SEQUENCE: 53

Phe Trp Leu Phe Arg Pro Xaa Asn
1               5

<210> SEQ ID NO 54
<211> LENGTH: 8
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: X at position 7 is Homoarginine

<400> SEQUENCE: 54

Phe Trp Leu Phe Arg Ala Xaa Asn
1               5

<210> SEQ ID NO 55
```

```
<211> LENGTH: 8
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: X at position 8 is Norleucine

<400> SEQUENCE: 55

Trp Phe Leu Phe Arg Ala Arg Xaa
1               5

<210> SEQ ID NO 56
<211> LENGTH: 8
<212> TYPE: PRT
<213> ORGANISM: Homo sapiens

<400> SEQUENCE: 56

Phe Trp Leu Phe Arg Ala Arg Asn
1               5

<210> SEQ ID NO 57
<211> LENGTH: 8
<212> TYPE: PRT
<213> ORGANISM: Homo sapiens

<400> SEQUENCE: 57

Trp Ala Leu Phe Arg Ala Arg Asn
1               5

<210> SEQ ID NO 58
<211> LENGTH: 8
<212> TYPE: PRT
<213> ORGANISM: Homo sapiens

<400> SEQUENCE: 58

Phe Ala Leu Phe Arg Pro Arg Asn
1               5

<210> SEQ ID NO 59
<211> LENGTH: 25
<212> TYPE: PRT
<213> ORGANISM: Homo sapiens
<220> FEATURE:
<221> NAME/KEY: MISC_FEATURE
<222> LOCATION: (24)..(24)
<223> OTHER INFORMATION: X at position 24 is Homoarginine

<400> SEQUENCE: 59

Phe Arg Val Asp Glu Glu Phe Gln Ser Pro Phe Ala Ser Gln Ser Arg
1               5                   10                  15

Gly Phe Trp Leu Phe Arg Pro Xaa Asn
            20                  25

<210> SEQ ID NO 60
<211> LENGTH: 25
<212> TYPE: PRT
<213> ORGANISM: Homo sapiens
<220> FEATURE:
<221> NAME/KEY: MISC_FEATURE
<222> LOCATION: (24)..(24)
<223> OTHER INFORMATION: X at position 24 is Homoarginine

<400> SEQUENCE: 60

Phe Arg Val Asp Glu Glu Phe Gln Ser Pro Phe Ala Ser Gln Ser Arg
1               5                   10                  15
```

-continued

Gly Phe Trp Leu Phe Arg Ala Xaa Asn
            20                  25

<210> SEQ ID NO 61
<211> LENGTH: 25
<212> TYPE: PRT
<213> ORGANISM: Homo sapiens
<220> FEATURE:
<221> NAME/KEY: MISC_FEATURE
<222> LOCATION: (25)..(25)
<223> OTHER INFORMATION: X at position 25 is Norleucine

<400> SEQUENCE: 61

Phe Arg Val Asp Glu Glu Phe Gln Ser Pro Phe Ala Ser Gln Ser Arg
1               5                   10                  15

Gly Phe Trp Leu Phe Arg Pro Arg Xaa
            20                  25

<210> SEQ ID NO 62
<211> LENGTH: 33
<212> TYPE: PRT
<213> ORGANISM: Homo sapiens

<400> SEQUENCE: 62

Ile Leu Gln Arg Gly Ser Gly Thr Ala Ala Val Asp Phe Thr Lys Lys
1               5                   10                  15

Asp His Thr Ala Thr Trp Gly Arg Pro Phe Phe Leu Phe Arg Pro Arg
            20                  25                  30

Asn

<210> SEQ ID NO 63
<211> LENGTH: 34
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION

<400> SEQUENCE: 63

Cys Ile Leu Gln Arg Gly Ser Gly Thr Ala Ala Val Asp Phe Thr Lys
1               5                   10                  15

Lys Asp His Thr Ala Thr Trp Gly Arg Pro Phe Phe Leu Phe Arg Pro
            20                  25                  30

Arg Asn

<210> SEQ ID NO 64
<211> LENGTH: 34
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (1)..(1)
<223> OTHER INFORMATION: Cys(N-ethylmaleimidyl)

<400> SEQUENCE: 64

Cys Ile Leu Gln Arg Gly Ser Gly Thr Ala Ala Val Asp Phe Thr Lys
1               5                   10                  15

Lys Asp His Thr Ala Thr Trp Gly Arg Pro Phe Phe Leu Phe Arg Pro
            20                  25                  30

Arg Asn

<210> SEQ ID NO 65
<211> LENGTH: 34
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (1)..(1)
<223> OTHER INFORMATION: Cys(PEG)2 40 kDa

<400> SEQUENCE: 65

Cys Ile Leu Gln Arg Gly Ser Gly Thr Ala Ala Val Asp Phe Thr Lys
1               5                   10                  15

Lys Asp His Thr Ala Thr Trp Gly Arg Pro Phe Phe Leu Phe Arg Pro
            20                  25                  30

Arg Asn

<210> SEQ ID NO 66
<211> LENGTH: 34
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (1)..(1)
<223> OTHER INFORMATION: Cys(Cholesteroyl)

<400> SEQUENCE: 66

Cys Ile Leu Gln Arg Gly Ser Gly Thr Ala Ala Val Asp Phe Thr Lys
1               5                   10                  15

Lys Asp His Thr Ala Thr Trp Gly Arg Pro Phe Phe Leu Phe Arg Pro
            20                  25                  30

Arg Asn

<210> SEQ ID NO 67
<211> LENGTH: 34
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (1)..(1)
<223> OTHER INFORMATION: Cys(PEG)20 kDa

<400> SEQUENCE: 67

Cys Ile Leu Gln Arg Gly Ser Gly Thr Ala Ala Val Asp Phe Thr Lys
1               5                   10                  15

Lys Asp His Thr Ala Thr Trp Gly Arg Pro Phe Phe Leu Phe Arg Pro
            20                  25                  30

Arg Asn

<210> SEQ ID NO 68
<211> LENGTH: 33
<212> TYPE: PRT
<213> ORGANISM: Homo sapiens -continued

```
<220> FEATURE:
<221> NAME/KEY: MISC_FEATURE
<222> LOCATION: (1)..(1)
<223> OTHER INFORMATION: Palmitoyl Isoleucine

<400> SEQUENCE: 68

Ile Leu Gln Arg Gly Ser Gly Thr Ala Ala Val Asp Phe Thr Lys Lys
1               5                   10                  15

Asp His Thr Ala Thr Trp Gly Arg Pro Phe Phe Leu Phe Arg Pro Arg
                20                  25                  30

Asn

<210> SEQ ID NO 69
<211> LENGTH: 288
<212> TYPE: PRT
<213> ORGANISM: Artificial Sequence
<220> FEATURE:
<223> OTHER INFORMATION: Synthetic

<400> SEQUENCE: 69

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
                20                  25                  30

Ser Pro Pro Ala Gly Gly Pro Leu Asp Gly Leu Pro Ala Arg Arg Thr
            35                  40                  45

Met Ser Arg Thr Arg Leu Pro Ser Pro Ala Pro Ser Pro Ala Phe
    50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
                100                 105                 110

Ala Ala Asp Ala Pro Pro Pro Thr Met Arg Val Ala Val Thr Ala Ala
            115                 120                 125

Arg Pro Pro Arg Ala Lys Pro Ala Pro Arg Arg Ala Ala Gln Pro
        130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Lys Tyr Gln Asp Met Ile Ala Ala Leu Pro Glu Ala Thr His Glu Ala
    210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
            260                 265                 270

Glu Ala Val His Ala Trp Arg Asn Ala Leu Thr Gly Ala Pro Leu Asn
        275                 280                 285
```

```
<210> SEQ ID NO 70
<211> LENGTH: 183
<212> TYPE: PRT
<213> ORGANISM: Artificial Sequence
<220> FEATURE:
<223> OTHER INFORMATION: Synthetic

<400> SEQUENCE: 70

Arg Pro Ala Leu Glu Ser Ile Val Ala Gln Leu Ser Arg Pro Asp Pro
1               5                   10                  15

Ala Leu Ala Ala Leu Thr Asn Asp His Leu Val Ala Leu Ala Cys Leu
                20                  25                  30

Gly Gly Arg Pro Ala Leu Asp Ala Val Lys Lys Gly Leu Pro His Ala
            35                  40                  45

Pro Ala Leu Ile Lys Arg Thr Asn Arg Arg Ile Pro Glu Arg Thr Ser
    50                  55                  60

His Arg Val Ala Asp His Ala Gln Val Val Arg Val Leu Gly Phe Phe
65                  70                  75                  80

Gln Cys His Ser His Pro Ala Gln Ala Phe Asp Asp Ala Met Thr Gln
                85                  90                  95

Phe Gly Met Ser Arg His Gly Leu Leu Gln Leu Phe Arg Arg Val Gly
                100                 105                 110

Val Thr Glu Leu Glu Ala Arg Ser Gly Thr Leu Pro Pro Ala Ser Gln
            115                 120                 125

Arg Trp Asp Arg Ile Leu Gln Ala Ser Gly Met Lys Arg Ala Lys Pro
            130                 135                 140

Ser Pro Thr Ser Thr Gln Thr Pro Asp Gln Ala Ser Leu His Ala Phe
145                 150                 155                 160

Ala Asp Ser Leu Glu Arg Asp Leu Asp Ala Pro Ser Pro Met His Glu
                165                 170                 175

Gly Asp Gln Thr Arg Ala Ser
                180
```